US012742021B2

(12) United States Patent
Gregory

(10) Patent No.: US 12,742,021 B2
(45) Date of Patent: Sep. 22, 2026

(54) INHIBITING THE RNA METHYLTRANSFERASE METTL3 OR ITS INTERACTION WITH EIF3H TO SUPPRESS ONCOGENE TRANSLATION AND TUMORIGENESIS

(71) Applicant: Children's Medical Center Corporation, Boston, MA (US)

(72) Inventor: Richard I. Gregory, Brookline, MA (US)

(73) Assignee: Children's Medical Center Corporation, Boston, MA (US)

( * ) Notice: Subject to any disclaimer, the term of this patent is extended or adjusted under 35 U.S.C. 154(b) by 1122 days.

(21) Appl. No.: 17/624,117

(22) PCT Filed: Jul. 2, 2020

(86) PCT No.: PCT/US2020/404593
§ 371 (c)(1),
(2) Date: Dec. 30, 2021

(87) PCT Pub. No.: WO2021/003330
PCT Pub. Date: Jan. 7, 2021

(65) Prior Publication Data

US 2023/0018989 A1 Jan. 19, 2023

Related U.S. Application Data

(60) Provisional application No. 62/870,342, filed on Jul. 3, 2019.

(51) Int. Cl.

| | |
|---|---|
| ***C07K 16/40*** | (2006.01) |
| ***A61K 38/17*** | (2006.01) |
| ***A61K 38/45*** | (2006.01) |
| ***C07K 16/18*** | (2006.01) |
| ***C12N 15/113*** | (2010.01) |

(52) U.S. Cl.
CPC .......... *C07K 16/40* (2013.01); *A61K 38/1709* (2013.01); *A61K 38/45* (2013.01); *C07K 16/18* (2013.01); *C12N 15/113* (2013.01); *C12N 15/1137* (2013.01); *C12N 2310/14* (2013.01)

(58) Field of Classification Search
None
See application file for complete search history.

(56) References Cited

U.S. PATENT DOCUMENTS

| | | | |
|---|---|---|---|
| 9,610,332 | B2 | 4/2017 | Yaffe et al. |
| 2016/0264934 | A1 | 9/2016 | Giallourakis et al. |

FOREIGN PATENT DOCUMENTS

| | | | | |
|---|---|---|---|---|
| CN | 107349217 A | 11/2017 | | |
| WO | 2017/176813 A1 | 10/2017 | | |
| WO | WO-2019074980 A1 * | 4/2019 | ............ | A61K 35/28 |
| WO | 2020/023360 A1 | 1/2020 | | |

OTHER PUBLICATIONS

Hickman, D. L., Johnson, J., Vemulapalli, T. H., Crisler, J. R., & Shepherd, R. (2017). Commonly Used Animal Models. Principles of Animal Research for Graduate and Undergraduate Students, 117-175. (Year: 2017).*

Bid, H. K., & Kerk, S. (2016). BET bromodomain inhibitor (JQ1) and tumor angiogenesis. Oncoscience, 3(11-12), 316-317 (Year: 2016).*

Lin, S., Choe, J., Du, P., Triboulet, R., & Gregory, R. I. (2016). The m(6)A Methyltransferase METTL3 Promotes Translation in Human Cancer Cells. Molecular cell, 62(3), 335-345. (Year: 2016).*

Tan, Y., Wang, L., Du, Y., Liu, X., Chen, Z., Weng, X., Guo, J., Chen, H., Wang, M., & Wang, X. (2018). Inhibition of BRD4 suppresses tumor growth in prostate cancer via the enhancement of FOXO1 expression. International journal of oncology, 53(6), 2503-2517. (Year: 2018).*

Choe, J., Lin, S., Zhang, W., Liu, Q., Wang, L., Ramirez-Moya, J., . . . & Gregory, R. I. (2018). mRNA circularization by METTL3-eIF3h enhances translation and promotes oncogenesis. Nature, 561(7724), 556-560. (Year: 2018).*

Havasi, A., Lu, W., Cohen, H. T., Beck, L., Wang, Z., Igwebuike, C., & Borkan, S. C. (2017). Blocking peptides and molecular mimicry as treatment for kidney disease. American Journal of Physiology-Renal Physiology, 312(6), F1016-F1025. (Year: 2017).*

Choe et al., mRNA circularization by METTL3-eIF3h enhances translation and promotes oncogenesis. Nature. Sep. 2018;561(7724):556-560. doi: 10.1038/s41586-018-0538-8. Epub Sep. 19, 2018.

Lin et al., The m(6)A Methyltransferase METTL3 Promotes Translation in Human Cancer Cells. Mol Cell. May 5, 2016;62(3):335-345. doi: 10.1016/j.molcel.2016.03.021. Epub Apr. 21, 2016.

* cited by examiner

*Primary Examiner* — Thomas J. Visone
(74) *Attorney, Agent, or Firm* — Wolf, Greenfield & Sacks, P.C.

(57) ABSTRACT

Provided herein are method of treating cancer using agents that inhibit the interaction between Methyltransferase like 3 (METTL3) and Eukaryotic Translation Initiation Factor 3 Subunit H (EIF3h), and optionally agents that inhibit Bromodomain-containing protein 4 (BRD4). The present disclosure demonstrates the topology of individual polyribosomes with single METTL3 foci found in close proximity to 5' cap-binding proteins, revealing a previously unknown direct physical and functional interaction between METTL3 and the eukaryotic translation initiation factor 3 subunit h (eIF3h).

19 Claims, 58 Drawing Sheets

Specification includes a Sequence Listing.

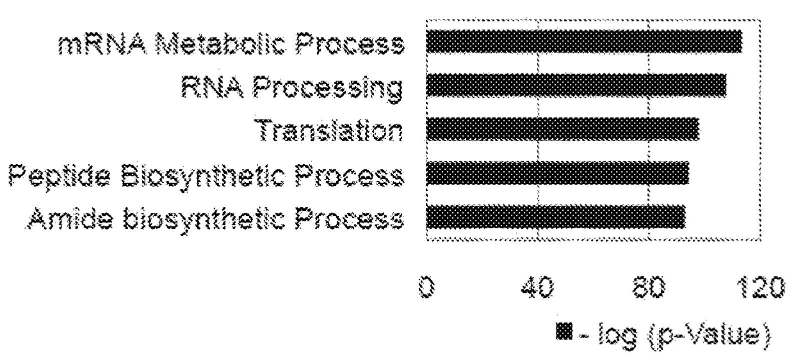
FIG. 4E
| Translation involving factors | |
|---|---|
| Name | No. of Proteins |
| Ribosomal proteins | 87 |
| Eukaryotic translation initiation factors | 21 |
| Eukaryotic translation elongation factors | 5 |
| Nuclear cap-binding protein, CBP80 | 1 |
FIG. 4F
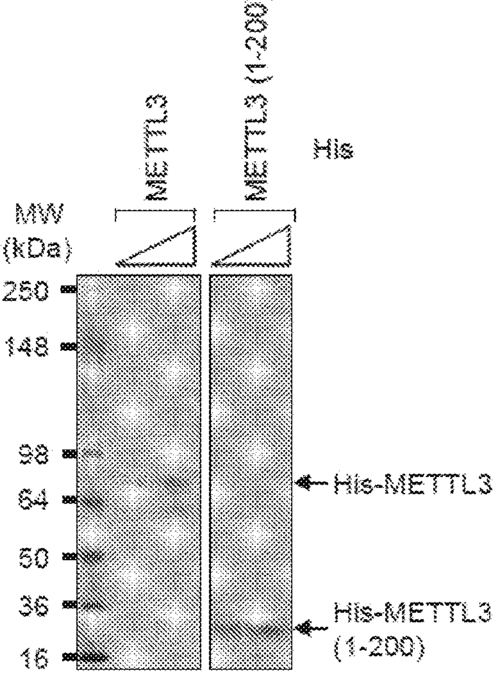
FIG. 5A

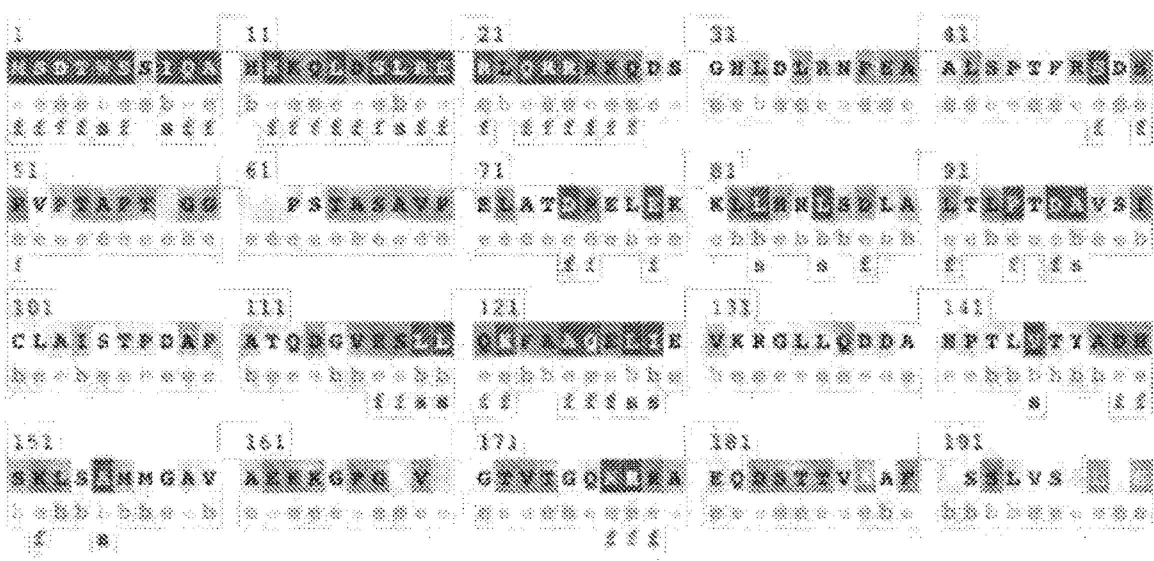

The conservation scale:

Variable Average Conserved e - An exposed residue according to the neural-network algorithm.

b - A buried residue according to the neural-network algorithm.

f - A predicted functional residue (highly conserved and exposed).

s - A predicted structural residue (highly conserved and buried).

. - Insufficient data - the calculation for this site was performed on less than 10% of the sequences.

FIG. 11B

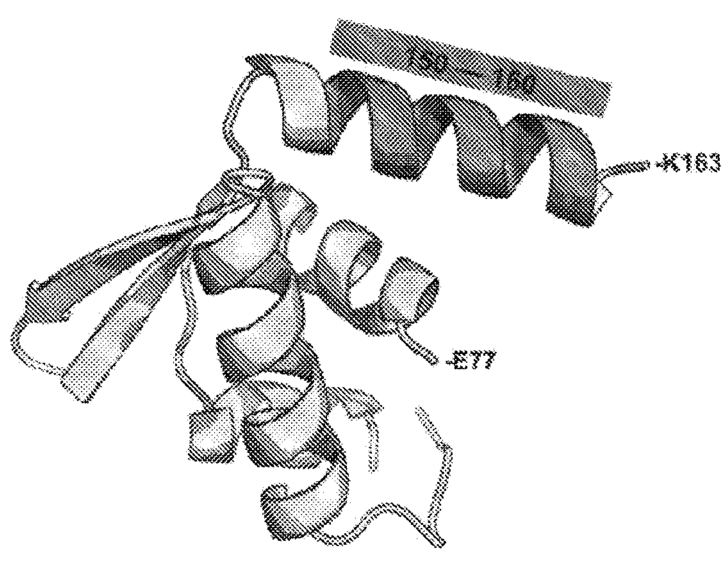

FIG. 11C

INHIBITING THE RNA METHYLTRANSFERASE METTL3 OR ITS INTERACTION WITH EIF3H TO SUPPRESS ONCOGENE TRANSLATION AND TUMORIGENESIS

RELATED APPLICATIONS

This application is a national stage filing under 35 U.S.C. § 371 of International Application No. PCT/US2020/040593, filed Jul. 2, 2020, which claims the benefit under 35 U.S.C. § 119(e) to U.S. Provisional Application No. 62/870,342, filed Jul. 3, 2019, and entitled "INHIBITING THE RNA METHYLTRANSFERASE METTL3 OR ITS INTERACTION WITH EIF3H TO SUPPRESS ONCOGENE TRANSLATION AND TUMORIGENESIS," the entire contents of each of which is incorporated herein by reference.

GOVERNMENT SUPPORT

This invention was made with government support under Grant Nos. GM086386 and CA211328 awarded by the National Institutes of Health. The Government has certain rights in the invention.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Dec. 15, 2021, is named C1233.70159US01-SEQ-RE.txt and is 50,800 bytes in size.

BACKGROUND

N6-Methyladenosine (m6A), the most abundant posttranscriptional messenger RNA (mRNA) modification, is emerging as an important regulator of gene expression. Manipulation of m6A impacts different developmental and biological processes, and altered m6A homeostasis is linked to cancer. m6A is catalyzed by METTL3 and enriched in the 3' untranslated region (3' UTR) of a large subset of mRNAs at sites close to the stop codon. METTL3 can promote translation but the mechanism and widespread relevance remain unknown.

SUMMARY

The present disclosure is based, at least in part, on the novel finding that METTL3 enhances translation only when tethered to mRNA at sites close to the stop codon, supporting a mRNA looping mechanism for ribosome recycling and translational control. The present disclosure demonstrates the topology of individual polyribosomes with single METTL3 foci found in close proximity to 5' cap-binding proteins, revealing a previously unknown direct physical and functional interaction between METTL3 and the eukaryotic translation initiation factor 3 subunit h (eIF3h). It was further demonstrated herein that, METTL3 promotes translation of a large subset of oncogenic mRNAs, including BRD4 that are also $m^6A$-modified in human primary lung tumors, and that the METTL3-eIF3h interaction is required for enhanced translation, formation of densely packed polyribosomes, and oncogenic transformation. The present disclosure further shows that, METTL3 depletion inhibits tumorigenicity and sensitizes cancer cells to BRD4 inhibition, suggesting that METTL3-eIF3h can serve as a potential cancer therapeutic target.

Accordingly, some aspects of the present disclosure provide methods of treating cancer, the method comprising administering to a subject in need thereof an effective amount of an agent that inhibits interaction between Methyltransferase like 3 (METTL3) and Eukaryotic Translation Initiation Factor 3 Subunit H (EIF3h).

In some embodiments, the agent inhibits of METTL3 expression. In some embodiments, the agent comprises a RNAi molecule that targets METTL3 mRNA. In some embodiments, the agent inhibits EIF3h expression. In some embodiments, the agent comprises a RNAi molecule that targets EIF3h mRNA.

In some embodiments, the agent inhibits binding of METTL3 to EIF3h. In some embodiments, the agent is an inhibitory peptide, a small molecule, or an antibody. In some embodiments, the agent is an inhibitory peptide. In some embodiments, the inhibitory peptide comprises an amino acid sequence corresponding to amino acids 150-200 of METTL3. In some embodiments, the inhibitory peptide comprises an amino acid sequence corresponding to amino acids 29-222 of EIF3h.

In some embodiments, the agent is an antibody. In some embodiments, the antibody binds to amino acids 150-200 of METTL3. In some embodiments, the antibody binds to amino acids 29-222 of EIF3h.

In some embodiments, the agent is a small molecule.

In some embodiments, the agent is an antibody. In some embodiments, the antibody binds to amino acids 150-200 of METTL3. In some embodiments, the antibody binds to amino acids 29-222 of EIF3h.

In some embodiments, the agent inhibits METTL3 activity. In some embodiments, the agent is a small molecule or an antibody.

In some embodiments, the method further comprises administering to the subject an effective amount of a second agent that inhibits Bromodomain-containing protein 4 (BRD4).

In some embodiments, the second agent inhibits BRD4 expression. In some embodiments, the second agent comprises a RNAi molecule that targets BRD4 mRNA. In some embodiments, the second agent inhibits BRD4 activity. In some embodiments, the second agent is selected from the group consisting of JQ1, I-BET762, OTX015, I-BET151, CPI203, PFI-1, MS436, CPI-0610, RVX2135, FT-1101, BAY1238097, INCB054329, TEN-010, GSK2820151, ZEN003694, BAY-299, BMS-986158, ABBV-075, GS-5829, and PLX51107.

In some embodiments, the cancer is lung cancer, colon cancer, neuroblastoma, esophageal carcinoma, liver cancer, or prostate cancer.

In some embodiments, the agent is administered systemically. In some embodiments, the second agent is administered systemically.

In some embodiments, the subject is human. In some embodiments, the subject is a rodent. In some embodiments, the rodent is a mouse or a rat.

Other aspects of the present disclosure provide compositions comprising a first agent that inhibits interaction between Methyltransferase like 3 (METTL3) and Eukaryotic Translation Initiation Factor 3 Subunit H (EIF3h) and a second agent that inhibits BRD4.

In some embodiments, the composition further comprises a pharmaceutically acceptable carrier.

The summary above is meant to illustrate, in a non-limiting manner, some of the embodiments, advantages, features, and uses of the technology disclosed herein. Other embodiments, advantages, features, and uses of the technology disclosed herein will be apparent from the Detailed Description, the Drawings, the Examples, and the Claims.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing.

(FIG. 1A) Schematic diagram of reporter plasmids containing Firefly luciferase cDNA and different positions of MS2 binding sites. (FIG. 1B) Western blotting with indicated antibodies. (FIG. 1C) qRT-PCR analysis of reporter mRNAs. Each tested reporter mRNAs were normalized to RLuc mRNAs. The FLuc:RLuc ratio for each construct with FLAG-MS2 expression was set to 1. Error bars represent mean±SD; n=3. (FIG. 1D) Tethering assay to measure translation efficiency of reporter mRNAs. Firefly luciferase (FLuc) activity was normalized to the *Renilla* luciferase (RLuc) activity. Relative FLuc activity was normalized to the relative FLuc mRNAs. The normalized FLuc activity (translation efficiency) in the presence of FLAG-MS2 was set to 1. Error bars represent mean±SD; n=3. p<0.01. (FIG. 1E) Colloidal blue staining of recombinant protein His-FLAG-MS2, His-FLAG-MS2-METTL3, or His-FLAG-MS2-METTL3 (1-200). (FIG. 1F) Ethidium bromide-stained agarose gel electrophoresis of the indicated in vitro transcribed reporter mRNAs; FLuc-MS2bs without poly (A) tail (Poly (A)−) or FLuc-MS2bs with 30 nt poly (A) tail (Poly (A)+). (FIG. 1G) In vitro translation of reporter mRNAs using either H1299 cell extracts or Rabbit reticulocyte lysate (RRL). The levels of in vitro-translated FLuc protein were analyzed using luciferase assays. Value of FLuc activity in the presence of His-FLAG-MS2 recombinant protein was set to 1.0. Error bars represent mean±SD; n=6. * p<0.001.

(FIG. 2A) Schematic diagram of METTL3 deletion mutants or mutation in METTL3 catalytic domain. (FIG. 2B) Western blotting with indicated antibodies. (FIG. 2C) qRT-PCR analysis of reporter mRNAs. FLuc-MS2bs mRNA levels were normalized to RLuc mRNAs. The FLuc:RLuc ratio obtained in FLAG-MS2 (control) was set to 1. Error bars represent mean±SD; n=3. (FIG. 2D) Tethering assay to measure translation efficiency of reporter mRNAs. Firefly luciferase (FLuc) activity was normalized to the *Renilla* luciferase (RLuc) activity. Relative FLuc activity was normalized to the relative FLuc-MS2bs mRNAs. The normalized FLuc activity (translation efficiency) in the presence of FLAG-MS2 was set to 1. Error bars represent mean±SD; n=3. **p<0.01.

(FIG. 3A) Diagram of the experimental procedure of the electron microscopy. The details are described in results and experimental procedure. (FIG. 3B) EM images of polyribosome with METTL3-gold particle labeling. Arrows indicate METTL3 with immuno-gold particle (6 nm). Scale bar, 50 nm. (FIG. 3C) Counting of METTL3 with gold particle labeling in each polyribosome. (FIG. 3D) EM images of polyribosome with METTL3 and CBP80. Black arrows indicate METTL3 with immuno-gold particle (6 nm) and white arrows indicate CBP80 with immuno-gold particle (10 nm). (FIG. 3E) EM images of polyribosome with METTL3 and eIF4E. Black arrows indicate METTL3 with immuno-gold particle (6 nm) and white arrows indicate eIF4E with immuno-gold particle (10 nm). (FIG. 3F) Average distance between immuno-gold particles was measured.

FIGS. 4A-4F. METTL3 associates with translation initiation factors. (FIG. 4A) Deletion mutants of METTL3 were expressed in HeLa cell. The total-cell extracts (Input) and the cap-associated protein samples were analyzed by Western blotting using the indicated antibodies. (FIG. 4B) Cap-association assay with METTL3 depletion. The total-cell extracts (Input) and the cap-bound protein samples were analyzed by Western blotting using the indicated antibodies. $m^7$GpppG cap analogue was used for antagonizing cap-associating proteins binding to $m^7$GTP-Agarose. (FIG. 4C) Same as FIG. 4B except HeLa cells were transfected with CTIF, eIF3b or eIF4GI siRNA. (FIGS. 4D-4F) Mass spectrometry of FLAG-METTL3 interacting proteins. (FIG. 4D) Proteins that were co-immunopurified with FLAG-METTL3 subjected to 4-12% Tris-Glycine SDS-PAGE. Colloidal blue staining was performed. (FIG. 4E) Gene ontology analysis of the identified proteins from Mass spectrometry. (FIG. 4F) Table showing the translation involving factors identified from Mass spectrometry.

FIGS. 5A-5I. N-terminal region of METTL3 directly interacts with MPN domain of eIF3h. (FIGS. 5A-5C) Far Western blotting analysis (FW) of purified eIF3 complex. (FIG. 5A) Colloidal blue staining of recombinant protein His-METTL3 or His-METTL3 1-200 amino acid fragments (1-200). (FIG. 5B) Colloidal blue staining results showing the integrities and relative abundances of input eIF3 protein subunits. The breakdown product of eIF3a is denoted as ΔeIF3a. (FIG. 5C) FW of purified eIF3 complex. Purified human eIF3 complex was resolved by SDS-PAGE. The purified His-METTL3 or His-METTL3 (1-200) (right), and α-METTL3 antibody were used as a probe and a primary antibody, respectively. (FIGS. 5D-5I) In vitro GST pull-down assay with indicated GST-tagged eIF3 protein subunits. (FIG. 5D) Colloidal blue staining of recombinant GST-tagged protein eIF3g, eIF3h, eIF3i, eIF3j or eIF3m. (FIG. 5E) Indicated purified GST-tagged eIF3 subunits were mixed with either His-METTL3 or His-METTL3 (1-200). After GST pull-down, co-purified His-METTL3 or His-METTL3 (1-200) was analyzed by Western blotting. (FIG. 5F) GST-eIF3h was co-purified with His-METTL3 in the presence of either rabbit IgG (rIgG) or α-METTL3 antibody. Levels of co-purified His-METTL3 were analyzed by Western blotting. (FIG. 5G) Schematic diagram of human eIF3h deletion mutants. (FIG. 5H) Colloidal blue staining of recombinant GST-eIF3h, -eIF3h (1-222) or -eIF3h (29-222). (FIG. 5I) GST pull-down of indicated eIF3h deletion mutants. Co-purified His-METTL3 was analyzed by Western blotting.

(FIG. 6A) In vivo interaction of METTL3 and eIF3h was examined by in situ proximity ligation assay (PLA). Cells were stained with rabbit α-METTL3 antibody and/or mouse α-eIF3h antibody, and in vivo protein interaction between METTL3 and eIF3h was detected with secondary proximity probes, α-rabbit-plus and α-mouse-minus. (FIG. 6B) Co-IPs of FLAG-METTL3 using the lysates collected from either control or eIF3h siRNA transfected cells. (FIGS. 6C-6F) Tethering of METTL3 upon knockdown of eIF3h. (FIG. 6C) Western blotting demonstrates efficient knockdown of eIF3h protein.

(FIG. 6D) qRT-PCR analysis demonstrates efficient down regulation of eIF3h mRNA. Error bars represent mean±SD; n=3. *p<0.001. (FIG. 6E) qRT-PCR analysis of reporter mRNAs. FLuc-MS2bs reporter mRNAs were normalized to RLuc mRNAs. The FLuc:RLuc ratio obtained in FLAG-MS2 was set to 1. Error bars represent mean±SD; n=3. (FIG. 6F) Translation efficiency of reporter mRNAs as described in FIG. 1B. Error bars represent mean±SD; n=3. p<0.01. (FIG. 6G) Model illustration of METTL3 dependent mRNA translation. CAP, cap; h, eIF3h; GGAC, $m^6A$ motif sequence; (A)n, poly(A) tail; 40S, 40S ribosomal subunit; 60S, 60S ribosomal subunit.

(FIGS. 7A-7E) Global profiling of METTL3 target genes in HeLa. Cytoplasmic extracts from control or METTL3 depleted cells were subjected to sucrose gradient centrifugation. Total RNA, RNA from sub-polysome fractions and RNA from polysome fractions were analyzed by RNA-seq. (FIG. 7A) Peak analysis of polysome profiling. (FIG. 7B) Scatter plot of RNA-Seq data in METTL3 knockdown (shMETTL3) and control (shGFP) HeLa cells. Average read number from two individual METTL3 knockdown is plotted on the y-axis. (FIG. 7C) Scatter plot of RNA-Seq data in shMETTL3 and shGFP HeLa cells. Average read number from two shMETTL3 samples were calculated by the ratio of polysome fraction to the read number in the sub-polysome fraction and plotted on the y-axis. (FIG. 7D) Venn diagram showing the overlap of 2-fold less translated genes and METTL3 PAR-CLIP data. (FIG. 7E) Average length of 5' UTR, CDS and 3' UTR in overlapping genes that is collected from FIG. 7D. (FIG. 7N) Quantification of apoptotic cells, numbers represent ratio between death cells in JQ1 and DMSO treatments. Death cells were considered as the sum of dead cells, and early and late apoptotic cells. Error bars represent mean±SD; n=3. * p<0.05, **p<0.01.

(FIG. 8A) Western blotting with indicated antibodies. (FIG. 8B) Gene ontology analysis of the overlapping mRNAs in FIG. 5D. (FIG. 8C) qRT-PCR analysis using indicated primers. (FIGS. 8D-8E) Half-life of endogenous mRNAs was analyzed by qRT-PCR using indicated primers. Error bars represent mean±SEM; n=6. There were no significant differences between the samples for all the tested mRNAs; p>0.05.

(FIG. 9A) IP of endogenous METTL3 and Western blotting analysis using indicated antibodies. (FIG. 9B) Density plot reflects the distribution of changes in percent spliced In (ΔPSI) values and according p-values for alternative splicing events detected by rMATs v3.2.5. Splicing events at a FDR <5% and deltaPSI >0.1 are considered as significant. Total mRNAs are indicated. 4,276 mRNAs indicate more than 2-fold less translating mRNAs in METTL3 depleted cells. (FIG. 9C) Western blot using indicated antibodies in control-, METTL3- or YTHDF1-knockdown cells. (FIG. 9D) qRT-PCR analysis of endogenous BRD4 mRNAs. (FIG. 9E) Annexin V/PI staining of METTL3 knockdown and control A549 cells upon JQ1 treatment that was analyzed by FACS.

(FIG. 10A) Co-IPs of FLAG-METTL3 or FLAG-METTL3 A155P analyzed by Western blotting using the indicated antibodies. Where indicated, lysates were treated with RNase A. (FIG. 10B) Tethering assay to measure translation efficiency of reporter mRNAs. Firefly luciferase (FLuc) activity was normalized to the *Renilla* luciferase (RLuc) activity. Relative FLuc activity was normalized to the relative FLuc-MS2bs mRNAs. The normalized FLuc activity (translation efficiency) in the presence of FLAG-MS2 was set to 1.0. Error bars represent mean±SD; n=6. *p<0.001. (FIG. 10C) Western blotting analysis using indicated antibodies. (FIG. 10D) qRT-PCR analysis of FLAG-METTL3 WT or FLAG-METTL3 A155P RNA IP with indicated primers. mRNAs level obtained from IP was normalized to their input mRNAs. Relative mRNAs level obtained in FLAG vector was set to 1. Error bars represent mean±SD; n=2. (FIG. 10E) In vitro translation of reporter mRNAs Rabbit reticulocyte lysate. The levels of in vitro-translated FLuc protein were analyzed using luciferase assays. Value of FLuc activity in the presence of His-FLAG-MS2 recombinant protein was set to 1.0. Error bars represent mean±SD; n=6. * p<0.001. (FIG. 10F) Counting the number of polysomes from 20 images of each sample in FIG. 10E. (FIG. 10G) Peak analysis of polysome profiling coupled with in vitro translation. (FIG. 10H) EM images of polyribosomes. Images were taken from the samples in FIG. 10G. Scale bar, 50 nm.

FIGS. 11A-11G. Identification of a conserved Alanine residue in the N-terminal region of METTL3 required for its interaction with eIF3h. (FIG. 11A) Secondary structure prediction of the N-terminal (1-200) region of METTL3 protein showing putative alpha helices (longest lines). (FIG. 11B) Evolutionary conservation of the N-terminal (1-200) region METTL3 protein (SEQ ID NO: 84). (FIG. 11C) Computational modeling of the 3D structure of the N-terminal (77-163) region METTL3 protein, based on the coordinates of PDB: 3HHH. (FIG. 11D) Western blotting analysis using indicated antibodies. (FIG. 11E) qRT-PCR analysis of reporter mRNAs. FLuc-MS2bs mRNA levels were normalized to RLuc mRNAs. The FLuc:RLuc ratio obtained in FLAG-MS2 (control) was set to 1. Error bars represent mean±SD; n=6. (FIG. 11F) IP of FLAG-METTL3 WT or A155P and Western blotting analysis using indicated antibodies. (FIG. 11G) Colloidal blue staining of recombinant protein His-FLAG-MS2-METTL3 WT or His-FLAG-MS2-METTL3 A155P.

(FIGS. 13A-13B) IHC staining of METTL3 expression in primary lung adenocarcinoma and control samples. (FIG. 13A) Staining score in lung adenocarcinoma samples and the paired adjacent normal controls. n=75, Wilcoxon signed-rank test, *** p<0.001.

(FIG. 13B) Staining scores in different stages of lung adenocarcinoma samples. Wilcoxon signed-rank test, ** $p<0.01$, * $p<0.05$. (FIG. 13C) Tumor-growth curves of xenografts derived from 100,000 A549 cells that is stably expressing either shGFP, shMETTL3-1 and shMETTL3-2. (FIGS. 13D-13E) Quantification of invasive BJ cells. Cells were transiently transfected with indicated siRNAs (FIG. 13D) or plasmids (FIG. 13E). Error bars represent mean±SEM; n=5 for FIG. 13D, n=9 for FIG. 13E. * $p<0.001$,  $p<0.01$. (FIG. 13F) Quantification of NIH-3T3 cells colony formation. 25 days after plating the cells into soft agar, colony numbers were counted. Error bars represent mean±SEM; n=3. *$P<0.001$; ns, not significant. (FIGS. 13G-13H) Quantification of MEFs (FIG. 13G) or MB352 (FIG. 13H) cells colony formation. 30 days after plating the cells into soft agar, colony numbers were counted. Error bars represent mean±SEM; n=3. $P<0.01$; ns, not significant. (FIG. 13I) Tumor weight of xenografts derived from 1,500,000 NIH-3T3 cells stably expressing empty vector, METTL3 WT, or METTL3 A155P. All the mice were euthanized on day 40 and the tumor weights were measured. There was no tumor formation in empty vector group during the observed period. Error bars represent mean±SEM; N=8. * $p<0.05$. (FIGS. 13J-13L) Global profiling of $m^6A$ targets in primary lung cancer samples. (FIG. 13J) Sequence motif identified in $m^6A$ MeRIP-seq from four lung cancer patient samples. (FIG. 13K) Metagene analysis of $m^6A$ peaks. (FIG. 13L) Integrative genomics viewer (IGV) plots of representative $m^6A$ containing genes. The boxes represent exons, and lines represent introns.

(FIG. 14A) Representative staining image of control and different stages lung cancer samples. Lower panels show the enlarged sections of the upper ones. Scale bar=30 μM. (FIG. 14B) Western blotting analysis using indicated antibodies. (FIGS. 14C-14D) Tumor images (FIG. 14C) and plot of tumor weight (FIG. 14D) at the endpoint in the xenograft experiment. Error bars represent mean±SEM; n=5. *$p<0.05$, *$p<0.001$. (FIG. 14E-14H) Western blotting analysis using indicated antibodies. (FIG. 141) Tumor images at the endpoint in the xenograft experiment. Scale bar, 20 mm. (FIG. 14J) Overlapping of $m^6A$ containing genes identified in four lung cancer patient samples. (FIG. 14**K) Distribution of $m^6A$ sites.

(FIG. 15A) Gene ontology analysis. Common methylated genes refers to the methylated genes in all four patient samples. Not methylated genes refers to the genes not methylated in any of the four patient samples. (FIG. 15B) Venn Diagram showing $m^6A$ peak overlap between patient tumor samples and cells (H1299 and A549).

(FIG. 16A) METTL3 gene expression among TCGA tumors. TP=primary solid tumor, NT=solid tissue normal. Wilcoxon signed-rank test, *$p<0.05$, $p<0.01$, *$p<0.001$. (FIG. 16B) eIF3h gene expression among TCGA tumors. TP=primary solid tumor, NT=solid tissue normal. Wilcoxon signed-rank test, $p<0.01$, *$p<0.001$. (FIG. 16C) Plot illustrating the Pearson's correlations of expression level between METTL3 and eIF3h in eight TCGA tumors, in which both METTL3 and eIF3h are significantly changed compared with normal tissues.

(FIG. 17A) correlation between METTL3 expression and neuroblastoma patient survival. (FIG. 17B) Western blot analysis of METTL3 knockdown and control cells. (FIG. 17C) Proliferation of METTL3 knockdown and control cells. (FIG. 17D) Apoptosis of METTL3 knockdown and control cells. (FIG. 17E) In vivo growth of METTL3 knockdown and control cells in mouse xenograft model.

Figure 1A:
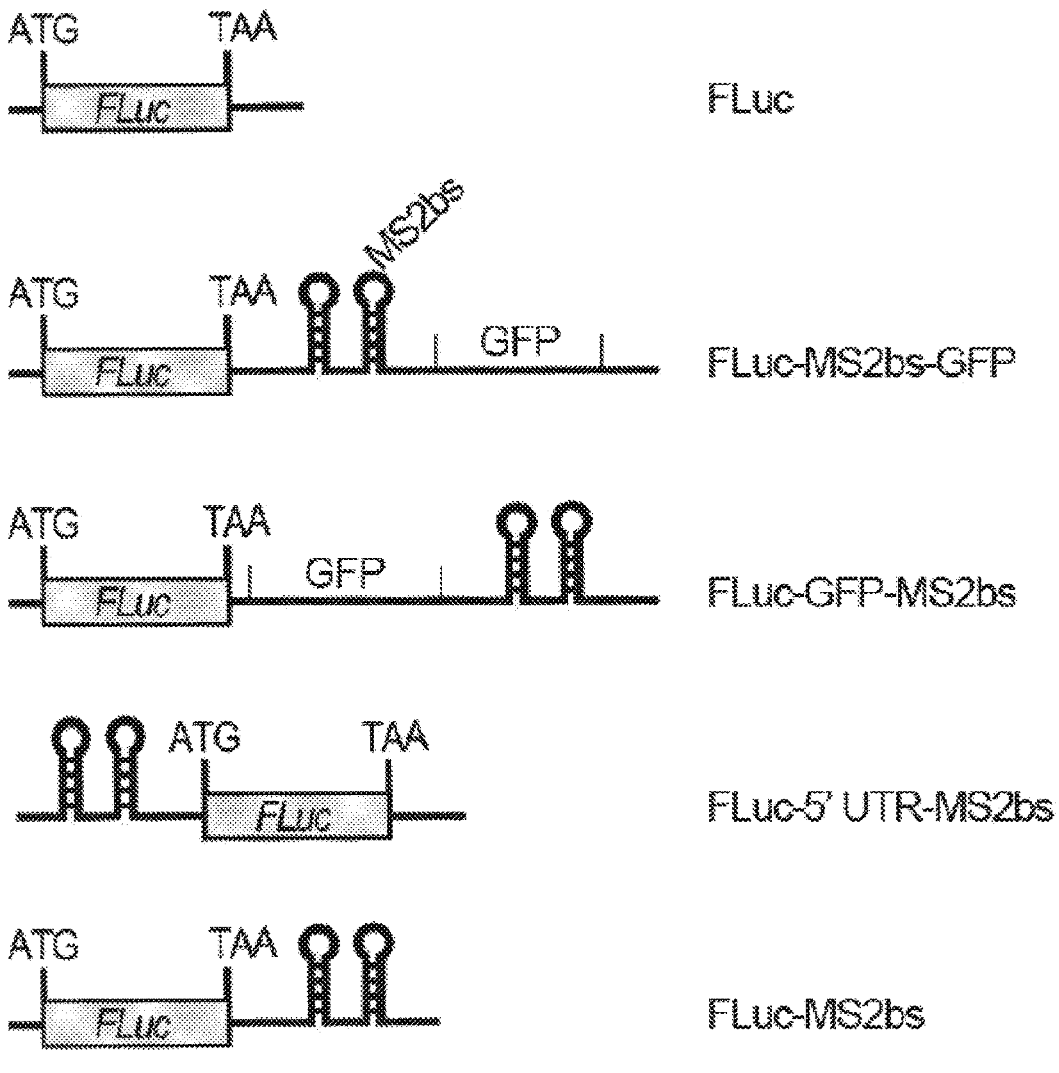
FIGS. 1A to 1G. METTL3 binding close to the stop codon enhances translation.

DETAILED DESCRIPTION OF CERTAIN EMBODIMENTS $N^6$-methyladenosine ($m^6A$) modification of mRNA catalyzed by METTL3 is enriched at a subset of stop codons. METTL3 can promote translation but the mechanism and widespread relevance remain unknown. It was demonstrated herein that, METTL3 enhances translation only when tethered to reporter mRNA at sites close to the stop codon, supporting a mRNA looping mechanism for ribosome recycling and translational control. Electron microscopy data revealed the topology of individual polyribosomes with single METTL3 foci found in close proximity to 5' cap-binding proteins. Further, the present disclosure revealed a previously unknown direct physical and functional interaction between METTL3 and a subunit of the eukaryotic translation initiation factor 3 (eIF3) complex. METTL3 promotes translation of a large subset of oncogenic mRNAs that are also $m^6A$-modified in human primary lung tumors, and the METTL3-eIF3 interaction is required for enhanced translation, formation of densely packed polyribosomes, and oncogenic transformation. These findings suggest that the interaction between METTL3-eIF3 can used as a potential cancer therapeutic target.

Accordingly, some aspects of the present disclosure provide methods of treating cancer, the methods comprising administering to a subject in need thereof an effective amount of an agent that inhibits interaction between Methyltransferase like 3 (METTL3) and Eukaryotic Translation Initiation Factor 3 Subunit H (EIF3h).

"Methyltransferase like 3 (METTL3)" is encoded by the METTL3 gene, and is the 70 kDa subunit of MT-A which is part of N6-adenosine-methyltransferase. METTL3 is involved in the posttranscriptional methylation of internal adenosine residues in eukaryotic mRNAs, forming N6-methyladenosine.

"Translation Initiation Factor 3 Subunit H (EIF3h)" is a component of the eukaryotic translation initiation factor 3 (eIF-3) complex, which is required for several steps in the initiation of protein synthesis (e.g., as described in Lee et al., Nature. 2016 Aug. 4; 536(7614):96-9, incorporated herein by reference). The eIF-3 complex associates with the 40S ribosome and facilitates the recruitment of various translation factors to form the 43S pre-initiation complex (43S PIC). The eIF-3 complex stimulates mRNA recruitment to the 43S PIC and scanning of the mRNA for AUG recognition. The eIF-3 complex is also required for disassembly and recycling of post-termination ribosomal complexes and subsequently prevents premature joining of the 40S and 60S ribosomal subunits prior to initiation (e.g., as described in Masutani et al., EMBO J. 2007 Jul. 25; 26(14):3373-83, incorporated herein by reference). The eIF-3 complex specifically targets and initiates translation of a subset of mRNAs involved in cell proliferation, including cell cycling, differentiation and apoptosis, and uses different modes of RNA stem-loop binding to exert either translational activation or repression.

The methods described herein use agents that inhibit the METTL3-eIF3h interaction. In some embodiments, the agent inhibits METTL3 expression. For example, in some embodiments, the agent may reduce the expression level of METTL3 by at least 20%, at least 30%, at least 40%, at least 50%, at least 60%, at least 70%, at least 80%, at least 90%, at least 95%, or 100%, compared to in the absence of the agent. In some embodiments, the agent reduces the expression level of METTL3 by 20%, 30%, 40%, 50%, 60%, 70%, 80%, 90%, 95%, or 100%, compared to in the absence of the agent.

In some embodiments, the agent inhibits eIF3h expression. For example, in some embodiments, the agent may reduce the expression level of eIF3h by at least 20%, at least 30%, at least 40%, at least 50%, at least 60%, at least 70%, at least 80%, at least 90%, at least 95%, or 100%, compared to in the absence of the agent. In some embodiments, the agent reduces the expression level of eIF3h by 20%, 30%, 40%, 50%, 60%, 70%, 80%, 90%, 95%, or 100%, compared to in the absence of the agent.

"Inhibition of gene expression" refers to the absence or observable decrease in the level of protein and/or mRNA product from a target gene (e.g., METTL3 and/or EIF3h). In some embodiments, the agent inhibits the expression of METTL3 without manifest effects on other genes of the cell. The consequences of inhibition can be confirmed by examination of the outward properties of the cell or organism or by biochemical techniques such as RNA solution hybridization, nuclease protection, Northern hybridization, reverse transcription, gene expression monitoring with a microarray, antibody binding, enzyme linked immunosorbent assay (ELISA), Western blotting, radioimmunoassay (RIA), other immunoassays, and fluorescence activated cell analysis (FACS). For RNA-mediated inhibition in a cell line or whole organism, gene expression is conveniently assayed by use of a reporter or drug resistance gene whose protein product is easily assayed. Such reporter genes include acetohydroxyacid synthase (AHAS), alkaline phosphatase (AP), beta galactosidase (LacZ), beta glucoronidase (GUS), chloramphenicol acetyltransferase (CAT), green fluorescent protein (GFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, methotrexate, phosphinothricin, puromycin, and tetracyclin.

Depending on the assay, quantitation of the amount of gene expression allows one to determine a degree of inhibition as compared to in the absence of the agent. As an example, the efficiency of inhibition may be determined by assessing the amount of gene product in the cell: mRNA may be detected with a hybridization probe having a nucleotide sequence outside the region used for the inhibitory nucleic acid, or translated polypeptide may be detected with an antibody raised against the polypeptide sequence of that region.

In some embodiments, the agent that inhibits METTL3 expression and/or EIF3h expression is a nucleic acid. A "nucleic acid" is at least two nucleotides covalently linked together, and in some instances, may contain phosphodiester bonds (e.g., a phosphodiester "backbone"). A nucleic acid may be DNA, both genomic and/or cDNA, RNA or a hybrid, where the nucleic acid contains any combination of deoxyribonucleotides and ribonucleotides (e.g., artificial or natural), and any combination of bases, including uracil, adenine, thymine, cytosine, guanine, inosine, xanthine, hypoxanthine, isocytosine and isoguanine. Nucleic acids of the present disclosure may be produced using standard molecular biology methods (see, e.g., Green and Sambrook, Molecular Cloning, A Laboratory Manual, 2012, Cold Spring Harbor Press).

In some embodiments, the agent comprises a RNA interference (RNAi) molecule that targets METTL3 mRNA and/or a RNAi molecule that targets EIF3h mRNA. "RNA interference (RNAi)" is a biological process in which RNA molecules inhibit gene expression or translation, by neutralizing targeted mRNA molecules. A "messenger RNA (mRNA)" is a RNA molecule that conveys genetic information from DNA to the ribosome, where they specify the amino acid sequence of the protein products of gene expression.

In some embodiments, the agent that inhibits METTL3 or EIF3h expression is a microRNA, a small interfering RNA (siRNA), or a short hairpin RNA (shRNA). A "microRNA" is a small non-coding RNA molecule (containing about 22 nucleotides) that functions in RNA silencing and post-transcriptional regulation of gene expression. A "siRNA" is a commonly used RNA interference (RNAi) tool for inducing short-term silencing of protein coding genes. siRNA is a synthetic RNA duplex designed to specifically target a particular mRNA for degradation. A "shRNA" an artificial RNA molecule with a tight hairpin turn that can be used to silence target gene expression via RNA interference (RNAi). Expression of shRNA in cells is typically accomplished by delivery of plasmids or through viral or bacterial vectors.

In some embodiment, vector-based RNAi modalities (e.g., siRNA or shRNA expression constructs) are used to reduce expression of METTL3 or EIF3h in a cell. In some embodiments, an isolated plasmid vector (e.g., any isolated plasmid vector known in the art or disclosed herein) that expresses a RNAi molecule such as an shRNA. The isolated plasmid may comprise a specific promoter operably linked to a gene encoding the small interfering nucleic acid. In some embodiments, the isolated plasmid vector is packaged in a virus capable of infecting the individual. Exemplary viruses include adenovirus, retrovirus, lentivirus, adeno-associated virus, and others that are known in the art and disclosed herein.

A broad range of RNAi-based modalities could be employed to inhibit expression METTL3 or EIF3h in a cell, such as siRNA-based oligonucleotides and/or altered siRNA-based oligonucleotides. Altered siRNA based oligonucleotides are those modified to alter potency, target affinity, safety profile and/or stability, for example, to render them resistant or partially resistant to intracellular degradation. Modifications, such as phosphorothioates, for example, can be made to oligonucleotides to increase resistance to nuclease degradation, binding affinity and/or uptake. In addition, hydrophobization and bioconjugation enhances siRNA delivery and targeting (De Paula et al., RNA. 13(4): 431-56, 2007) and siRNAs with ribo-difluorotoluyl nucleotides maintain gene silencing activity (Xia et al., ASC Chem. Biol. 1(3):176-83, (2006)). siRNAs with amide-linked oligoribonucleosides have been generated that are more resistant to S1 nuclease degradation than unmodified siRNAs (Iwase R et al. 2006 Nucleic Acids Symp Ser 50: 175-176). In addition, modification of siRNAs at the 2'-sugar position and phosphodiester linkage confers improved serum stability without loss of efficacy (Choung et al., Biochem. Biophys. Res. Commun. 342(3):919-26, 2006). Other molecules that can be used to inhibit expression of METTL3 or EIF3h include ribozymes, peptides, DNAzymes, peptide nucleic acids (PNAs), triple helix forming oligonucleotides, antibodies, and aptamers and modified form(s) thereof directed to sequences in gene(s), RNA transcripts, or proteins. Antisense and ribozyme suppression strategies have led to the reversal of a tumor phenotype by reducing expression of a gene product or by cleaving a mutant transcript at the site of the mutation (Carter and Lemoine Br. J. Cancer. 67(5):869-76, 1993; Lange et al., Leukemia. 6(11):1786-94, 1993; Valera et al., J. Biol. Chem. 269(46):28543-6, 1994; Dosaka-Akita et al., Am. J. Clin. Pathol. 102(5):660-4, 1994; Feng et al., Cancer Res. 55(10):2024-8, 1995; Quattrone et al., Cancer Res. 55(1):90-5, 1995; Lewin et al., Nat Med. 4(8):967-71, 1998). Ribozymes have also been proposed as a means of both inhibiting gene expression of a mutant gene and of correcting the mutant by targeted trans-splicing (Sullenger and Cech Nature 371(6498):619-22, 1994; Jones et al., Nat. Med. 2(6):643-8, 1996). Ribozyme activity may be augmented by the use of, for example, non-specific nucleic acid binding proteins or facilitator oligonucleotides (Herschlag et al., Embo J. 13(12):2913-24, 1994; Jankowsky and Schwenzer Nucleic Acids Res. 24(3):423-9, 1996). Multitarget ribozymes (connected or shotgun) have been suggested as a means of improving efficiency of ribozymes for gene suppression (Ohkawa et al., Nucleic Acids Symp Ser. (29):121-2, 1993).

Triple helix approaches have also been investigated for sequence-specific gene suppression. Triple helix forming oligonucleotides have been found in some cases to bind in a sequence-specific manner (Postel et al., Proc. Natl. Acad. Sci. U.S.A. 88(18):8227-31, 1991; Duval-Valentin et al., Proc. Natl. Acad. Sci. U.S.A. 89(2):504-8, 1992; Hardenbol and Van Dyke Proc. Natl. Acad. Sci. U.S.A. 93(7):2811-6, 1996; Porumb et al., Cancer Res. 56(3):515-22, 1996). Similarly, peptide nucleic acids have been shown to inhibit gene expression (Hanvey et al., Antisense Res. Dev. 1(4):307-17, 1991; Knudsen and Nielson Nucleic Acids Res. 24(3):494-500, 1996; Taylor et al., Arch. Surg. 132(11):1177-83, 1997). Minor-groove binding polyamides can bind in a sequence-specific manner to DNA targets and hence may represent useful small molecules for suppression at the DNA level (Trauger et al., Chem. Biol. 3(5):369-77, 1996). In addition, suppression has been obtained by interference at the protein level using dominant negative mutant peptides and antibodies (Herskowitz Nature 329(6136):219-22, 1987; Rimsky et al., Nature 341(6241):453-6, 1989; Wright et al., Proc. Natl. Acad. Sci. U.S.A. 86(9):3199-203, 1989). The diverse array of suppression strategies that can be employed includes the use of DNA and/or RNA aptamers that can be selected to target METTL3 or EIF3h mRNA.

In some embodiments, the agent that inhibits expression of METTL3 or EIF3h is an anti-sense nucleic acid. An "anti-sense nucleic acid" is a nucleic acid that is an oligoribonucleotide, oligodeoxyribonucleotide, modified oligoribonucleotide, or modified oligodeoxyribonucleotide which hybridizes under physiological conditions to DNA comprising a particular gene or to an mRNA transcript of that gene and, thereby, inhibits the transcription of that gene and/or the translation of that mRNA. The antisense molecules are designed so as to interfere with transcription or translation of a target gene upon hybridization with the target gene or transcript. Antisense nucleic acids include modified or unmodified RNA, DNA, or mixed polymer nucleic acids, and primarily function by specifically binding to matching sequences resulting in modulation of peptide synthesis (Wu-Pong, November 1994, BioPharm, 20-33). Antisense nucleic acid binds to target RNA by Watson Crick base-pairing and blocks gene expression by preventing ribosomal translation of the bound sequences either by steric blocking or by activating RNase H enzyme. Antisense molecules may also alter protein synthesis by interfering with RNA processing or transport from the nucleus into the cytoplasm (Mukhopadhyay & Roth, 1996, Crit. Rev. in Oncogenesis 7, 151-190).

The mRNA sequences of METTL3 and EIF3h are known. For example, human METLL3 mRNA sequence has the ID number of NM_019852.5 in NCBI reference sequence database. The DNA sequence encoding human METLL3 mRNA is provided as SEQ ID NO: 1. Human EIF3h mRNA sequence has the ID number of NM_003756.3 in NCBI reference sequence database. The DNA sequence encoding human EIF3h mRNA is provided as SEQ ID NO: 2.

DNA sequence encoding human METLL3 mRNA
(NM_019852.5, SEQ ID NO: 1)

```
ATTTTCCGGTTAGCCTTCGGGGTGTCCGCGTGAGAATTGGCTATATCCTGGAGCGAGTGCTGGGAGG

TGCTAGTCCGCCGCGCCTTATTCGAGAGGTGTCAGGGCTGGGAGACTAGGATGTCGGACACGTGGA

GCTCTATCCAGGCCCACAAGAAGCAGCTGGACTCTCTGCGGGAGAGGCTGCAGCGGAGGCGGAAGC

AGGACTCGGGGCACTTGGATCTACGGAATCCAGAGGCAGCATTGTCTCCAACCTTCCGTAGTGACAG

CCCAGTGCCTACTGCACCCACCTCTGGTGGCCCTAAGCCCAGCACAGCTTCAGCAGTTCCTGAATTA

GCTACAGATCCTGAGTTAGAGAAGAAGTTGCTACACCACCTCTCTGATCTGGCCTTAACATTGCCCA

CTGATGCTGTGTCCATCTGTCTTGCCATCTCCACGCCAGATGCTCCTGCCACTCAAGATGGGGTAGA

AAGCCTCCTGCAGAAGTTTGCAGCTCAGGAGTTGATTGAGGTAAAGCGAGGTCTCCTACAAGATGA

TGCACATCCTACTCTTGTAACCTATGCTGACCATTCCAAGCTCTCTGCCATGATGGGTGCTGTGGCAG

AAAAGAAGGGCCCTGGGGAGGTAGCAGGGACTGTCACAGGGCAGAAGCGGCGTGCAGAACAGGAC

TCGACTACAGTAGCTGCCTTTGCCAGTTCGTTAGTCTCTGGTCTGAACTCTTCAGCATCGGAACCAGC

AAAGGAGCCAGCCAAGAAATCAAGGAAACATGCTGCCTCAGATGTTGATCTGGAGATAGAGAGCCT

TCTGAACCAACAGTCCACTAAGGAACAACAGAGCAAGAAGGTCAGTCAGGAGATCCTAGAGCTATT

AAATACTACAACAGCCAAGGAACAATCCATTGTTGAAAAATTTCGCTCTCGAGGTCGGGCCCAAGT

GCAAGAATTCTGTGACTATGGAACCAAGGAGGAGTGCATGAAAGCCAGTGATGCTGATCGACCCTG

TCGCAAGCTGCACTTCAGACGAATTATCAATAAACACACTGATGAGTCTTTAGGTGACTGCTCTTTC
```

-continued

CTTAATACATGTTTCCACATGGATACCTGCAAGTATGTTCACTATGAAATTGATGCTTGCATGGATTC

TGAGGCCCCTGGCAGCAAAGACCACACGCCAAGCCAGGAGCTTGCTCTTACACAGAGTGTCGGAGG

TGATTCCAGTGCAGACCGACTCTTCCCACCTCAGTGGATCTGTTGTGATATCCGCTACCTGGACGTCA

GTATCTTGGGCAAGTTTGCAGTTGTGATGGCTGACCCACCCTGGGATATTCACATGGAACTGCCCTA

TGGGACCCTGACAGATGATGAGATGCGCAGGCTCAACATACCCGTACTACAGGATGATGGCTTTCTC

TTCCTCTGGGTCACAGGCAGGGCCATGGAGTTGGGGAGAGAATGTCTAAACCTCTGGGGGTATGAA

CGGGTAGATGAAATTATTTGGGTGAAGACAAATCAACTGCAACGCATCATTCGGACAGGCCGTACA

GGTCACTGGTTGAACCATGGGAAGGAACACTGCTTGGTTGGTGTCAAAGGAAATCCCCAAGGCTTC

AACCAGGGTCTGGATTGTGATGTGATCGTAGCTGAGGTTCGTTCCACCAGTCATAAACCAGATGAAA

TCTATGGCATGATTGAAAGACTATCTCCTGGCACTCGCAAGATTGAGTTATTTGGACGACCACACAA

TGTGCAACCCAACTGGATCACCCTTGGAAACCAACTGGATGGGATCCACCTACTAGACCCAGATGTG

GTTGCACGGTTCAAGCAAAGGTACCCAGATGGTATCATCTCTAAACCTAAGAATTTATAGAAGCACT

TCCTTACAGAGCTAAGAATCCATAGCCATGGCTCTGTAAGCTAAACCTGAAGAGTGATATTTGTACA

ATAGCTTTCTTCTTTATTTAAATAAACATTTGTATTGTAGTTGGGA

DNA sequence encoding human EIF3h mRNA (NM_003756.3, SEQ ID NO: 2)

CTCTTTCTTCCTGTCTGCTTGGAAAGATGGCGTCCCGCAAGGAAGGTACCGGCTCTACTGCCACCTCT

TCCAGCTCCACCGCCGGCGCAGCAGGGAAAGGCAAAGGCAAAGGCGGCTCGGGAGATTCAGCCGT

GAAGCAAGTGCAGATAGATGGCCTTGTGGTATTAAAGATAATCAAACATTATCAAGAAGAAGGACA

AGGAACTGAAGTTGTTCAAGGAGTGCTTTTGGGTCTGGTTGTAGAAGATCGGCTTGAAATTACCAAC

TGCTTTCCTTTCCCTCAGCACACAGAGGATGATGCTGACTTTGATGAAGTCCAATATCAGATGGAAA

TGATGCGGAGCCTTCGCCATGTAAACATTGATCATCTTCACGTGGGCTGGTATCAGTCCACATACTA

TGGCTCATTCGTTACCCGGGCACTCCTGGACTCTCAGTTTAGTTACCAGCATGCCATTGAAGAATCTG

TCGTTCTCATTTATGATCCCATAAAAACTGCCCAAGGATCTCTCTCACTAAAGGCATACAGACTGAC

TCCTAAACTGATGGAAGTTTGTAAAGAAAAGGATTTTTCCCCTGAAGCATTGAAAAAAGCAAATATC

ACCTTTGAGTACATGTTTGAAGAAGTGCCGATTGTAATTAAAAATTCACATCTGATCAATGTCCTAA

TGTGGGAACTTGAAAAGAAGTCAGCTGTTGCAGATAAACATGAATTGCTCAGCCTTGCCAGCAGCA

ATCATTTGGGGAAGAATCTACAGTTGCTGATGGACAGAGTGGATGAAATGAGCCAAGATATAGTTA

AATACAACACATACATGAGGAATACTAGTAAACAACAGCAGCAGAAACATCAGTATCAGCAGCGTC

GCCAGCAGGAGAATATGCAGCGCCAGAGCCGAGGAGAACCCCCGCTCCCTGAGGAGGACCTGTCCA

AACTCTTCAAACCACCACAGCCGCCTGCCAGGATGGACTCGCTGCTCATTGCAGGCCAGATAAACAC

TTACTGCCAGAACATCAAGGAGTTCACTGCCCAAAACTTAGGCAAGCTCTTCATGGCCCAGGCTCTT

CAAGAATACAACAACTAAGAAAAGGAAGTTTCCAGAAAAGAAGTTAACATGAACTCTTGAAGTCAC

ACCAGGGCAACTCTTGGAAGAAATATATTTGCATATTGAAAAGCACAGAGGATTTCTTTAGTGTCAT

TGCCGATTTTGGCTATAACAGTGTCTTTCTAGCCATAATAAAATAAAACAAAATCTTGACTGCTTGCT

CATTTGATTTTAGATGTATTTTCTCTGGCTTACTTTTGTTTGCTTATACTTGTTTATTTCTAAAAGCTA

AAACAAGCCCTGACCGGAAGTTTCACCAGGCAGAAACCTATAGGCTCCACCACTTTTGCTGCCTCTC

AGGTGCCACCTTTCAACCCACTTCTCCCAACTACTTATCCCAGCTCCTGACCCCGAGGCCCTGGCATC

TACTGTGAATATTTTTTTTTTGAATTTTTATACTTCGCTGCTCCCAAATGAGCACCCCGAGAGAAGTC

CAGGCTTCATGTACTTGCCCAGGAATTCCTTGTCCCCGGACCCGGAATCACTTGGCCTAATTCCGGTC

AGTCTGCCTTTTCATTTCTGCAGGTGATGGTCAACCAGTCCCCGTACTCATAGGCCATGGGACACAA

-continued

```
GATTATTATTATCATCATTATTTTTAAAGACAGAGTCTCACTTTGTTGCCCAGGCTGGAGTGTAGTGG
CACAATCTCAGCTCGCTGCAACCTCCACCTTCTGAGTTCAAGCGATTCTCCCACCTCAGCCTCCCAAG
TAGCTGGGACTACAGGCGTGTGCCATCACGCCTGGCTAATTTTTGTATTTTTAGTAGAGATGGGGTTT
CACCATGTTGGCCAGGCTGGTCTGCATCTCCTGACCTCAAGTGATTCACCTGCTTCTGTCTCCCAAAG
TGCTGGGAATACAGGCATGAGCCACCACTCCTGGACAGGCCACAGAAATTTTAAAGAAAAGAATCA
TGCCACCACAAGTAAACTTCATTTTGTTTATATTATTTAGGACTTCACATTTGTCTTCCGAAACCATG
AAGTATAATTCTGCTAACAGCAAGTGTTGTGAATGAGGAATTAGGAATTAGGAGAATGGTAGTACA
TTGGGAAAAACATATTTTAGTAATTTTTATATTTTAAAGATAATCACAGATTTTGCTGTTTGTGCATC
ACCAAAATCAGTGAGATCTGCCAGCTGGTGGGGGTGTGCCTATGAGAATTTTTGATTATGATCCCCT
AGGAGGGTTATCAAAAAAGGAGATGGGTGAAAGATCAGGAGAGTCGAGAAATTCATTTTTTGGACA
ACATTGTTTTGAAGGCACTACTGGGGCTCTGGGATCAGGCAGCCAGATTGAAACCTGGCTCCTCCTT
TTCCTAAGTTATTTAACCTCCCTGTGCCTCACTTTTTGTCAACCAGATAAGATAAGAAATGAGAGCA
GGTCTGTTACCTCACAAGGTGGCTGTGAGTGTTGAAGACGTTTGTTGGGGGTTTGGGTGAAGCATGC
AAACTCTGGTTGGTATGTGGCAGCCACTCAGCCTGTATTTATGATGAGGGAGGCATTCTAGGCACCC
CTTCCAGGATGTTGGGTTGTTGGCTGGGTTTTACTTTAAAAAGCTCAGGGCCTAGAACATTCTAGAA
TCCAAGTACTTGCTCACATATATAATTATTTCTTTAGGATAATCTTTGATATAGACTTACGAGTCAAA
GGGTATGTAAAATGTCAGCCCTTTTACCTGTATTGCCAAATTGCCTTCAAAAGTTTCTGCTGTTTTGC
CCTCCTACCCATAGTGATAACCTTAAATTGGAGTCAACACAAATTTGAGTGTGACTGTGTTAGACAG
AAGGGATATATTAACAGGTAAAACTGGCCATGGCCCCTGCCCTTGTGGAGTATATGCTCTGTTGGTT
CATTTCCTCTGCATTCTAATTTTCTAGACTTGGGATCTTATTGTGGAGTTAAACAAAGCACCCTTAAA
GTAGCAAGCGAGCAAAATAAAAGCAAGGAAAATCAGTTGGAACATAACTTATGTATTTTTTAGGAT
TAAGAGTAATTTAACTGAGTCAATTCAATATGTTTTTAAAGGTGTGATTCTTAAATTCTTTATGATTG
TTTAGATTTCTATATCTTGGTAACATGAATACACACTTAATGAAAGATTTCAGTAATTTTTGATTTGG
GAATTAATCATAGTGGGAAAAACTGTTTAGGAAAACATGTCAGTGGAAATTAACTCGCCACAGTAT
GTAGTGTTAGGGAATAGCTTCTGTTCGGCATTTGATTTGAGTGCTGTATTCTGACATTTTTCAGGAAC
AAATACATGTGATTCATCTTCTATAAATATTTGCAGTTTCTTCAAGTTGAAATGAGAAAAGCTCGTA
AATTGAGCACCAGGTCTAATAAATCATTCACTTACCCAAGAACAGAAAGACAGGAAAAGCTAGCAT
GTTAATCTAATGAAAAAATCGAATGTTAAAAAACCAAGAAAGTAGAAGATATTTGACATTAACTTT
CTAATCATTGATAATAATCTAATAATCATAACATTATTCTTAAAACCTGAAAGAATGGATTCCTGCT
CCCAATGTGTTTTTAATATCAACTTAAACTAAAATAATTTTTTTACCTATTTTTGGAAGCTTGGAAAT
TGAGATGTAGTTGTCTAATGTTAACCTAATTAAGAGAGCTTGGTGTGATTTCTCATATACAGCATCTA
AATATTTAAGTTTTAATGTCTTCTAAAATATTATTACATTCTTCATACTATAGTTTTTTAACATCCTTT
AGAAAACTTGTATCAGCTTCACTTTCAAACCATGCTGGCATCGAACTCAGGTGTAGTGGTATCAGAA
TGTTATGAAATAATTTTTTATTTTCATTATAAACTCCATTTTTACAATAAACACTTCTCAACCAAA
```

Those skilled in the art will be able to design the anti-sense nucleic acids targeting of METTL3 or EIF3h based on the of METTL3 and EIF3h mRNA sequences, and recognize that the exact length of the antisense nucleic acid and its degree of complementarity with its target will depend upon the specific target selected, including the sequence of the target and the particular bases which comprise that sequence. An anti-sense nucleic acid is generally designed to have partial or complete complementarity with one or more target sequences (i.e., complementarity with one or more transcripts of the of METTL3 or EIF3h gene). Depending on the particular target sequence, the nature of the inhibitory nucleic acid and the level of expression of anti-sense nucleic acid (e.g. depending on copy number, promoter strength) the procedure may provide partial or complete loss of function for the target gene. Quantitation of gene expression in a cell may show similar amounts of inhibition at the level of accumulation of target mRNA or translation of target protein.

In some embodiments, the agent inhibits binding of METTL3 to EIF3h. "Inhibit binding" of METTL3 to EIF3h means disrupting (inhibiting or reducing) the interaction between METTL3 and EIF3h. In some embodiments, the agent reduces the interaction between METTL3 and EIF3h by at least 20%, at least 30%, at least 40%, at least 50%, at least 60%, at least 70%, at least 80%, at least 90%, at least 95%, or 100%, compared to in the absence of the agent. In some embodiments, the agent reduces the interaction between METTL3 and EIF3h by 20%, 30%, 40%, 50%, 60%, 70%, 80%, 90%, 95%, or 100%, compared to in the absence of the agent. Non-limiting examples of agents that inhibit the interaction between METTL3 and EIF3h include, without limitation: inhibitory peptides, small molecules, and antibodies.

In some embodiments, the agent that inhibits the interaction between METTL3 and EIF3h is an inhibitory peptide. An "inhibitory peptide" refers to a peptide that blocks the interaction between METTL3 and EIF3h. In some embodiments, the inhibitory peptide blocks the interaction between METTL3 and EIF3h via competitive binding.

In some embodiments, the inhibitory peptide may be a peptide corresponding to the binding site in METTL3 that interacts with EIF3h. For example, the inhibitory peptide may comprise an amino acid sequence corresponding to amino acids 150-200 (e.g., amino acids 150-200, 150-190, 150-180, 150-170, 150-160, 160-200, 160-190, 160-180, 160-170, 170-200, 170-190, 170-180, 180-200, 180-190, or 190-200) of METTL3. In some embodiments, the inhibitory peptide comprises an amino acid sequence that is at least 80%, at least 85%, at least 90%, at least 95%, or at least 99%, identical to the amino acid sequence of SEQ ID NO: 4. In some embodiments, the inhibitory peptide comprises the amino acid sequence of SEQ ID NO: 4. In some embodiments, the inhibitory peptide consists of the amino acid sequence of SEQ ID NO: 4. The amino acid sequence of full-length human METTL3 is provided as SEQ ID NO: 3 and amino acids 150-200 of human METTL3 is provided as SEQ ID NO: 4.

```
METTL3 full-length amino acid sequence
                    (Uniprot ID Q86U44, SEQ ID NO: 3)
MSDTWSSIQAHKKQLDSLRERLQRRRKQDSGHLDLRNPEAALSPTFRSDS

PVPTAPTSGGPKPSTASAVPELATDPELEKKLLHHLSDLALTLPTDAVSI

CLAISTPDAPATQDGVESLLQKFAAQELIEVKRGLLQDDAHPTLVTYADH

SKLSAMMGAVAEKKGPGEVAGTVTGQKRRAEQDSTTVAAFASSLVSGLNS

SASEPAKEPAKKSRKHAASDVDLEIESLLNQQSTKEQQSKKVSQEILELL

NTTTAKEQSIVEKFRSRGRAQVQEFCDYGTKEECMKASDADRPCRKLHFR

RIINKHTDESLGDCSFLNTCFHMDTCKYVHYEIDACMDSEAPGSKDHTPS

QELALTQSVGGDSSADRLFPPQWICCDIRYLDVSILGKFAVVMADPPWDI

HMELPYGTLTDDEMRRLNIPVLQDDGFLFLWVTGRAMELGRECLNLWGYE

RVDEIIWVKTNQLQRIIRTGRTGHWLNHGKEHCLVGVKGNPQGFNQGLDC

DVIVAEVRSTSHKPDEIYGMIERLSPGTRKIELFGRPHNVQPNWITLGNQ

LDGIHLLDPDVVARFKQRYPDGIISKPKNL

METTL3 amino acids 150-200
                                   (SEQ ID NO: 4)
PVPTAPTSGGPKPSTASAVPELATDPELEKKLLHHLSDLALTLPTDAVSI

CLAISTPDAPATQDGVESLLQKFAAQELIEVKRGLLQDDAHPTLVTYADH

SKLSAMMGAVAEKKGPGEVAGTVTGQKRRAEQDSTTVAAFASSLVSGLNS
```

In some embodiments, the inhibitory peptide may be a peptide corresponding to the binding site in EIF3h that interacts with METTL3. For example, the inhibitory peptide may comprise an amino acid sequence corresponding to amino acids 29-222 (e.g., amino acids 29-222, 29-200, 29-150, 29-100, 29-50, 50-222, 50-200, 20-150, 50-100, 100-222, 100-200, 100-150, 150-222, 150-200, or 200-229) of EIF3h. In some embodiments, the inhibitory peptide comprises an amino acid sequence that is at least 80%, at least 85%, at least 90%, at least 95%, or at least 99%, identical to the amino acid sequence of SEQ ID NO: 6. In some embodiments, the inhibitory peptide comprises the amino acid sequence of SEQ ID NO: 6. In some embodiments, the inhibitory peptide consists of the amino acid sequence of SEQ ID NO: 6. The amino acid sequence of full-length human EIF3h is provided as SEQ ID NO: 5 and amino acids 29-222 of human EIF3h is provided as SEQ ID NO: 6.

```
EIF3h full-length amino acid sequence
                  (Uniprot ID 015372, SEQ ID NO: 5)
MASRKEGTGSTATSSSSTAGAAGKGKGKGGSGDSAVKQVQIDGLVVLKII

KHYQEEGQGTEVVQGVLLGLVVEDRLEITNCFPFPQHTEDDADFDEVQYQ

MEMMRSLRHVNIDHLHVGWYQSTYYGSFVTRALLDSQFSYQHAIEESVVL

IYDPIKTAQGSLSLKAYRLTPKLMEVCKEKDFSPEALKKANITFEYMFEE

VPIVIKNSHLINVLMWELEKKSAVADKHELLSLASSNHLGKNLQLLMDRV

DEMSQDIVKYNTYMRNTSKQQQQKHQYQQRRQQENMQRQSRGEPPLPEED

LSKLFKPPQPPARMDSLLIAGQINTYCQNIKEFTAQNLGKLFMAQALQEY

NN

EIF3h amino acids 29-222
                                    (SEQ ID NO: 6)
GSGDSAVKQVQIDGLVVLKIIKHYQEEGQGTEVVQGVLLGLVVEDRLEIT

NCFPFPQHTEDDADFDEVQYQMEMMRSLRHVNIDHLHVGWYQSTYYGSFV

TRALLDSQFSYQHAIEESVVLIYDPIKTAQGSLSLKAYRLTPKLMEVCKE

KDFSPEALKKANITFEYMFEEVPIVIKNSHLINVLMWELEKKS
```

In some embodiments, the agent that inhibits the interaction between METTL3 and EIF3h is an antibody. An "antibody" or "immunoglobulin (Ig)" is a large, Y-shaped protein produced mainly by plasma cells that is used by the immune system to neutralize an exogenous substance (e.g., a pathogens such as bacteria and viruses). Antibodies are classified as IgA, IgD, IgE, IgG, and IgM. "Antibodies" and "antibody fragments" include whole antibodies and any antigen binding fragment (i.e., "antigen-binding portion") or single chain thereof. An "antibody" refers to a glycoprotein comprising at least two heavy (H) chains and two light (L) chains inter-connected by disulfide bonds, or an antigen binding portion thereof. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system. An antibody may be a polyclonal antibody or a monoclonal antibody.

The basic 4-chain antibody unit is a heterotetrameric glycoprotein composed of two identical L chains and two H chains (an IgM antibody consists of 5 of the basic heterotetramer unit along with an additional polypeptide called J chain, and therefore contain 10 antigen binding sites, while secreted IgA antibodies can polymerize to form polyvalent assemblages comprising 2-5 of the basic 4-chain units along with J chain). In the case of IgGs, the 4-chain unit is generally about 150,000 daltons. Each L chain is linked to a H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain (VH) followed by three constant domains (CH) for each of the $\alpha$ and $\gamma$ chains and four CH domains for $\mu$ and $\varepsilon$ isotypes. Each L chain has at the N-terminus, a variable domain (VL) followed by a constant domain (CL) at its other end. The VL is aligned with the VH and the CL is aligned with the first constant domain of the heavy chain (CH1). Particular amino acid residues are believed to form an interface between the light chain and heavy chain variable domains. The pairing of a VH and VL together forms a single antigen-binding site. For the structure and properties of the different classes of antibodies, (e.g., Basic and Clinical Immunology, 8th edition, Daniel P. Stites, Abba I. Ten and Tristram G. Parslow (eds.), Appleton & Lange, Norwalk, Conn., 1994, page 71 and Chapter 6, incorporated herein by reference).

The L chain from any vertebrate species can be assigned to one of two clearly distinct types, called kappa and lambda, based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG, and IgM, having heavy chains designated $\alpha$, $\delta$, $\varepsilon$, $\gamma$ and $\mu$, respectively. The $\gamma$ and $\alpha$ classes are further divided into subclasses on the basis of relatively minor differences in CH sequence and function, e.g., humans express the following subclasses: IgG1, IgG2, IgG3, IgG4, IgA1, and IgA2.

The V domain mediates antigen binding and define specificity of a particular antibody for its particular antigen. However, the variability is not evenly distributed across the 110-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a $\beta$-sheet configuration, connected by three hypervariable regions, which form loops connecting, and in some cases forming part of, the $\beta$-sheet structure. The hypervariable regions in each chain are held together in close proximity by the FRs and, with the hypervariable regions from the other chain, contribute to the formation of the antigen-binding site of antibodies (see, e.g., Kabat et al., Sequences of Proteins of Immunological Interest, 5th Ed. Public Health Service, National Institutes of Health, Bethesda, Md. (1991), incorporated herein by reference). The constant domains are not involved directly in binding an antibody to an antigen, but exhibit various effector functions, such as participation of the antibody in antibody dependent cellular cytotoxicity (ADCC).

An "antibody fragment" for use in accordance with the present disclosure contains the antigen-binding portion of an antibody. The antigen-binding portion of an antibody refers to one or more fragments of an antibody that retain the ability to specifically bind to an antigen. It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (e.g., as described in Ward et al., (1989) Nature 341:544-546, incorporated herein by reference), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883, incorporated herein by reference). Such single chain antibodies are also intended to be encompassed within the term "antigen-binding portion" of an antibody. These antibody fragments are obtained using conventional techniques known to those with skill in the art, and the fragments are screened for utility in the same manner as are full-length antibodies.

In some embodiments, an antibody fragment may be a Fc fragment, a Fv fragment, or a single-change Fv fragment. The Fc fragment comprises the carboxy-terminal portions of both H chains held together by disulfides. The effector functions of antibodies are determined by sequences in the Fc region, which region is also the part recognized by Fc receptors (FcR) found on certain types of cells.

The Fv fragment is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

Single-chain Fv also abbreviated as "sFv" or "scFv" are antibody fragments that comprise the VH and VL antibody domains connected into a single polypeptide chain. Preferably, the sFv polypeptide further comprises a polypeptide linker between the VH and VL domains which enables the sFv to form the desired structure for antigen binding (e.g., as described in Pluckthun in The Pharmacology of Monoclonal Antibodies, vol. 113, Rosenburg and Moore eds., Springer-Verlag, New York, pp. 269-315 (1994); Borrebaeck 1995, incorporated herein by reference).

In some embodiments, the antibody is a diabody. A diabody is a dimeric antibody fragment designed to form two antigen binding sites. Diabodies are composed of two single-chain variable fragments (scFvs) in the same polypeptide connected by a linker peptide which is too short (~3-6 amino acids) to allow pairing between the two domains on the same chain, forcing the domains to pair with complementary domains of another chain to form two antigen binding sites. Alternately, the two scFvs can also be connected with longer linkers, such as leucine zippers.

In some embodiments, the antibody is an affibody. An affibody is an antibody mimetics engineered to bind to a large number of target proteins or peptides with high affinity, imitating monoclonal antibodies. These molecules can be used for molecular recognition in diagnostic and therapeutic applications.

In some embodiments, the antibody is a single chain antibody (e.g., VHH). A single chain antibody refers to an antibody that has only a heavy chain or a light chain, but not both (e.g., a heavy chain-only antibody). It is known that Camilids produce heavy chain-only antibodies (e.g., as described in Hamers-Casterman et al., 1992, incorporated herein by reference). The single-domain variable fragments of these heavy chain-only antibodies are termed VHHs or nanobodies. VHHs retain the immunoglobulin fold shared by antibodies, using three hypervariable loops, CDR1, CDR2 and CDR3, to bind to their targets. Many VHHs bind to their targets with affinities similar to conventional full-size antibodies, but possess other properties superior to them. Therefore, VHHs are attractive tools for use in biological research and therapeutics. VHHs are usually between 10 to 15 kDa in size, and can be recombinantly expressed in high yields, both in the cytosol and in the periplasm in *E. coli*. VHHs can bind to their targets in mammalian cytosol. A VHH fragment (e.g., NANOBODY®) is a recombinant, antigen-specific, single-domain, variable fragment derived from camelid heavy chain antibodies. Although they are small, VHH fragments retain the full antigen-binding capacity of the full antibody. VHHs are small in size, highly soluble and stable, and have greater set of accessible epitopes, compared to traditional antibodies. They are also easy to use as the extracellular target-binding moiety of the chimeric receptor described herein, because no reformatting is required.

In some embodiments, the antibody binds METTL3 (e.g., at a site of METTL3 that interacts with EIF3h). In some embodiments, the antibody binds EIF3h (e.g., at a site of EIF3h that binds METTL3). In some embodiments, the antibody binds to amino acids 150-200 (e.g., amino acids 150-200, 150-190, 150-180, 150-170, 150-160, 160-200, 160-190, 160-180, 160-170, 170-200, 170-190, 170-180, 180-200, 180-190, or 190-200) of METTL3. In some embodiments, the antibody binds to amino acids 29-222 (e.g., amino acids 29-222, 29-200, 29-150, 29-100, 29-50, 50-222, 50-200, 20-150, 50-100, 100-222, 100-200, 100-150, 150-222, 150-200, or 200-229) of EIF3h.

In some embodiments, the agent that inhibits the interaction between METTL3 and EIF3h is a small molecule. A "small molecule," as used herein, refers to an organic compound, whether naturally-occurring or artificially created (e.g., via chemical synthesis) that has a relatively low molecular weight. Typically, an organic compound contains carbon. An organic compound may contain multiple carbon-carbon bonds, stereocenters, and other functional groups (e.g., amines, hydroxyl, carbonyls, or heterocyclic rings). In some embodiments, small molecules are monomeric organic compounds that have a molecular weight of less than about 1500 g/mol. In some embodiments, the molecular weight of the small molecule is less than about 1000 g/mol or less than about 500 g/mol. In some embodiments, the small molecule is a drug, for example, a drug that has already been deemed safe and effective for use in humans or animals by the appropriate governmental agency or regulatory body.

In some embodiments, the agent inhibits METTL3 activity. For example, in some embodiments, the agent may reduce the activity of METTL3 (e.g., as measured by degree of N6-Methyladenosine modification on RNAs) by at least 20%, at least 30%, at least 40%, at least 50%, at least 60%, at least 70%, at least 80%, at least 90%, at least 95%, or 100%, compared to in the absence of the agent. In some embodiments, the agent reduces the activity of METTL3 (e.g., as measured by degree of N6-Methyladenosine modification on RNAs) of eIF3h by 20%, 30%, 40%, 50%, 60%, 70%, 80%, 90%, 95%, or 100%, compared to in the absence of the agent. Agents that inhibit METTL3 activity may be, without limitation, small molecules and antibodies (e.g., antibodies that bind METTL3).

In some embodiments, the method described herein further comprises administering to the subject an effective amount of a second agent that inhibits Bromodomain-containing protein 4 (BRD4). "Bromodomain-containing protein 4 (BRD4)" is a protein that in humans is encoded by the BRD4 gene. BRD4 is a member of the BET (bromodomain and extra terminal domain) family, which also includes BRD2, BRD3, and BRDT. BRD4, similar to other BET family members, contains two bromodomains that recognize acetylated lysine residues. BRD4 also has an extended C-terminal domain with little sequence homology to other BET family members. BRD4 is a chromatin reader protein that recognizes and binds acetylated histones and plays a key role in transmission of epigenetic memory across cell divisions and transcription regulation. BRD4 remains associated with acetylated chromatin throughout the entire cell cycle and provides epigenetic memory for postmitotic G1 gene transcription by preserving acetylated chromatin status and maintaining high-order chromatin structure (e.g., as described in Patel et al., Mol Cell Biol. 2013 June; 33(12): 2497-507, incorporated herein by reference). During interphase, BRD4 plays a key role in regulating the transcription of signal-inducible genes by associating with the P-TEFb complex and recruiting it to promoters. Most cases of NUT midline carcinoma (a rare genetically defined, very aggressive squamous cell epithelial cancer that usually arises in the midline of the body and is characterized by a chromosomal rearrangement in the nuclear protein in testis gene) involve translocation of the BRD4 with NUT genes. BRD4 is often required for expression of Myc and other "tumor driving" oncogenes in hematologic cancers including multiple myeloma, acute myelogenous leukemia and acute lymphoblastic leukemia (e.g., as described in Da Costa et al., Blood Cancer Journal. 3 (7): e126, 2013, incorporated herein by reference).

In some embodiments, the second agent inhibits BRD4 expression. For example, in some embodiments, the second agent may reduce the expression level of BRD4 by at least 20%, at least 30%, at least 40%, at least 50%, at least 60%, at least 70%, at least 80%, at least 90%, at least 95%, or 100%, compared to in the absence of the second agent. In some embodiments, the second agent reduces the expression level of BRD4 by 20%, 30%, 40%, 50%, 60%, 70%, 80%, 90%, 95%, or 100%, compared to in the absence of the second agent.

In some embodiments, the second agent comprises a RNAi molecule that targets BRD4 mRNA. Any type of the RNAi molecules described herein and/or known to those skilled in the art can be used to inhibit BRD4 expression. BRD4 mRNA sequences are known in the art. For example, human BRD4 mRNA isoforms have the ID number of NM_001330384.2, NM_014299.2, and NM_058243.2 in NCBI reference sequence database. The DNA sequence encoding human BRD4 is provided as SEQ ID NOs: 7-9. The RNAi molecule can target any one of the BRD4 mRNA isoforms to inhibit BRD4 expression.

```
DNA sequence encoding human BRD4 mRNA isoform 3
                                           (NM_001330384.2, SEQ ID NO: 7)
AGTGCGCTGGCGGCGGCGGCGGCGGCGGCGGCGGCTGGGCTGTTTGTTCTGGTCTCCCGCAGC

CGAGGAGCCGAAGCAGTGGCGGCGGCAGCGGCTGCGGCGGCTGCCGGCGGTGCCCGCGGGCGAGC

GCGGCCTGTGAGCTCGGCAGAGCGGCGGGCGGGCCCCGGCGCCGCGCAGGCAGCTCGGGGAGGGG

GCGGCGGCAGCGGGCGGACGGCCGGCGGGGGCGGCGTGCGGCCTAGCGTCTCAGAGTGCCTGGTGA

AGAATGTGATGGGATCACTAGCATGTCTGCGGAGAGCGGCCCTGGGACGAGATTGAGAAATCTGCC

AGTAATGGGGGATGGACTAGAAACTTCCCAAATGTCTACAACACAGGCCCAGGCCCAACCCCAGCC

AGCCAACGCAGCCAGCACCAACCCCCCGCCCCCAGAGACCTCCAACCCTAACAAGCCCAAGAGGCA

GACCAACCAACTGCAATACCTGCTCAGAGTGGTGCTCAAGACACTATGGAAACACCAGTTTGCATG

GCCTTTCCAGCAGCCTGTGGATGCCGTCAAGCTGAACCTCCCTGATTACTATAAGATCATTAAAACG

CCTATGGATATGGGAACAATAAAGAAGCGCTTGGAAAACAACTATTACTGGAATGCTCAGGAATGT

ATCCAGGACTTCAACACTATGTTTACAAATTGTTACATCTACAACAAGCCTGGAGATGACATAGTCT

TAATGGCAGAAGCTCTGGAAAAGCTCTTCTTGCAAAAAATAAATGAGCTACCCACAGAAGAAACCG

AGATCATGATAGTCCAGGCAAAAGGAAGAGGACGTGGGAGGAAAGAAACAGGGACAGCAAAACCT

GGCGTTTCCACGGTACCAAACACAACTCAAGCATCGACTCCTCCGCAGACCCAGACCCCTCAGCCGA

ATCCTCCTCCTGTGCAGGCCACGCCTCACCCCTTCCCTGCCGTCACCCCGGACCTCATCGTCCAGACC

CCTGTCATGACAGTGGTGCCTCCCCAGCCACTGCAGACGCCCCCGCCAGTGCCCCCCCAGCCACAAC

CCCCACCCGCTCCAGCTCCCCAGCCCGTACAGAGCCACCCACCCATCATCGCGGCCACCCCACAGCC

TGTGAAGACAAAGAAGGGAGTGAAGAGGAAAGCAGACACCACCACCCCCACCACCATTGACCCCA

TTCACGAGCCACCCTCGCTGCCCCCGGAGCCCAAGACCACCAAGCTGGGCCAGCGGCGGGAGAGCA

GCCGGCCTGTGAAACCTCCAAAGAAGGACGTGCCCGACTCTCAGCAGCACCCAGCACCAGAGAAGA

GCAGCAAGGTCTCGGAGCAGCTCAAGTGCTGCAGCGGCATCCTCAAGGAGATGTTTGCCAAGAAGC

ACGCCGCCTACGCCTGGCCCTTCTACAAGCCTGTGGACGTGGAGGCACTGGGCCTACACGACTACTG

TGACATCATCAAGCACCCCATGGACATGAGCACAATCAAGTCTAAACTGGAGGCCCGTGAGTACCG

TGATGCTCAGGAGTTTGGTGCTGACGTCCGATTGATGTTCTCCAACTGCTATAAGTACAACCCTCCTG

ACCATGAGGTGGTGGCCATGGCCCGCAAGCTCCAGGATGTGTTCGAAATGCGCTTTGCCAAGATGCC

GGACGAGCCTGAGGAGCCAGTGGTGGCCGTGTCCTCCCCGGCAGTGCCCCCTCCCACCAAGGTTGTG

GCCCCGCCCTCATCCAGCGACAGCAGCAGCGATAGCTCCTCGGACAGTGACAGTTCGACTGATGACT

CTGAGGAGGAGCGAGCCCAGCGGCTGGCTGAGCTCCAGGAGCAGCTCAAAGCCGTGCACGAGCAG

CTTGCAGCCCTCTCTCAGCCCCAGCAGAACAAACCAAAGAAAAAGGAGAAAGACAAGAAGGAAAA

GAAAAAAGAAAAGCACAAAAGGAAAGAGGAAGTGGAAGAGAATAAAAAAAGCAAAGCCAAGGAA

CCTCCTCCTAAAAAGACGAAGAAAAATAATAGCAGCAACAGCAATGTGAGCAAGAAGGAGCCAGC

GCCCATGAAGAGCAAGCCCCCTCCCACGTATGAGTCGGAGGAAGAGGACAAGTGCAAGCCTATGTC

CTATGAGGAGAAGCGGCAGCTCAGCTTGGACATCAACAAGCTCCCCGGCGAGAAGCTGGGCCGCGT

GGTGCACATCATCCAGTCACGGGAGCCCTCCCTGAAGAATTCCAACCCCGACGAGATTGAAATCGA

CTTTGAGACCCTGAAGCCGTCCACACTGCGTGAGCTGGAGCGCTATGTCACCTCCTGTTTGCGGAAG

AAAAGGAAACCTCAAGCTGAGAAAGTTGATGTGATTGCCGGCTCCTCCAAGATGAAGGGCTTCTCG
```

-continued

TCCTCAGAGTCGGAGAGCTCCAGTGAGTCCAGCTCCTCTGACAGCGAAGACTCCGAAACAGCTTTCT

GCACCAGTGGAGACTTCGTGTCCCCAGGGCCTTCCCCGTATCACAGTCACGTGCAGTGCGGCCGCTT

CAGGGAGATGCTTCGCTGGTTTCTGGTGGATGTGGAGCAGACTGCAGCTGGCCAGCCGCATCGCCA

GTCTGCTGCTGGCCCTGCCATCACCTGGGCCCCAGCCATTGCCTACCCCTCCCCAGAGTGTGCTCGTT

GCTGTGTTGGCTGCTCCTGAATCTGCCCTAACTCCACACGCACCTGGACTTGCGTGTCCCTCCTGCAG

TTCTAACTAACAGTCCCTTCTTTTCAAGCCCCGTGGGTCTGCACGTTGGACCCTGGGTTCCCCATTAG

AGCCCACCTTCTGAGCAGCAGCCTCAGTGGGAGGTGGAGGCAGGTAGTGATGCTGGGTGCCAGGTG

GGAGTGGAGAGGGGACTGCTCTCCTCCAAGTGTGCACTTTCCTCATTATTCTCAGGGGCGCAGATGC

TCAGGCTGGCGCAGGGGAGAGGCTAGGGAGGGAGCCATGGTGCCCAGAAGGCCTGGCGACCAGCC

CCTGCTGAGAGATGGAGCTAACATCCTGTGTTTACGGCCAACGGGGTTGCCGCTAGGCTGGTGCAGC

TGTCAGTGAGCTGGCGTGCTGCAGACCACCTGAGAGCTGGCCCTAGGGTCTCAGGCAGACTGGGGA

GTGGGGATCCACAGTGGGAAACCTGTGTTTTGGCAGTAGACTCCTGCATGTTCTCCCACGGGCCTGT

CCCATCCCTGGGATTTTATTCTAACTAGAAATAAATGCTAACCCTCAATAA

DNA sequence encoding human BRD4 mRNA isoform short
(NM_014299.2, SEQ ID NO: 8)

ATTCTTTGGAATACTACTGCTAGAAGTCTGACTTAAGACCCAGCTTATGGGCCACATGGCACCCAGC

TGCTTCTGCAGAGAAGGCAGGCCACTGATGGGTACAGCAAAGTGTGGTGCTGCTGGCCAAGCCAAA

GACCCGTGTAGGATGACTGGGCCTCTGCCCCTTGTGGGTGTTGCCACTGTGCTTGAGTGCCTGGTGA

AGAATGTGATGGGATCACTAGCATGTCTGCGGAGAGCGGCCCTGGGACGAGATTGAGAAATCTGCC

AGTAATGGGGGATGGACTAGAAACTTCCCAAATGTCTACAACACAGGCCCAGGCCCAACCCCAGCC

AGCCAACGCAGCCAGCACCAACCCCCCGCCCCCAGAGACCTCCAACCCTAACAAGCCCAAGAGGCA

GACCAACCAACTGCAATACCTGCTCAGAGTGGTGCTCAAGACACTATGGAAACACCAGTTTGCATG

GCCTTTCCAGCAGCCTGTGGATGCCGTCAAGCTGAACCTCCCTGATTACTATAAGATCATTAAAACG

CCTATGGATATGGGAACAATAAAGAAGCGCTTGGAAAACAACTATTACTGGAATGCTCAGGAATGT

ATCCAGGACTTCAACACTATGTTTACAAATTGTTACATCTACAACAAGCCTGGAGATGACATAGTCT

TAATGGCAGAAGCTCTGGAAAAGCTCTTCTTGCAAAAAATAAATGAGCTACCCACAGAAGAAACCG

AGATCATGATAGTCCAGGCAAAAGGAAGAGGACGTGGGAGGAAAGAAACAGGGACAGCAAAACCT

GGCGTTTCCACGGTACCAAACACAACTCAAGCATCGACTCCTCCGCAGACCCAGACCCCTCAGCCGA

ATCCTCCTCCTGTGCAGGCCACGCCTCACCCCTTCCCTGCCGTCACCCCGGACCTCATCGTCCAGACC

CCTGTCATGACAGTGGTGCCTCCCCAGCCACTGCAGACGCCCCCGCCAGTGCCCCCCCAGCCACAAC

CCCCACCCGCTCCAGCTCCCCAGCCCGTACAGAGCCACCCACCCATCATCGCGGCCACCCCACAGCC

TGTGAAGACAAAGAAGGGAGTGAAGAGGAAAGCAGACACCACCACCCCCACCACCATTGACCCCA

TTCACGAGCCACCCTCGCTGCCCCCGGAGCCCAAGACCACCAAGCTGGGCCAGCGGCGGGAGAGCA

GCCGGCCTGTGAAACCTCCAAAGAAGGACGTGCCCGACTCTCAGCAGCACCCAGCACCAGAGAAGA

GCAGCAAGGTCTCGGAGCAGCTCAAGTGCTGCAGCGGCATCCTCAAGGAGATGTTTGCCAAGAAGC

ACGCCGCCTACGCCTGGCCCTTCTACAAGCCTGTGGACGTGGAGGCACTGGGCCTACACGACTACTG

TGACATCATCAAGCACCCCATGGACATGAGCACAATCAAGTCTAAACTGGAGGCCCGTGAGTACCG

TGATGCTCAGGAGTTTGGTGCTGACGTCCGATTGATGTTCTCCAACTGCTATAAGTACAACCCTCCTG

ACCATGAGGTGGTGGCCATGGCCCGCAAGCTCCAGGATGTGTTCGAAATGCGCTTTGCCAAGATGCC

GGACGAGCCTGAGGAGCCAGTGGTGGCCGTGTCCTCCCCGGCAGTGCCCCCTCCCACCAAGGTTGTG

GCCCCGCCCTCATCCAGCGACAGCAGCAGCGATAGCTCCTCGGACAGTGACAGTTCGACTGATGACT

CTGAGGAGGAGCGAGCCCAGCGGCTGGCTGAGCTCCAGGAGCAGCTCAAAGCCGTGCACGAGCAG

-continued

CTTGCAGCCCTCTCTCAGCCCCAGCAGAACAAACCAAAGAAAAAGGAGAAAGACAAGAAGGAAAA

GAAAAAAGAAAAGCACAAAAGGAAAGAGGAAGTGGAAGAGAATAAAAAAAGCAAAGCCAAGGAA

CCTCCTCCTAAAAAGACGAAGAAAAATAATAGCAGCAACAGCAATGTGAGCAAGAAGGAGCCAGC

GCCCATGAAGAGCAAGCCCCCTCCCACGTATGAGTCGGAGGAAGAGGACAAGTGCAAGCCTATGTC

CTATGAGGAGAAGCGGCAGCTCAGCTTGGACATCAACAAGCTCCCCGGCGAGAAGCTGGGCCGCGT

GGTGCACATCATCCAGTCACGGGAGCCCTCCCTGAAGAATTCCAACCCCGACGAGATTGAAATCGA

CTTTGAGACCCTGAAGCCGTCCACACTGCGTGAGCTGGAGCGCTATGTCACCTCCTGTTTGCGGAAG

AAAAGGAAACCTCAAGCTGAGAAAGTTGATGTGATTGCCGGCTCCTCCAAGATGAAGGGCTTCTCG

TCCTCAGAGTCGGAGAGCTCCAGTGAGTCCAGCTCCTCTGACAGCGAAGACTCCGAAACAGGTCCT

GCCTAATCATTGGACACGGACTCTTAATAAAACGGTCTTCAGTTCCAGATTCCTTCCCAGCAAGCTA

TAGCTTAAGTCCATTTTCTTCCGTGAAAGGGACAGGACTCCATCAAGTTATGGAATTCCTCAGAGCC

CTGGGCCTGTCCCCCGGGGTGGATTAGTCATGTCCAGCAGCACACGCCTAGTCCCGCCTTCGGGAAG

GCTGCCTGCCTGGCCAGCCGCCCAGGCCTCTCTGTGTAAAGACTGCCTGGCTGTCCTGCCCAGCCTT

CCTGGTTCTCTGGGGTCCTCTGGGTGGGTGGCATCTCCTGGAGGGTGATGACAATCCCCAACACATG

CATTCATGTGGTGCTACTCTGTGTGCAAAGCCAGACCCCAAGTATGTTTTCTCTCTTTGTCCCATCCC

TCTTTTTCTGGGACTTTGGACCCTAACTACTTCCCTCCTGAACCTTGCAGTGACATCAGTCCAGGAGA

GCTCTCGTTCAGTGTGCGGAAGAACACTCTGACCTCTAGAGCTGTCCTAGATAAGGAGTGGGAGCTT

TAGAGGCAAGGCCTCTAGACCCTGGAAGGCTCAGTGAGGCTCTTCCCACAGCATGCTTCTCACTGGT

GCCCTGTAAGGCTCGAGCCACCGCTGACTCTGAGCCTTTTGGAGTCTTTCCTCCTTCGTCTCCATTGT

TCCCGTGCATTTCCAAAAGCTTAAGTTGCCTGGTGGGCATTTCCCCAGTTTCTTTGGCCTCCGTCTTC

TCAAGTCACATAGGGAAAGTACCTCCTGGAACCAGGCTGCAGTATGCAGGACCTGCCAGGCAGGCA

CTGGTGAAGGGCCTTGGGCCTATCATCCCCCCAACCCCACCTCACCCCACCCGCCTCCTCTAGTGGG

GTGAGTCTGGGCTGGTGGACCAGAGAGGGTGTCACAGACCCTCAGGGACTGCCCCATGGACACCTC

TGACTGGTGTTAACAGTGTGAACATTTTCCCCGTCTTCAGTCCCTTAGAATGACGACAGCCCCTGGG

GTTGGGGCAGGCGAGTGTGGCCACATCATCCAAGCCCTCCCAGAGACACAAATAGGCTTTTTTGCTC

TAAAAATAAATACCAGCCCTTTTTTGGTCACAAATCCAGCATCTCAGCAGAAAACTGCCTGACATGA

AAAGTCCCCTGAGGAACTGCATCTGCGTTTCAGGGGCTTTTCATTTTTTCTCCTTTTTTAAAGTGTAG

ATTGTGGGTGCTTCCTAGAGGCCTGCCTTCTTCTGGAACTGGAAGTGGGCTATCACCATGGGCAAGC

CCTTGGGTGCAGGCTCCCCACCTGCCTGGGAACTCTGGCAGCTCTCCTCAGCTCCTTGGGCTTGAGC

AGCTGCAACTGCCCCAGATTTGCTGTGGAAGCAGGGGCTAGCCCTGGCCTCACCAGGGCCTCCCGG

GGCCCTGCATTGATGCTCAGGAGTTCCTGGGCTGCTCTTGATCCTTTCTGGGCATCCAGCTTCCAGTT

AAGCTCTGTTTGCCAAACAAACTATTCTCAGCTGCCCTTTGGCCTGCGCCTGATGTGTTCCTGTTGCA

GTCCCGCCTGCCTGAGACAGGAGCAGGCAGGAGAGCCTTCATGCCCAGATTCCCACAGGACAATTG

GGGAGCTGCTGGCATTGTCTTTCTGGGAAGATTCTGCTTTCTTGGACCAAATGGCAGCCTGATTACC

AGTGTCGGGCCTGCATGCTGCCCCCGACACACGCACGCACGCGCACACACGTGTGCACATGGGCCA

TAGCCACAAGCCAGCTCTCCTCCAGGGTCCTTTCAACCTCGCTGTCCAGGGACCCTGTCCTTCTTGCC

CGTGGGGCTTCCATCTGGCAGAGAACGTTCAGGGCTTGTTGAACTTGAAAGCTCATTAGACTTAAGC

TGTCACCTGTGCTTGGTGCCCCAGGAACAGCCAGAGAGGACAGTGCCCACTCACTTCTTGTTGGCAG

CCTCCTGTGCAGGAAGTGCCAGCCGGGCCTCGACGCACCAGCTGGCTGTGGGTCCTGAGGAGGGGC

GGGAGGCGGCCGCTCAGTGCAGATGGGGACTCCTCTCCTCTGCCCTGACCTTACCCTCCATTACCTC

-continued

CTTCACTGGAGTGGGGCTGGGGGGTGGGTGGAATCAGTGTTTTAATCGGATTTTTAAAAAACATTTT

ATTTCTTTGTACAATTACCATCCTATGTAAAGATGAAATTTGTGTTGAGTTGAAGATTGTCATGGAAT

AAAGATCACACCGTACTTGAGGCCATCTTCATGTAA

DNA sequence encoding human BRD4 mRNA isoform long (NM_058243.2, SEQ ID NO: 9)

ATTCTTTGGAATACTACTGCTAGAAGTCTGACTTAAGACCCAGCTTATGGGCCACATGGCACCCAGC

TGCTTCTGCAGAGAAGGCAGGCCACTGATGGGTACAGCAAAGTGTGGTGCTGCTGGCCAAGCCAAA

GACCCGTGTAGGATGACTGGGCCTCTGCCCCTTGTGGGTGTTGCCACTGTGCTTGAGTGCCTGGTGA

AGAATGTGATGGGATCACTAGCATGTCTGCGGAGAGCGGCCCTGGGACGAGATTGAGAAATCTGCC

AGTAATGGGGGATGGACTAGAAACTTCCCAAATGTCTACAACACAGGCCCAGGCCCAACCCCAGCC

AGCCAACGCAGCCAGCACCAACCCCCCGCCCCCAGAGACCTCCAACCCTAACAAGCCCAAGAGGCA

GACCAACCAACTGCAATACCTGCTCAGAGTGGTGCTCAAGACACTATGGAAACACCAGTTTGCATG

GCCTTTCCAGCAGCCTGTGGATGCCGTCAAGCTGAACCTCCCTGATTACTATAAGATCATTAAAACG

CCTATGGATATGGGAACAATAAAGAAGCGCTTGGAAAACAACTATTACTGGAATGCTCAGGAATGT

ATCCAGGACTTCAACACTATGTTTACAAATTGTTACATCTACAACAAGCCTGGAGATGACATAGTCT

TAATGGCAGAAGCTCTGGAAAAGCTCTTCTTGCAAAAAATAAATGAGCTACCCACAGAAGAAACCG

AGATCATGATAGTCCAGGCAAAAGGAAGAGGACGTGGGAGGAAAGAAACAGGGACAGCAAAACCT

GGCGTTTCCACGGTACCAAACACAACTCAAGCATCGACTCCTCCGCAGACCCAGACCCCTCAGCCGA

ATCCTCCTCCTGTGCAGGCCACGCCTCACCCCTTCCCTGCCGTCACCCCGGACCTCATCGTCCAGACC

CCTGTCATGACAGTGGTGCCTCCCCAGCCACTGCAGACGCCCCCGCCAGTGCCCCCCCAGCCACAAC

CCCCACCCGCTCCAGCTCCCCAGCCCGTACAGAGCCACCCACCCATCATCGCGGCCACCCCACAGCC

TGTGAAGACAAAGAAGGGAGTGAAGAGGAAAGCAGACACCACCACCCCCACCACCATTGACCCCA

TTCACGAGCCACCCTCGCTGCCCCCGGAGCCCAAGACCACCAAGCTGGGCCAGCGGCGGGAGAGCA

GCCGGCCTGTGAAACCTCCAAAGAAGGACGTGCCCGACTCTCAGCAGCACCCAGCACCAGAGAAGA

GCAGCAAGGTCTCGGAGCAGCTCAAGTGCTGCAGCGGCATCCTCAAGGAGATGTTTGCCAAGAAGC

ACGCCGCCTACGCCTGGCCCTTCTACAAGCCTGTGGACGTGGAGGCACTGGGCCTACACGACTACTG

TGACATCATCAAGCACCCCATGGACATGAGCACAATCAAGTCTAAACTGGAGGCCCGTGAGTACCG

TGATGCTCAGGAGTTTGGTGCTGACGTCCGATTGATGTTCTCCAACTGCTATAAGTACAACCCTCCTG

ACCATGAGGTGGTGGCCATGGCCCGCAAGCTCCAGGATGTGTTCGAAATGCGCTTTGCCAAGATGCC

GGACGAGCCTGAGGAGCCAGTGGTGGCCGTGTCCTCCCCGGCAGTGCCCCCTCCCACCAAGGTTGTG

GCCCCGCCCTCATCCAGCGACAGCAGCAGCGATAGCTCCTCGGACAGTGACAGTTCGACTGATGACT

CTGAGGAGGAGCGAGCCCAGCGGCTGGCTGAGCTCCAGGAGCAGCTCAAAGCCGTGCACGAGCAG

CTTGCAGCCCTCTCTCAGCCCCAGCAGAACAAACCAAAGAAAAAGGAGAAAGACAAGAAGGAAAA

GAAAAAAGAAAAGCACAAAAGGAAAGAGGAAGTGGAAGAGAATAAAAAAAGCAAAGCCAAGGAA

CCTCCTCCTAAAAAGACGAAGAAAAATAATAGCAGCAACAGCAATGTGAGCAAGAAGGAGCCAGC

GCCCATGAAGAGCAAGCCCCCTCCCACGTATGAGTCGGAGGAAGAGGACAAGTGCAAGCCTATGTC

CTATGAGGAGAAGCGGCAGCTCAGCTTGGACATCAACAAGCTCCCCGGCGAGAAGCTGGGCCGCGT

GGTGCACATCATCCAGTCACGGGAGCCCTCCCTGAAGAATTCCAACCCCGACGAGATTGAAATCGA

CTTTGAGACCCTGAAGCCGTCCACACTGCGTGAGCTGGAGCGCTATGTCACCTCCTGTTTGCGGAAG

AAAAGGAAACCTCAAGCTGAGAAAGTTGATGTGATTGCCGGCTCCTCCAAGATGAAGGGCTTCTCG

TCCTCAGAGTCGGAGAGCTCCAGTGAGTCCAGCTCCTCTGACAGCGAAGACTCCGAAACAGAGATG

GCTCCGAAGTCAAAAAAGAAGGGGCACCCCGGGAGGGAGCAGAAGAAGCACCATCATCACCACCA

-continued

TCAGCAGATGCAGCAGGCCCCGGCTCCTGTGCCCCAGCAGCCGCCCCCGCCTCCCCAGCAGCCCCCA

CCGCCTCCACCTCCGCAGCAGCAACAGCAGCCGCCACCCCCGCCTCCCCCACCCTCCATGCCGCAGC

AGGCAGCCCCGGCGATGAAGTCCTCGCCCCCACCCTTCATTGCCACCCAGGTGCCCGTCCTGGAGCC

CCAGCTCCCAGGCAGCGTCTTTGACCCCATCGGCCACTTCACCCAGCCCATCCTGCACCTGCCGCAG

CCTGAGCTGCCCCCTCACCTGCCCCAGCCGCCTGAGCACAGCACTCCACCCCATCTCAACCAGCACG

CAGTGGTCTCTCCTCCAGCTTTGCACAACGCACTACCCCAGCAGCCATCACGGCCCAGCAACCGAGC

CGCTGCCCTGCCTCCCAAGCCCGCCCGGCCCCCAGCCGTGTCACCAGCCTTGACCCAAACACCCCTG

CTCCCACAGCCCCCCATGGCCCAACCCCCCCAAGTGCTGCTGGAGGATGAAGAGCCACCTGCCCCAC

CCCTCACCTCCATGCAGATGCAGCTGTACCTGCAGCAGCTGCAGAAGGTGCAGCCCCCTACGCCGCT

ACTCCCTTCCGTGAAGGTGCAGTCCCAGCCCCCACCCCCCCTGCCGCCCCCACCCCACCCCTCTGTGC

AGCAGCAGCTGCAGCAGCAGCCGCCACCACCCCCACCACCCCAGCCCCAGCCTCCACCCCAGCAGC

AGCATCAGCCCCCTCCACGGCCCGTGCACTTGCAGCCCATGCAGTTTTCCACCCACATCCAACAGCC

CCCGCCACCCCAGGGCCAGCAGCCCCCCCATCCGCCCCCAGGCCAGCAGCCACCCCCGCCGCAGCC

TGCCAAGCCTCAGCAAGTCATCCAGCACCACCATTCACCCCGGCACCACAAGTCGGACCCCTACTCA

ACCGGTCACCTCCGCGAAGCCCCCTCCCCGCTTATGATACATTCCCCCCAGATGTCACAGTTCCAGA

GCCTGACCCACCAGTCTCCACCCCAGCAAAACGTCCAGCCTAAGAAACAGGAGCTGCGTGCTGCCT

CCGTGGTCCAGCCCCAGCCCCTCGTGGTGGTGAAGGAGGAGAAGATCCACTCACCCATCATCCGCA

GCGAGCCCTTCAGCCCCTCGCTGCGGCCGGAGCCCCCCAAGCACCCGGAGAGCATCAAGGCCCCCG

TCCACCTGCCCCAGCGGCCGGAAATGAAGCCTGTGGATGTCGGGAGGCCTGTGATCCGGCCCCCAG

AGCAGAACGCACCGCCACCAGGGGCCCCTGACAAGGACAAACAGAAACAGGAGCCGAAGACTCCA

GTTGCGCCCAAAAAGGACCTGAAAATCAAGAACATGGGCTCCTGGGCCAGCCTAGTGCAGAAGCAT

CCGACCACCCCCTCCTCCACAGCCAAGTCATCCAGCGACAGCTTCGAGCAGTTCCGCCGCGCCGCTC

GGGAGAAAGAGGAGCGTGAGAAGGCCCTGAAGGCTCAGGCCGAGCACGCTGAGAAGGAGAAGGA

GCGGCTGCGGCAGGAGCGCATGAGGAGCCGAGAGGACGAGGATGCGCTGGAGCAGGCCCGGCGGG

CCCATGAGGAGGCACGTCGGCGCCAGGAGCAGCAGCAGCAGCAGCGCCAGGAGCAACAGCAGCAG

CAGCAACAGCAAGCAGCTGCGGTGGCTGCCGCCGCCACCCCACAGGCCCAGAGCTCCCAGCCCCAG

TCCATGCTGGACCAGCAGAGGGAGTTGGCCCGGAAGCGGGAGCAGGAGCGAAGACGCCGGGAAGC

CATGGCAGCTACCATTGACATGAATTTCCAGAGTGATCTATTGTCAATATTTGAAGAAAATCTTTTCT

GAGCGCACCTAGGTGGCTTCTGACTTTGATTTTCTGGCAAAACATTGACTTTCCATAGTGTTAGGGG

CGGTGGTGGAGGTGGGATCAGCGGCCAGGGGATGCCTCAGGGCCTGGCCCTCCTGCATGCTATGCC

CGGGGCAGGCCTGACGGGCAGCTGAGGATTGCAGAGCCTGTCTGCCTTACGGCCAGTCGGACAGAC

GTCCCGCCACCCACCACCCCTCACAGGACGTCCGCTCAGCACACGCCTTGTTACGAGCAAGTGCCGG

CTGGACCCAAGCCCTGCATCCCCACATGCGGGGCAGAGGCCCTTCTCTCCGCCAAATGTCTACACAG

TATACACAGGACATCGTTGCTGCCGCCGTGACTGGTTTTCTGTCCCCAAGAACGTGACGTTCGTGAT

GTCCTGCCCGCCGGGAGTCTTTCCCCACACCCCAGCCATCGCCGCCCGCTCCCAGGAGGCCAGGGCA

GGCCTGCGTGGGCTGGAGGCGGGCGAGGCCGGCCCACCCCCTCGCTGGCACTGACTTTGCCTTGAAC

AGACCCCCCGACCCTCCCCCACAAGCCTTTAATTGAGAGCCGCTCTCTGTAAGTGTTTGCTTGTGCA

AAAGGGAATAGTGCCGTGGAGGTGTGTGTGTCCATGGCATCCGGAGCGAGGCGACTGTCCTGCGTG

GGTAGCCCTCGGCCGGGGAGTGAGGCCACCAACCAAAGTCAGTTCCTTCCCACCTGTGTTTCTGTTT

CGTTTTTTTTTTTCTTTTTTTTCTATATATATTTTTTGTTGAATTCTATTTTATTTTTAATTCTCTCTTCT

-continued

```
CCTCCAGACACAATGGCACTGCTTATCTCCGAAATGGTGTGATCGTCTCCTCATTGAGCAGCGGCTG

CCACCGCGCTGTGGGTA
```

In some embodiments, the second agent inhibits BRD4 activity. For example, in some embodiments, the second agent may reduce BRD4 activity by at least 20%, at least 30%, at least 40%, at least 50%, at least 60%, at least 70%, at least 80%, at least 90%, at least 95%, or 100%, compared to in the absence of the second agent. In some embodiments, the second agent reduces BRD4 activity by 20%, 30%, 40%, 50%, 60%, 70%, 80%, 90%, 95%, or 100%, compared to in the absence of the second agent.

The second agent that inhibits BRD4 activity may be, without limitation, small molecules and anti-BRD4 antibodies. Small molecule BRD4 inhibitors are known in the art (e.g., as described in Perez-Salvia et al., Epigenetics, 2017, VOL. 12, NO. 5, 323-339, incorporated herein by reference). In some embodiments, the second agent is selected from the group consisting of: JQ1, I-BET762, OTX015, I-BET151, CPI203, PFI-1, MS436, CPI-0610, RVX2135, FT-1101, BAY1238097, INCB054329, TEN-010, GSK2820151, ZEN003694, BAY-299, BMS-986158, ABBV-075, GS-5829, and PLX51107. In some embodiments, the second agent is JQ1.

It was shown herein that METTL3 inhibition reduced the expression of BRD4, and makes cells more sensitive to the BRD4 inhibitors. In some embodiments, co-administration of an agent that inhibits the interaction between METTL3 and EIF3h and a second agent that inhibits BRD4 improves the potency of the second agent that inhibits BRD4 (e.g., by at least 20%, at least 30%, at least 50%, at least 100%, at least 2-fold, at least 10-fold, at least 100-fold, or more).

In some aspects, the present disclosure provides compositions comprising a first agent that inhibits interaction between METTL3 and EIF3h, and/or a second agent that inhibits BRD4. The first agent that inhibits interaction between METTL3 and EIF3h and the second agent that inhibits BRD4 may be formulated separately (in two compositions) or in one composition.

In some embodiments, any of the compositions is formulated as a pharmaceutical composition. In some embodiments, the pharmaceutical composition further comprises a pharmaceutically acceptable carrier. "Pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. A "pharmaceutically acceptable carrier" may be a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body. Each carrier must be "acceptable" in the sense of being compatible with the other ingredients of the formulation and not injurious to the tissue of the patient (e.g., physiologically compatible, sterile, physiologic pH, etc.). The term "carrier" denotes an organic or inorganic ingredient, natural or synthetic, with which the active ingredient is combined to facilitate the application. The components of the pharmaceutical compositions also are capable of being co-mingled with the molecules of the present disclosure, and with each other, in a manner such that there is no interaction which would substantially impair the desired pharmaceutical efficacy. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) C2-C12 alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation.

The pharmaceutical compositions may conveniently be presented in unit dosage form and may be prepared by any of the methods well-known in the art of pharmacy. The term "unit dose" when used in reference to a pharmaceutical composition of the present disclosure refers to physically discrete units suitable as unitary dosage for the subject, each unit containing a predetermined quantity of active material calculated to produce the desired therapeutic effect in association with the required diluent; i.e., carrier, or vehicle.

The formulation of the pharmaceutical composition may dependent upon the route of administration. Injectable preparations suitable for parenteral administration or intratumoral, peritumoral, intralesional or perilesional administration include, for example, sterile injectable aqueous or oleaginous suspensions and may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3 propanediol or 1,3 butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid find use in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

Compositions suitable for oral administration may be presented as discrete units, such as capsules, tablets, lozenges, each containing a predetermined amount of the anti-inflammatory agent. Other compositions include suspensions in aqueous liquids or non-aqueous liquids such as a syrup, elixir or an emulsion.

In some embodiments, the pharmaceutical compositions used for therapeutic administration must be sterile. Sterility is readily accomplished by filtration through sterile filtration membranes (e.g., 0.2 micron membranes). Alternatively, preservatives can be used to prevent the growth or action of microorganisms. Various preservatives are well known and include, for example, phenol and ascorbic acid. The pharmaceutical composition ordinarily will be stored in lyophilized form or as an aqueous solution if it is highly stable to thermal and oxidative denaturation. The pH of the preparations typically will be about from 6 to 8, although higher or lower pH values can also be appropriate in certain instances.

In some embodiments, the agent described herein (i.e., agent inhibiting the interaction between METTL3 and EIF3h, and/or agent inhibiting BRD4) or the composition described (i.e., composition comprising one or both of the agent inhibiting the interaction between METTL3 and EIF3h and the agent inhibiting BRD4) is administered systemically (e.g., via intravenous injection or infusion), orally, or intratumorally (e.g., via injection).

In some embodiments, the agent inhibiting the interaction between METTL3 and EIF3h and the agent inhibiting BRD4 are administered simultaneously (e.g., in one composition) or sequentially (e.g., in two compositions). When the two agents are administered sequentially, either can be administered first and the other one administered second.

"A therapeutically effective amount" as used herein refers to the amount of each therapeutic agent (e.g., therapeutic agents for treating any of the cancer described herein) of the present disclosure required to confer therapeutic effect on the subject, either alone or in combination with one or more other therapeutic agents. Effective amounts vary, as recognized by those skilled in the art, depending on the particular condition being treated, the severity of the condition, the individual subject parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a subject may insist upon a lower dose or tolerable dose for medical reasons, psychological reasons or for virtually any other reasons.

Empirical considerations, such as the half-life, generally will contribute to the determination of the dosage. For example, therapeutic agents that are compatible with the human immune system, such as polypeptides comprising regions from humanized antibodies or fully human antibodies, may be used to prolong half-life of the polypeptide and to prevent the polypeptide being attacked by the host's immune system. Frequency of administration may be determined and adjusted over the course of therapy, and is generally, but not necessarily, based on treatment and/or suppression and/or amelioration and/or delay of a disease. Alternatively, sustained continuous release formulations of a polypeptide may be appropriate. Various formulations and devices for achieving sustained release are known in the art.

In some embodiments, dosage is daily, every other day, every three days, every four days, every five days, or every six days. In some embodiments, dosing frequency is once every week, every 2 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy is easily monitored by conventional techniques and assays. The dosing regimen (including the anti-cancer agent used) can vary over time.

In some embodiments, for an adult subject of normal weight, doses ranging from about 0.01 to 1000 mg/kg may be administered. In some embodiments, the dose is between 1 to 200 mg. The particular dosage regimen, i.e., dose, timing and repetition, will depend on the particular subject and that subject's medical history, as well as the properties of the anti-cancer agent (such as the half-life of the anti-cancer agent, and other considerations well known in the art).

For the purpose of the present disclosure, the appropriate dosage of a therapeutic agent as described herein will depend on the specific agent (or compositions thereof) employed, the formulation and route of administration, the type and severity of the disease, whether the anti-cancer agent is administered for preventive or therapeutic purposes, previous therapy, the subject's clinical history and response to the antagonist, and the discretion of the attending physician. Typically the clinician will administer an anti-cancer agent until a dosage is reached that achieves the desired result. Administration of one or more anti-cancer agents can be continuous or intermittent, depending, for example, upon the recipient's physiological condition, whether the purpose of the administration is therapeutic or prophylactic, and other factors known to skilled practitioners. The administration of an anti-cancer agent may be essentially continuous over a preselected period of time or may be in a series of spaced dose, e.g., either before, during, or after developing a disease.

As used herein, the term "treating" refers to the application or administration of an anti-cancer agent to a subject in need thereof. "A subject in need thereof", refers to an individual who has cancer, a symptom of cancer, or a predisposition toward cancer, with the purpose to cure, heal, alleviate, relieve, alter, remedy, ameliorate, improve, or affect the disease, the symptom of the disease, or the predisposition toward the cancer.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In some embodiments, the non-human animal is a mammal (e.g., rodent (e.g., mouse or rat), primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). The non-human animal may be a male or female at any stage of development. The non-human animal may be a transgenic animal or genetically engineered animal.

In some embodiments, the subject is a companion animal (a pet). "A companion animal," as used herein, refers to pets and other domestic animals. Non-limiting examples of companion animals include dogs and cats; livestock such as horses, cattle, pigs, sheep, goats, and chickens; and other animals such as mice, rats, guinea pigs, and hamsters. In some embodiments, the subject is a research animal. Non-limiting examples of research animals include: rodents (e.g., rats, mice, guinea pigs, and hamsters), rabbits, or non-human primates.

Alleviating a disease includes delaying the development or progression of the disease, or reducing disease severity. Alleviating the disease does not necessarily require curative results. As used therein, "delaying" the development of a disease means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detectable and assessed using standard clinical techniques as well known in the art. However, development also refers to progression that may be undetectable. For purpose of this disclosure, development or progression refers to the biological course of the symptoms. "Development" includes occurrence, recurrence, and onset. As used herein "onset" or "occurrence" of a disease includes initial onset and/or recurrence.

Conventional methods, known to those of ordinary skill in the art of medicine, can be used to administer the anti-cancer agent the subject, depending upon the type of disease to be treated or the site of the disease. The anti-cancer agent can also be administered via other conventional routes, e.g., administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. In addition, it can be administered to the subject via injectable depot routes of administration such as using 1-, 3-, or 6-month depot injectable or biodegradable materials and methods.

The term "cancer" refers to a class of diseases characterized by the development of abnormal cells that proliferate uncontrollably and have the ability to infiltrate and destroy normal body tissues. See, e.g., Stedman's Medical Dictionary, 25th ed.; Hensyl ed.; Williams & Wilkins: Philadelphia, 1990. Exemplary cancers that may be treated using the methods described herein include, but are not limited to, hematological malignancies. Additional exemplary cancers include, but are not limited to, lung cancer (e.g., bronchogenic carcinoma, small cell lung cancer (SCLC), non-small cell lung cancer (NSCLC), adenocarcinoma of the lung); kidney cancer (e.g., nephroblastoma, a.k.a. Wilms' tumor, renal cell carcinoma); acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); heavy chain disease (e.g., alpha chain disease, gamma chain disease, mu chain disease; hemangioblastoma; hypopharynx cancer; inflammatory myofibroblastic tumors; immunocytic amyloidosis; liver cancer (e.g., hepatocellular cancer (HCC), malignant hepatoma); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendoctrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

In some embodiments, the cancer is lung cancer, colon cancer, esophageal carcinoma, liver cancer, prostate cancer, or neuroblastoma. In some embodiments, the cancer is colon cancer. In some embodiments, the cancer is lung cancer. In some embodiments, the cancer is neuroblastoma.

In some embodiments, Other cancer therapeutics (e.g., chemotherapeutic agents and/or immunotherapeutic agents) are used in combination with the methods described herein. A "chemotherapeutic agent" refers is a chemical agent or drugs that are selectively destructive to malignant cells and tissues. Non-limiting, exemplary chemopharmaceutically compositions that may be used in accordance with the present disclosure include, Neratinib or lapatinib, Actinomycin, All-trans retinoic acid, Azacitidine, Azathioprine, Bleomycin, Bortezomib, Carboplatin, Capecitabine, Cisplatin, Chlorambucil, Cyclophosphamide, Cytarabine, Daunorubicin, Docetaxel, Doxifluridine, Doxorubicin, Epirubicin, Epothilone, Etoposide, Fluorouracil, Gemcitabine, Hydroxyurea, Idarubicin, Imatinib, Irinotecan, Mechlorethamine, Mercaptopurine, Methotrexate, Mitoxantrone, Oxaliplatin, Paclitaxel, Pemetrexed, Teniposide, Tioguanine, Topotecan, Valrubicin, Vinblastine, Vincristine, Vindesine, and Vinorelbine. An "immunotherapeutic agent" refers to an agent that modulates (e.g., suppresses or activates) the immune response to treat a disease. Immunetheraepeutic agents are known to those skilled in the art, e.g., those listed on www.ncbi.nlm.nih.gov/medgen/2637.

In some embodiments, the immunotherapeutic agent is an immune checkpoint inhibitor. An "immune checkpoint" is a protein in the immune system that either enhances an immune response signal (co-stimulatory molecules) or reduces an immune response signal. Many cancers protect themselves from the immune system by exploiting the inhibitory immune checkpoint proteins to inhibit the T cell signal. Exemplary inhibitory checkpoint proteins include, without limitation, Cytotoxic T-Lymphocyte-Associated protein 4 (CTLA-4), Programmed Death 1 receptor (PD-1), T-cell Immunoglobulin domain and Mucin domain 3 (TIM3), Lymphocyte Activation Gene-3 (LAG3), V-set domain-containing T-cell activation inhibitor 1 (VTVN1 or B7-H4), Cluster of Differentiation 276 (CD276 or B7-H3), B and T Lymphocyte Attenuator (BTLA), Galectin-9 (GALS), Checkpoint kinase 1 (Chk1), Adenosine A2A receptor (A2aR), Indoleamine 2,3-dioxygenase (IDO), Killer-cell Immunoglobulin-like Receptor (KIR), Lymphocyte Activation Gene-3 (LAG3), and V-domain Ig suppressor of T cell activation (VISTA).

Some of these immune checkpoint proteins need their cognate binding partners, or ligands, for their immune inhibitory activity. For example, A2AR is the receptor of adenosine A2A and binding of A2A to A2AR activates a negative immune feedback loop. As another example, PD-1 associates with its two ligands, PD-L1 and PD-L2, to down regulate the immune system by preventing the activation of T-cells. PD-1 promotes the programmed cell death of antigen specific T-cells in lymph nodes and simultaneously reduces programmed cell death of suppressor T cells, thus achieving its immune inhibitory function. As yet another example, CTLA4 is present on the surface of T cells, and when bound to its binding partner CD80 or CD86 on the surface of antigen-present cells (APCs), it transmits an inhibitory signal to T cells, thereby reducing the immune response.

An "immune checkpoint inhibitor" is a molecule that prevents or weakens the activity of an immune checkpoint protein, For example, an immune checkpoint inhibitor may inhibit the binding of the immune checkpoint protein to its cognate binding partner, e.g., PD-1, CTLA-4, or A2aR. In some embodiments, the immune checkpoint inhibitor is a small molecule. In some embodiments, the immune checkpoint inhibitors is a nucleic acid aptamer (e.g., a siRNA targeting any one of the immune checkpoint proteins). In some embodiments, the immune checkpoint inhibitor is a recombinant protein. In some embodiments, the immune checkpoint inhibitor is an antibody. In some embodiments, the antibody comprises an anti-CTLA-4, anti-PD-1, anti-PD-L1, anti-TIM3, anti-LAG3, anti-B7-H3, anti-B7-H4, anti-BTLA, anti-GALS, anti-Chk, anti-A2aR, anti-IDO, anti-KIR, anti-LAG3, anti-VISTA antibody, or a combination of any two or more of the foregoing antibodies. In some embodiments, the immune checkpoint inhibitor is a monoclonal antibody. In some embodiments, the immune checkpoint inhibitor comprises anti-PD1, anti-PD-L1, anti-CTLA-4, or a combination of any two or more of the foregoing antibodies. For example, the anti-PD-1 antibody is pembrolizumab (Keytruda®) or nivolumab (Opdivo®) and the anti-CTLA-4 antibody is ipilimumab (Yervoy®). Thus, in some embodiments, the immune checkpoint inhibitor comprises pembrolizumab, nivolumab, ipilimumab, or any combination of two or more of the foregoing antibodies. The examples described herein are not meant to be limiting and that any immune checkpoint inhibitors known in the art and any combinations thereof may be used in accordance with the present disclosure.

Some of the embodiments, advantages, features, and uses of the technology disclosed herein will be more fully understood from the Examples below. The Examples are intended to illustrate some of the benefits of the present disclosure and to describe particular embodiments, but are not intended to exemplify the full scope of the disclosure and, accordingly, do not limit the scope of the disclosure.

EXAMPLES $N^6$-Methyladenosine ($m^6A$), the most abundant posttranscriptional modification on messenger RNA (mRNA), is emerging as an important regulator of gene expression[1]. $m^6A$ modification is catalyzed by a protein complex comprising METTL3 (methyltransferase-like 3) together with its cofactor METTL14 (methyltransferase-like 14), and accessory proteins[2-6]. The mapping of $m^6A$ sites throughout the transcriptome of mammalian cells revealed that this modification occurs at a GGAC sequence motif and is typically enriched at a position close to the translation stop codon of a large subset of mRNAs[7-9]. On the other hand, the demethylases FTO (fat mass and obesity-associated protein) and ALKBH5 (alkB homolog 5, RNA demethylase) can remove $m^6A$, facilitating the dynamic regulation of $m^6A$ modification in the cells[10,11]. It was however recently found that FTO activity might be more relevant for removing methylation at N6,2'-O-dimethyladenosine ($m^6Am$) sites in 5' mRNA cap structures[12].

Manipulation of $m^6A$ modification impacts different developmental and biological processes including meiosis in yeast[13], plant development[14], mouse spermatogenesis[10], circadian clock[15], ultraviolet-induced DNA damage response[16], embryonic stem cell (ESC) self-renewal and mouse embryogenesis[17-19], X-chromosome inactivation[20], and sex determination in *Drosophila*[21,22], supporting the physiological importance of $m^6A$ mRNA modification. Altered $m^6A$ homeostasis is linked to cancer cell growth and tumorigenicity, where depending on the cell type and specific mRNA targets, $m^6A$ can have either oncogenic or tumor suppressive functions[8,23-25]. Despite this growing awareness of the biological roles of $m^6A$ in a variety of organisms, the mechanisms for how $m^6A$ regulates gene expression remain poorly understood. Several YTH-domain containing proteins can specifically recognize $m^6A$-modified RNA to regulate mRNA splicing, export, stability, and translation[26-33]. In addition, it was found that METTL3 itself can promotes the translation of oncogenes such as EGFR and TAZ in lung cancer cells[8]. However, the molecular mechanism and the functional relevance of METTL3 in translation remain unclear.

Translation of most mRNAs is controlled at the rate-limiting step of initiation, leading to the assembly of an elongation-competent 80S ribosome from the 40S (small) and 60S (large) ribosomal subunits. The 43S ribosome pre-initiation complex comprising the 40S subunit, the initiating methionyl tRNA (Met-tRNA$_i$) and a group of eukaryotic initiation factors (eIFs), including eIF2 which is recruited to the 5' end of the mRNA by the eIF4F complex. eIF4F comprises the eIF4E subunit that binds m$^7$GpppN at the mRNA 5' cap (cap-binding protein), the RNA helicase eIF4A, and a scaffolding protein eIF4G. Also associated with eIF4F are several other initiation factors, including the multisubunit eIF3 complex, and mRNA binding proteins such as the polyA tail binding protein PABPC1. Mammalian eIF3 is composed of 13 different subunits that are involved in bridging the interaction between the 43S pre-initiation complex and the eIF4F-bound mRNA. eIF3 has been implicated in numerous steps of translation initiation, termination, and ribosomal recycling[34-36]. Cryo-EM has revealed the organization of the structure core of 8 eIF3 subunits. This includes 6 subunits (a, c, e, k, 1 and m) possessing the PCI (Proteasome-COP9 signalosome-eIF3) domain and 2 subunits (f and h) possessing the MPN (Mpr1-Pad1N-terminal) domain[37]. While eIF3 is believed to be used in almost all mRNA translation, it is emerging that individual eIF3 subunits have distinct roles in cell viability, development, and disease[38 39,40].

A closed-loop model of enhanced mRNA translation was proposed many years ago and is supported by the discovery of the functional and physical interaction between the capped 5' terminus and the polyadenylated 3' terminus of mRNA mediated by translation initiation factors eIF4G and PABPC1 (poly(A) binding protein cytoplasmic 1)[41-44]. However, there remains limited direct evidence of such mRNA loops. The functional and structural data support an alternative closed loop model, where circularization of the mRNA is mediated by association between the translation initiation complex at the 5'-end of the mRNA and METTL3 bound to specific sites near the translation stop codon. A specific interaction between METTL3 and the eIF3h subunit of the eIF3 translation initiation complex was furthermore identified. Using cancer cell lines and primary lung tumor samples, it was found that METTL3 promotes translation of a large subset of oncogenic mRNAs including Bromodomain Containing 4 (BRD4). In addition, METTL3 depletion inhibits tumorigenesis and sensitizes lung cancer cells to BRD4 pharmacological inhibition. These findings provide new insights into the mechanism of translation control and suggest that METTL3-eIF3h and downstream oncogenes could be potential therapeutic targets for cancer therapy.

METTL3 Enhances Translation when Bound Close to the mRNA Stop Codon

Figure 1B:
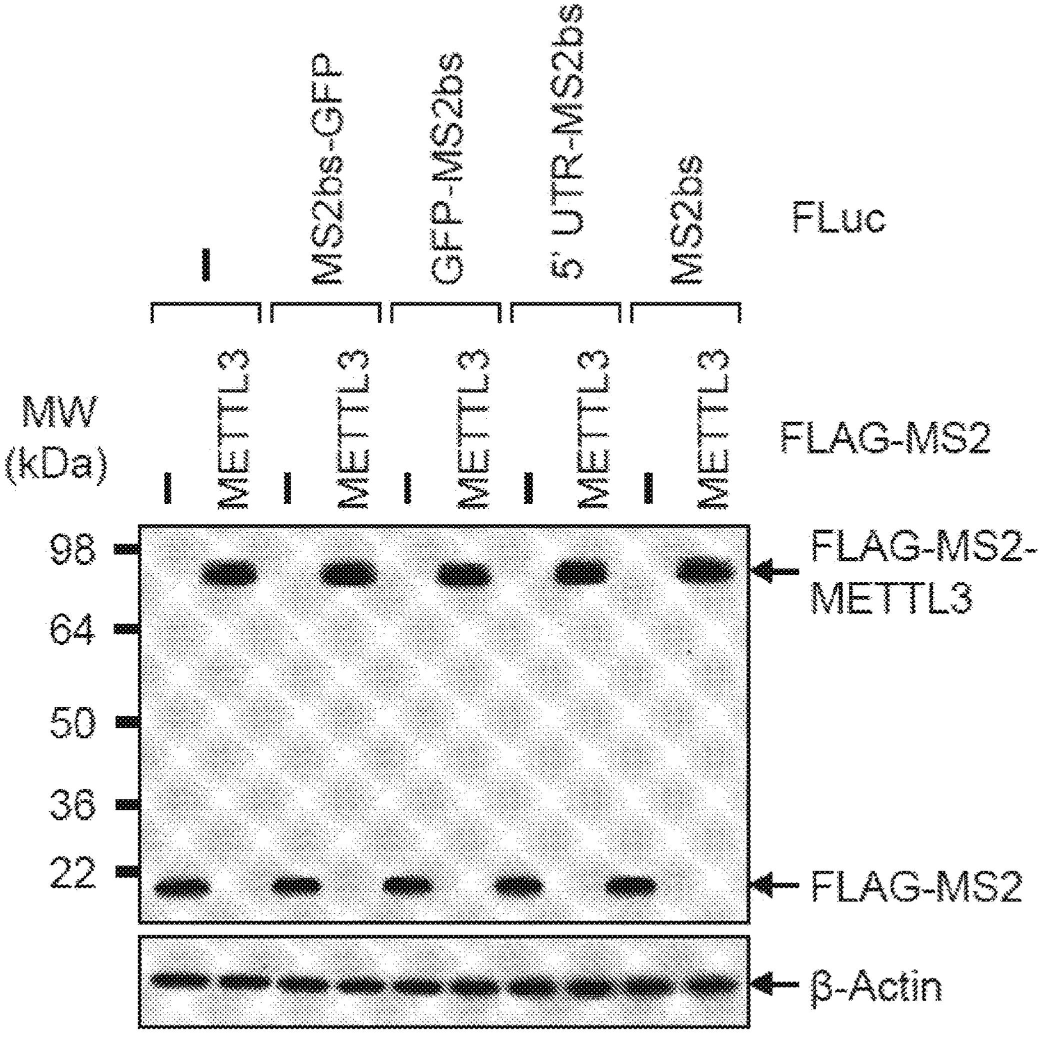
Figure 1C:
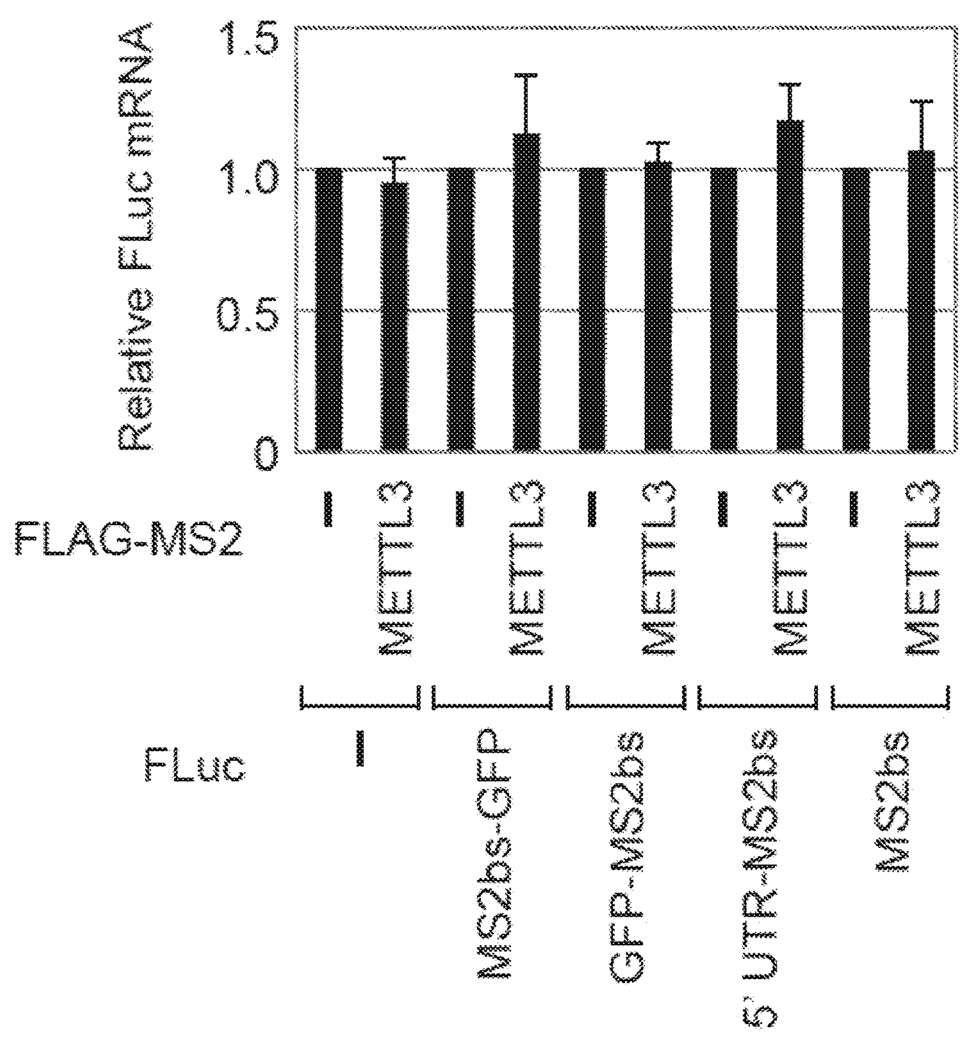
Figure 1D:
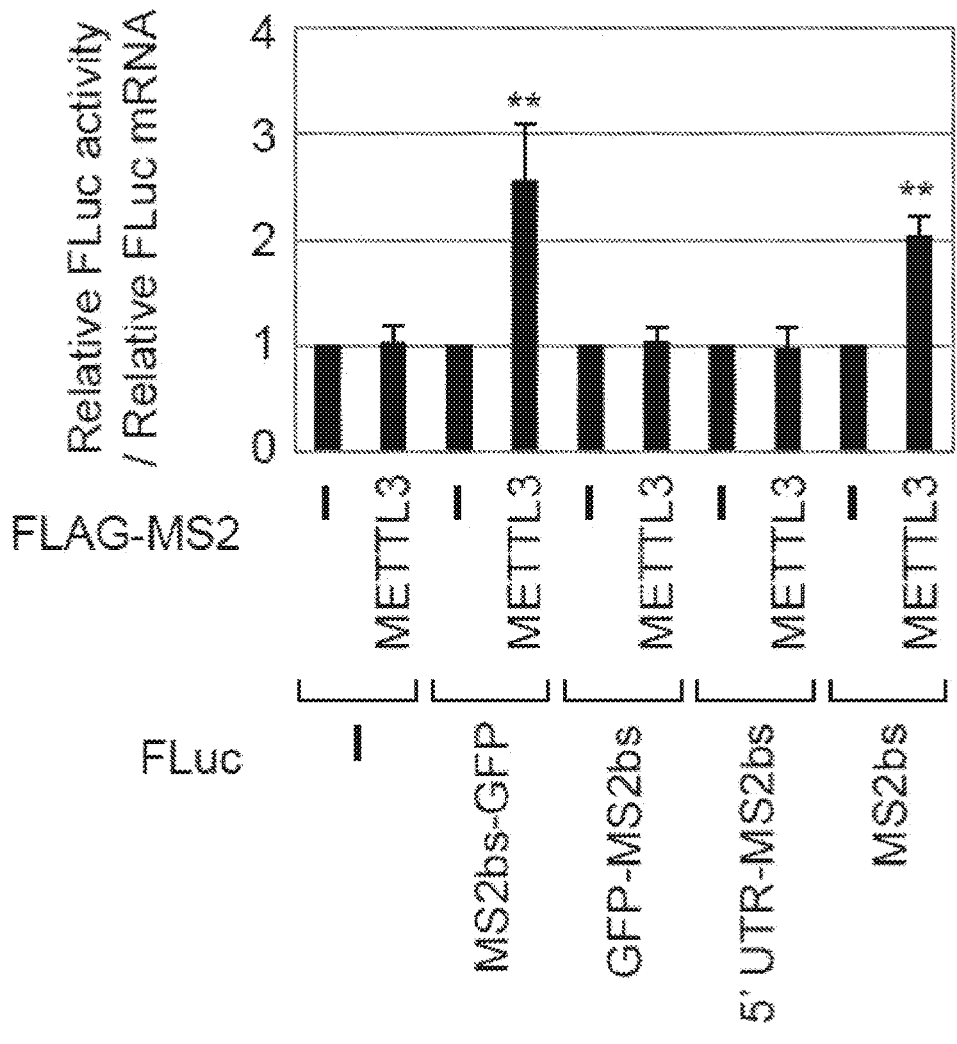

It was previously found that METTL3 when tethered to a reporter mRNA can enhance translation of a reporter mRNA. To directly test a mRNA looping model it was examined whether the METTL3 binding position on mRNA is important for its ability to enhance translation. To this end, tethering reporter plasmids containing firefly luciferase (FLuc) with MS2 binding sites located at different positions were generated (FIG. 1A). FLuc-MS2bs-GFP was generated with MS2 binding sites located in the 3' UTR close to the stop codon followed by an extended 3' UTR sequence (sequence from green fluorescent protein (GFP)). FLuc-GFP-MS2bs was constructed with the MS2 binding sites at the end of the long 3' UTR by inserting the MS2 sites downstream of the GFP sequence. A construct with MS2 binding sites in the 5' UTR was also generated to test the possible translation enhancement role of METTL3 at the 5' UTR. The FLuc plasmid without MS2 binding sites was used as a negative control and FLuc-MS2bs was used as a positive control. The relative expression of effector proteins including FLAG-MS2 (negative control), and FLAG-MS2-METTL3 was measured by western blot (FIG. 1B). Intriguingly, it was found that direct tethering of FLAG-MS2-METTL3 to the FLuc-MS2bs-GFP and FLuc-MS2bs robustly enhanced translation efficiency by more than 2-fold without changing the mRNA level, while tethering METTL3 to FLuc-GFP-MS2bs or FLuc-5' UTR-MS2bs had no effect on translation (FIGS. 1C-1D). Furthermore, stronger effects on translation were reproducibly detected when METTL3 is tethered upstream of a long 3' UTR compared with a short 3' UTR. These results indicate that METTL3 can promote translation only when bound to the 3' UTR at a position near the stop codon, supporting a mRNA looping mechanism for METTL3 function.

Figure 1E:
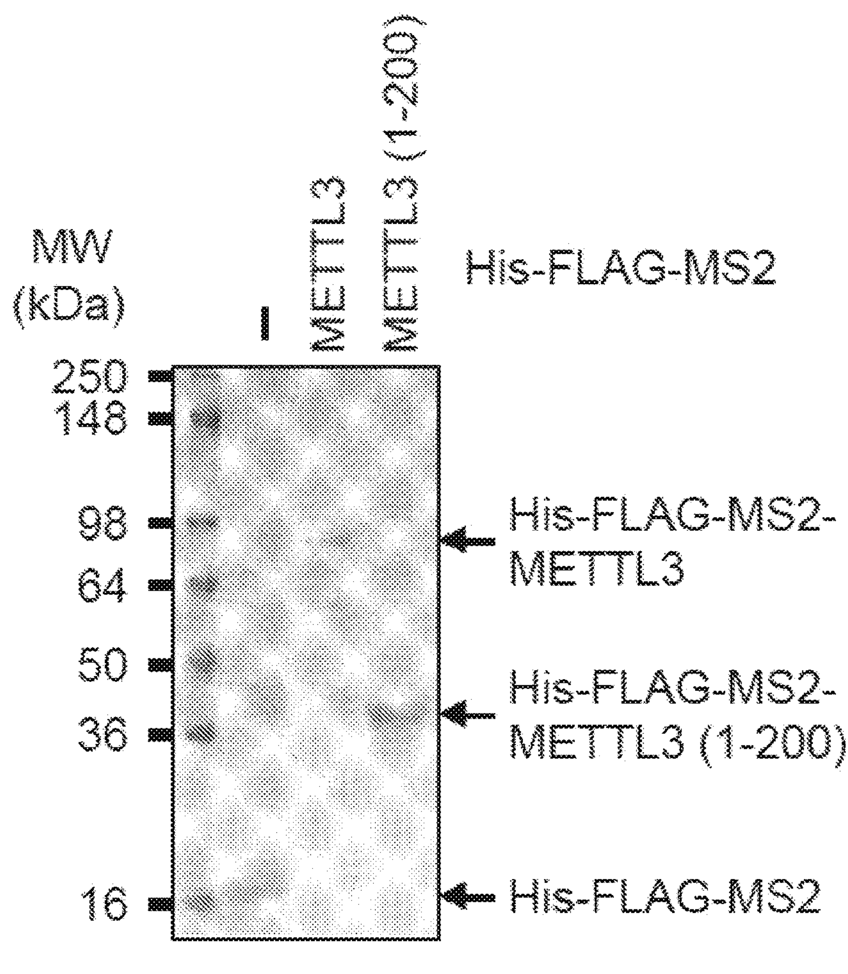
Figure 1F:
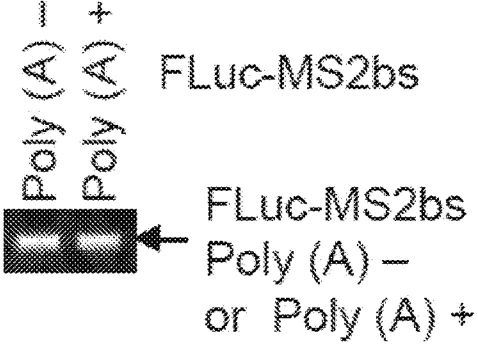
Figure 1G:
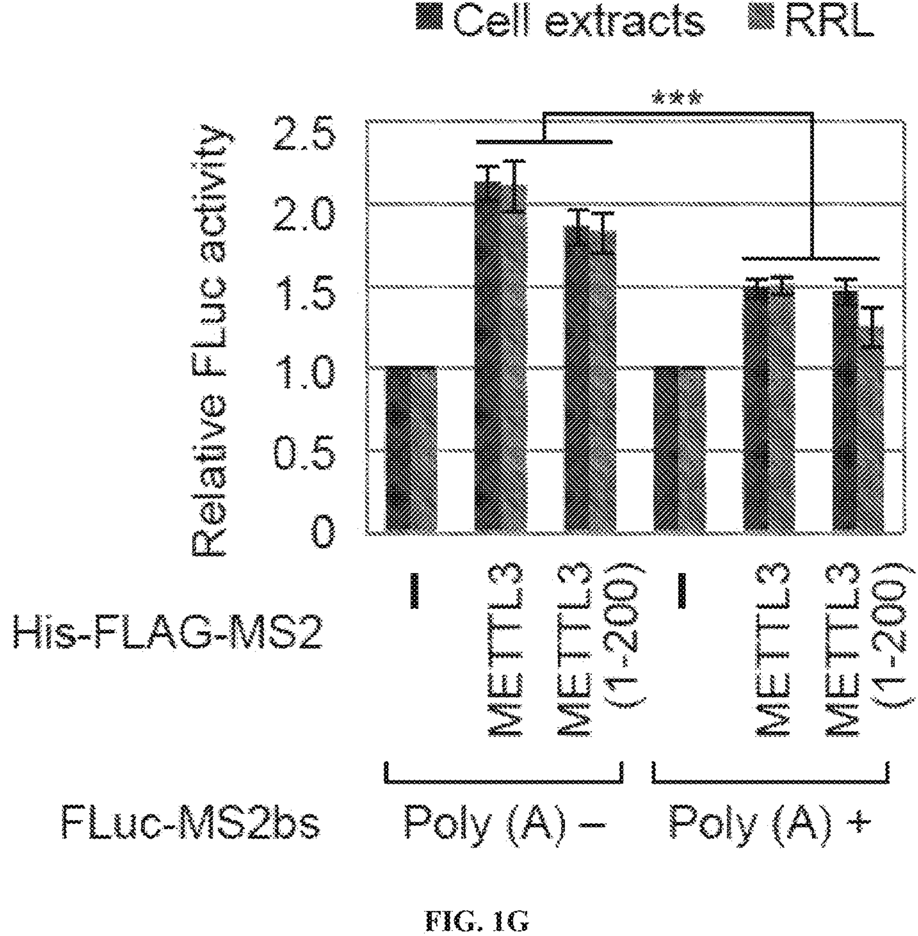
Figure 2A:
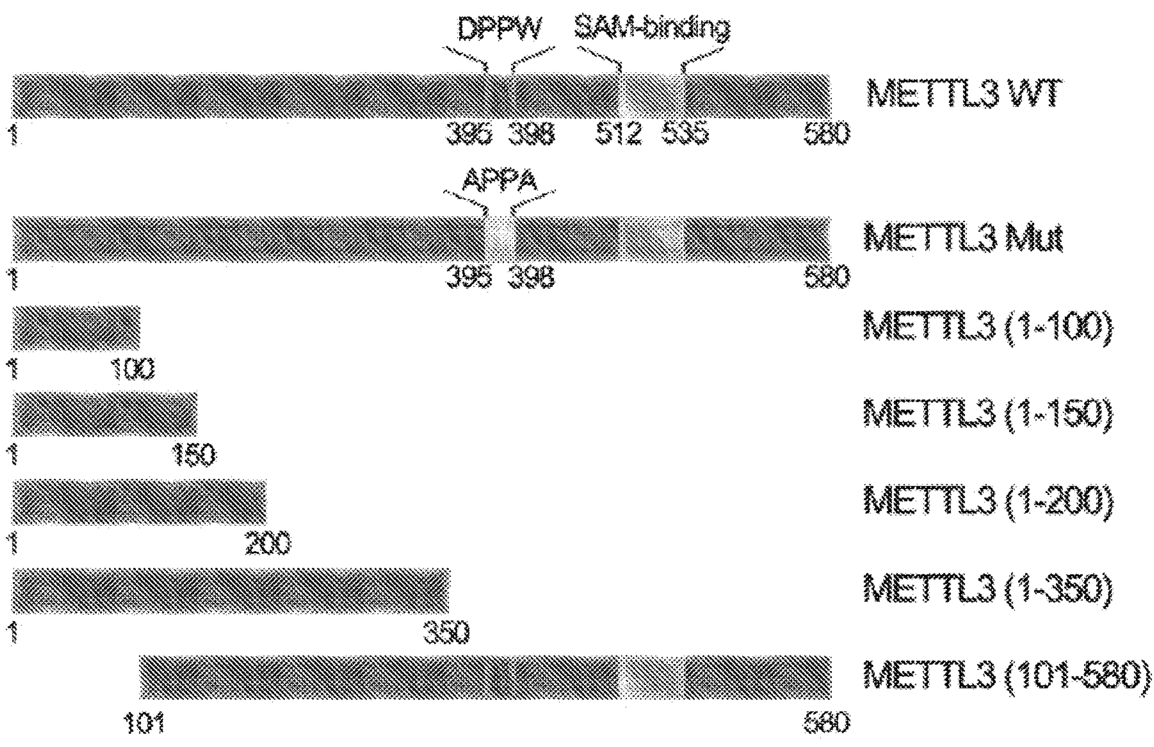
FIGS. 2A-2D. N-terminal region of METTL3 promotes translation.
Figure 2B:
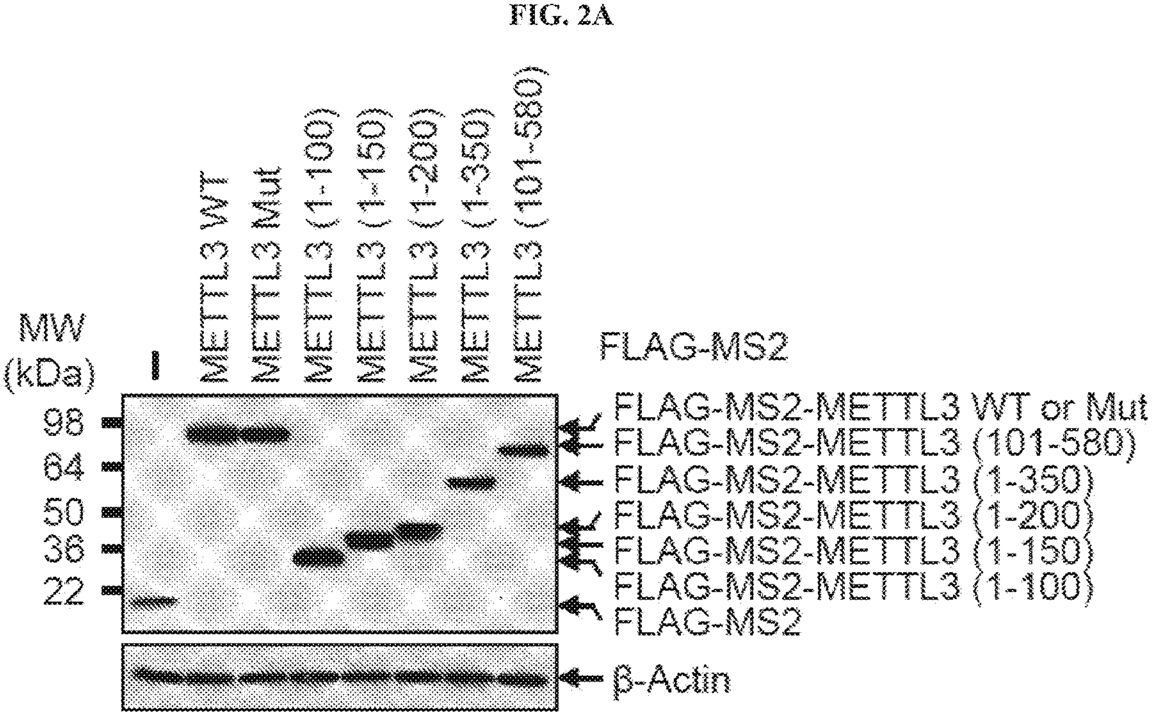
Figure 2C:
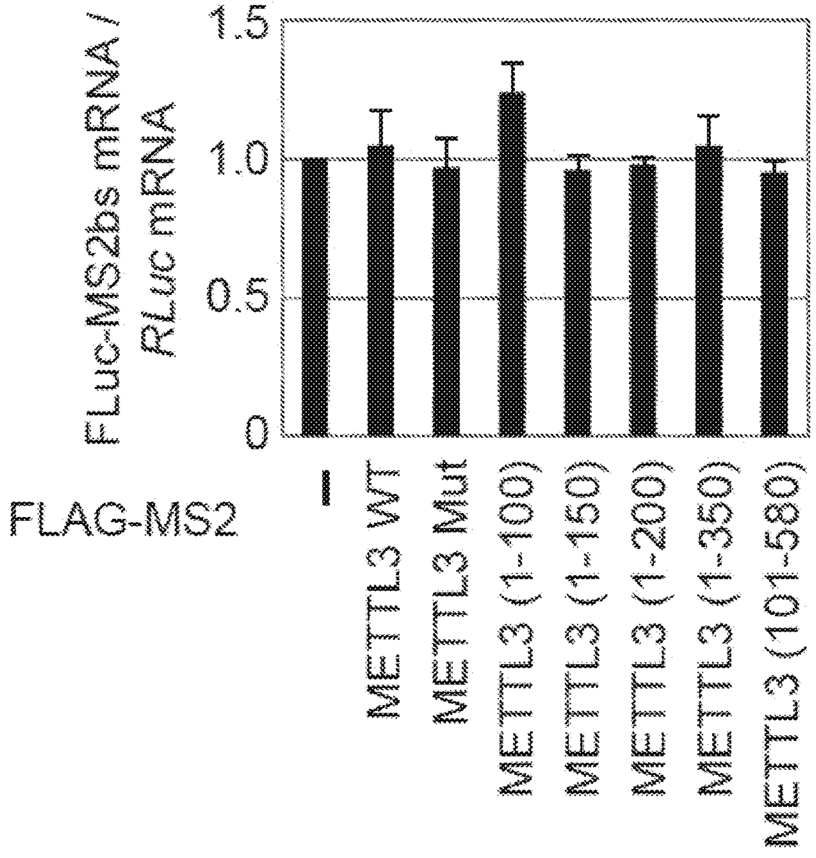
Figure 2D:
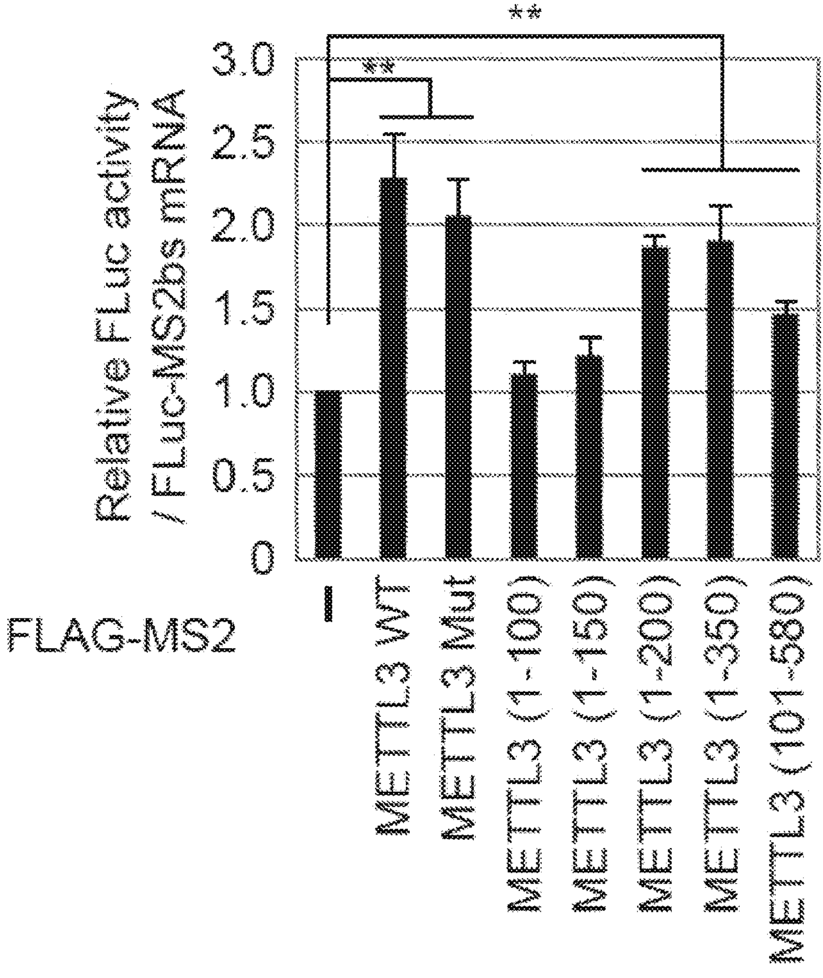

To further confirm these findings and to examine possible functional redundancy with a eIF4G-PABPC1 looping mechanism, in vitro translation assays were performed. The addition of recombinant His-FLAG-MS2-METTL3 protein (expressed and purified from bacteria) to lysates prepared from either human cells or rabbit reticulocytes was found to enhance translation of a luciferase reporter mRNA bearing a 5' m$^7$GpppG cap and MS2 binding sites close to the mRNA stop codon (FIGS. 1E-1G). Similarly, an amino-terminal fragment (1-200) of METTL3, that was found to be sufficient to promote reporter translation when expressed in cells (FIG. 2), was also sufficient to promote translation in vitro (FIGS. 1E-1G). Moreover, METTL3 tethering had a stronger effect on translation of reporter mRNAs without a poly (A) tail than the same reporter mRNA with a poly (A) tail (FIG. 1G), which is consistent with some redundancy between METTL3 and a eIF4G/PABPC1-mediated looping mechanism for poly (A)-containing mRNAs in these in vitro assays.

Figure 3A:
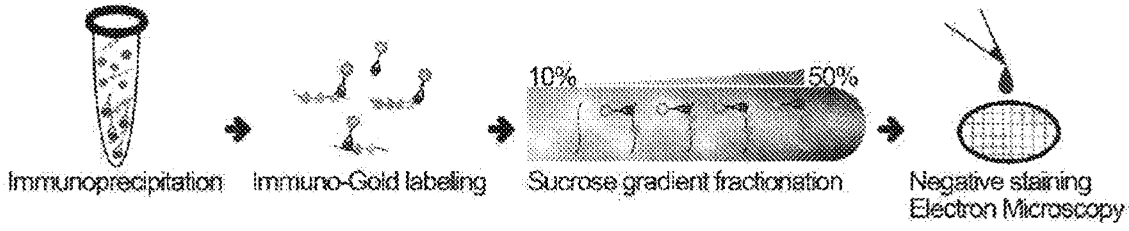
FIGS. 3A-3F. Topology of METTL3 and cap-binding proteins on individual mRNPs.
Figure 3B:
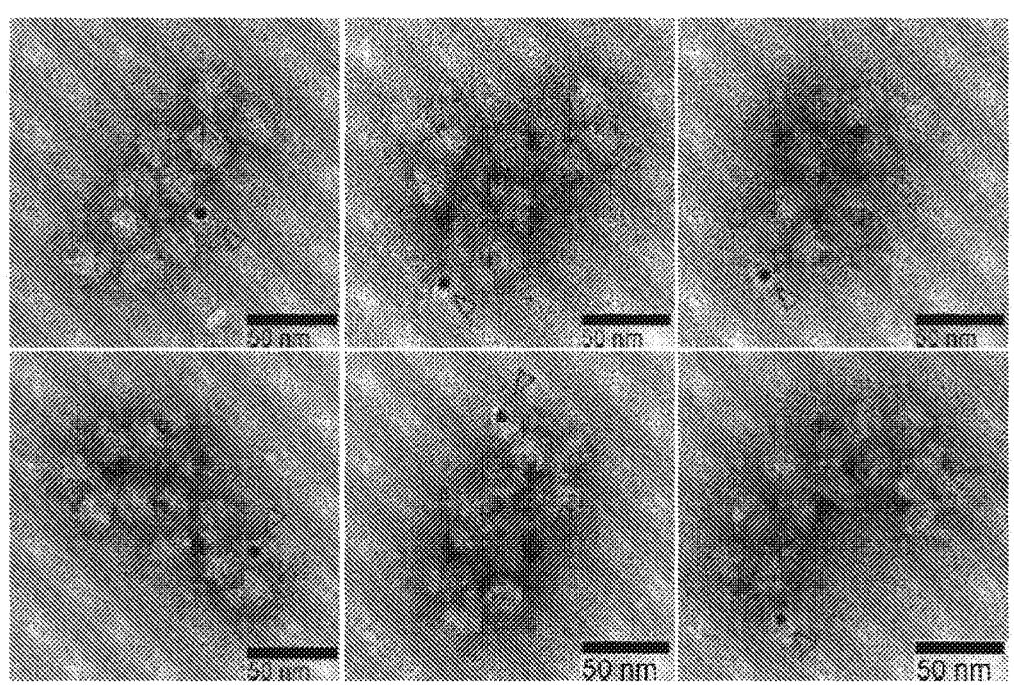
Figure 3C:
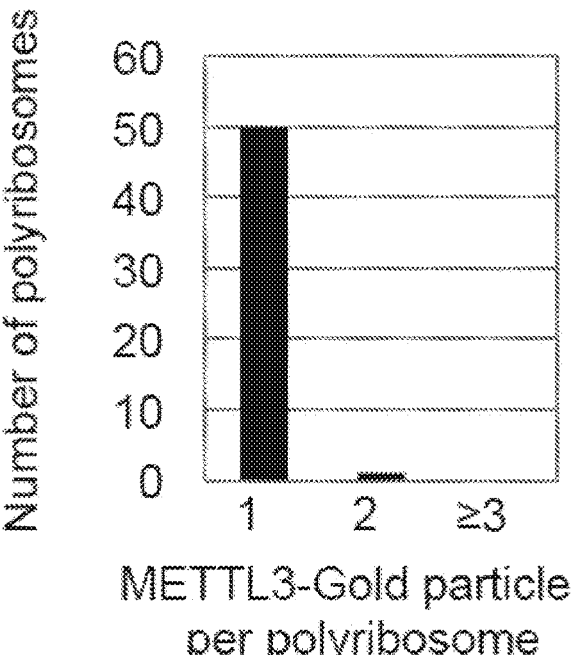
Figure 3D:
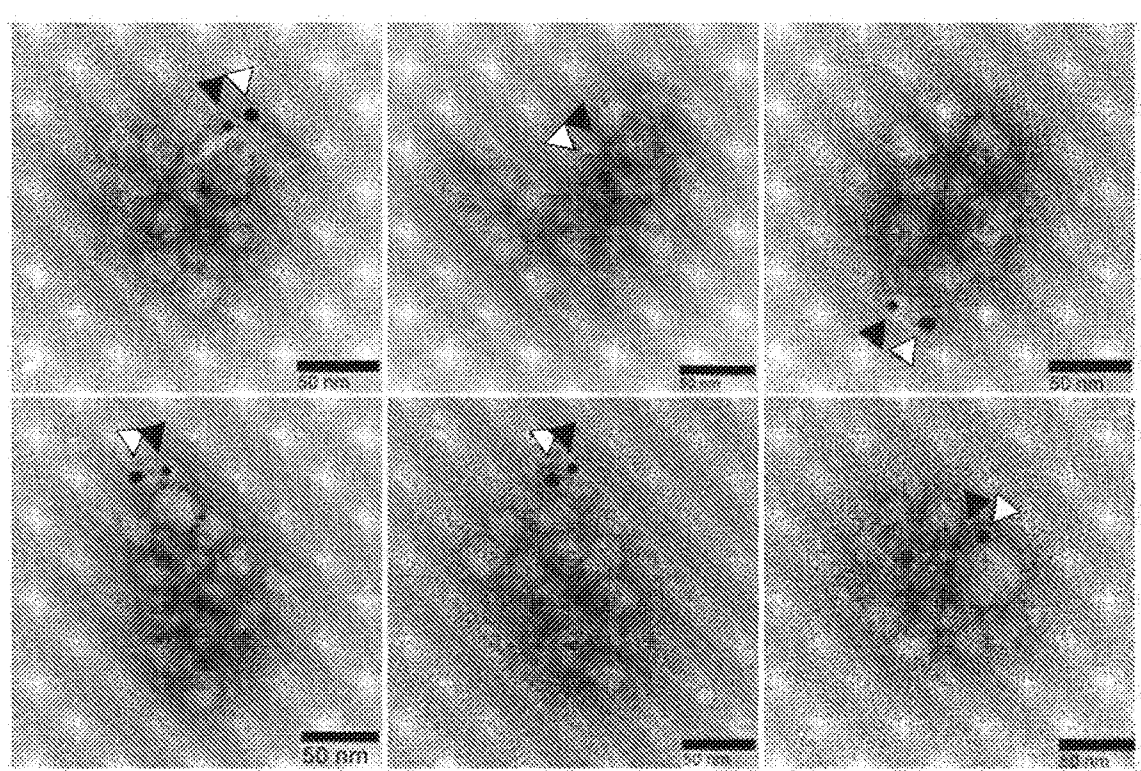
Figure 3E:
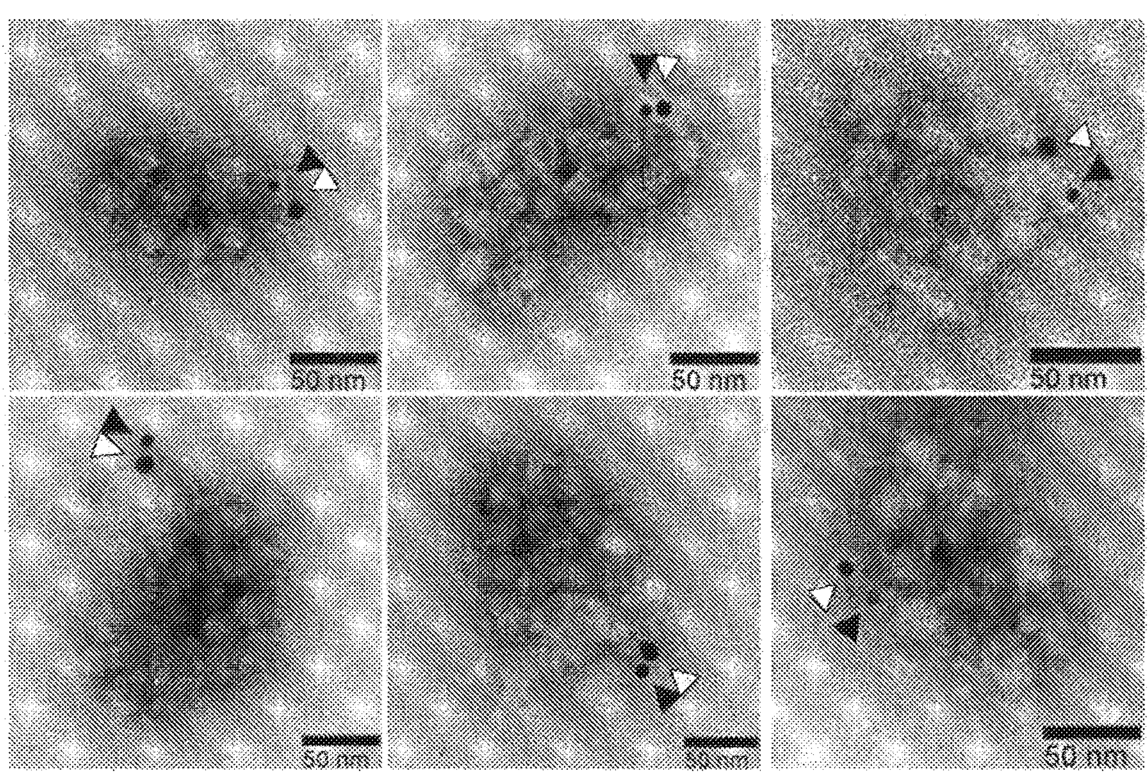
Figure 3F:
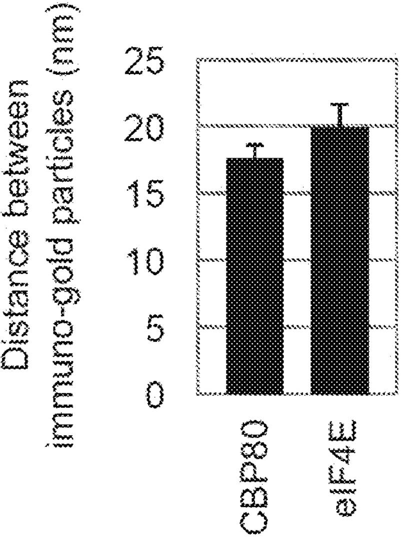

Individual Polyribosomes Contain METTL3 Proximal to Translation Initiation Factors More direct evidence that METTL3 is bound to polyribosomes was sought next. To this end, FLAG-METTL3-containing mRNA ribonucleoprotein complexes (mRNP) were affinity purified, incubated with α-METTL3 immuno-gold nano-particles (6 nm gold), then subjected to sucrose gradient fractionation. The gold-labeled messenger ribonucleoprotein (mRNP) complexes were then analyzed by electron microscopy (EM) (FIG. 3A). This analysis confirmed that polyribosomes were co-purified with FLAG-METTL3 and that the sucrose gradient fractionation successfully separated heavy mRNPs containing multiple ribosomes (polyribosomes) from the lighter complexes. This also clearly revealed the presence of gold-labeled METTL3 in the individual polyribosomes (FIG. 3B). Almost all (98%) mRNPs with METTL3 showed a single gold label (FIG. 3C). Similar experiments were performed using either α-CBP80 or α-eIF4E immuno-gold nano-particles together with the α-METTL3 immuno-gold nano-particles, since the α-CBP80 and α-eIF4E immuno-gold nano-particles were larger (10 nm gold) they could readily be distinguished from the (6 nm gold) α-METTL3 particles. Strikingly, individual polyribosomes containing double-labeled gold particles show that each METTL3 signal is in close proximity (<20 nm) to a cap-binding protein (FIGS. 3D-3F). These results reveal the topology of individual endogenous METTL3-bound polyribosomes and support that METTL3 mediates the looping of mRNA to promote efficient translation.

METTL3 Binds to Translation Initiation Factors

5' cap binding assays revealed a physical association between METTL3 and the translation initiation machinery.

Figure 4A:
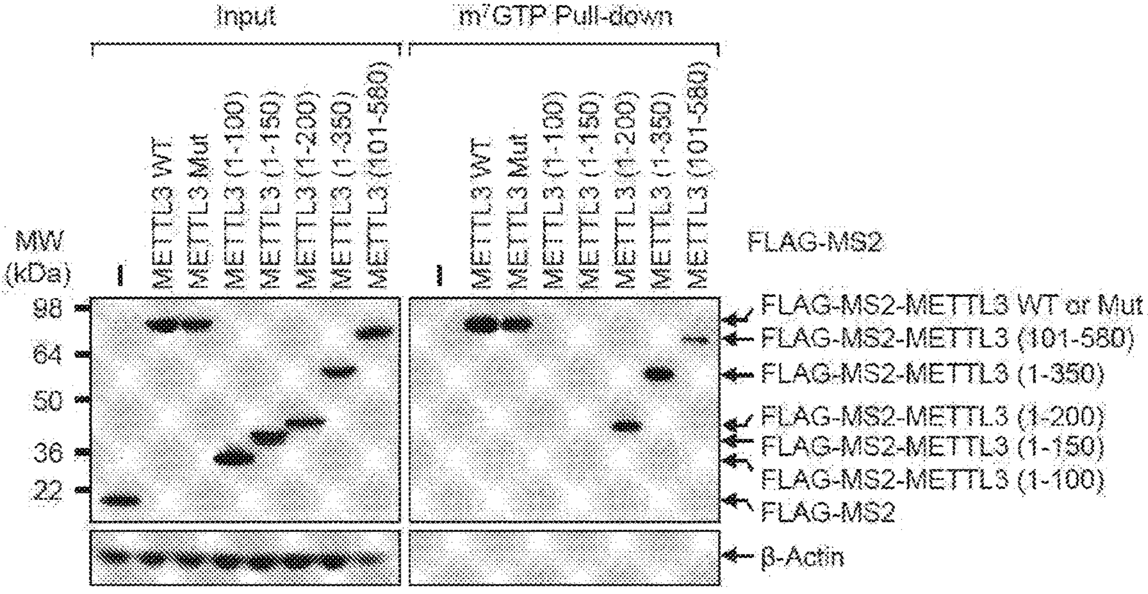

Cell lysates expressing different METTL3 deletion mutants were incubated with the 5' cap analogue, $m^7$GTP-Agarose, and pull-down assays were performed. Western blotting analysis of these cap-binding assays showed that full length FLAG-MS2-METTL3 as well as the FLAG-MS2-METTL3 (1-200, and 1-350) deletion mutants associate with $m^7$GTP-Agarose (FIG. 4A). FLAG-MS2-METTL3 (101-580) was also weekly associated in these assays. This result is highly consistent with the tethering assays (FIG. 2) and support that the 1-200 amino acid (aa) fragment of METTL3 interacts with translation initiation factor(s) to promote translation.

Figure 4B:
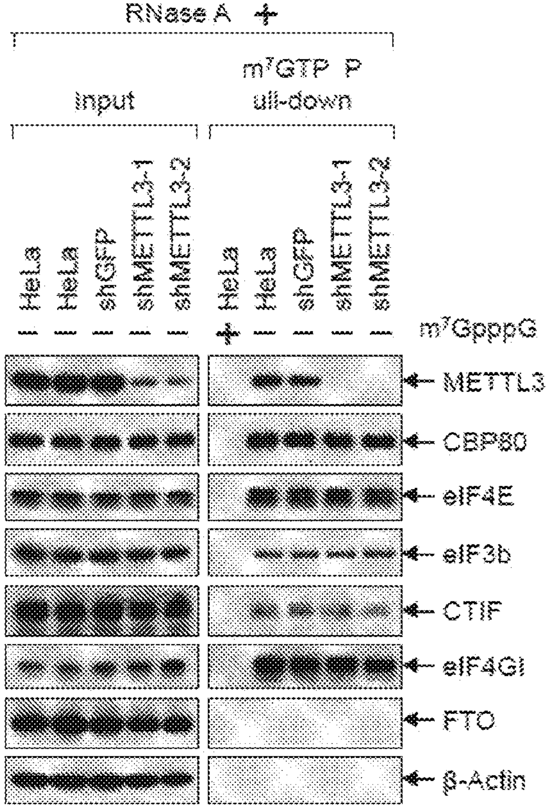
Figure 4C:
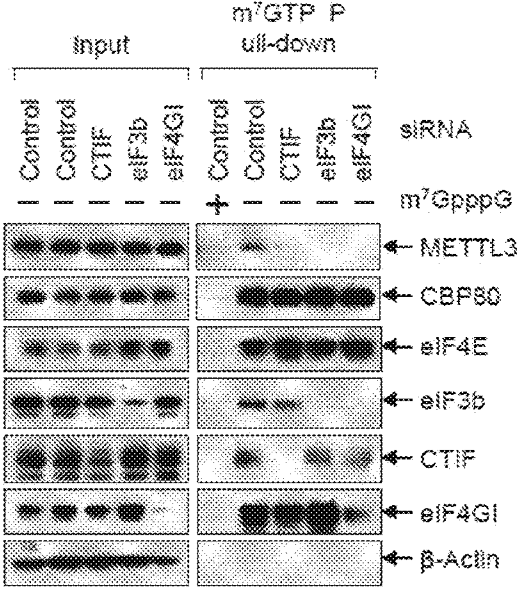

Considering knockdown of METTL3 inhibits translation of target mRNAs from the previous finding, the possible effect of METTL3 in general translation initiation complex formation was tested next. To this end, METTL3-depleted cell lysates were used for cap-binding assays (FIG. 4B). Addition of $m^7$GpppG cap analogue was used as a negative control to antagonize the binding of cap-associating proteins to $m^7$GTP-Agarose. Knockdown of METTL3 had no significant effect on the association of cap-binding proteins (CBP80 and eIF4E) or translation initiation factors (CTIF, eIF4GI and eIF3b) with $m^7$GTP-Agarose. As controls, the $m^6$A demethylase, FTO and β-Actin did not associate with $m^7$GTP-Agarose. This result indicates translation initiation complex formation does not require METTL3 and that the reduced translation observed for specific target mRNAs upon METTL3 knockdown is not due to abrogation of the general translation initiation complex. Conversely, the association of METTL3 with $m^7$GTP-Agarose in these cap-binding assays was dramatically diminished using lysates depleted for CTIF, eIF4GI or eIF3b, supporting that the association of METTL3 with $m^7$GTP-Agarose beads is mediated through a physical interaction with general translation initiation complex components (FIG. 4C).

Figure 4D:
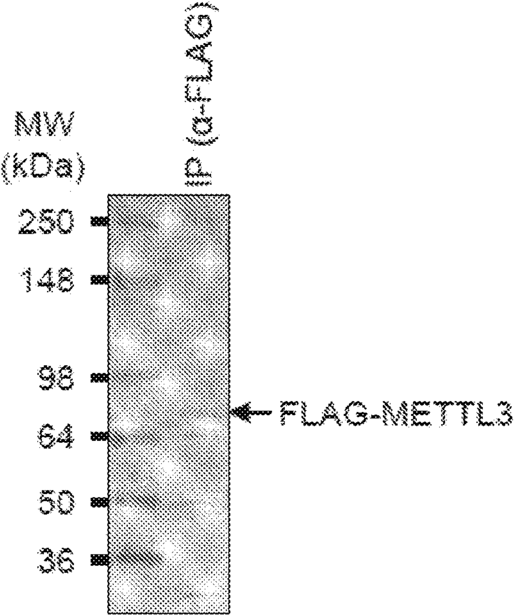

A large-scale purification and mass spectroscopy characterization of FLAG-METTL3-containing complexes identified numerous translation factors, several of which were confirmed by independent co-IP and western blot analysis (FIG. 4D). As expected, METTL14 was also identified. Indeed, gene ontology (GO) analysis of the METTL3-interacting proteins identified 'mRNA metabolic processes', 'RNA processing', and 'Translation' as the most significantly enriched biological process annotations (FIG. 4E). Among the METTL3 associated translation factors, numerous ribosome subunits and translation initiation factors were identified (FIG. 4F). Considering these results, as well as the previous observation that METTL3 knockdown diminishes the association of eIF3 with cap-binding proteins (CBP80 and eIF4E) in co-IP experiments, one possible outcome was that METTL3 (through its N-terminal domain) might interact directly with certain component(s) of the multi-subunit eIF3 complex to promote translation.

METTL3 Directly Interacts with eIF3h

Figure 5B:
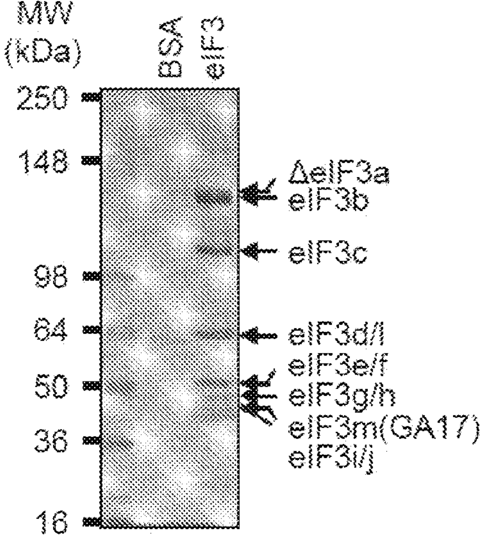
Figure 5C:
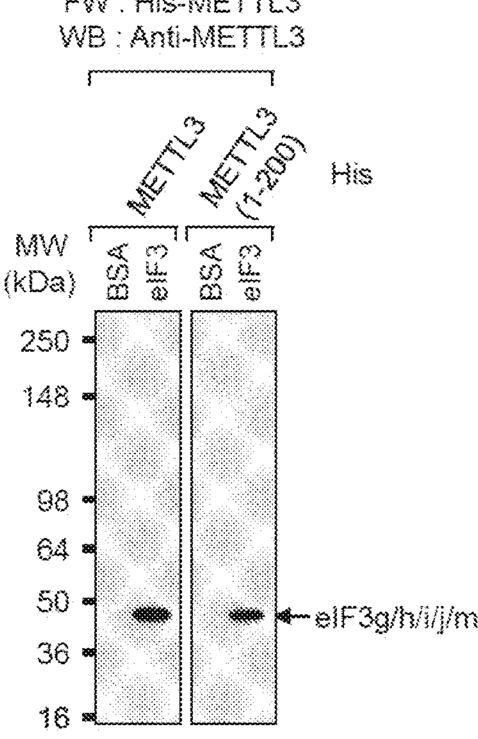
Figure 5D:
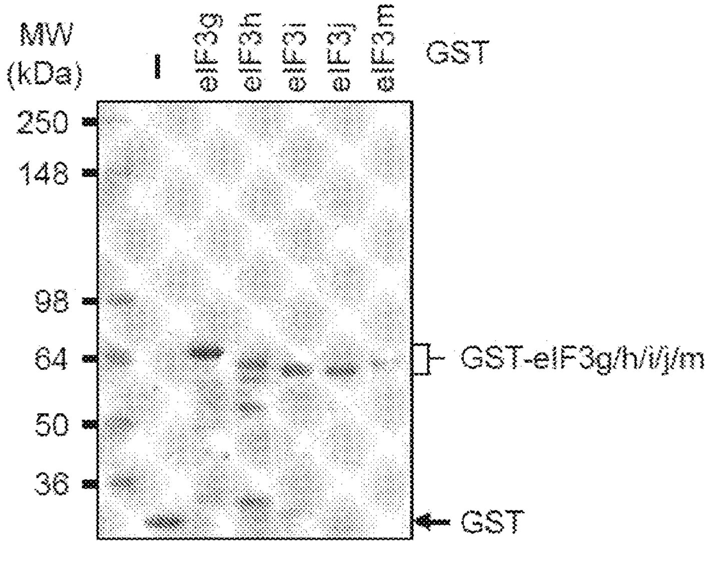
Figure 5E:
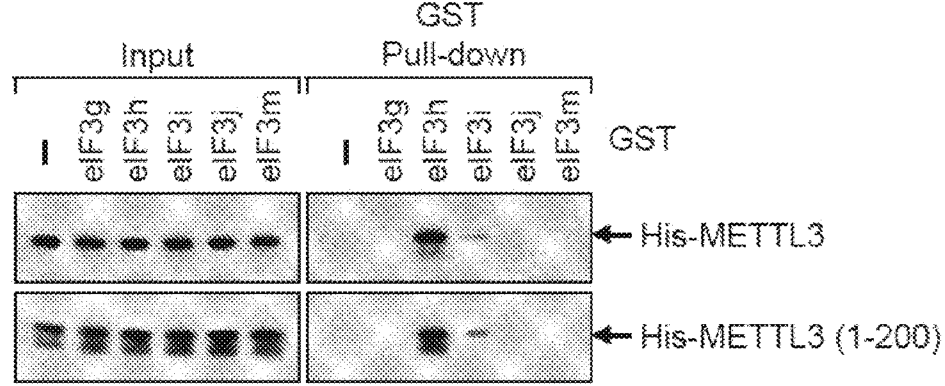
Figure 5F:
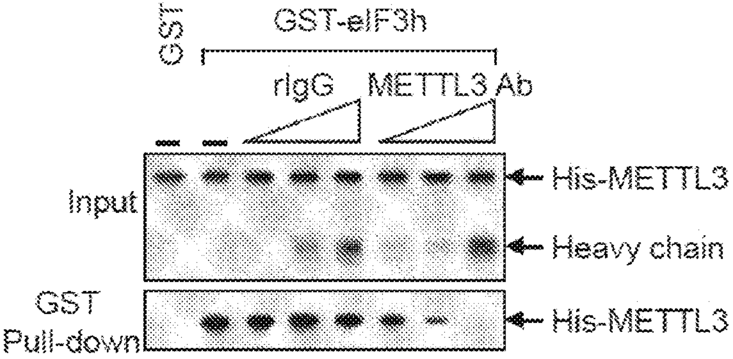
Figures 5G, 5H, 5I:
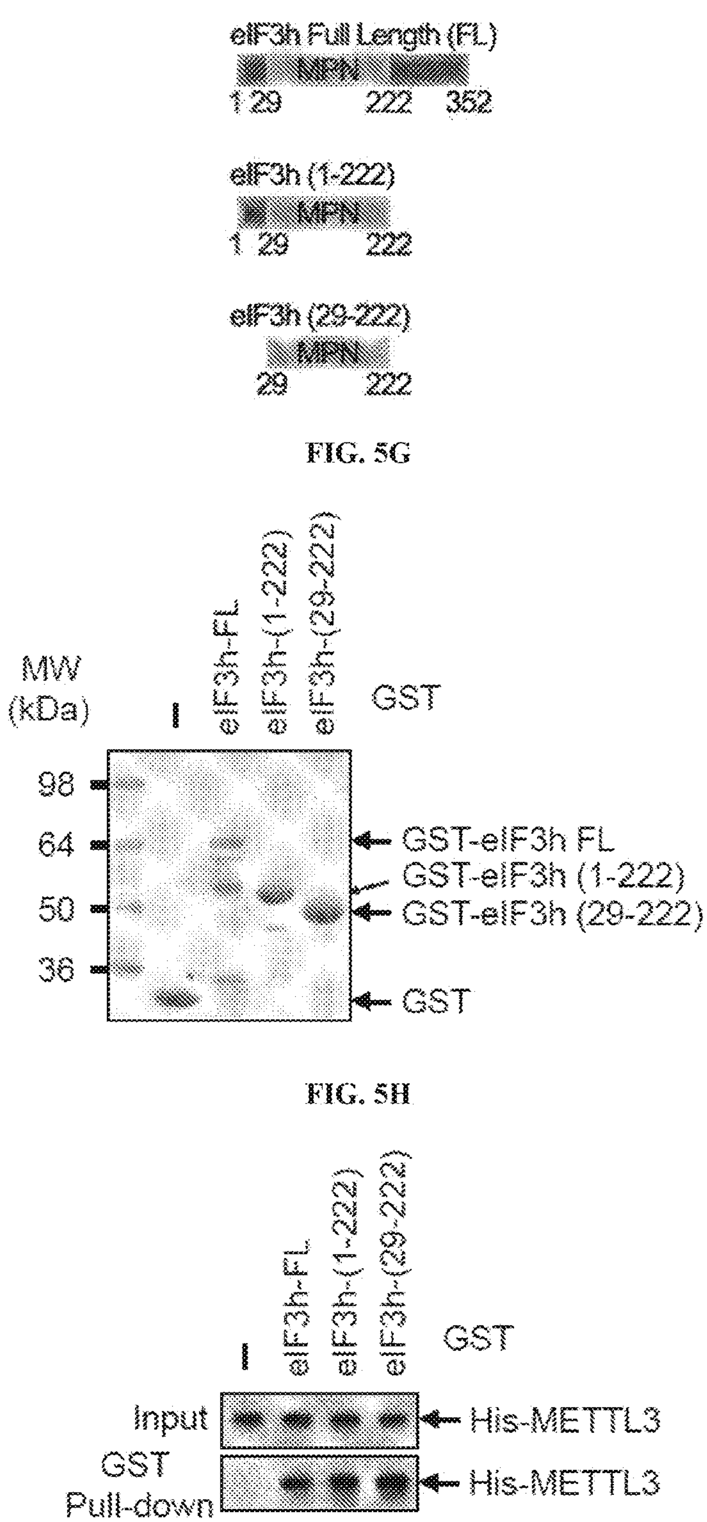

It was next sought to test whether METTL3 interacts with eIF3 directly, and if so, to identify which of the 13 subunit(s) of eIF3 interacts with METTL3. To this end, recombinant His-tagged human METTL3 (full-length) and METTL3 (1-200) proteins were purified from *E. coli*, and these purified proteins were used in a Far-Western blotting assay with a biochemically isolated human eIF3 complex (FIGS. 5A-5B). The striking results of Far-Western blotting using purified eIF3 complex and, as a probe, either purified recombinant His-METTL3 or His-METTL3 (1-200) showed that both specifically bound to a single band that based on size most likely corresponds to eIF3g, eIF3h, eIF3i, eIF3j, or eIF3m (FIG. 5C). To further confirm this interaction and to define the particular subunit(s) that interacts with METTL3, each of the GST-tagged eIF3 subunits from bacteria was individually expressed and purified (FIG. 5D) and tested for binding to His-METTL3 using in vitro binding assays with either His-METTL3 or His-METTL3 (1-200). The result showed that both METTL3 and METTL3 (1-200) specifically interact with eIF3h (FIG. 5E). A much weaker interaction with eIF3i was also detected in these GST-pull down assays (FIG. 5E). Structurally, it is noteworthy that eIF3i is part of the eIF3h-3i-3g module located at the mRNA channel whereas eIF3h maintains the core eIF3 scaffold with some of its structure including the MPN domain facing the solvent side of the ribosome that is likely accessible for interaction with METTL3 without impairing 80S assembly[37]. The interaction between eIF3h with METTL3 was further confirmed by another GST pull-down assay that included a titration of α-METTL3 antibody (that recognizes a 1-250 aa METTL3 epitope) or control IgG to specifically inhibit this interaction between METTL3 and eIF3h (FIG. 5F). To further specify which region of eIF3h interacts with METTL3 additional fragments (1-222, and 29-222) of eIF3h protein were generated and purified (FIGS. 5G-5H). The GST pull-down results showed that the eIF3h Mpr1p/Pad1p N-terminal (MPN) domain (29-222)[37] is necessary and sufficient to interact with METTL3 protein (FIG. 5I).

METTL3 Promotes Translation Via an Interaction with eIF3h

Figure 6A:
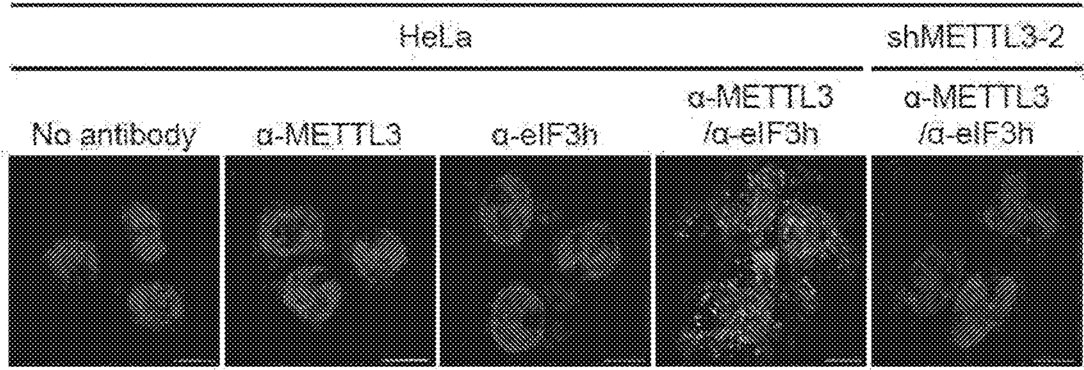
FIGS. 6A-6G. METTL3 enhances translation of target mRNAs by interacting with eIF3h.
Figure 6B:
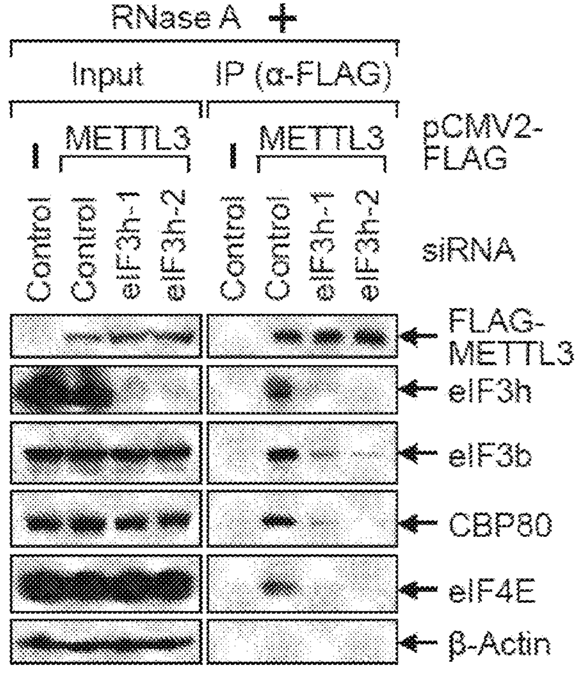

To examine whether METTL3 and eIF3h interact in cells an in situ proximity ligation assay (PLA) was performed using α-METTL3 antibody with α-eIF3h antibody and an appropriate secondary proximity probe (FIG. 6A). This analysis confirmed the METTL3-eIF3h interaction in vivo, with a widespread PLA signal detected in both the nuclear and cytoplasmic compartments. METTL3 knockdown drastically reduced the detectable PLA signal, and no signal was detected using either of the single antibodies alone, thereby further confirming the specificity of this interaction. Moreover, co-IP experiments performed on control- or eIF3h-knockdown cells revealed that METTL3 association with translation initiation factors is dependent on eIF3h (FIG. 6B). The association of METTL3 with another eIF3 subunit, eIF3b, and two cap-binding proteins were significantly reduced upon eIF3h knockdown, thus confirming that eIF3h is required for the association of METTL3 with translation initiation factors.

Figure 6C:
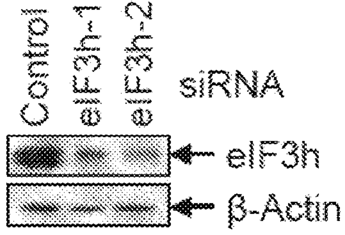
Figure 6D:
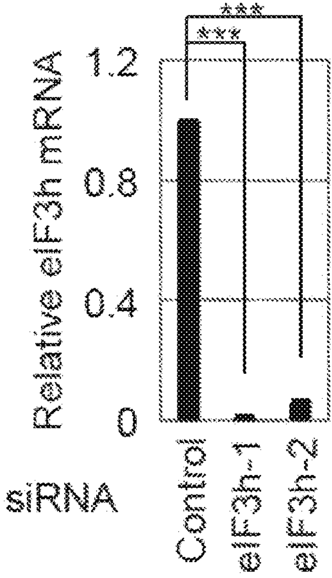
Figure 6E:
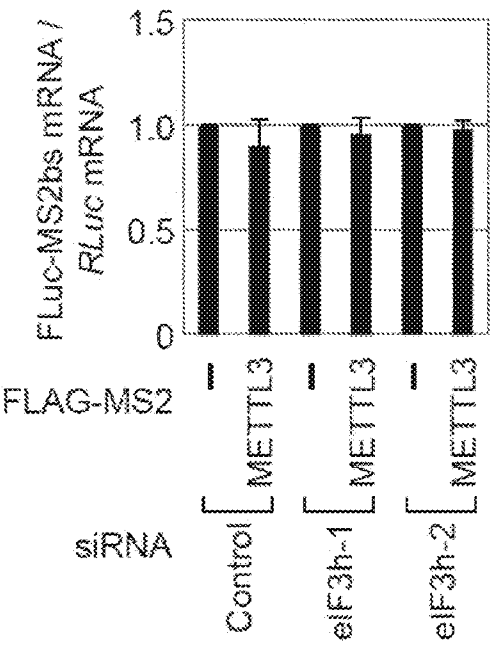
Figures 6F, 6G:
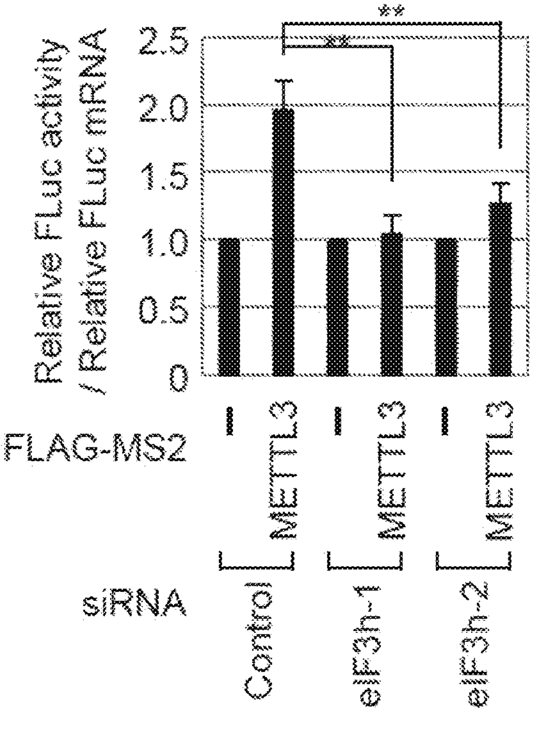

The functional interaction between METTL3 and eIF3h, and in particular whether eIF3h is required for METTL3 to promote translation, was tested next. METTL3 reporter tethering assays were performed with control siRNA and eIF3h knockdown. Western blotting and quantitative RT-PCR (qRT-PCR) confirmed efficient eIF3h knockdown at the protein and mRNA level (FIGS. 6C-6D). While METTL3 tethering led to ~2-fold enhanced translation of the reporter mRNA, the depletion of eIF3h (with two independent siRNAs) abrogated this effect without affecting mRNA levels (FIGS. 6E-6F). Taken together, these data support the functional effects of METTL3 in promoting mRNA translation through its physical interaction with eIF3h. Overall, the results showing the physical and functional METTL3-eIF3h interaction support a model where circularization of the mRNA is mediated by the direct association between eIF3h in the translation initiation complex at the 5'-end of the mRNA and METTL3 bound to specific sites in the 3' UTR (FIG. 6G). This interaction may help efficient translation by looping the mRNA such that the stop codon is in close proximity to the 5' translation initiation factors to facilitate multiple rounds of mRNA translation.

METTL3 Promotes Translation of a Large Subset of mRNAs

Figure 7A:
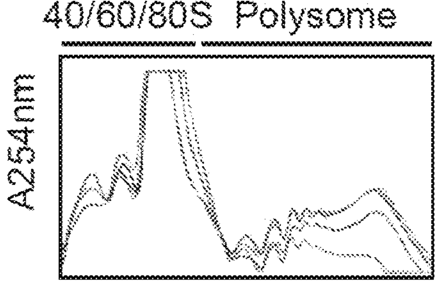
FIGS. 7A-7N. METTL3 promotes translation of a large subset of mRNAs.
Figure 7B:
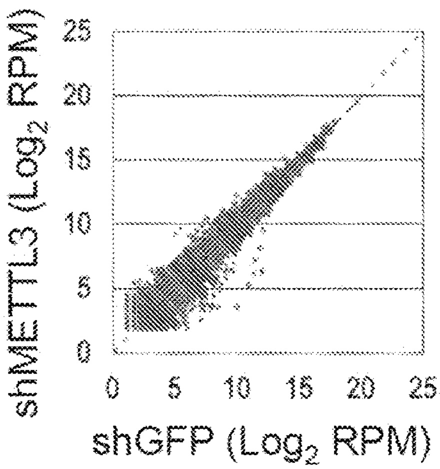
Figure 7C:
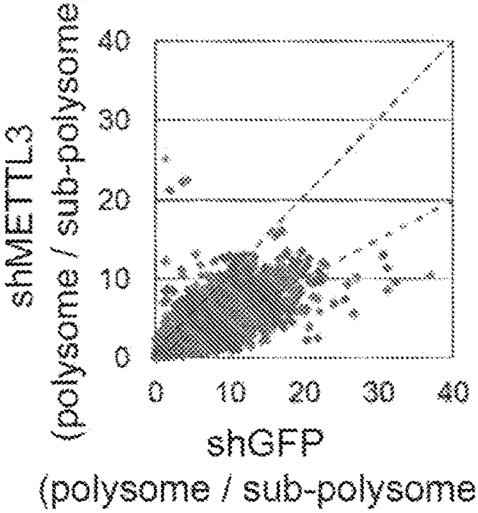
Figure 7D:
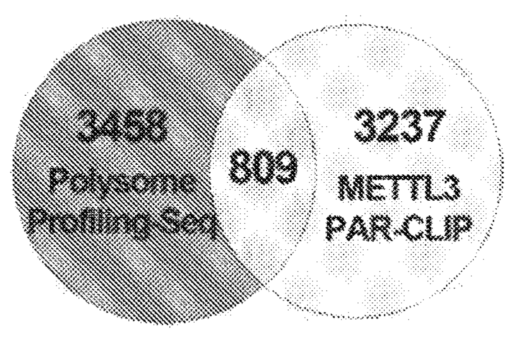
Figure 7E:
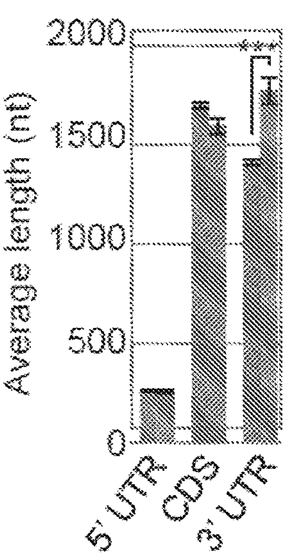
Figure 7F:
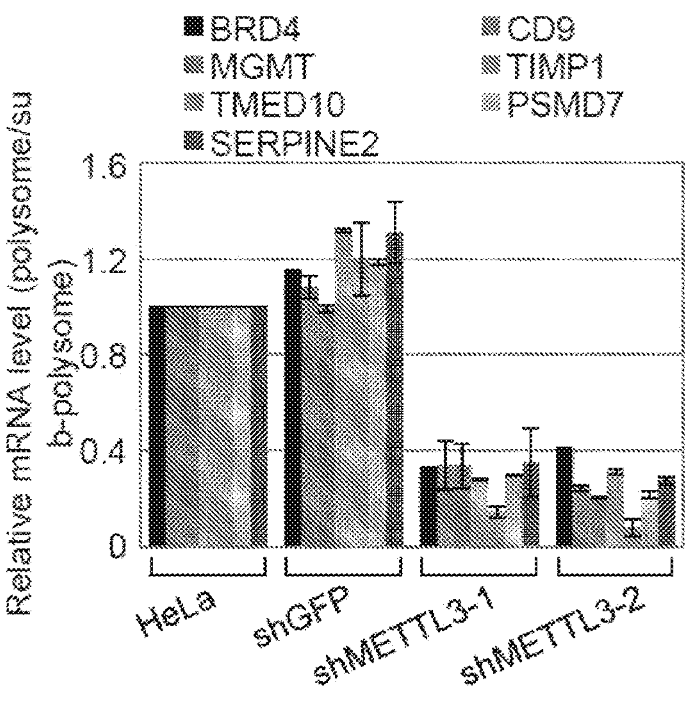
(FIG. 7F) qRT-PCR analysis of indicated mRNA levels. mRNAs were first normalized to SLC7A1 mRNA. The level of mRNAs obtained from polysome fraction was divided by the level of mRNAs obtained from sub-polysome fraction. Relative ratio (fold change) obtained in HeLa cell was set to 1. Error bars represent mean±SD; n=3.
Figure 7G:
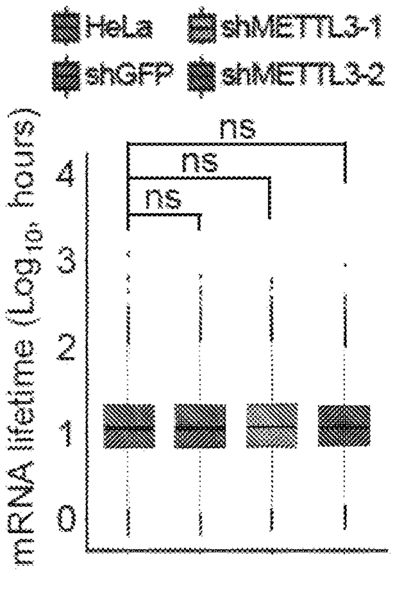
(FIG. 7G) Box plot represents global mRNA lifetime profiling from two biological replicates. ns, not significant.
Figure 7H:
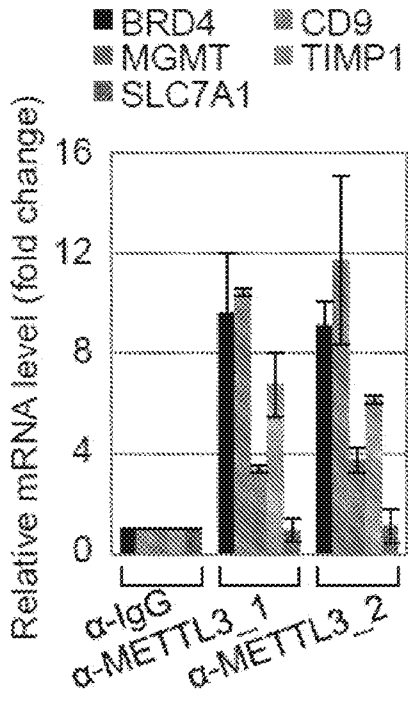
(FIG. 7H) qRT-PCR analysis of endogenous METTL3 RNA IP with indicated primers using two different METTL3 antibodies. mRNAs level obtained from IP was normalized to their input mRNAs. Relative mRNA levels obtained in rabbit IgG control (rIgG) was set to 1. Error bars represent mean±SD; n=2.
Figure 7I:
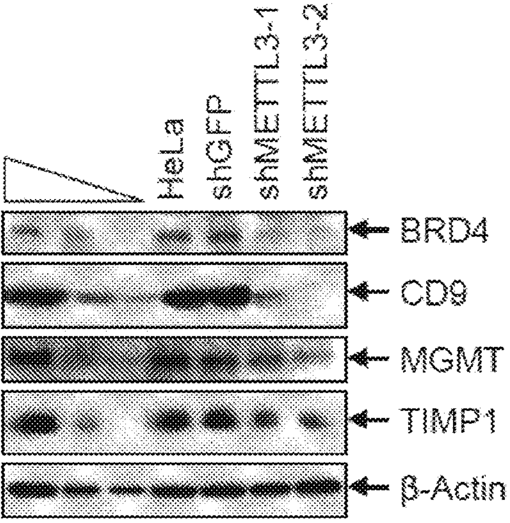
(FIGS. 7I-7L) Western blotting with indicated antibodies.
Figure 7J:
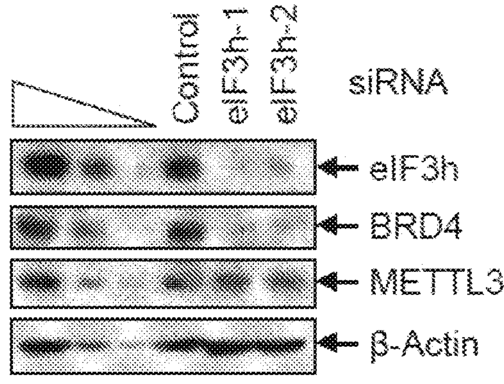
Figure 7K:
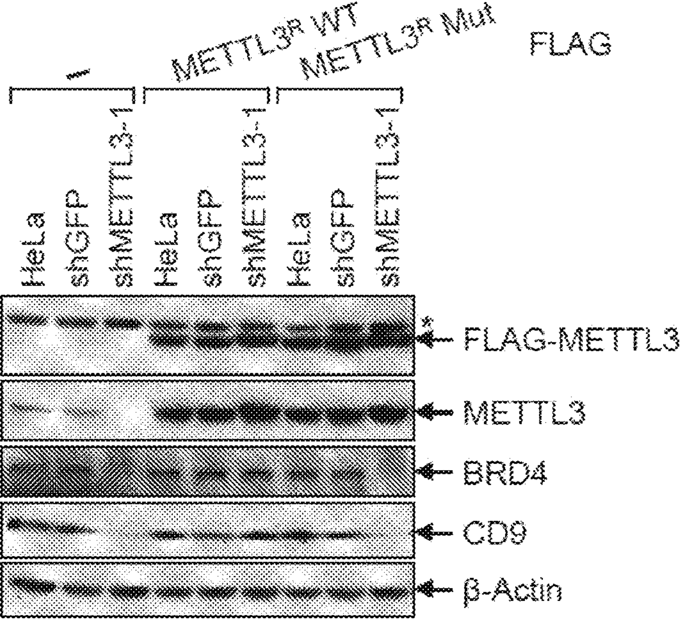
Figure 7L:
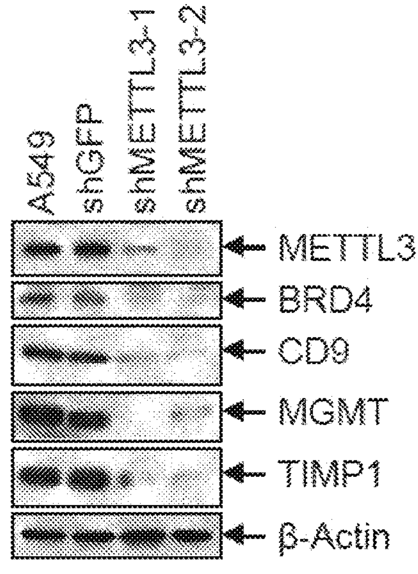
Figure 7M:
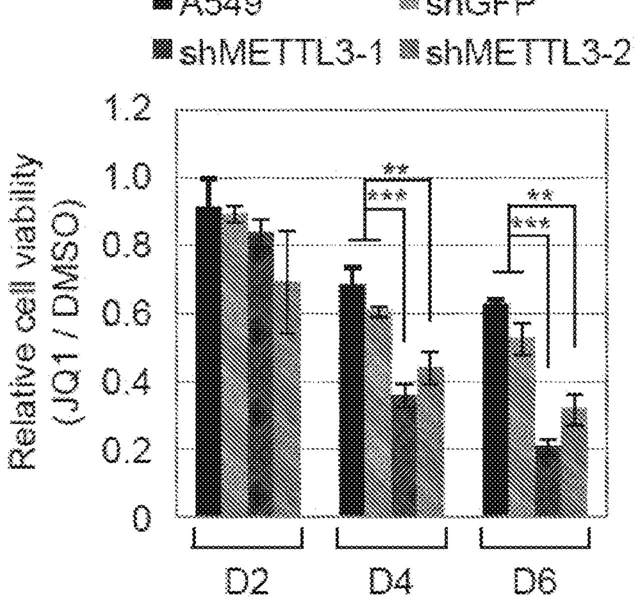
(FIG. 7M) MTS assay of cellular proliferation in A549 cells upon 500 nM JQ1 treatment. The numbers represent the ratio between the proliferation data (OD490) in JQ1 and DMSO treatments. Error bars represent mean±SD; n=3. * p<0.001, p<0.01.
Figure 7N:
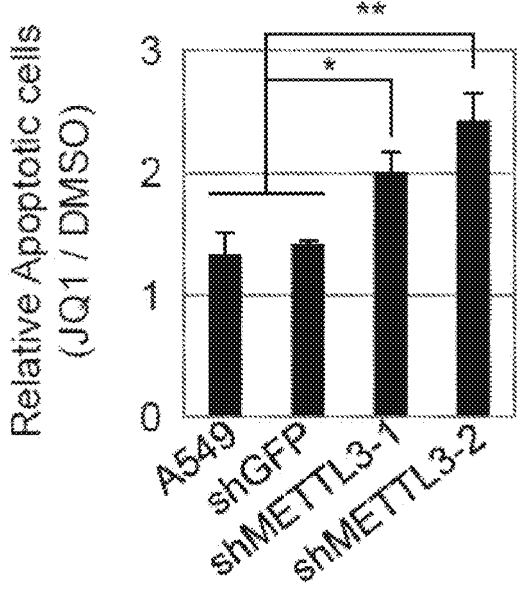
Figure 8A:
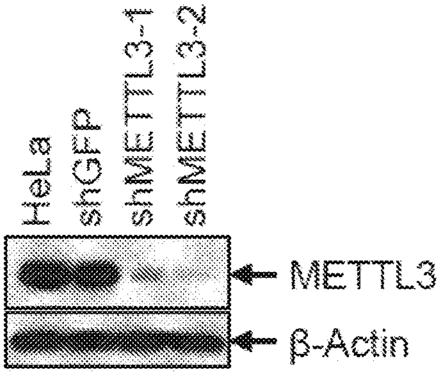
FIGS. 8A-8E. METTL3 has no significant effect on mRNA stability.
Figure 8B:
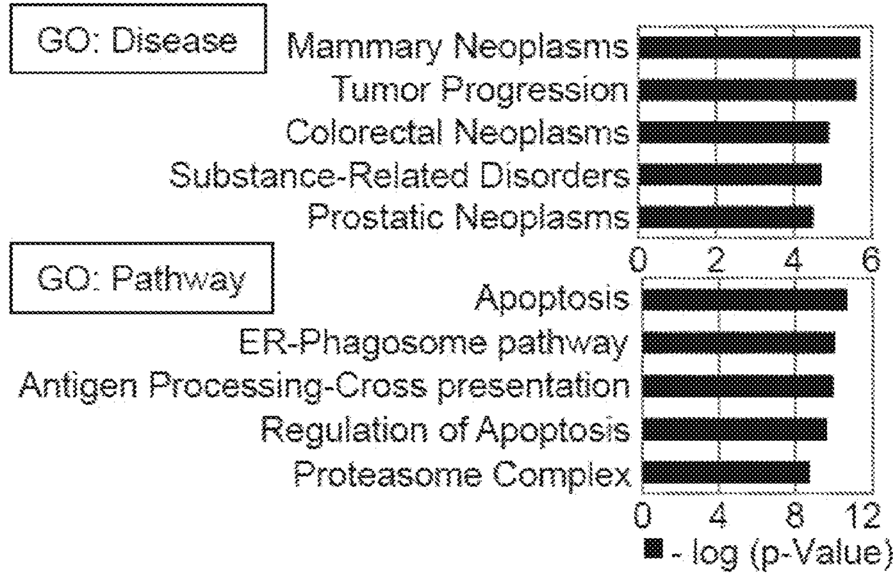
Figure 8C:
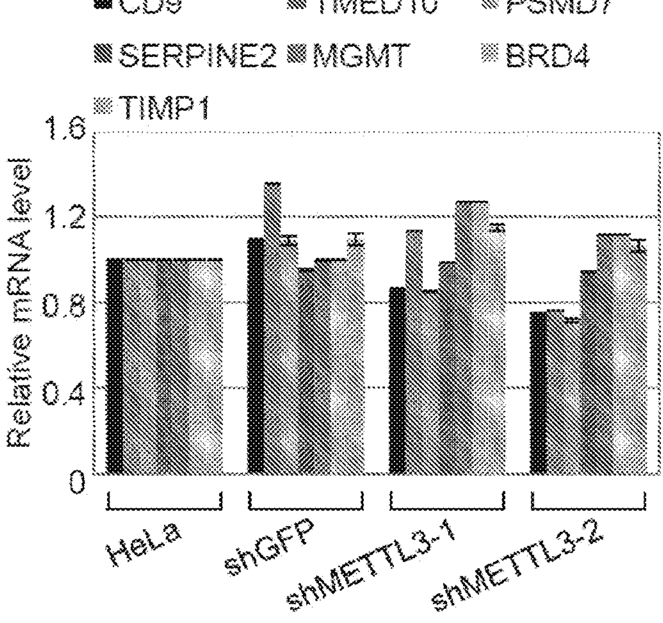
Figure 8D:
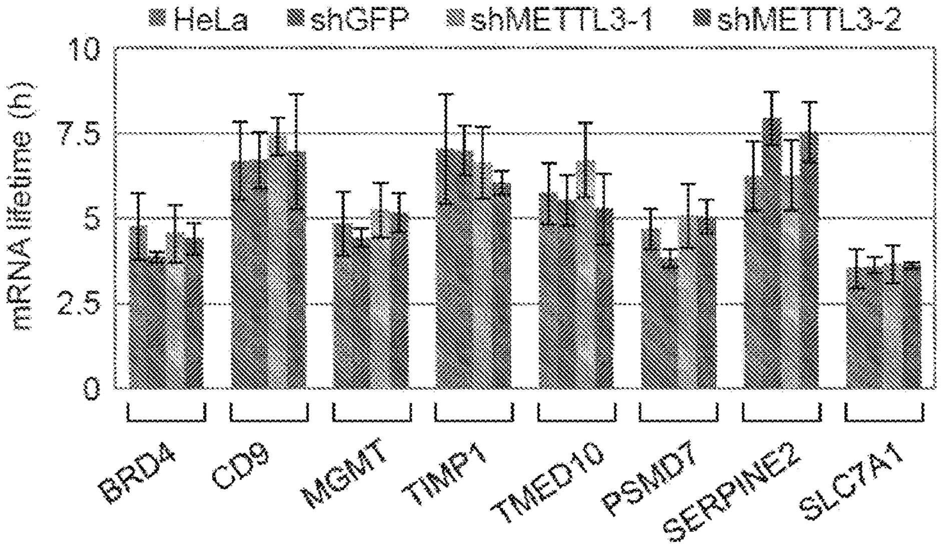
Figure 8E:
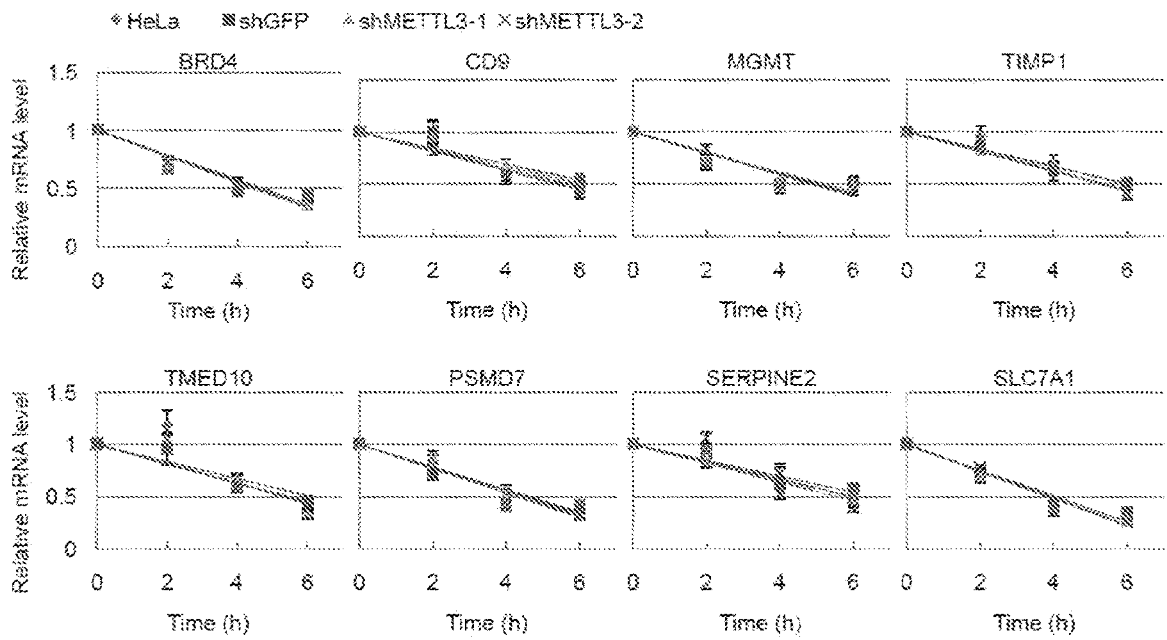
Figure 9A:
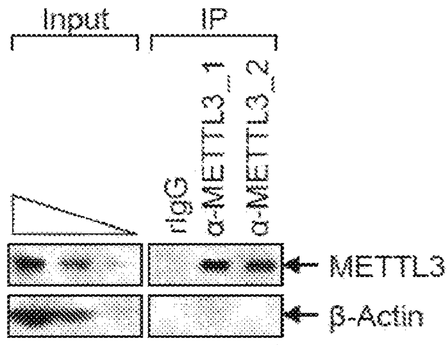
FIGS. 9A-9E. Widespread role of METTL3 in oncogene translation.
Figure 9B:
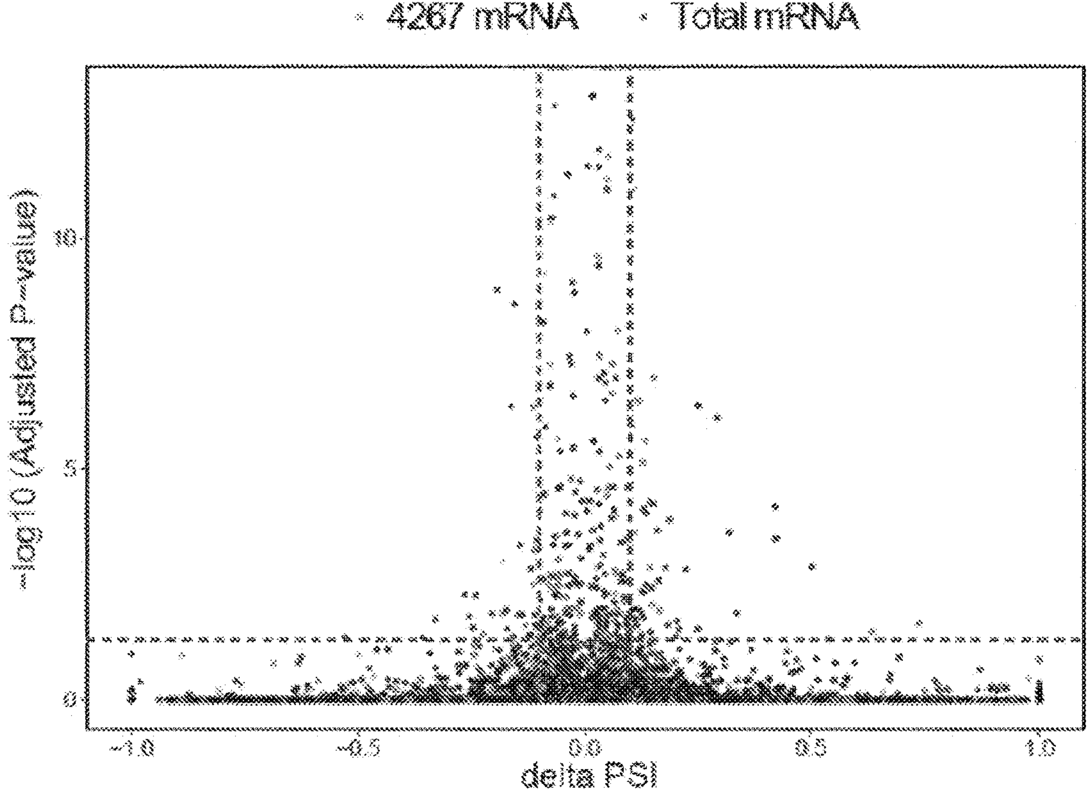
Figure 9C:
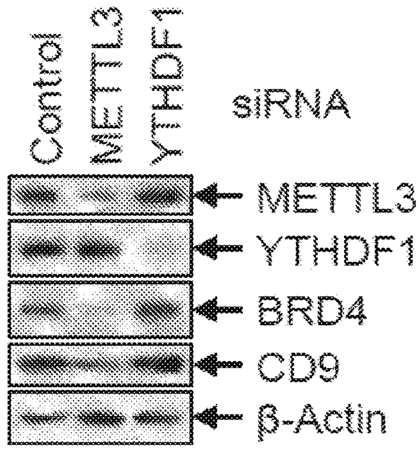

To investigate the global target genes that are translationally regulated by METTL3, sucrose gradient fractionation was performed on METTL3 knockdown cells followed by RNA-seq (FIG. 7). Two different shRNAs were used to stably knockdown METTL3 in Hela cells (FIG. 8A). METTL3 depletion caused an increase in the 80S ribosome peak and a corresponding reduction of polyribosome peak (FIG. 7A). METTL3 depletion had a negligible effect on steady state mRNA abundance (FIG. 7B). Translation efficiency of mRNAs was also analyzed by calculating the ratio of the mRNA sequence read numbers obtained from polysome fraction compared to the sub-polysome fraction (FIG. 7C). This revealed the translation efficiency of a large subset (4,267) of mRNAs was reduced by more than 2-fold in METTL3 depleted cells compared to control cells (shGFP) (FIGS. 7C-7D). Comparison of these genes with previously reported METTL3 PAR-CLIP data[2] revealed that 809 mRNAs are bound and translationally regulated by METTL3 (FIG. 7D). Interestingly, mRNAs on this list of high-confidence METTL3 target mRNAs have on average longer 3' UTRs compared to the average length of all mRNAs (FIG. 7E). Gene ontology (GO) disease and pathway annotation showed that these METTL3 targeted genes are significantly involved in tumor progression and apoptosis (FIG. 8B). qRT-PCR analysis confirmed that METTL3 depletion had a modest effect on individual target mRNA abundance (FIG. 8C), but largely decreased translation of target genes (FIG. 7F). Moreover, neither global mRNA stability analysis by RNA-seq (FIG. 7G) nor qRT-PCR analysis of individual genes (FIGS. 8D-8E) showed any significant differences in mRNA stability upon METTL3 depletion. It was further verified whether these mRNAs are directly targeted by METTL3 by performing qRT-PCR on isolated endogenous METTL3 mRNPs using two individual METTL3 antibodies (FIGS. 7H and 9A). Bromodomain containing 4 (BRD4), CD9 molecule (CD9), O-6-methylguanine-DNA methyltransferase (MGMT), and TIMP metallopeptidase inhibitor 1 (TIMP1) were specifically associated with endogenous METTL3 protein but not a non-methylated control mRNA solute carrier family 7 member 1 (SLC7A1) (FIG. 7H). Western blotting showed decreased protein expression from these target mRNAs in the METTL3 knockdown samples (FIG. 7I), whereas analysis of mRNA sequencing data revealed that the splicing patterns of these target mRNAs was unaltered in METTL3 depleted cells (FIG. 9B). Furthermore, depletion of YTHDF1, a $m^6A$-reader protein implicated in translational control had no effect on the expression of these METTL3 targets (FIG. 9C)[30].

Figure 9D:
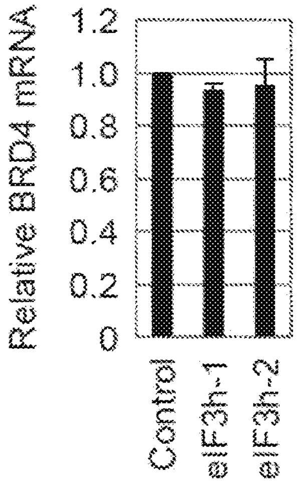

Considering the findings of a physical and functional interaction between METTL3 and eIF3h, it was next tested whether depletion of eIF3h might also affect expression of METTL3 target mRNAs. Western blotting showed strongly reduced endogenous BRD4 protein expression upon knockdown of eIF3h without affecting the mRNA abundance of BRD4 or the levels of METTL3 protein (FIGS. 7J and 9D). Next, to further confirm the requirement of METTL3 for efficient translation of target mRNAs, rescue experiments in METTL3 knockdown cells were performed (FIG. 7K). Expression of a shRNA-resistant FLAG-METTL3 (FLAG-METTL3$^R$ WT) in METTL3 depleted cells rescued the expression of BRD4 and CD9 proteins. However, expression of a catalytic domain mutant of METTL3 (FLAG-METTL3$^R$ Mut) failed to recover the protein expression of the target genes, supporting that METTL3 catalytic activity and its ability to promote translation are important for the expression of endogenous target mRNAs.

Figure 9E:
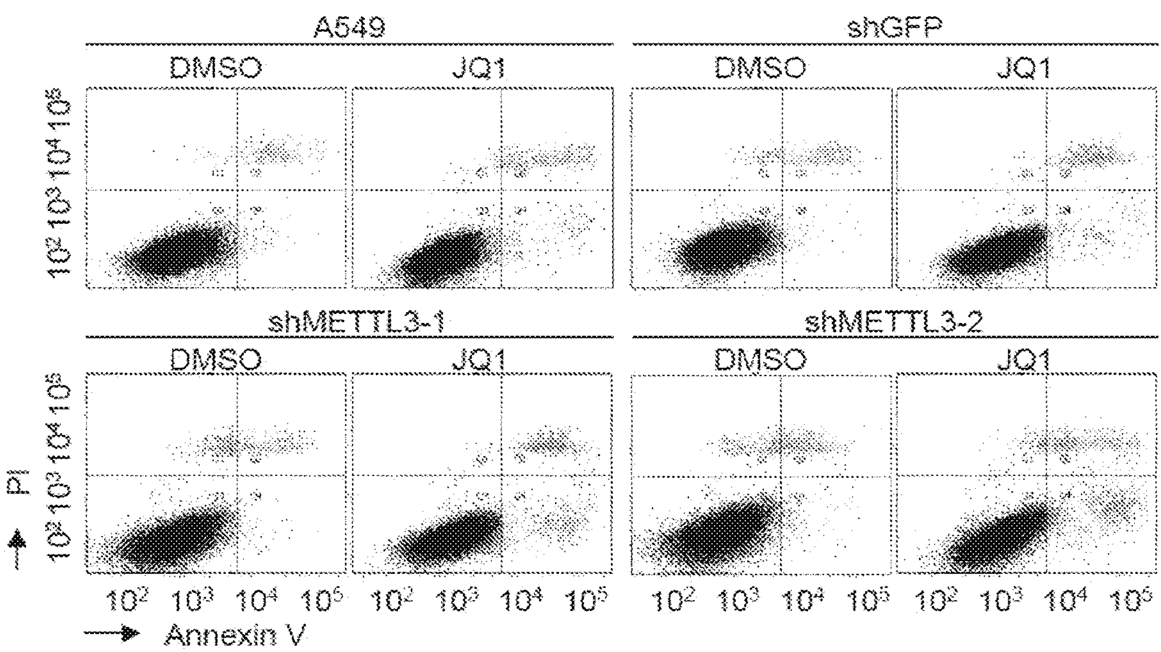

It was next determined whether inhibition of both METTL3 and its downstream target BRD4 has synergistic effect in lung cancer cells. It was found that knockdown of METTL3 decreases the expression of BRD4 and other target genes in A549 lung cancer cells (FIG. 7L), and importantly, treatment of METTL3-depleted and control-A549 cells with BRD4 inhibitor JQ1 revealed that the METTL3 depleted cells are more sensitive to pharmacological BRD4 inhibition. JQ1 treatment induced a stronger proliferation defect and increased the number of apoptotic cells in the METTL3 depleted cells than the control cells (FIGS. 7M, 7N, and 9E), suggesting that targeting both METTL3 and its downstream BRD4 can synergistically inhibit lung cancer cell growth and survival.

METTL3-eIF3h Interaction is Crucial for Enhanced Translation of Target mRNAs

Figure 10A:
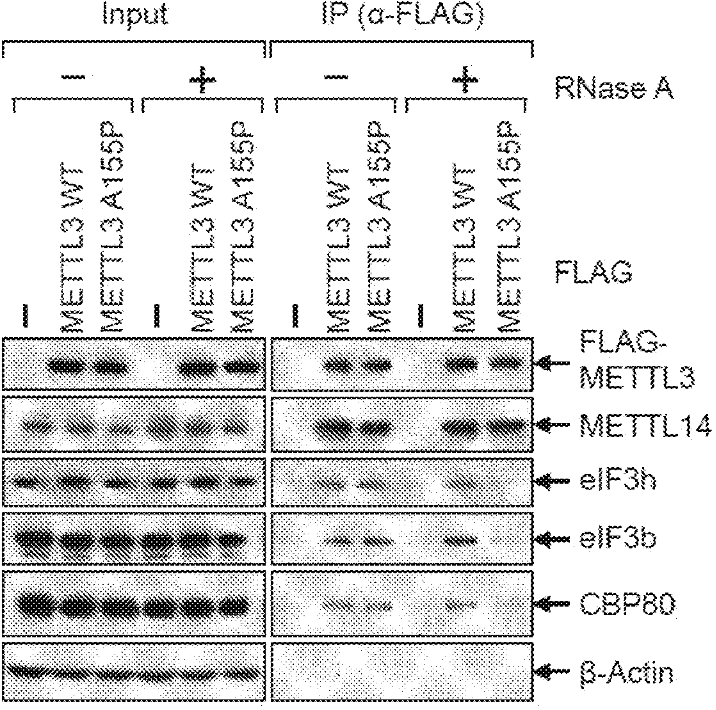
FIGS. 10A-10H. METTL3-eIF3h interaction is crucial for enhanced translation of target mRNAs and effects on polysome conformation.
Figure 10B:
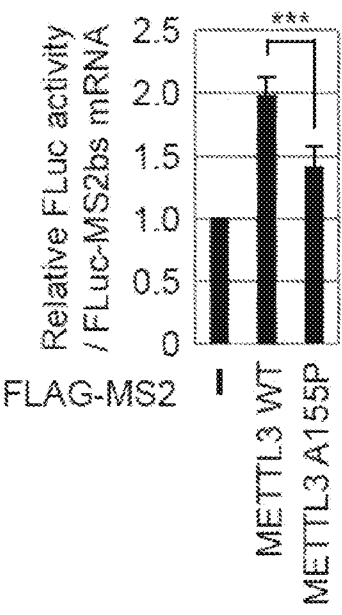
Figure 10C:
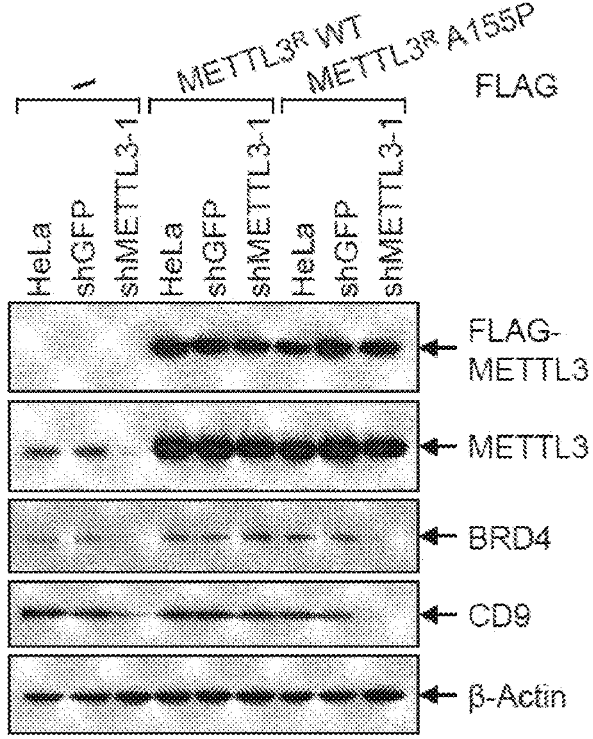
Figure 10D:
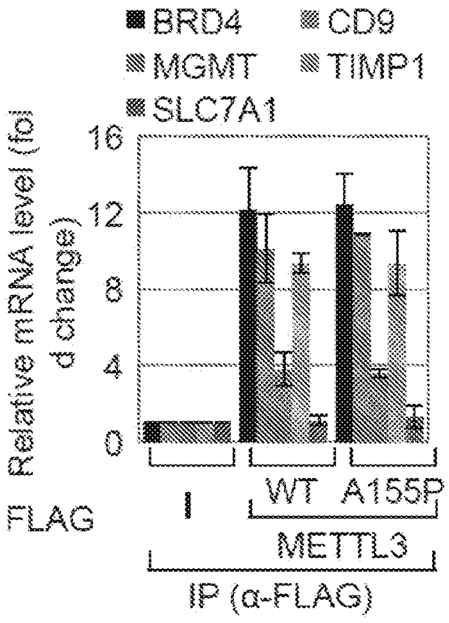
Figure 11A:
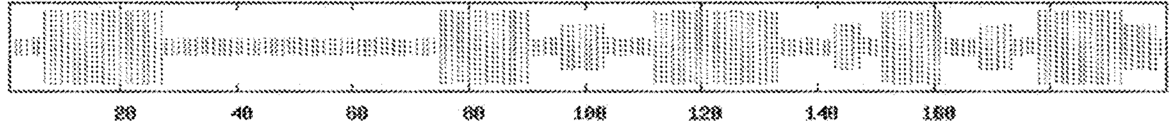
Figure 11D:
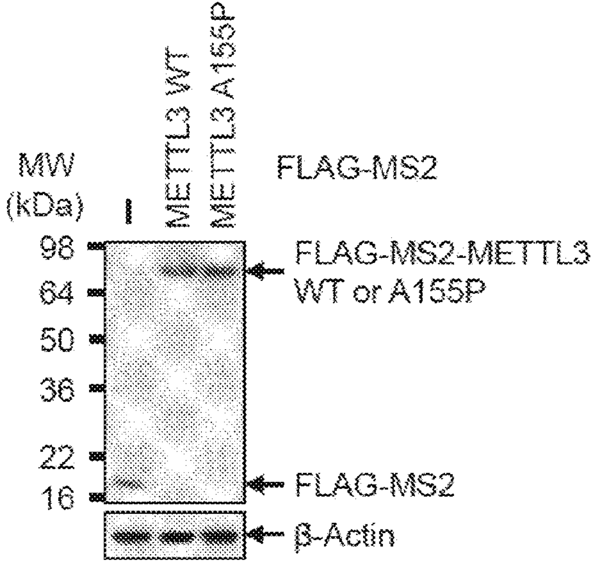
Figure 11E:
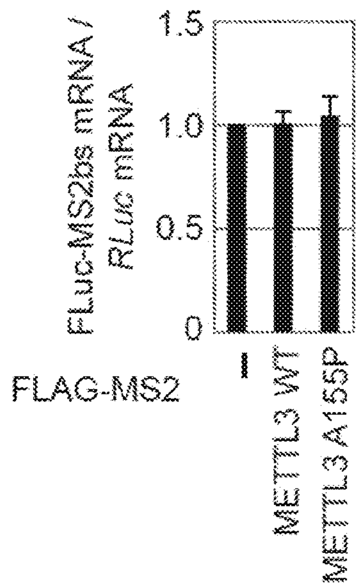
Figure 11F:
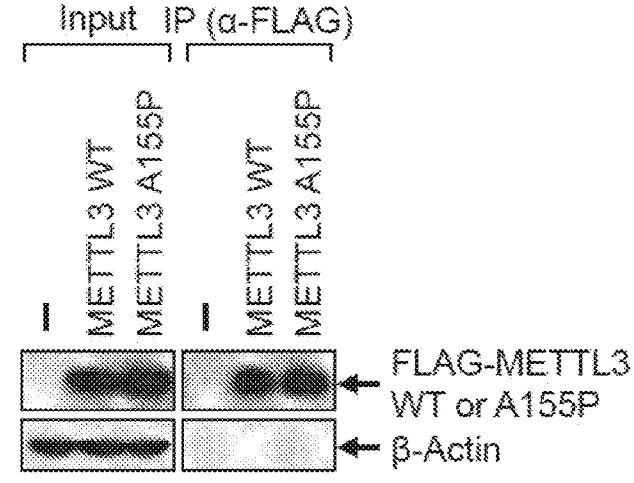
Figure 11G:
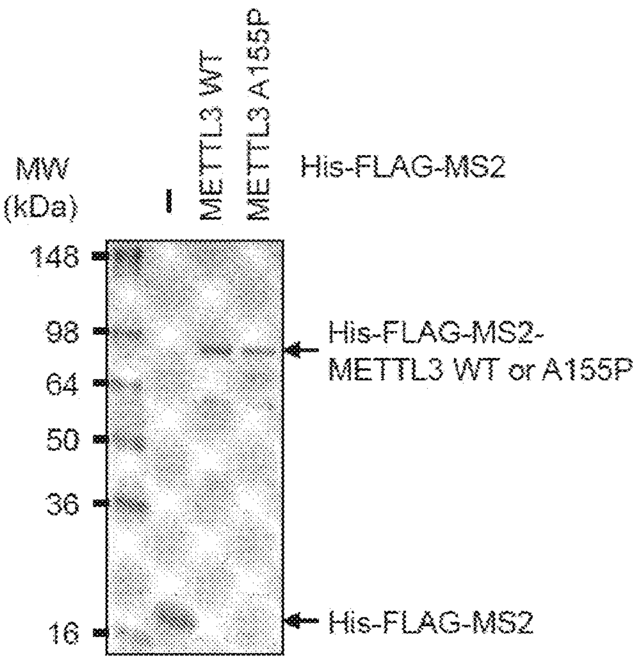

Given that METTL3 regulates the translation of a large subset of mRNAs and directly interacts with eIF3h, the functional importance of the METTL3-eIF3h interaction and the possible outcome that METTL3 promotes efficient translation through mRNA looping were sought to be investigated. Considering the findings that amino acids (aa) 1-200 of METTL3 is sufficient to directly interact withe IF3h (FIG. 5E) and that aa 1-200 can promote translation in tethering experiments whereas aa 1-150 does not (FIG. 2). Thus, the region between aa 150-200 must be important for the physical and functional METTL3-eIF3h interaction. Secondary structure computational predictions identified a putative alpha helix (aa 150-161) within this region that is highly conserved in mammals (FIGS. 11A-11B)[45,46]. Moreover, 3D modeling identified a putative structured module comprising aa 77-163 that is based on a crystal structure (PDB: 3HHH) of a bacterial transcriptional regulator (FIG. 11C)[47]. Therefore, a mutant version of METTL3 was generated with a single amino acid substitution of a highly conserved Alanine to Proline (METTL3 A155P) to disrupt this putative helical structure of METTL3. It was first investigated by co-IP experiments whether METTL3 A155P can associate with translation initiation factors. It was found that compared to wild-type (WT) METTL3 the interaction of A155P with eIF3h, eIF3b and a cap-binding protein CBP80, was substantially impaired, specifically in the RNase-treated samples (FIG. 10A). Importantly, the A155P mutation did not affect the METTL3 interaction with METTL14 (FIG. 10A). It was next tested whether this A155P mutation affects METTL3 function in promoting translation. To this end, a tethering experiment was performed using plasmids expressing WT or A155P METTL3 (FIG. 11*d*) and it was found that the A155P mutant is strongly impaired in promoting reporter mRNA translation (FIGS. 10B and 11E). Moreover, unlike WT METTL3, expression of METTL3 A155P in METTL3-depleted cells failed to rescue the expression of endogenous target proteins BRD4 and CD9 (FIG. 10C). This effect was not due to altered mRNA association since both WT and A155P were comparably bound to target mRNAs as measured by RNA IP and qRT-PCR (FIGS. 10D and 11F). In summary, these results indicate that while METTL3 A155P mutant can associate with METTL14 and be loaded on mRNAs, its ability to interact with initiation factors and promote mRNA translation is severely compromised.

Figure 10E:
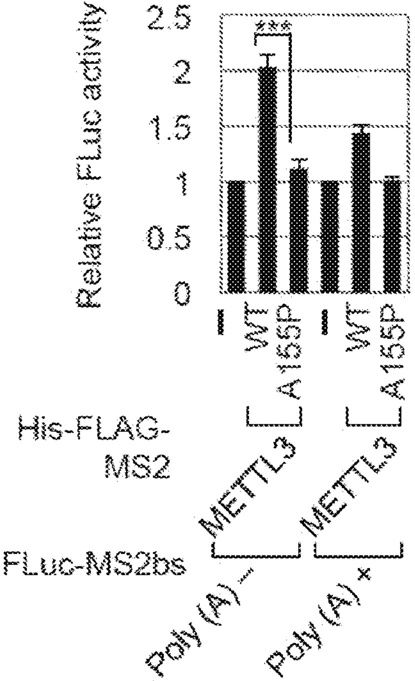
Figure 10F:
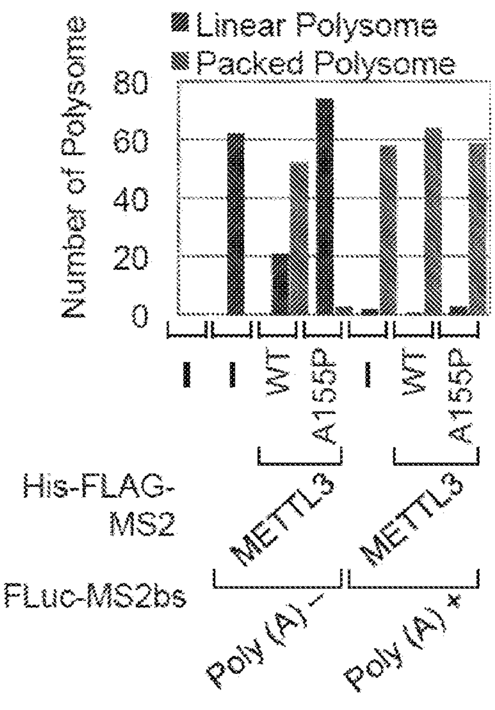
Figure 10G:
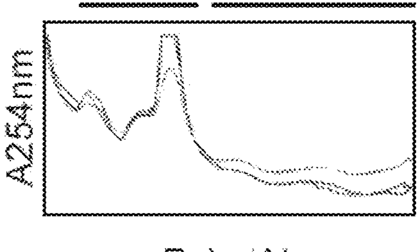
Figure 10H:
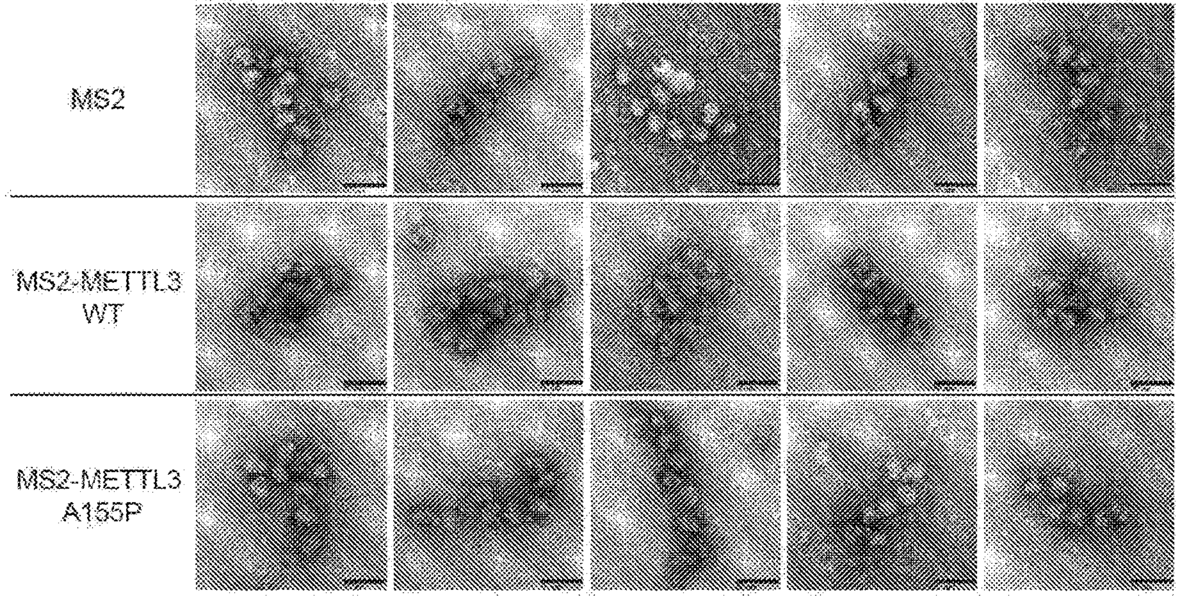
Figure 12:
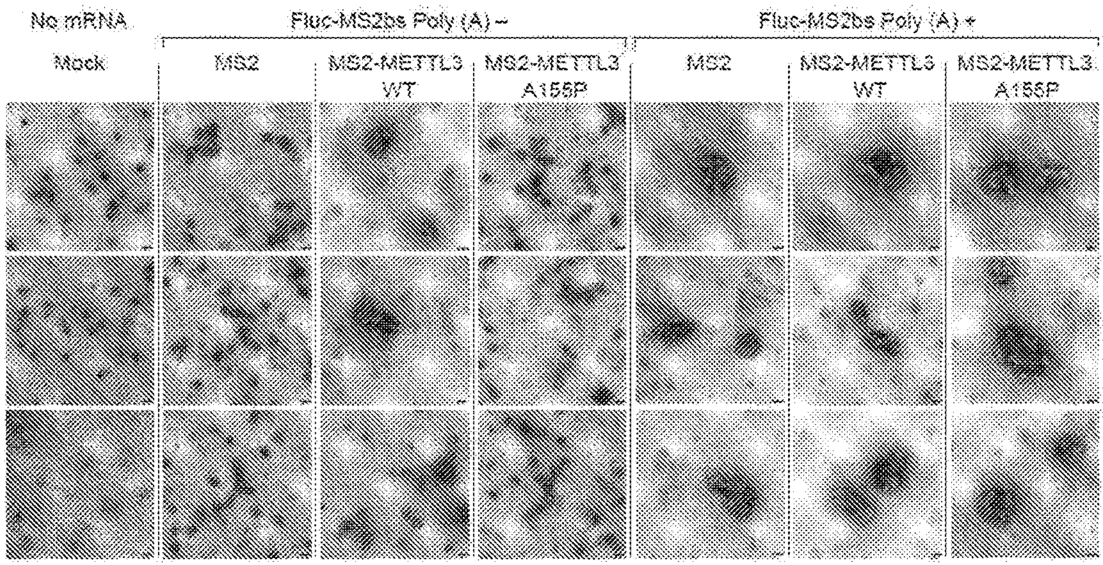
FIG. 12. EM images of polyribosomes. Images were taken from the samples in FIG. 10E. Scale bar, 50 nm.

In vitro translation assays combined with EM analysis were next used to directly visualize actively translating polyribosomes and to explore the effect of 3' UTR-bound METTL3 on translation efficiency and polysome conformation (FIGS. 10A-10F, 11G and 12A). Consistent with FIG. 1G, tethering of recombinant protein His-FLAG-MS2-METTL3 WT to the 3' UTR of reporter mRNA increased its translation efficiency, with a stronger effect on mRNA without a poly (A) tail (FIG. 10E). In contrast, tethered His-FLAG-MS2-METTL3 A155P had no significant effect on translation efficiency (FIG. 10E). EM analysis was performed on samples from the in vitro translation reactions (FIG. 12A) to visualize the actively translating polysomes. A sample taken from an in vitro translation reaction performed in the absence of mRNA was analyzed as a control, and only dispersed individual ribosomes could be observed. Strikingly, mostly densely packed polysome structures formed when His-FLAG-MS2-METTL3 WT was tethered to reporter mRNAs without a poly (A) tail. In contrast, almost all the polysomes observed in the His-FLAG-MS2-METTL3 A155P sample appeared as linear polysomes (similar to those observed in the His-FLAG-MS2 control sample) (FIGS. 10F and 12A). In all samples with poly (A)+ containing mRNAs mostly packed polysomes were observed irrespective of the protein that was tethered. Since the reporter mRNA contains a very short 3'UTR (with the poly (A) tail close to the translation stop codon) it was expected that the known eIF4GI-PABP interaction can efficiently promote mRNA looping. This mechanism is likely responsible for observed packed polysomes in the poly (A)+ samples and the redundancy of METTL3 in this context (FIGS. 10F and 12A). In vitro translation assays were further analyzed by resolving polysomes using sucrose gradient fractionation. Tethering of His-FLAG-MS2-METTL3 WT to reporter mRNAs without a poly (A) tail resulted in a larger polysome peak compared to His-FLAG-MS2-METTL3 A155P (FIG. 10G). Individual polysomes from these sucrose gradients were visualized by EM (FIGS. 10G-10H). This EM analysis revealed that the polysomes formed with the His-FLAG-MS2-METTL3 WT appeared more densely packed compared to the more linear polysomes that formed with the His-FLAG-MS2-METTL3 A155P mutant or MS2 control (FIG. 10H). Taken together, these results strongly support the model that METTL3 through its interaction with eIF3h promotes translation through its effects on polysome conformation involving mRNA looping to facilitate multiple rounds of mRNA translation.

METTL3 Expression Correlates with Lung Tumor Stage and Promotes Tumorigenicity

Figure 13A:
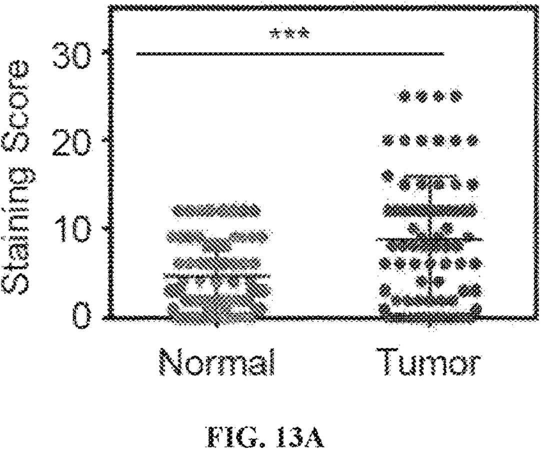
FIGS. 13A-13L. Role of METTL3 and $m^6A$ in lung cancer cells and primary human tumors.
Figure 13B:
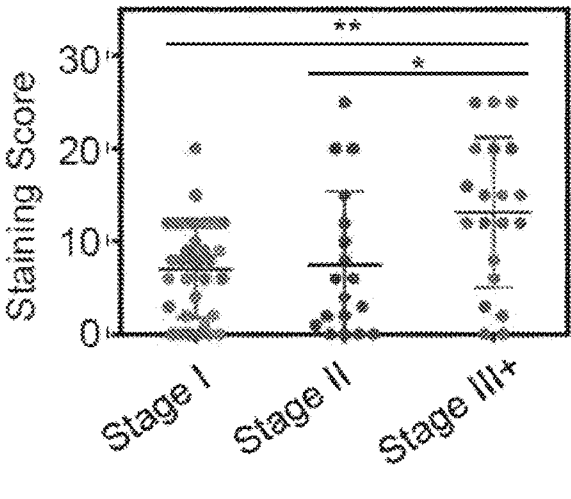
Figure 13C:
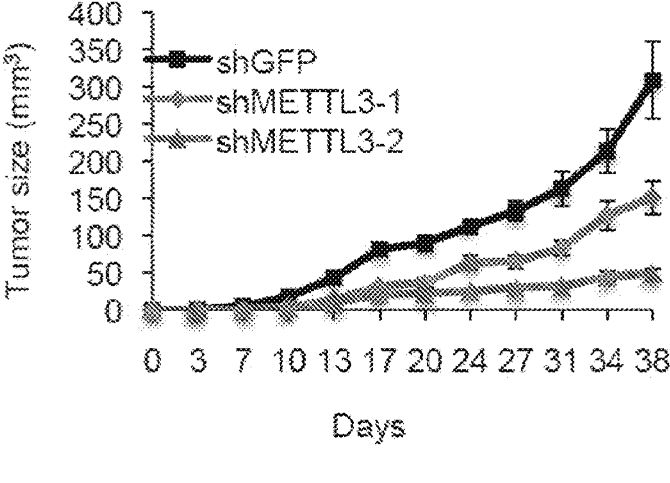
Figure 14A:
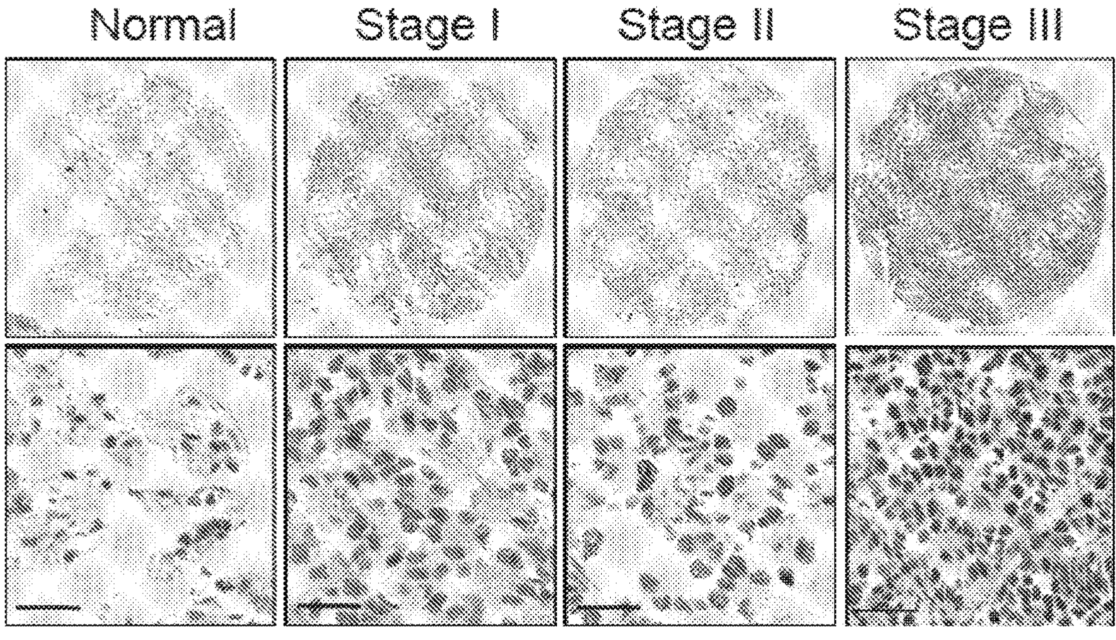
FIGS. 14A-14K.
Figure 14B:
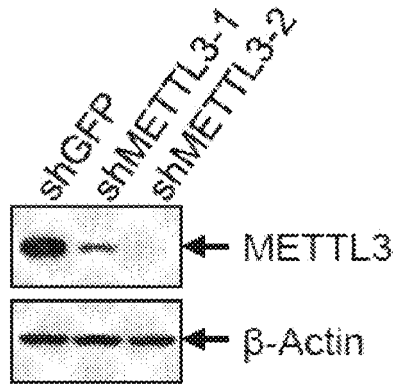
Figure 14C:
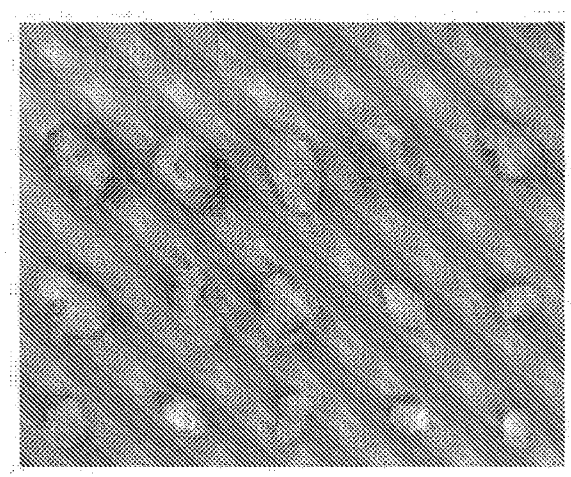
Figure 14D:
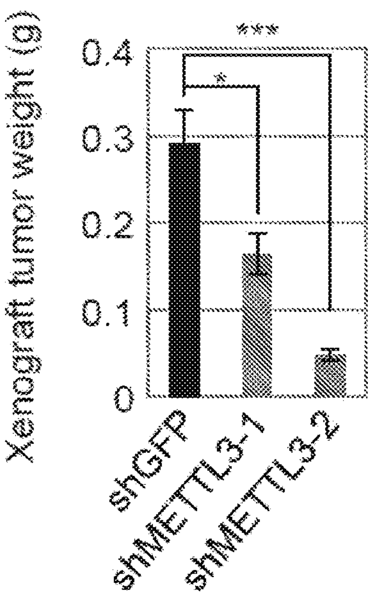

Given that METTL3 regulates the translation of a large subset of genes that are involved in tumor progression and apoptosis (FIG. 8B), the role of METTL3 in cancer was further determined. Immunohistochemistry (IHC) staining of primary lung adenocarcinoma patient samples and adjacent normal controls revealed that METTL3 expression is significantly up-regulated in lung cancer samples compared to the normal controls (FIGS. 13A and 14A). Moreover, METTL3 expression is associated with advanced tumor stage (FIGS. 13B and 14B). The role of METTL3 in lung cancer growth was next determined using a mouse xenograft model. Depletion of METTL3 expression in A549 lung cancer cells resulted in significant decrease in the tumor size and weight (FIGS. 13C and 14B-14D), suggesting that METTL3 is essential for tumor growth in vivo.

Figure 13D:
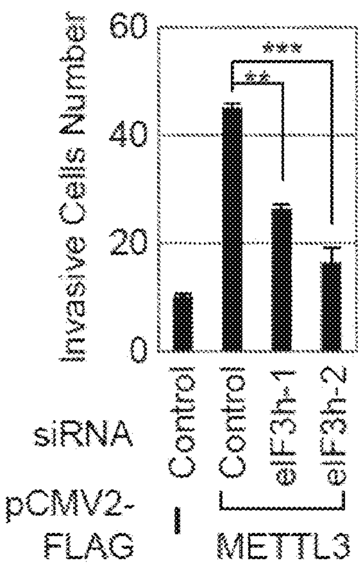
Figure 13E:
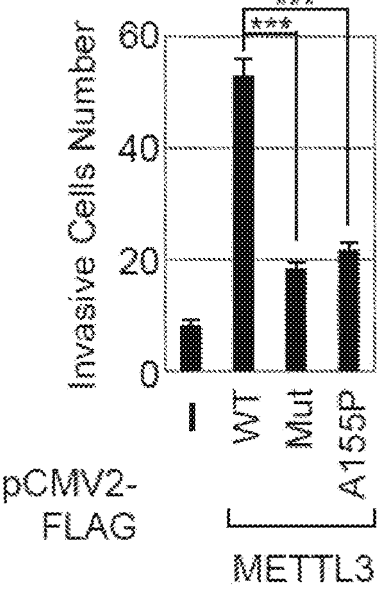
Figure 13F:
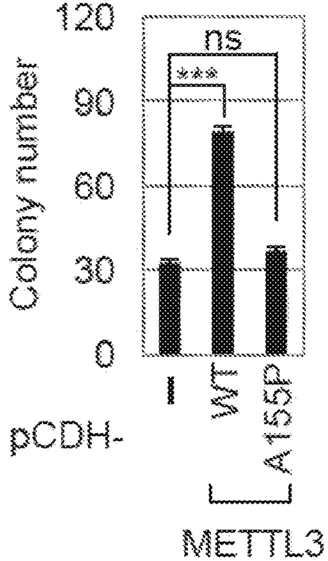
Figure 13G:
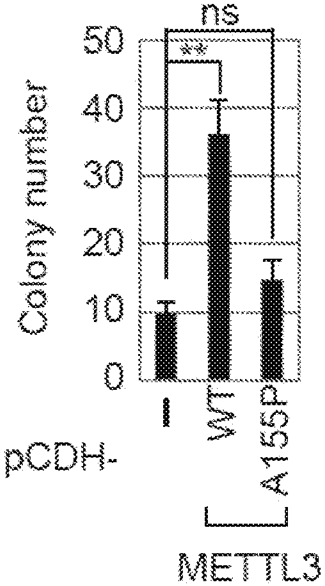
Figure 13H:
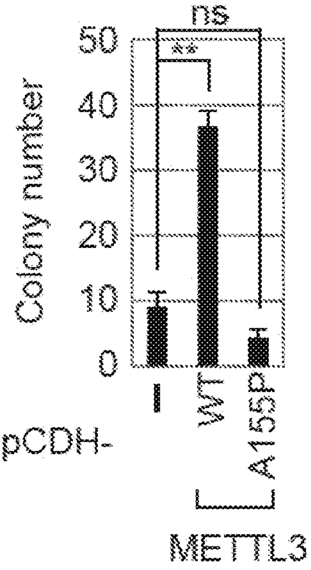
Figure 13I:
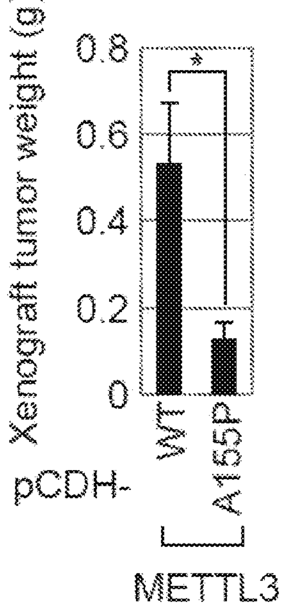
Figure 14E:
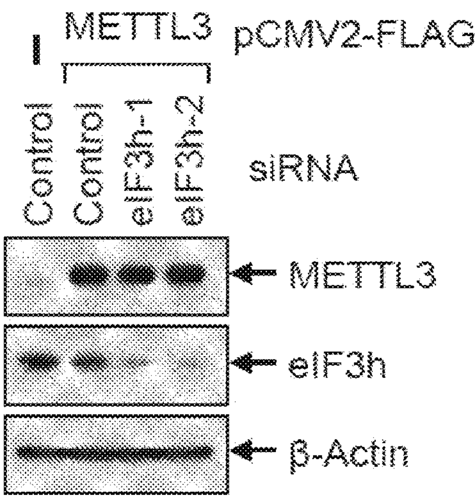
Figure 14F:
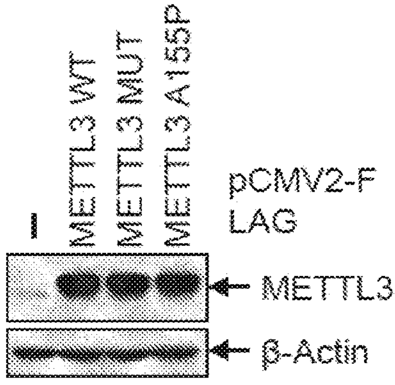
Figure 14G:
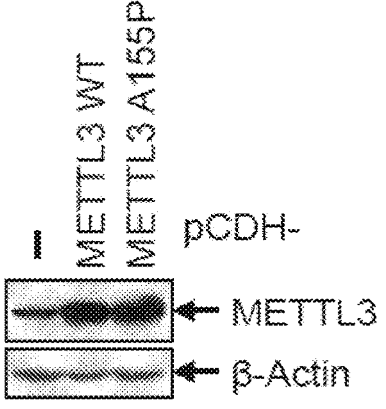
Figure 14H:
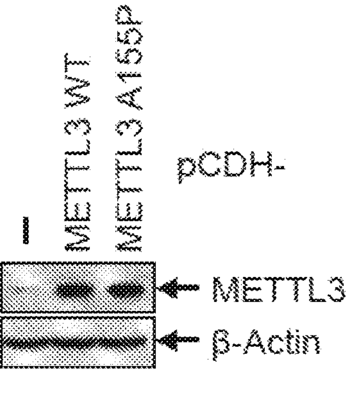
Figure 14I:
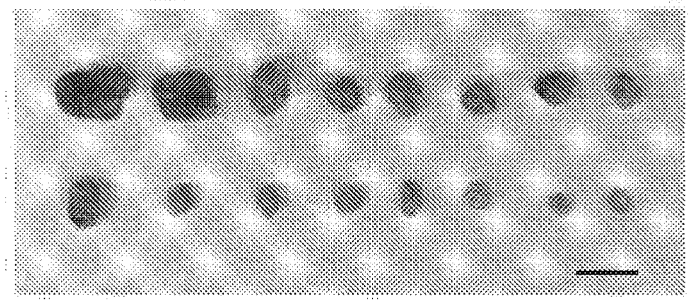

The relevance of the METTL3-eIF3h interaction and mRNA looping was next examined in the context of cancer cell biology. Knockdown of eIF3h suppressed the ability of METTL3 to promote cellular invasion (FIGS. 13D and 14E). Moreover, it was found that unlike the WT METTL3 protein, expression of either a catalytically inactive mutant (Mut) METTL3, or the A155P mutant form of METTL3 (that specifically disrupts its interaction with eIF3h and its ability to facilitate mRNA looping and translation) is unable to promote the invasive capability of lung fibroblast cells (FIGS. 13E and 14F). It was further shown that METTL3 WT overexpression is sufficient to promote the oncogenic transformation of NIH-3T3 cells, mouse embryonic fibroblasts (MEFs) or MB352 (p53 null MEFs) cells, whereas METTL3 A155P had no significant effect in 2D colony formation assays and 3D soft agar colony formation assays (FIGS. 13F-13H and 14H). Moreover, the oncogenic function of METTL3 was also studied in a mouse xenograft model. NIH-3T3 cells with ectopic expression of METTL3 WT, METTL3 A155P, or the empty vector control were injected into nude mice to determine their in vivo tumorigenic capacities. The data revealed that METTL3 WT overexpression promoted in vivo tumor growth, whereas METTL3 A155P showed an impaired ability to promote tumor growth. As control, no tumors were detected in mice injected with control NIH-3T3 cells (that were transduced with the empty vector) (FIGS. 13I and 14I). Overall, these results support that the METTL3-eIF3h mediated mRNA looping and the effects on mRNA translation are critical for the oncogenic function of METTL3.

m$^6$A Modification in Primary Human Lung Tumors

Figure 13J:
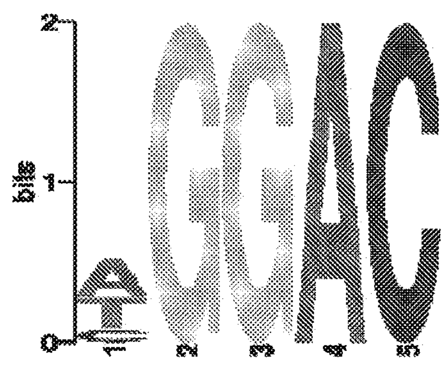
Figure 13K:
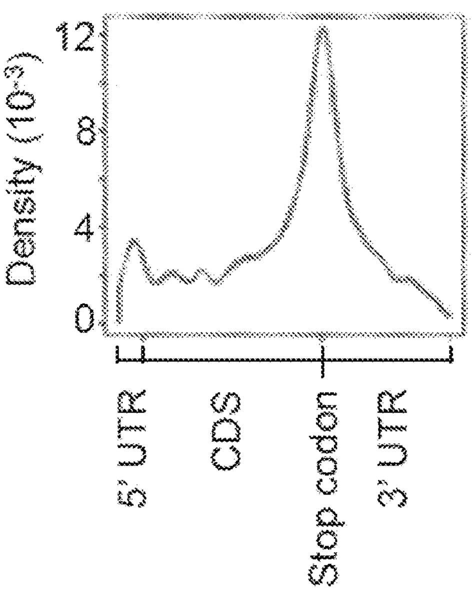
Figure 13L:
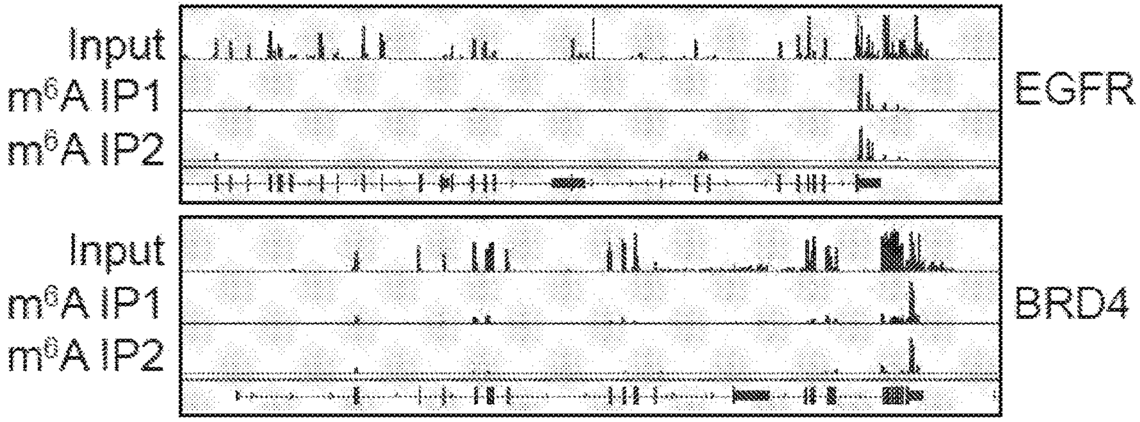
Figure 14J:
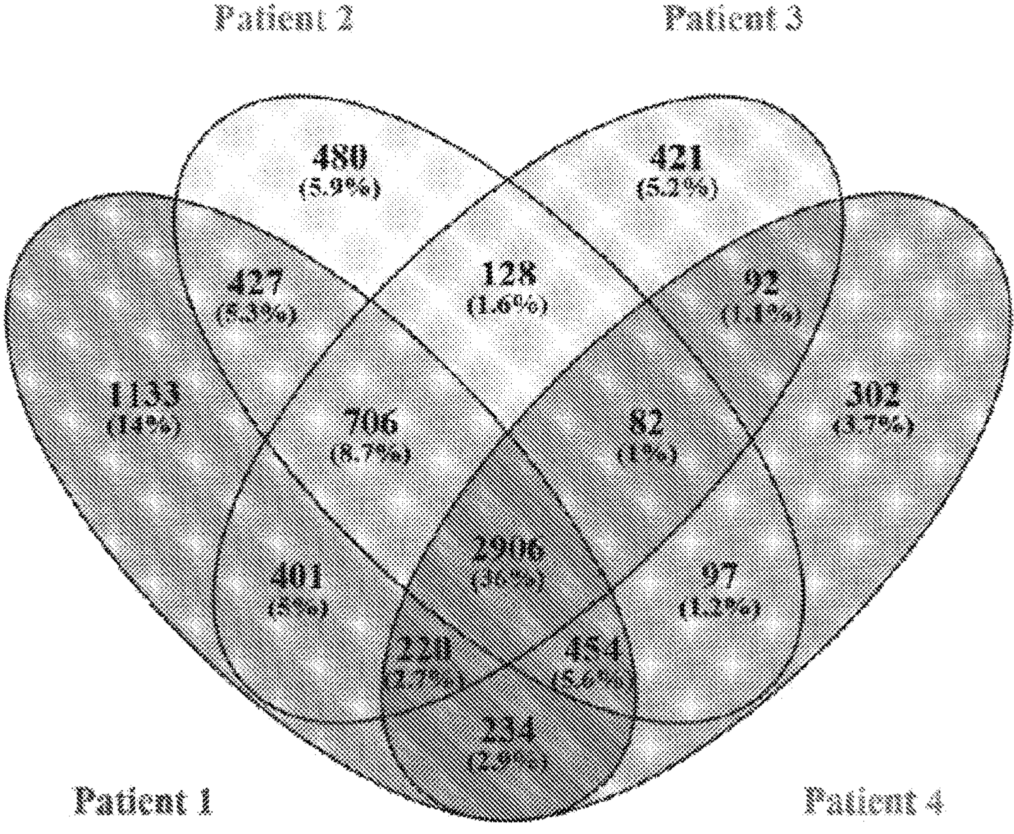
Figure 14K:
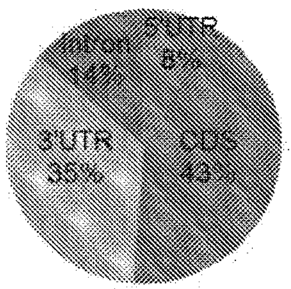
Figure 15A:
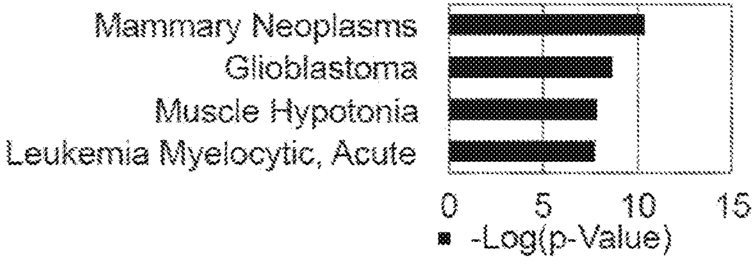
FIGS. 15A-15B.
Figure 15A:
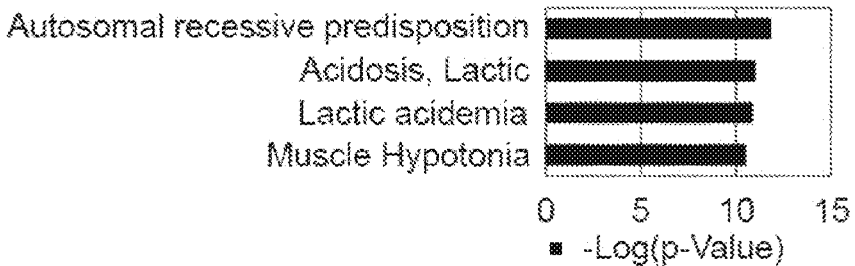
Figure 15B:
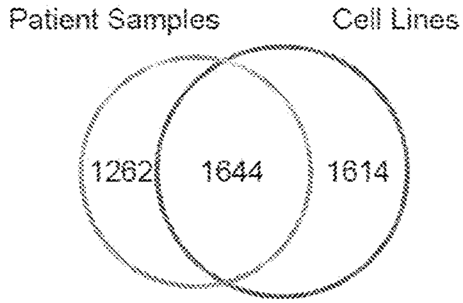

To further study the role of METTL3 mediated m$^6$A modification in cancer, transcriptome-wide mapping of m$^6$A was performed in primary human lung adenocarcinoma samples. Profiling of m$^6$A by meRIP-seq (methylated RNA immunoprecipitation and sequencing) in four primary human tumors identified patient specific and commonly methylated genes in lung cancer samples (FIG. 14J and Table S3). A "GGAC" motif was identified in the lung cancer m$^6$A peaks, and metagene analysis revealed that the m$^6$A peaks are predominantly localized near the translation stop codons, with a subset of peaks located in the 5'UTR and internal exons (FIGS. 13J-13K and 14K). Gene ontology analysis revealed that the common methylated genes are enriched in the signature genes of neoplasms and cancer, including the known oncogenes EGFR and BRD4 (FIGS. 13L and 15A). These data were consistent with the published m$^6$A features identified in cell lines, and more than 50% of the peaks found in lung tumors are also present in lung cancer cell lines (FIG. 15B), suggesting that the m$^6$A profiling successfully identified the specific m$^6$A targets in lung cancer patient samples.

Discussion

In this study, a mechanism and role of METTL3 in promoting translation is uncovered. It is concluded that METTL3 promotes translation through an mRNA looping mechanism. This contention is supported by; 1) the position-dependent effects of METTL3 tethering on the translation of reporter mRNAs, 2) the EM visualization of METTL3 bound to endogenous polyribosomes and its close proximity to the cap-binding proteins, 3) the present discovery that the N-terminal region (1-200) of METTL3 directly interacts with the MPN-domain of the eIF3h subunit of the eIF3 translation initiation complex, and 4) the evidence that disruption of the METTL3-eIF3h interaction via a single amino acid substitution abolished the ability of METTL3 to promote translation and affect polysome conformation in vitro when directly tethered to a site in the mRNA 3'UTR. This physical and functional interaction is critical for METTL3 to associate with the translation initiation complex, to promote translation of a reporter as well as endogenous target mRNAs, and for promoting oncogenic transformation. The widespread consequences of METTL3 deficiency for mRNA translation were uncovered and BRD4 is identified as one of the important downstream genes that is controlled by METTL3-eIF3h, and it was found that many of the same METTL3 target RNAs found in lung cancer cell lines are also $m^6A$-modified in primary lung adenocarcinomas.

A closed-loop model of enhanced mRNA translation was suggested earlier and the model is supported by work from several groups including the discovery of the functional synergism and the physical interaction between the capped 5' terminus and the polyadenylated 3' terminus of mRNA mediated by translation initiation factors eIF4G and PABPC1 (poly(A) binding protein cytoplasmic 1)[41-44]. The data that METTL3 promotes mRNA translation only when bound to sites close to the stop codon in the 3' UTR, as well as the polyribosome topology observed by EM, support the existence of an alternative closed loop model mediated by METTL3-eIF3h that brings the 5' cap in close proximity to the translation stop codon. This METTL3-eIF3h loop presumably promotes translation through ribosome recycling in a way similar to that proposed for the eIF4G-PABPC1-mediated mRNA looping model. Indeed, while there is likely some redundancy between these mRNA circularization mechanisms, looping between the stop codon and the 5' end might represent a more productive way to recycle ribosomes rather than via the 3' end, especially for mRNAs with long 3' UTRs since the ribosomes will dissociate from the mRNP once released at the stop codon. Interestingly, and in support of this outcome mRNAs with longer 3' UTRs are especially sensitive to METTL3 depletion (FIG. 7E), and METTL3 has a stronger effect on translation when tethered close to the stop codon of reporter with a long 3' UTR compared to that with a shorter 3' UTR (FIG. 1D). Furthermore, METTL3 has a stronger effect on boosting translation of reporters without a poly (A) tail in vitro presumably due to some redundancy with eIF4G-PABPC1-mediated mRNA looping for polyadenylated mRNAs in these biochemical experiments. It will be of interest to explore the relationship between the closed loops mediated by either METTL3-eIF3h or eIF4GI-PABPC1 and the different polysome shapes (circular, spiral, or other) that have been observed in vivo[48].

Figure 16A:
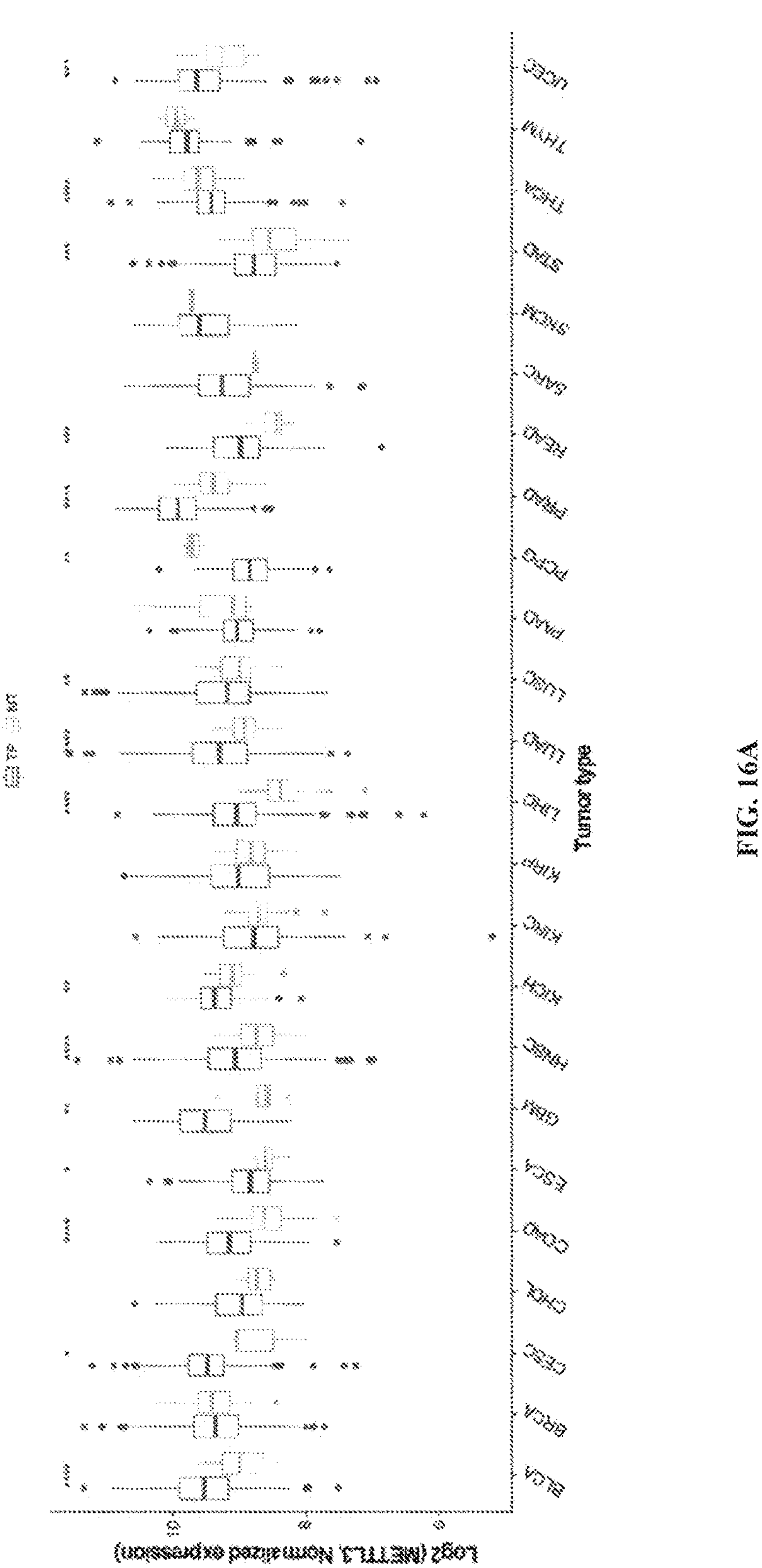
FIGS. 16A-16C.
Figure 16B:
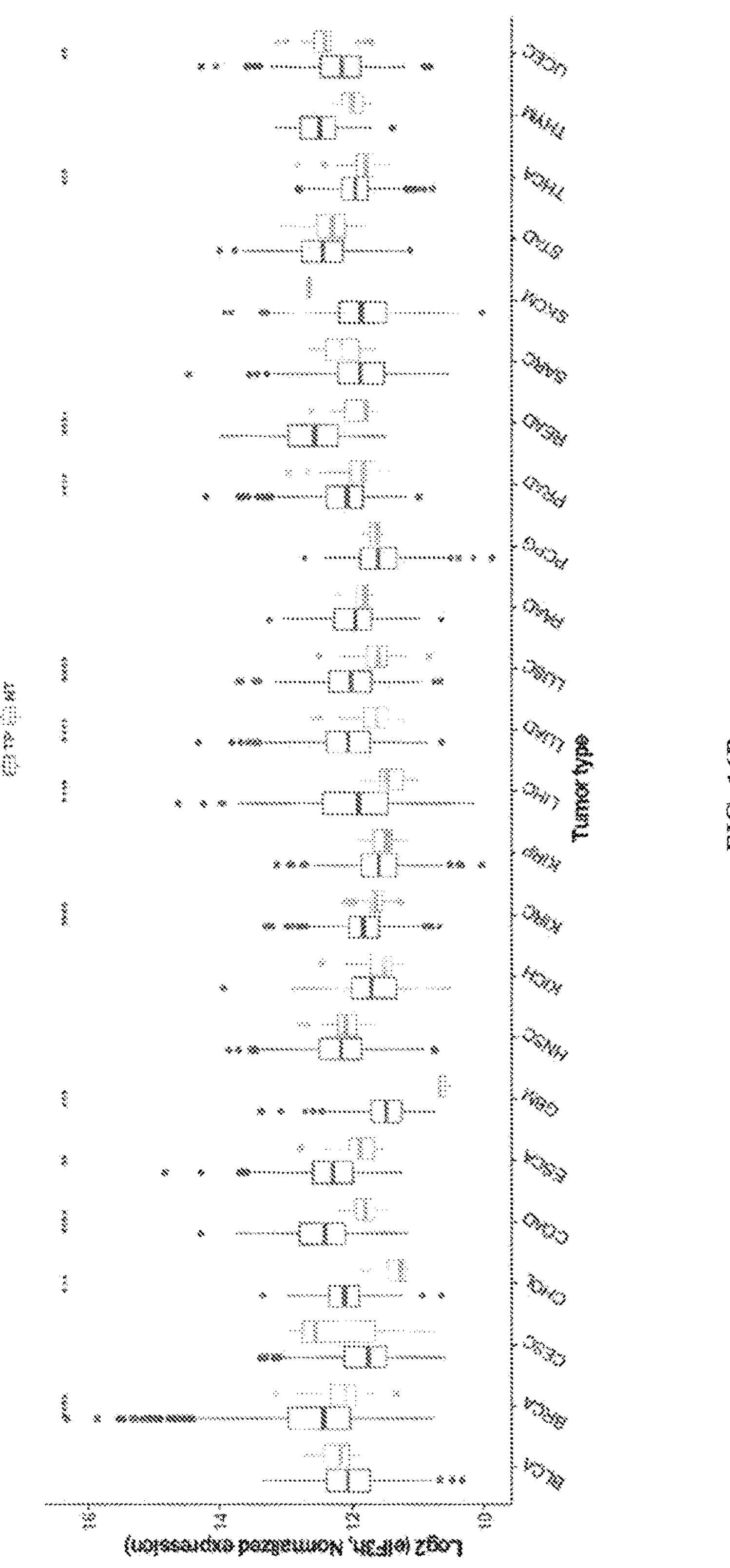
Figure 16C:
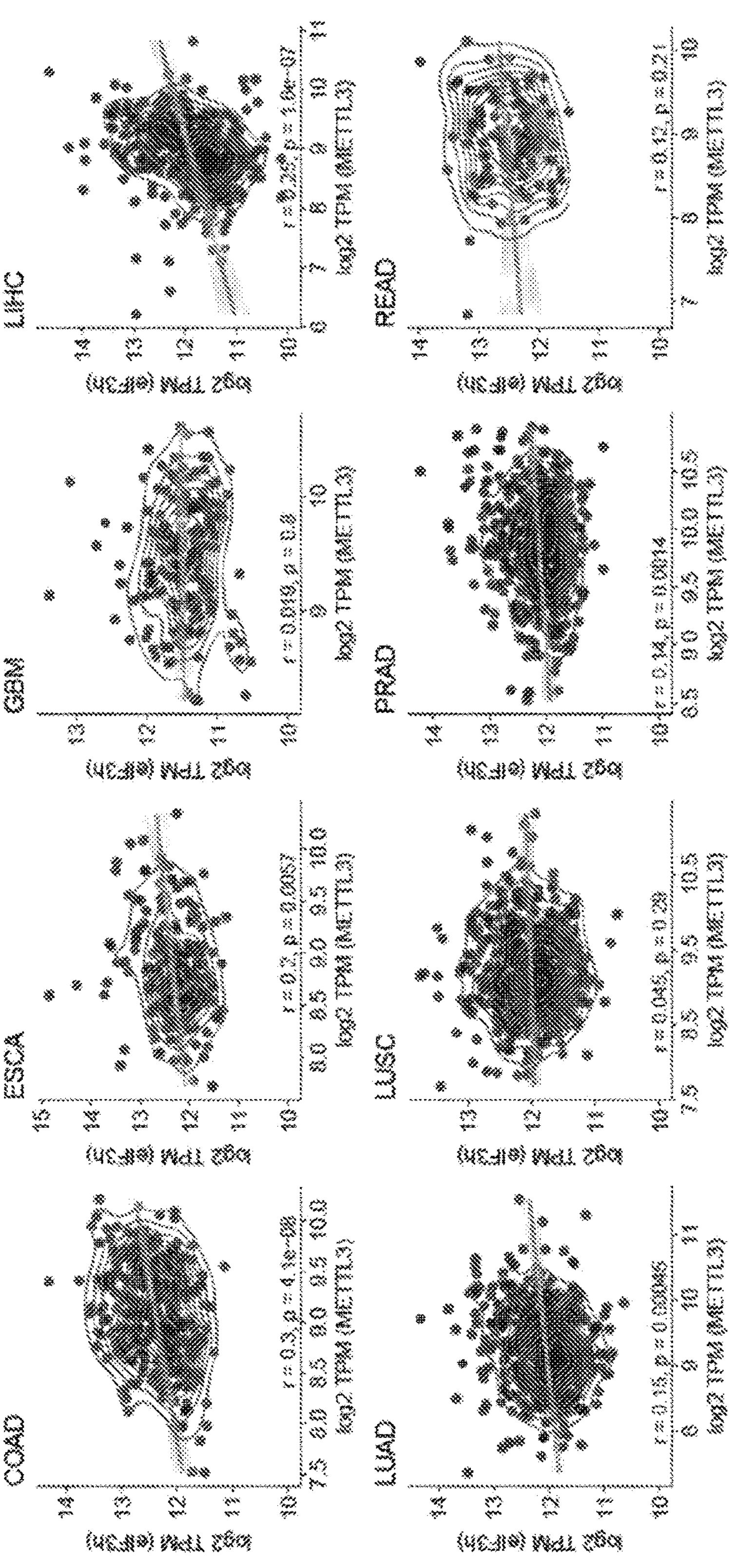
Figure 17A:
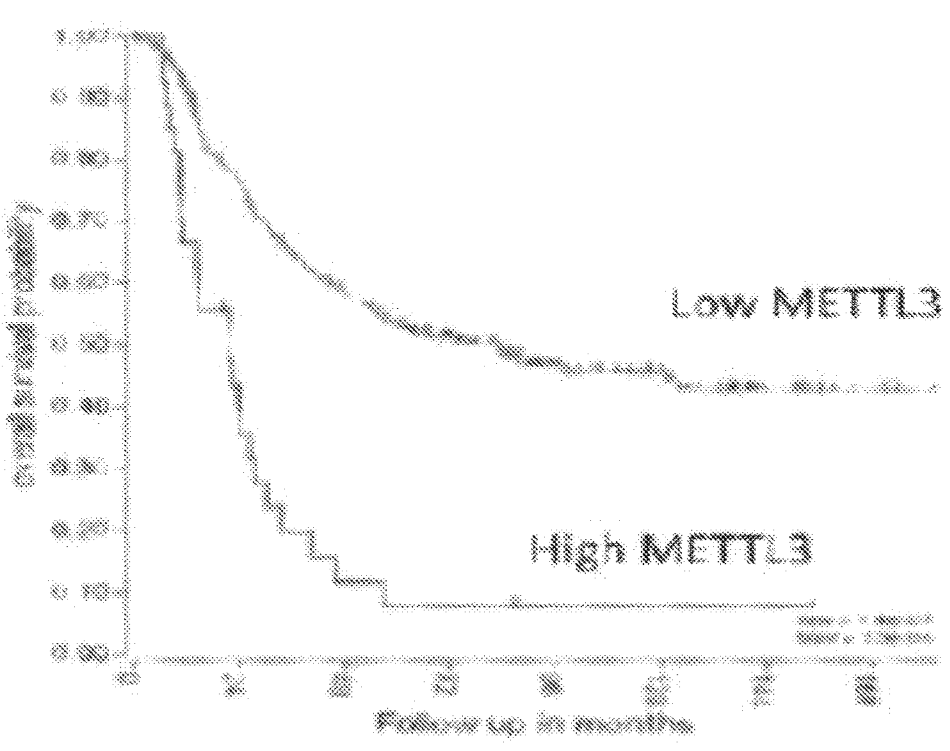
FIGS. 17A-17E. METTL3 regulates proliferation and survival in neuroblastomas.
Figure 17B:
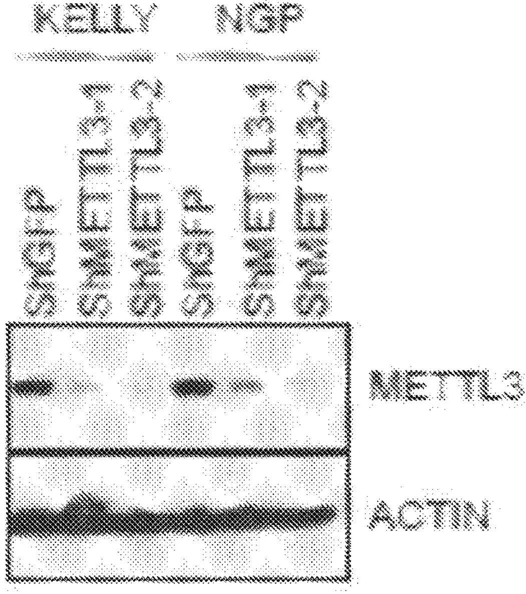
Figures 17C, 17D:
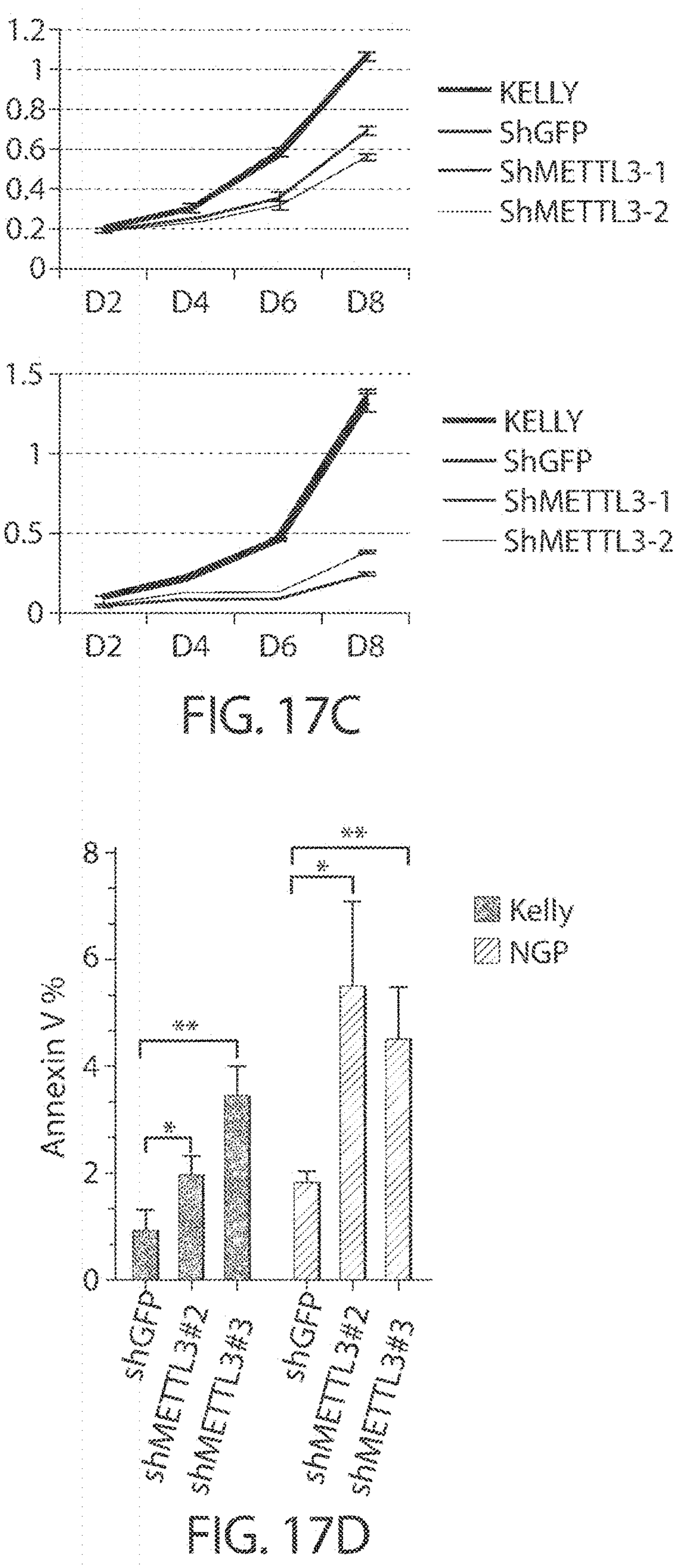
Figure 17E:
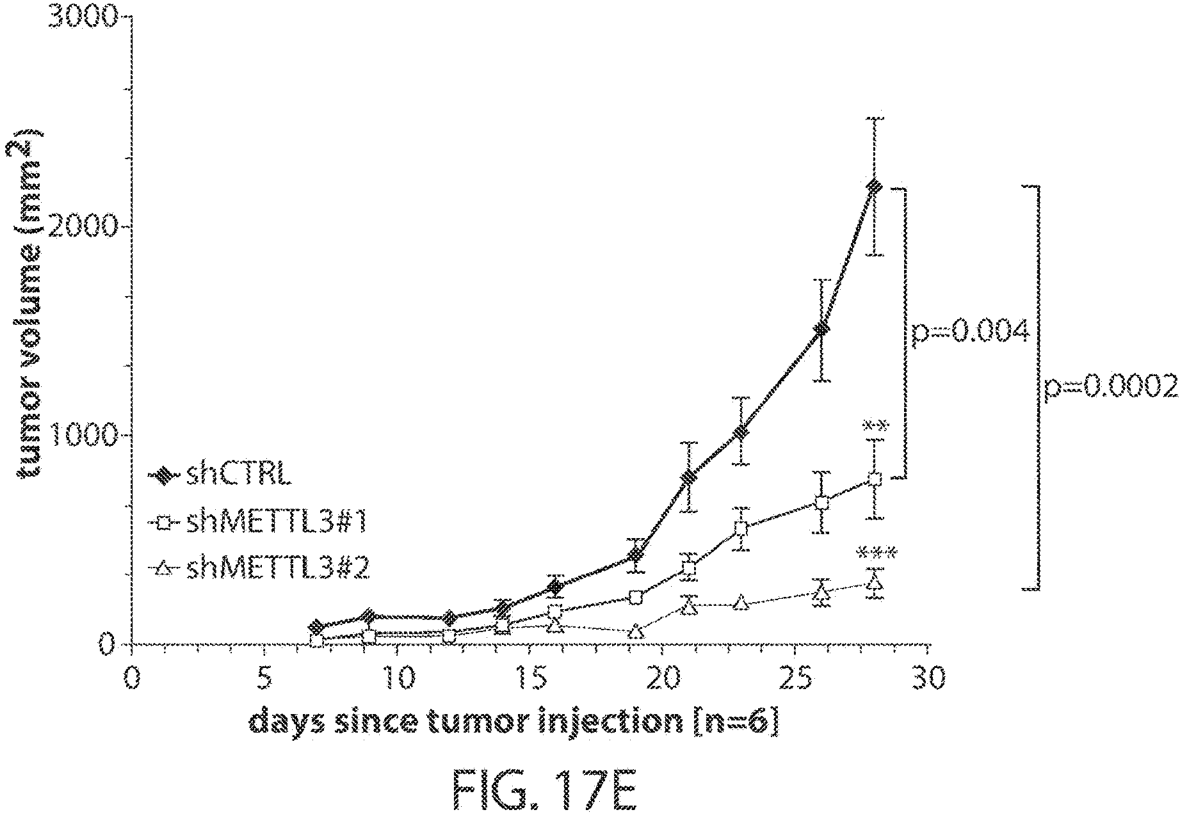

The complexity of eIF3 and the specialized roles of each of the subunits is only beginning to be appreciated. Indeed, eIF3d knockdown results in severe proliferation defects with no impact on eIF3 integrity[39]. In addition, c-Jun mRNA uses eIF3d as a cap-binding protein which recruits other eIF3 subunits to initiate translation[38], while BTG1 mRNA shows a translational defect upon eIF3 binding to its 5' UTR[40]. Thus it is emerging that eIF3 is not only a general translation factor but that individual subunits can have more specialized roles for controlling distinct subsets of mRNAs. Imbalanced expression of eIF3 subunits can be found in various tumors including eIF3a, -3b, -3c, -3h, -3i and −3 m[36]. Moreover, ectopic overexpression of these subunits in fibroblasts can promote malignant transformation[49]. In humans, overexpression of eIF3h has been found in prostate, breast, and liver cancer. This overexpression, in many cases, is due to amplification of 8q23 region of chromosome 8 that includes the eIF3h gene at 8q23.3[50]. Previous studies demonstrated that eIF3h is often co-amplified with Myc that is relatively nearby at 8q24.1, suggesting possible cooperation between MYC and eIF3 to further up-regulate translation initiation[51]. Inspection of TCGA data identify that METTL3 is overexpressed in several different types of cancer compared with the corresponding normal tissues (FIG. 16). eIF3h is also overexpressed in a variety of tumor types (FIG. 16B). Interestingly, the expression of METTL3 and eIF3h is positively correlated in many tumor types that show increased expression of both genes, including Lung Adenocarcinoma, Colon Adenocarcinoma, Esophageal Carcinoma, Liver Hepatocellular Carcinoma, and Prostate Adenocarcinoma (FIG. 16C). Considering the emerging data showing a more widespread oncogenic role of METTL3 it will be of interest the functional role of METTL3-eIF3h in other cancer types[52-58].

Epidermal growth factor receptor (EGFR) and the Hippo pathway effector TAZ were previously identified as METTL3 target genes[8]. Here a global mRNA profiling was performed to identify the widespread impact of METTL3 on target mRNA translation. A selection of this large group of mRNAs was validated that are less efficiently translated in METTL3-depleted cells. Considering, the emerging relevance of METTL3 in various human malignancies, the follow up studies were focused on one of the newly identified METTL3 target genes, BRD4, a member of bromodomain (BRD) and extra-terminal domain (BET) family, that itself has been shown to play an important role in the transcriptional regulation of growth-associated genes and has profound effects on cell proliferation and apoptosis[59]. It was shown that METTL3 depletion reduced the expression of BRD4, and makes cells more sensitive to the BRD4 inhibitor JQ1 in cell proliferation and apoptosis assays. Considering also the findings that 1) METTL3 protein expression is increased in advanced stages of lung cancer, 2) METTL3 depletion can suppress tumor progression in mouse xenograft assays and METTL3 WT overexpression promoted in vivo tumor growth whereas METTL3 A155P showed impaired effect in mouse xenograft assays, 3) METTL3 WT overexpression increased invasive ability of cells whereas knockdown of eIF3h or overexpression of METTL3 mutants diminished the invasive ability, and 4) METTL3 overexpression in NIH-3T3, MEFs, or MB352 cells promoted oncogenic transformation whereas METTL3 A155P did not, indicating that METTL3 is a promising cancer therapeutic target. Indeed, the very first $m^6A$ profiling of any primary tumor type is provided herein and the results from meRIP-seq analysis in lung tumors support that several important oncogenes including EGFR and BRD4 are enriched for $m^6A$ modification with a peak distribution comparable to that observed in lung cancer cell lines. Taken together, the results provide strong evidence that METTL3 promotes translation through an interaction with eIF3h and mRNA looping, and contributes to tumorigenesis by promoting oncogene expression, cell proliferation, and inhibiting apoptosis.

Methods

Cell Culture and Transfection

Human lung cancer cell lines (A549 and H1299), HEK293T, BJ, NIH-3T3, HeLa, MEFs, or p53 null MEFs (MB352) cells were cultured with DMEM supplemented with 10% fetal bovine serum (FBS) and antibiotics. Cells were grown in a 5% $CO_2$ cell culture incubator at 37° C. Transfection of plasmids was performed using Lipofectamine 2000 (Invitrogen) according to the manufacturer's instructions. Down regulation of target genes by siRNA was performed using Lipofectamine RNAi Max (Invitrogen). The following siRNA sequences were used in this study: 5'-r(GAUAGAUGGCCUUGUGGUA)(UU)-3' (SEQ ID NO: 10) for eIF3h-1; 5'-r(GCGGAGCCUUCGCCAUGUA)(UU)-3' (SEQ ID NO: 11) for eIF3h-2; 5'-r(UGAGAAAGGAGGAGAGGAA)d(TT)-3' (SEQ ID NO: 12) for eIF4GI; 5'-r(UCAACCUCUUUACGGAUUU)d(TT)-3' (SEQ ID NO: 13) for eIF3b; and 5'-r(GCAUCAAC-CUGAAUGACAU)(UU)-3' (SEQ ID NO: 14) for CTIF.

Virus Production and Generation of Stable Knockdown and Over-Expression Cells

Virus mediated generation of stable knockdown and over-expression cells were was performed as described previously[8]. Briefly, shRNA containing pLKO.1 vector was co-transfected with pLP1, pLP2, and VSVG into 293T cells. For over-expression, pCDH vectors containing the METTL3 WT and A155 P cDNA were co-transfected with Delta 8.9 and VSVG plasmids into 293T cells. Viruses were collected at 48 hr and 72 hr after transfection and then used to infect cells with Polybrene (8 mg/ml, Sigma); 48 hr after infection, puromycin was added to the culture medium to select the infected cells.

Plasmid Construction pFLAG-METTL3 WT, pFLAG-MS2-METTL3 and pFLAG-MS2-METTL3 Mut, were described previously[8]. pFLAG-METTL3 A155P plasmids was generated by inducing point mutation in pFLAG-METTL3 WT using Q5® Site-Directed Mutagenesis Kit (NEB E0554). Plasmids pFLAG-MS2-METTL3 (1-100), pFLAG-MS2-METTL3 (1-150), pFLAG-MS2-METTL3 (1-200), pFLAG-MS2-METTL3 (1-350) and pFLAG-MS2-METTL3 (101-580) was constructed by substitution of PCR amplified each METTL3 fragment into NotI-METTL3 WT-BglII site of pFLAG-MS2-METTL3. For stable METTL3 over-expression, METTL3 WT and A155P sequence were PCR amplified and cloned into the NheI and NotI sites of pCDH-CMV-MCS-EF1-Puro plasmid. For expression of recombinant METTL3 proteins, METTL3 full length and N-terminal amino acids 1-200 cDNA were cloned into the pETDuet-1 and pET His6 GST TEV LIC cloning vector individually. For expression of recombinant METTL3 proteins for in vitro translation, FLAG-MS2, FLAG-MS2-METTL3 (1-200), FLAG-MS2-METTL3, FLAG-MS2-METTL3 A155P were cloned into pETDuet-1. For bacteria protein expression of human eIF3h, eIF3j and eIF3m that express N-terminal GST-fused proteins, BamHI/EcoRI fragment of pGEX2TK vector was ligated to the PCR amplified BamHI/EcoRI fragment that contained either eIF3h, eIF3j, or eIF3m. In addition, for the pGEX2TK-eIF3g or -eIF3i, BglII/EcoRI fragment of pGEX2TK vector was ligated to the PCR amplified BglII/EcoRI fragment that contained either eIF3g or eIF3i, respectively. For bacteria expression of eIF3h deletion mutants were generated by ligation of BamHI/EcoRI fragment of pGEX2TK vector with BamHI/EcoRI fragment of either PCR amplified eIF3h (1-222) or eIF3h (29-222). The pGL3c_TK luciferase reporter (FLuc) and pGL3c_TK luciferase reporter containing 2× MS2 binding sites near the stop codon (FLuc-MS2bs) were described previously[8]. The 2× MS2 binding site sequence was PCR amplified from FLuc-MS2bs and inserted into the NcoI site of pGL3c_TK luciferase reporter to make the FLuc-5'UTR-MS2bs reporter that the MS2 binding sites are located in the 5'UTR region of luciferase gene. The 2× MS2 binding site sequence and GFP sequence (from CAG-GFP, Addgene Plasmid #16664) were cloned into the XbaI site of pGL3c_TK luciferase reporter (FLuc) to make the FLuc-MS2bs-GFP and FLuc-GFP-MS2bs reporters. For pFLAG-tethering effector plasmids, METTL3 shRNA resistance plasmids were generated by introducing synonymous mutations in the shRNA targeting sequence using the Q5® Site-Directed Mutagenesis Kit (NEB E0554). All cloning primers are listed in Table 51.

TABLE 1

List of primers for cloning

| Cloning primer | | SEQ ID NO: |
|---|---|---|
| NotI-METTL3 (1-100)-F | ATAAGAATGCGGCCGCGTCGGACACGTG GAGCTCTATCCAGGC | 15 |
| BglII-METTL3 (1-100)-R | GAAGATCTAGATGGACACAGCATCAGTG GGCAATG | 16 |
| NotI-METTL3 (1-150)-F | ATAAGAATGCGGCCGCGTCGGACACGTG GAGCTCTATCCAGGC | 17 |
| BglII-METTL3 (1-150)-R | GAAGATCTAATGGTCAGCATAGGTTACA AGAGTAG | 18 |
| NotI-METTL3 (1-200)-F | AACAAGCGGCCGCGTCGGACACGTGGAG CTCTAT | 19 |
| BglII-METTL3 (1-200)-R | AACAAAGATCTTAAGAGTTCAGACCAGA GACTAACGAAC | 20 |
| NotI-METTL3 (1-350)-F | AACAAGCGGCCGCGTCGGACACGTGGAG CTCTAT | 21 |
| BglII-METTL3 (1-350)-R | AACAAAGATCTTAGCTTGGCGTGTGGTCT TT | 22 |
| NotI-METTL3 (101-580)-F | ATAAGAATGCGGCCGCGTGTCTTGCCATC TCCACGCCAGATGC | 23 |
| BglII-METTL3 (101-580)-R | GAAGATCTCTATAAATTCTTAGGTTTAGA GATGATACCATCTGGGTACC | 24 |
| SalI-METTL3-F for His-METTL3 | ACGCGTCGACTCGGACACGTGGAGCTCTA TC | 25 |

TABLE 1-continued

| List of primers for cloning | | |
|---|---|---|
| Cloning primer | | SEQ ID NO: |
| NotI-METTL3-R for His-METTL3 | ATAAGAATGCGGCCGCCTATAAATTCTTAGGTTTAGAGATGATACCAT | 26 |
| NheI-METTL3-F for pCDH-METTL3 | GTCATGCTAGCGCCACCATGTCGGACACGTGGAGCTCTATCC | 27 |
| NotI-METTL3-R for pCDH-METTL3 | AACAAGCGGCCGCCTATAAATTCTTAGGTTTAG | 28 |
| METTL3 (1-200)-F for His-METTL3 (1-200) | TACTTCCAATCCAATGCA ATGTCGGACACGTGGAGCTC | 29 |
| METTL3 (1-200)-R for His-METTL3 (1-200) | TTATCCACTTCCAATGTTATTAGTTCAGACCAGAGACTAACGAAC | 30 |
| BglII-eIF3g-F | GGAAGATCTCCTACTGGAGACTTTGATTCGAAGCC | 31 |
| EcoRI-eIF3g-R | CCGGAATTCTTAGTTGGTGGACGGCTTGGCCCACTC | 32 |
| BamHI-eIF3h-F | CGCGGATCCGCGTCCCGCAAGGAAGGTACCGGCTC | 33 |
| EcoRI-eIF3h-R | CCGGAATTCTTAGTTGTTGTATTCTTGAAGAGCCTG | 34 |
| BamHI-eIF3m-F | CGCGGATCCAGCGTCCCGGCCTTCATCGACATCAG | 35 |
| EcoRI-eIFm-R | CCGGAATTCTCAGGTATCAGAAAGACTCAAAAGGCTG | 36 |
| BglII-eIF3i-F | GGAAGATCTAAGCCGATCCTACTGCAGGGCCATG | 37 |
| EcoRI-eIF3i-R | CCGGAATTCTTAAGCCTCAAACTCAAATTCGAAGTAC | 38 |
| BamHI-eIF3j-F | CGCGGATCCCACGCTCACACCCGGCTCGAGATG | 39 |
| EcoRI-eIF3j-R | CCGGAATTCTCACATGAAGTCTTCATAGTCTTGTAC | 40 |
| BamHI-eIF3h (1-222)-F | CGCGGATCCGCGTCCCGCAAGGAAGGTACCGGCTC | 41 |
| EcoRI-eIF3h (1-222)-R | CCGGAATTCTTATGACTTCTTTTCAAGTTCCCACATTAGG | 42 |
| BamHI-eIF3h (29-222)-F | CGCGGATCCGGCGGCTCGGGAGATTCAGCCGTGAAG | 43 |
| EcoRI-eIF3h (29-222)-R | CCGGAATTCTTATGACTTCTTTTCAAGTTCCCACATTAGG | 44 |
| NcoI-MS2bs-F for FLuc-5'UTR-MS2bs | CATGCCATGGCGCGTACACGATCACGGTAC | 45 |
| NcoI-MS2bs-R for FLuc-5'UTR-MS3bs | CATGCCATGGCCCCGGGAGCATGGGTGAT | 46 |
| XbaI-MS2bs-F for FLuc-MS2bs-GFP | CTAGTCTAGACGCGTACACGATCACGGTAC | 47 |
| EcoRI-MS2bs-R for FLuc-MS2bs-GFP | CCGGAATTCCCCCGGGAGCATGGGTGAT | 48 |
| EcoRI-GFP-F for FLuc-MS2bs-GFP | CCGGAATTCGTGAGCAAGGGCGAGGAGCT | 49 |
| XbaI-GFP-R for FLuc-MS2bs-GFP | CTAGTCTAGACTTGTACAGCTCGTCCATGC | 50 |

TABLE 1-continued

| List of primers for cloning | | |
|---|---|---|
| Cloning primer | | SEQ ID NO: |
| XbaI-GFP-F for FLuc GFP-MS2bs | CTAGTCTAGAGTGAGCAAGGGCGAGGAGCT | 51 |
| EcoRI-GFP-R for FLuc GFP-MS2bs | CCGGAATTCCTTGTACAGCTCGTCCATGC | 52 |
| EcoRI-MS2bs-F for FLuc GFP-MS2bs | CCGGAATTCCGCGTACACGATCACGGTAC | 53 |
| XbaI-MS2bs-R for FLuc GFP-MS2bs | CTAGTCTAGACCCCGGGAGCATGGGTGAT | 54 |
| METTL3 A155P-F | CAAGCTCTCTcccATGATGGGTG | 55 |
| METTL3 A155P-R | GAATGGTCAGCATAGGTTAC | 56 |
| METTL3$^R$-F | CATTACGAGATTGATGCTTGCATGGATTCTG | 57 |
| METTL3$^R$-R | TACGTATTTACAGGTATCCATGTGGAAACATG | 58 |
| SalI-CMV2-FLAG F for His-FLAG-MS2, His-FLAG-MS2-METTL3 or His-FLAG-METTL3 (1-200) | ACGCGTCGACGACTACAAAGACGATGACGACAAG | 59 |
| AflII-CMV2-FLAG R for His-FLAG-MS2, His-FLAG-MS2-METTL3 or His-FLAG-METTL3 (1-200) | ACGACTTAAGTTATGGTACCGATATCAGATCT | 60 |

In Vitro Translation Assay

H1299 cells were harvested and resuspended in hypotonic buffer [10 mM Hepes (pH 7.4), 10 mM potassium acetate, 1.5 mM magnesium acetate, and 2.5 mM DTT]. Cells were then incubated on ice for 30 min and ruptured by passing 10 times through a 25-gauge needle attached to a 3-mL syringe. The cell homogenate was centrifuged at 13,000×g for 15 min at 4° C. The supernatant was collected and used for in vitro translation. In vitro translation reactions were performed for 1 hour at 30° C. using either H1299 cytoplasmic cell extracts or rabbit reticulocyte lysate (RRL) (Thermo FisherScientific, AM1200) in 20 μL reaction mixtures containing 100 ng of in vitro transcribed reporter mRNAs and 500 ng of either purified recombinant His-FLAG-MS2, His-FLAG-MS2-METTL3 or His-FLAG-MS2-METTL3 (1-200) protein. The activity of in vitro-translated luciferase was measured by Luciferase assay kit (Promega, E1960) according to the manufacturer's instructions. Reporter mRNAs either presence or absence of poly (A) tails were in vitro transcribed using PCR amplified FLuc-MS2bs fragment with following primers; 5'-GACTAGTAATACGACTCACTATAGGGGCCACCATGGAAGACGCCAAAAACATAAA G-3' (SEQ ID NO: 61) (sense) and 5'-TCTAGACCCCGGGAGCATGGGTGAT-3' (SEQ ID NO: 62) (antisense) for the FLuc-MS2bs Poly (A)-mRNA, and 5'-GACTAGTAATACGACTCACTATAGGGGCCACCATGGAAGACGCCAAAAACATAAA G-3' (sense) (SEQ ID NO: 61) and 5'-TTTTTTTTTTTTTTTTTTTTTTTTTTTTTTTTCTAGACCCCGGGAGCATGGGTGAT-3' (SEQ ID NO: 63) (antisense) for the FLuc-MS2bs Poly $(A)^+$ mRNAs.

RNA Isolation and qRT-PCR

The details of RNA isolation and qRT-PCR assays are as described previously[8]. In brief, RNA was extracted from cells, co-immunoprecipitation or sucrose gradient fractionation samples using Trizol (Invitrogen) following the manufacturer's instructions. qRT-PCR analyses were performed using SYBR Green PCR Master Mix with the Step One Real-Time PCR System (AppliedBiosystems). All primers used in this study are listed in Table S2. For the analysis of global or individual mRNA lifetime, METTL3-depleted or control HeLa cells (60-mm culture dishes) were treated with Actinomycin D (5 μg/ml), then harvested at 0h, 2h, 4h, and 6h.

TABLE 2

| List of primers for qRT-PCR | | |
|---|---|---|
| Primer | Sequence | SEQ ID NO: |
| Firefly-luc-F | GGTACTGTTGGTAAAGCCAC | 64 |
| Firefly-luc-R | CTCTTCATAGCCTTATGCAG | 65 |
| Renilla-luc-F | CACTGGGCAGGTGTCCACTC | 66 |
| Renilla-luc-R | GTTCTGGATCATAAACTTTC | 67 |
| hBRD4-F | GACATGAGCACAATCAAGTC | 68 |
| hBRD4-R | GAACACATCCTGGAGCTTGC | 69 |
| hCD9-F | CTGAAAGCCATCCACTATGC | 70 |
| hCD9-R | GTCGAAGACCTCTTTGATGG | 71 |
| hMGMT-F | CGTTTGCGACTTGGTACTTG | 72 |

TABLE 2-continued

| List of primers for qRT-PCR | | |
|---|---|---|
| Primer | Sequence | SEQ ID NO: |
| hMGMT-R | GAGCTTTATTTCGTGCAGAC | 73 |
| hTIMP1-F | CTTCTGCAATTCCGACCTCG | 74 |
| hTIMP1-R | CATCCCCTAAGGCTTGGAAC | 75 |
| hTMED10-F | CCACTGAAGATTATGACATG | 76 |
| hTMED10-R | GCTCTACCTCTAATGGTTTG | 77 |
| hPSMD7-F | GAATGACATTGCCATCAACG | 78 |
| hPSMD7-R | GAGGTTGGAGTTCCATCATC | 79 |
| hSERPINE2-F | GCTTCAGCAGCAACAACTGC | 80 |
| hSERPINE2-R | CATGAATAACACAGCACCTG | 81 |
| hSLC7A1-F | GCTCACGGAGGAGGATTTTG | 82 |
| hSLC7A12-R | CGAAGGCATAGAAGCAAGTC | 83 |

Polysome Fractionation and RNA-Seq

METTL3-depleted or control HeLa cells (four 150-mm culture dishes) were treated with 100 μg/ml cycloheximide (Sigma) for 10 min at 37° C. Cells were then lysed and layered onto 10%-50% sucrose gradient tube and centrifuged at 36,000 rpm in a Beckman SW-41Ti rotor for 2.5 hr at 4° C. Gradients were fractionated and monitored at absorbance 254 nm (Brandel). Collected fractions were pulled into sub-polysome fraction and polysome fraction. Then, total RNA, sub-polysome and polysome samples were subjected to RNA-seq. Poly-A selected mRNAs were purified and used for library construction using TruSeq Stranded mRNA Sample Prep Kits (Illumina RS-122-2101) and sequenced with Illumina NextSeq 500. ERCC RNA Spike-In Control Mixes (Ambion) were added into each sample before constructing the library to normalize the reads.

Co-Immunoprecipitation, Mass Spectrometry, and Western Blot

Co-immunoprecipitation (co-IP) and western blot were performed as previously described[8,60]. Briefly, FLAG-METTL3 expressing HeLa or H1299 cells was harvested and lysed using NET-2 buffer [50 mM Tris-HCl (pH 7.4), 150 mM NaCl, 1 mM phenylmethanesulfonylfluoride, 2 mM benzamidine, 1% NP-40] then the supernatant was subjected to IP using Anti-Flag M2 Affinity Gel (Sigma-Aldrich). Where indicated, the affinity elute was subjected to SDS-PAGE followed by either Colloidal blue staining or Western blotting. Bands were excised and subjected to Mass spectrometric sequencing as previously described[61]. The following antibodies were used for Western blotting: METTL3 (Proteintech, 15073-1-AP; Abcam, ab195352), β-actin (Abcam, ab8227), eIF3h (Abcam, ab60942) CBP80[60], CTIF[60], eIF4E (Cell Signaling Technology, #2067), eIF3b (Santa Cruz Biotechnology, sc-16377), eIF4GI (Cell Signaling Technology, #2498), FLAG (Sigma, A8592), BRD4 (Abcam, ab128874), CD9 (Cell Signaling Technology, #13174), MGMT (Cell Signaling Technology, #2739), TIMP1 (Cell Signaling Technology, #8946) and FTO (Phosphosolution, 597-FTO).

Protein Expression, Purification, and GST Pull-Down Assay.

The recombinant protein induction and purification were performed as previously described[62]. Briefly, the plasmids expressing the recombinant proteins were transformed into BL21 *Escherichia coli* then the recombinant proteins were induced by IPTG at 20° C. overnight. The bacteria were pelleted and resuspended in protease inhibitor containing PBST buffer and then lysed by sonication. His-tag recombinant proteins were purified using Ni-NTA agarose (Qiagen 30210). The GST-tagged proteins were purified using the glutathione sepharose (BioVision 6655) following the manufacturer's protocol. For GST pull down assay, equal amount of GST fusion proteins or GST control bound to glutathione sepharose were incubated with purified recombinant His-tagged METTL3 full length or N-terminal (1-200) fragment for 1 hour at 4° C., after extensive washing, the proteins bound to the sepharose were resolved on SDS—polyacrylamide gels and detected by western blot analysis.

Far-Western Blotting

Far western blotting was performed as previously described[60]. Briefly, the purified human eIF3 protein complex was resolved by SDS-PAGE and then transferred to Hybond ECL nitrocellulose membrane. The membrane was first incubated in blocking buffer (100 mM Tris (pH 7.5), 100 mM potassium acetate, 2 mM magnesium acetate, 0.1 mM EDTA, 10% glycerol, 1 mM PMSF, 1 mM benzamidine, and 0.05% Tween 20, 5% non-fat milk) at 4° C. overnight, then the membrane was incubated with blocking buffer containing 5 μg of purified recombinant METTL3 full-length or METTL3 (1-200) proteins at 4° C. for another 24 hours. After that, the membrane was incubated with METTL3 antibody for Western blotting analysis.

Electron Microscopy

FLAG-METTL3 expressing H1299 cells were harvested and lysed using NET-2 buffer, then the supernatant was subjected to IP using Anti-Flag M2 Affinity Gel (Sigma-Aldrich). Resin-bound mRNP complexes were eluted using 3×FLAG peptides (Sigma, F3290). Where indicated, during the elution, α-METTL3 antibody (Proteintech, 15073-1-AP) and gold nanoparticle (6 nm) conjugated α-rabbit IgG were added with/without either α-CBP80 antibody or α-eIF4E antibody that was gold nanoparticle (10 nm) conjugated using GOLD conjugation kit (Abcam, ab201808) according to the manufacturer's instructions. The elutes were then fractionated using 10%-50% sucrose gradients. Each fraction was applied to an EM grid (EMS, G400-Cu) covered with a thin layer of carbon and after 1 min the excess suspension was sucked up with a filter paper. The grid was washed twice with water and 0.7% uranyl formate, and then negatively stained for 20 seconds with 0.7% uranyl formate. The specimens were examined in Tecnai G2 Spirit BioTWIN Transmission Electron Microscope (FEI company) with AMT 2k CCD camera equipped. Direct magnification of 68,000× was used to detect images in and S6a, whereas magnification of 98,000× was used to detect images from FIGS. 3B, 3D-3E, and 10H. Polysome numbers were counted using 20 individual pictures for each sample with direct magnification of 30,000× in FIG. 10F. All the images shown in the figures were cropped sections. The average distance between immuno-gold particles in FIG. 3F were measured from the images in FIGS. 2D-2E using the electron microscope software (AMT Capture engine). In vitro translation reactions were performed for 1 hour at 30° C. using RRL, and then the total reaction mixture was subjected to Illustra™ MicroSpin™ S-400 HR Columns (FIGS. 10F and 12A) or sucrose gradient fractionation (FIGS. 10G-10H). The elutes were then applied to an EM grid and analyzed by electron microscopy.

Cap-Association Assay Using $m^7$GTP-Agarose

To analyze the interaction of METTL3 to cap-binding protein complex, cells were lysed using NET2 buffer and total cell extracts were incubated with $m^7$GTP-Agarose (Jena Bioscience, AC-155S) for 2 hours at 4° C. Then, the beads were washed for five times and suspended in SDS sample buffer. The eluted samples were analyzed by Western blot. Where indicated, 75 μM of $m^7$G(5')ppp(5')G Cap Analog (Ambion, AM8048) was added into the sample and incubated with $m^7$GTP-Agarose.

Cell Proliferation and Apoptosis Assays

Cell proliferation and apoptosis assays were performed as described previously[8]. Briefly, for cell proliferation, 700 cells were seeded in a 96-well plate on day 0 with the pertinent treatment. 500 nM of JQ1 were used. Absorbances at 490 nm were measured using CellTiter 96 AQueous One Solution Cell Proliferation Assay kit (Promega) on day 2, day 4, and day 6 to measure the cellular proliferation. The numbers of apoptotic cells were quantified by flow cytometric assays using Annexin V-FITC Apoptosis Detection Kit (BioVision) five days after 500 nM of JQ1 treatment and cell seeding.

Soft Agar Colony Formation Assays

NIH-3T3 cells, MEFs, and MB352 cells at 30% confluence were infected with the lentivirus expressing indicated protein for 48 h in the presence of 8 μg/ml polybrene (Sigma). Two days after infection, puromycin was added to the media at 2.5 μg/ml, and cells were selected for 1 week. Selected 50,000 live NIH-3T3 cells, 100,000 live MEFs, or 100,000 live MB352 (p53 null MEFs) cells were mixed with 0.35% top-agar and were plated onto 0.6% base-agar in six-well plates. The cells were incubated for 4 weeks. The colony numbers were counted by openCFU.

In Situ Proximity Ligation Assay (PLA)

HeLa Cells were incubated with primary antibodies (rabbit α-METTL3 antibody and mouse α-eIF3h antibody) in blocking solution at 4° C. for 2 h. Cells were then washed for five times for 5 min in PBS plus 0.1% Tween 20. Then, cells were incubated with secondary proximity probes (α-Rabbit-PLUS and α-Mouse-MINUS) (Sigma, DU092101) for 90 min at 37° C. Cells were washed five times for 5 min in 10 mM Tris-HCl (pH 7.5) plus 0.1% Tween 20 at 37° C., then twice for 5 min in PBS plus 0.1% Tween 20. All subsequent steps were performed according to the manufacturer's instruction. Cells were observed with a Zeiss LSM 710 Multiphoton Laser Scanning Confocal.

Immunohistochemistry (IHC) Staining

The human lung cancer tumor array was purchased from Biomax (HLug-Ade150CS-01). Slide was baked for 60 minutes in an oven set to 60° C. and then loaded into the Bond III staining platform with appropriate labels. Antigen was retrieved by Bond Epitope Retrieval 2 for 20 minutes. Then the slide was incubated with METLL3 antibody (Abcam, ab195352) at 1:500 for 30 minutes at RT. Primary antibody was detected using Bond Polymer Refine Detection kit. Slides were developed in DAB then dehydrated and coverslipped. Each sample was score by the percentage of positive stained cells (percentage score: 1-5) and the staining intensity (intensity score: 1-5). Then the sample staining score was calculated by multiplying the percentage score and the intensity score.

In Vivo Tumor Xenograft

All research involving animals was complied with protocols approved by the Beth Israel Deaconess Medical Center Institutional Animal Care and Use Committee. 4-6 weeks old female NU/J (Nude) immunodeficient mice (Jackson Laboratory #002019) were used for subcutaneous injections. 100,000 A549 cells or 1,500,000 NIH-3T3 cells in serum-free medium and growth factor reduced Matrigel (Corning #354230) (1:1) were inoculated into the flank of nude mice. The xenograft tumor formation was monitored by calipers twice a week. The recipient mice were monitored and euthanized when the tumors reached 1 cm in diameter. The tumor volume was calculated by use of a formula ½ (length×width)[62].

$m^6$A MeRIP-Seq and Data Analysis $m^6$A MeRIP-Seq and data analysis were performed as previously described[8]. All the studies involving human patient samples were complied with protocols approved by Institutional Review Board (IRB). Portions of fresh tumor tissue approximately 0.5×0.5×0.5 cm were snap frozen and preserved at −80 C, pulverized in liquid nitrogen and stabilized in Trizol for total RNA isolation. Then the mRNA purification from total RNA was performed using PolyATtract mRNA Isolation Systems (Promega). 2 μg of the purified mRNA was fragmented and immunoprecipitated with α-$m^6$A antibody (Synaptic Systems, 202003). The purified RNA fragments from $m^6$A MeRIP were used for library construction using the TruSeq Stranded mRNA Sample Prep Kits (Illumina RS-122-2101) and sequenced with Illumina NextSeq 500. Reads mapping, peak calling, metagene analysis and motif search were performed as previously described[8]. To identify the alternative splicing events, all the clean RNA-Seq reads of control and METTL3 knockdown samples were firstly trimmed to same length with 72 bp, which were then alighted against the human hg19 (GRCh37) reference genome using Tophat2[63]. rMATS v3.2.5[64] was used to detect the splicing events and significant splicing differences between METTL3 knockdown and control samples. To analyze the global profiling of mRNA lifetime, the clean reads were aligned to human reference genome (hg19) using Tophat2[63] after trimming the adapters and filtering low quality sequences from the raw data. The reads mapped to each gene were counted using HTSeq[65] based on the GENCODE gene model (v19)[66]. The raw counts were then normalized as Reads per kilobase per million mapped reads (RPKM). ERCC RNA Spike-In Control Mixes (Ambion) were added into each sample before constructing the library to normalize the reads. mRNA lifetime was calculated according to the method in the previous study[26]. To analyze METTL3 or eIF3h expression level among TCGA tumors, RNA-Seq data for 33 TCGA tumor types were downloaded from Genomic Data Commons Data Portal (GDC) of TCGA (cancergenome.nih.gov/) using R package TCGAbiolinks[67]. The expression matrix was then constructed by merging the TPM (Transcripts Per Million) values of all downloaded RNA-seq samples. The tumor types without corresponding normal tissue samples were excluded and the retained 24 tumor types with normal tissues were used to draw the boxplot of gene expression. p-values are calculated by Wilcoxon rank-sum test, with asterisks indicating statistical significance. Script and code used for data analysis can be found at github.com/rnabioinfor/rnamethy.

Statistical Analysis

Data are presented as the mean±SEM or mean±SD. Statistical significance was determined by a Student's two-tailed t-test for qRT-PCRs and Luciferase assays. Where it is applicable, Shapiro-Wilk test and Q-Q plotting (quantile-quantile plot,) were performed prior to Student's two-tailed t-test to assess if the data plausibly came from a normal distribution. Where indicated, Wilcoxon signed-rank test was used. P<0.05 was considered statistically significant.

REFERENCES

1. Gilbert, W. V., Bell, T. A. & Schaening, C. Messenger RNA modifications: Form, distribution, and function. Science 352, 1408-1412, doi:10.1126/science.aad8711 (2016).
2. Liu, J. et al. A METTL3-METTL14 complex mediates mammalian nuclear RNA N6-adenosine methylation. Nat Chem Biol 10, 93-95, doi:10.1038/nchembio.1432 (2014).
3. Ping, X. L. et al. Mammalian WTAP is a regulatory subunit of the RNA N6-methyladenosine methyltransferase. Cell Res 24, 177-189, doi:10.1038/cr.2014.3 (2014).
4. Sledz, P. & Jinek, M. Structural insights into the molecular mechanism of the m(6)A writer complex. Elife 5, doi:10.7554/eLife.18434 (2016).
5. Wang, P., Doxtader, K. A. & Nam, Y. Structural Basis for Cooperative Function of Mett13 and Mett114 Methyltransferases. Molecular cell 63, 306-317, doi:10.1016/j.molcel.2016.05.041 (2016).
6. Wang, X. et al. Structural basis of N(6)-adenosine methylation by the METTL3-METTL14 complex. Nature 534, 575-578, doi:10.1038/nature18298 (2016).
7. Dominissini, D. et al. Topology of the human and mouse m6A RNA methylomes revealed by m6A-seq. Nature 485, 201-206, doi:nature11112 [pii]10.1038/nature11112 (2012).
8. Lin, S., Choe, J., Du, P., Triboulet, R. & Gregory, R. I. The m(6)A Methyltransferase METTL3 Promotes Translation in Human Cancer Cells. Molecular cell 62, 335-345, doi:10.1016/j.molcel.2016.03.021 (2016).
9. Meyer, K. D. et al. Comprehensive analysis of mRNA methylation reveals enrichment in 3' UTRs and near stop codons. Cell 149, 1635-1646, doi:S0092-8674(12)00536-3 [pii]10.1016/j.cell.2012.05.003 (2012).
10. Zheng, G. et al. ALKBH5 is a mammalian RNA demethylase that impacts RNA metabolism and mouse fertility. Mol Cell 49, 18-29, doi:10.1016/j.molcel.2012.10.015 (2013).
11. Jia, G. et al. N6methyladenosine in nuclear RNA is a major substrate of the obesity-associated FTO. Nat Chem Biol 7, 885-887, doi:nchembio.687 [pii]10.1038/nchembio.687 (2011).
12. Mauer, J. et al. Reversible methylation of m6Am in the 5' cap controls mRNA stability. Nature 541, 371-375, doi:10.1038/nature21022 (2017).

Schwartz, S. et al. High resolution mapping reveals a conserved, widespread, dynamic mRNA methylation program in yeast meiosis. Cell 155, 1409-1421, doi:10.1016/j.cell.2013.10.047 (2013).

13. Shen, L. et al. N(6)-Methyladenosine RNA Modification Regulates Shoot Stem Cell Fate in *Arabidopsis*. Developmental cell 38, 186-200, doi:10.1016/j.devcel.2016.06.008 (2016).
14. Fustin, J. M. et al. RNA-methylation-dependent RNA processing controls the speed of the circadian clock. Cell 155, 793-806, doi:10.1016/j.cell.2013.10.026 (2013).
15. Xiang, Y. et al. RNA m6A methylation regulates the ultraviolet-induced DNA damage response. Nature 543, 573-576, doi:10.1038/nature21671 (2017).
16. Geula, S. et al. Stem cells. m6A mRNA methylation facilitates resolution of naive pluripotency toward differentiation. Science 347, 1002-1006, doi:10.1126/science.1261417 (2015).
17. Batista, P. J. et al. m(6)A RNA modification controls cell fate transition in mammalian embryonic stem cells. Cell Stem Cell 15, 707-719, doi:10.1016/j.stem.2014.09.019 (2014).
18. Wang, Y. et al. N6-methyladenosine modification destabilizes developmental regulators in embryonic stem cells. Nat Cell Biol 16, 191-198, doi:10.1038/ncb2902 (2014).
19. Patil, D. P. et al. m(6)A RNA methylation promotes XIST-mediated transcriptional repression. Nature 537, 369-373, doi:10.1038/nature19342 (2016).
20. Haussmann, I. U. et al. m6A potentiates Sxl alternative pre-mRNA splicing for robust *Drosophila* sex determination. Nature 540, 301-304, doi:10.1038/nature20577 (2016).
21. Lence, T. et al. m6A modulates neuronal functions and sex determination in *Drosophila*. Nature 540, 242-247, doi:10.1038/nature20568 (2016).
22. Li, Z. et al. FTO Plays an Oncogenic Role in Acute Myeloid Leukemia as a N6-Methyladenosine RNA Demethylase. Cancer Cell 31, 127-141, doi:10.1016/j.ccell.2016.11.017 (2017).
23. Zhang, S. et al. m6A Demethylase ALKBH5 Maintains Tumorigenicity of Glioblastoma Stem-like Cells by Sustaining FOXM1 Expression and Cell Proliferation Program. Cancer Cell 31, 591-606 e596, doi:10.1016/j.ccell.2017.02.013 (2017).
24. Cui, Q. et al. m6A RNA Methylation Regulates the Self-Renewal and Tumorigenesis of Glioblastoma Stem Cells. Cell Rep 18, 2622-2634, doi:10.1016/j.celrep.2017.02.059 (2017).
25. Wang, X. et al. N6-methyladenosine-dependent regulation of messenger RNA stability. Nature 505, 117-120, doi:10.1038/nature12730 (2014).
26. Zhou, J. et al. Dynamic m(6)A mRNA methylation directs translational control of heat shock response. Nature 526, 591-594, doi:10.1038/nature15377 (2015).
27. Meyer, K. D. et al. 5' UTR m(6)A Promotes Cap-Independent Translation.

Cell 163, 999-1010, doi:10.1016/j.cell.2015.10.012 (2015).

28. Meyer, K. D. & Jaffrey, S. R. The dynamic epitranscriptome: N6-methyladenosine and gene expression control. Nat Rev Mol Cell Biol 15, 313-326, doi:10.1038/nrm3785 (2014).
29. Wang, X. et al. N(6)-methyladenosine Modulates Messenger RNA Translation Efficiency. Cell 161, 1388-1399, doi:10.1016/j.cell.2015.05.014 (2015).
30. Xu, C. et al. Structural basis for selective binding of m6A RNA by the YTHDC1 YTH domain. Nat Chem Biol 10, 927-929, doi:10.1038/nchembio.1654 (2014).
31. Zhu, T. et al. Crystal structure of the YTH domain of YTHDF2 reveals mechanism for recognition of N6-methyladenosine. Cell Res 24, 1493-1496, doi:10.1038/cr.2014.152 (2014).
32. Li, F., Zhao, D., Wu, J. & Shi, Y. Structure of the YTH domain of human YTHDF2 in complex with an m(6)A mononucleotide reveals an aromatic cage for m(6)A recognition. Cell Res 24, 1490-1492, doi:10.1038/cr.2014.153 (2014).
33. Beznoskova, P. et al. Translation initiation factors eIF3 and HCR1 control translation termination and stop codon read-through in yeast cells. PLoS Genet 9, e1003962, doi:10.1371/journal.pgen.1003962 (2013).
34. Pisarev, A. V., Hellen, C. U. & Pestova, T. V. Recycling of eukaryotic posttermination ribosomal complexes. Cell 131, 286-299, doi:10.1016/j.cell.2007.08.041 (2007).

35. Hershey, J. W. The role of eIF3 and its individual subunits in cancer. Biochim Biophys Acta 1849, 792-800, doi:10.1016/j.bbagrm.2014.10.005 (2015).
36. des Georges, A. et al. Structure of mammalian eIF3 in the context of the 43S preinitiation complex. Nature 525, 491-495, doi:10.1038/nature14891 (2015).
37. Lee, A. S., Kranzusch, P. J., Doudna, J. A. & Cate, J. H. eIF3d is an mRNA cap-binding protein that is required for specialized translation initiation. Nature 536, 96-99, doi:10.1038/nature18954 (2016).
38. Wagner, S., Herrmannova, A., Sikrova, D. & Valasek, L. S. Human eIF3b and eIF3a serve as the nucleation core for the assembly of eIF3 into two interconnected modules: the yeast-like core and the octamer. Nucleic Acids Res 44, 10772-10788, doi:10.1093/nar/gkw972 (2016).
39. Lee, A. S., Kranzusch, P. J. & Cate, J. H. eIF3 targets cell-proliferation messenger RNAs for translational activation or repression. Nature 522, 111-114, doi:10.1038/nature14267 (2015).
40. Imataka, H., Gradi, A. & Sonenberg, N. A newly identified N-terminal amino acid sequence of human eIF4G binds poly(A)-binding protein and functions in poly(A)-dependent translation. Embo J 17, 7480-7489, doi:10.1093/emboj/17.24.7480 (1998).
41. Wells, S. E., Hillner, P. E., Vale, R. D. & Sachs, A. B. Circularization of mRNA by eukaryotic translation initiation factors. Molecular cell 2, 135-140 (1998).
42. Borman, A. M., Michel, Y. M., Malnou, C. E. & Kean, K. M. Free poly(A) stimulates capped mRNA translation in vitro through the eIF4G-poly(A)-binding protein interaction. J Biol Chem 277, 36818-36824, doi:10.1074/jbc.M205065200 (2002).
43. Tarun, S. Z., Jr. & Sachs, A. B. Association of the yeast poly(A) tail binding protein with translation initiation factor eIF-4G. The EMBO journal 15, 7168-7177 (1996).
44. Ashkenazy, H. et al. ConSurf 2016: an improved methodology to estimate and visualize evolutionary conservation in macromolecules. Nucleic Acids Res 44, W344-350, doi:10.1093/nar/gkw408 (2016).
45. Kouza, M., Faraggi, E., Kolinski, A. & Kloczkowski, A. The GOR Method of Protein Secondary Structure Prediction and Its Application as a Protein Aggregation Prediction Tool. Methods Mol Biol 1484, 7-24, doi:10.1007/978-1-4939-6406-2_2 (2017).
46. Kelley, L. A., Mezulis, S., Yates, C. M., Wass, M. N. & Sternberg, M. J. The Phyre2 web portal for protein modeling, prediction and analysis. Nat Protoc 10, 845-858, doi:10.1038/nprot.2015.053 (2015).
47. Christensen, A. K., Kahn, L. E. & Bourne, C. M. Circular polysomes predominate on the rough endoplasmic reticulum of somatotropes and mammotropes in the rat anterior pituitary. The American journal of anatomy 178, 1-10, doi:10.1002/aja.1001780102 (1987).
48. Zhang, L., Pan, X. & Hershey, J. W. Individual overexpression of five subunits of human translation initiation factor eIF3 promotes malignant transformation of immortal fibroblast cells. J Biol Chem 282, 5790-5800, doi:10.1074/jbc.M606284200 (2007).
49. Mahmood, S. F. et al. A siRNA screen identifies RAD21, EIF3H, CHRAC1 and TANC2 as driver genes within the 8q23, 8q24.3 and 17q23 amplicons in breast cancer with effects on cell growth, survival and transformation. Carcinogenesis 35, 670-682, doi:10.1093/carcin/bgt351 (2014).
50. Zhang, L., Smit-McBride, Z., Pan, X., Rheinhardt, J. & Hershey, J. W. An oncogenic role for the phosphorylated h-subunit of human translation initiation factor eIF3. J Biol Chem 283, 24047-24060, doi:10.1074/jbc.M800956200 (2008).
51. Chen, M. et al. RNA N6-methyladenosine methyltransferase METTL3 promotes liver cancer progression through YTHDF2 dependent post-transcriptional silencing of SOCS2. Hepatology, doi:10.1002/hep.29683 (2017).
52. Barbieri, I. et al. Promoter-bound METTL3 maintains myeloid leukaemia by m(6)A-dependent translation control. Nature 552, 126-131, doi:10.1038/nature24678 (2017).
53. Taketo, K. et al. The epitranscriptome m6A writer METTL3 promotes chemo- and radioresistance in pancreatic cancer cells. Int J Oncol 52, 621-629, doi:10.3892/ijo.2017.4219 (2018).
54. Deng, X., Su, R., Feng, X., Wei, M. & Chen, J. Role of N(6)-methyladenosine modification in cancer. Curr Opin Genet Dev 48, 1-7, doi:10.1016/j.gde.2017.10.005 (2017).
55. Vu, L. P. et al. The N(6)-methyladenosine (m(6)A)-forming enzyme METTL3 controls myeloid differentiation of normal hematopoietic and leukemia cells. Nat Med 23, 1369-1376, doi:10.1038/nm.4416 (2017).
56. Visvanathan, A. et al. Essential role of METTL3-mediated m6A modification in glioma stem-like cells maintenance and radioresistance. Oncogene, doi:10.1038/onc.2017.351 (2017).
57. Lin, S., Choe, J., Du, P., Triboulet, R. & Gregory, R. I. The m(6)A Methyltransferase METTL3 Promotes Translation in Human Cancer Cells. Mol Cell 62, 335-345, doi:10.1016/j.molcel.2016.03.021 (2016).
58. Belkina, A. C. & Denis, G. V. BET domain co-regulators in obesity, inflammation and cancer. Nature reviews. Cancer 12, 465-477, doi:10.1038/nrc3256 (2012).
59. Choe, J. et al. Translation initiation on mRNAs bound by nuclear cap-binding protein complex CBP80/20 requires interaction between CBP80/20-dependent translation initiation factor and eukaryotic translation initiation factor 3g. J Biol Chem 287, 18500-18509, doi:10.1074/jbc.M111.327528 (2012).
60. Chang, H. M., Triboulet, R., Thornton, J. E. & Gregory, R. I. A role for the Perlman syndrome exonuclease Dis312 in the Lin28-let-7 pathway. Nature 497, 244-248, doi:10.1038/nature12119 (2013).
61. Lin, S. et al. DDX5 is a positive regulator of oncogenic NOTCH1 signaling in T cell acute lymphoblastic leukemia. Oncogene 32, 4845-4853, doi:10.1038/onc.2012.482 (2013).
62. Kim, D. et al. TopHat2: accurate alignment of transcriptomes in the presence of insertions, deletions and gene fusions. Genome Biol 14, R36, doi:10.1186/gb-2013-14-4-r36 (2013).
63. Shen, S. et al. rMATS: robust and flexible detection of differential alternative splicing from replicate RNA-Seq data. Proc Natl Acad Sci USA 111, E5593-5601, doi:10.1073/pnas.1419161111 (2014).
64. Harrow, J. et al. GENCODE: the reference human genome annotation for The ENCODE Project. Genome Res 22, 1760-1774, doi:10.1101/gr.135350.111 (2012).
65. Anders, S., Pyl, P. T. & Huber, W. HTSeq-a Python framework to work with high-throughput sequencing data. Bioinformatics 31, 166-169, doi:10.1093/bioinformatics/btu638 (2015).
66. Colaprico, A. et al. TCGAbiolinks: an R/Bioconductor package for integrative analysis of TCGA data. Nucleic Acids Res 44, e71, doi:10.1093/nar/gkv1507 (2016).

All publications, patents, patent applications, publication, and database entries (e.g., sequence database entries) mentioned herein, e.g., in the Background, Summary, Detailed Description, Examples, and/or References sections, are hereby incorporated by reference in their entirety as if each individual publication, patent, patent application, publication, and database entry was specifically and individually incorporated herein by reference. In case of conflict, the present application, including any definitions herein, will control.

EQUIVALENTS AND SCOPE

Those skilled in the art will recognize, or be able to ascertain using no more than routine experimentation, many equivalents of the embodiments described herein. The scope of the present disclosure is not intended to be limited to the above description, but rather is as set forth in the appended claims.

Articles such as “a,” “an,” and “the” may mean one or more than one unless indicated to the contrary or otherwise evident from the context. Claims or descriptions that include “or” between two or more members of a group are considered satisfied if one, more than one, or all of the group members are present, unless indicated to the contrary or otherwise evident from the context. The disclosure of a group that includes “or” between two or more group members provides embodiments in which exactly one member of the group is present, embodiments in which more than one members of the group are present, and embodiments in which all of the group members are present. For purposes of brevity those embodiments have not been individually spelled out herein, but it will be understood that each of these embodiments is provided herein and may be specifically claimed or disclaimed.

It is to be understood that the disclosure encompasses all variations, combinations, and permutations in which one or more limitation, element, clause, or descriptive term, from one or more of the claims or from one or more relevant portion of the description, is introduced into another claim. For example, a claim that is dependent on another claim can be modified to include one or more of the limitations found in any other claim that is dependent on the same base claim. Furthermore, where the claims recite a composition, it is to be understood that methods of making or using the composition according to any of the methods of making or using disclosed herein or according to methods known in the art, if any, are included, unless otherwise indicated or unless it would be evident to one of ordinary skill in the art that a contradiction or inconsistency would arise.

Where elements are presented as lists, e.g., in Markush group format, it is to be understood that every possible subgroup of the elements is also disclosed, and that any element or subgroup of elements can be removed from the group. It is also noted that the term “comprising” is intended to be open and permits the inclusion of additional elements or steps. It should be understood that, in general, where an embodiment, product, or method is referred to as comprising particular elements, features, or steps, embodiments, products, or methods that consist, or consist essentially of, such elements, features, or steps, are provided as well. For purposes of brevity those embodiments have not been individually spelled out herein, but it will be understood that each of these embodiments is provided herein and may be specifically claimed or disclaimed.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in some embodiments, to the tenth of the unit of the lower limit of the range, unless the context clearly dictates otherwise. For purposes of brevity, the values in each range have not been individually spelled out herein, but it will be understood that each of these values is provided herein and may be specifically claimed or disclaimed. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

Where websites are provided, URL addresses are provided as non-browser-executable codes, with periods of the respective web address in parentheses. The actual web addresses do not contain the parentheses.

In addition, it is to be understood that any particular embodiment of the present disclosure may be explicitly excluded from any one or more of the claims. Where ranges are given, any value within the range may explicitly be excluded from any one or more of the claims. Any embodiment, element, feature, application, or aspect of the compositions and/or methods of the disclosure, can be excluded from any one or more claims. For purposes of brevity, all of the embodiments in which one or more elements, features, purposes, or aspects is excluded are not set forth explicitly herein.

What is claimed is:

1. A method of treating cancer, the method comprising administering to a subject in need thereof an effective amount of an agent that inhibits interaction between Methyltransferase like 3 (METTL3) and Eukaryotic Translation Initiation Factor 3 Subunit H (EIF3h).

2. The method of claim 1, wherein the agent inhibits METTL3 expression or EIF3 h expression.

3. The method of claim 2, wherein the agent comprises a RNAi molecule that targets METTL3 mRNA or EIF3 h mRNA.

4. The method of claim 1, wherein the agent inhibits binding of METTL3 to EIF3h.

5. The method of claim 1, wherein the agent is an inhibitory peptide, a small molecule, or an antibody.

6. The method of claim 5, wherein the inhibitory peptide comprises an amino acid sequence corresponding to amino acids 150-200 of METTL3 or amino acids 29-222 of EIF3h.

7. The method of claim 5, wherein the antibody binds to amino acids 150-200 of METTL3 or amino acids 29-222 of EIF3h.

8. The method of claim 1, wherein the agent inhibits METTL3 activity.

9. The method of claim 1, further comprising administering to the subject an effective amount of a second agent that inhibits Bromodomain-containing protein 4 (BRD4).

10. The method of claim 9, wherein the second agent inhibits BRD4 expression.

11. The method of claim 10, wherein the second agent comprises a RNAi molecule that targets BRD4 mRNA.

12. The method of claim 9, wherein the second agent inhibits BRD4 activity.

13. The method of claim 12, wherein the second agent is selected from the group consisting of JQ1, I-BET762, OTX015, I-BET151, CPI203, PFI-1, MS436, CPI-0610, RVX2135, FT-1101, BAY1238097, INCB054329, TEN-010, GSK2820151, ZEN003694, BAY-299, BMS-986158, ABBV-075, GS-5829, and PLX51107.

14. The method of claim 1, wherein the cancer is lung cancer, colon cancer, neuroblastoma, esophageal carcinoma, liver cancer, or prostate cancer.

15. The method of claim 9, wherein the agent or the second agent is administered systemically.

16. The method of claim 1, wherein the subject is human.

17. The method of claim 1, wherein the subject is a rodent, wherein the rodent is a mouse or a rat.

18. A composition comprising a first agent that inhibits interaction between Methyltransferase like 3 (METTL3) and Eukaryotic Translation Initiation Factor 3 Subunit H (EIF3h) and a second agent that inhibits BRD4.

19. The composition of claim 18, further comprising a pharmaceutically acceptable carrier.

* * * * *

SEQUENCE LISTING

```
<160> NUMBER OF SEQ ID NOS: 84

<210> SEQ ID NO 1
<211> LENGTH: 1980
<212> TYPE: DNA
<213> ORGANISM: Homo Sapiens

<400> SEQUENCE: 1

attttccggt tagccttcgg ggtgtccgcg tgagaattgg ctatatcctg gagcgagtgc      60

tgggaggtgc tagtccgccg cgccttattc gagaggtgtc agggctggga gactaggatg     120

tcggacacgt ggagctctat ccaggcccac aagaagcagc tggactctct gcgggagagg     180
```

```
ctgcagcgga ggcggaagca ggactcgggg cacttggatc tacggaatcc agaggcagca    240

ttgtctccaa ccttccgtag tgacagccca gtgcctactg cacccacctc tggtggccct    300

aagcccagca cagcttcagc agttcctgaa ttagctacag atcctgagtt agagaagaag    360

ttgctacacc acctctctga tctggcctta acattgccca ctgatgctgt gtccatctgt    420

cttgccatct ccacgccaga tgctcctgcc actcaagatg ggtagaaag cctcctgcag    480

aagtttgcag ctcaggagtt gattgaggta aagcgaggtc tcctacaaga tgatgcacat    540

cctactcttg taacctatgc tgaccattcc aagctctctg ccatgatggg tgctgtggca    600

gaaaagaagg gccctgggga ggtagcaggg actgtcacag ggcagaagcg gcgtgcagaa    660

caggactcga ctacagtagc tgcctttgcc agttcgttag tctctggtct gaactcttca    720

gcatcggaac cagcaaagga gccagccaag aaatcaagga aacatgctgc ctcagatgtt    780

gatctggaga tagagagcct tctgaaccaa cagtccacta aggaacaaca gagcaagaag    840

gtcagtcagg agatcctaga gctattaaat actacaacag ccaaggaaca atccattgtt    900

gaaaaatttc gctctcgagg tcgggcccaa gtgcaagaat tctgtgacta tggaaccaag    960

gaggagtgca tgaaagccag tgatgctgat cgaccctgtc gcaagctgca cttcagacga   1020

attatcaata aacacactga tgagtcttta ggtgactgct ctttccttaa tacatgtttc   1080

cacatggata cctgcaagta tgttcactat gaaattgatg cttgcatgga ttctgaggcc   1140

cctggcagca aagaccacac gccaagccag gagcttgctc ttacacagag tgtcggaggt   1200

gattccagtg cagaccgact cttcccacct cagtggatct gttgtgatat ccgctacctg   1260

gacgtcagta tcttgggcaa gtttgcagtt gtgatggctg acccaccctg ggatattcac   1320

atggaactgc cctatgggac cctgacagat gatgagatgc gcaggctcaa catacccgta   1380

ctacaggatg atggctttct cttcctctgg gtcacaggca gggccatgga gttggggaga   1440

gaatgtctaa acctctgggg gtatgaacgg gtagatgaaa ttatttgggt gaagacaaat   1500

caactgcaac gcatcattcg gacaggccgt acaggtcact ggttgaacca tgggaaggaa   1560

cactgcttgg ttggtgtcaa aggaaatccc caaggcttca accagggtct ggattgtgat   1620

gtgatcgtag ctgaggttcg ttccaccagt cataaaccag atgaaatcta tggcatgatt   1680

gaaagactat ctcctggcac tcgcaagatt gagttatttg gacgaccaca caatgtgcaa   1740

cccaactgga tcacccttgg aaaccaactg gatgggatcc acctactaga cccagatgtg   1800

gttgcacggt tcaagcaaag gtacccagat ggtatcatct ctaaacctaa gaatttatag   1860

aagcacttcc ttacagagct aagaatccat agccatggct ctgtaagcta aacctgaaga   1920

gtgatatttg tacaatagct ttcttcttta tttaaataaa catttgtatt gtagttggga   1980
```

<210> SEQ ID NO 2
<211> LENGTH: 3961
<212> TYPE: DNA
<213> ORGANISM: Homo Sapiens

<400> SEQUENCE: 2

```
ctctttcttc ctgtctgctt ggaaagatgg cgtcccgcaa ggaaggtacc ggctctactg     60

ccacctcttc cagctccacc gccggcgcag cagggaaagg caaaggcaaa ggcggctcgg    120

gagattcagc cgtgaagcaa gtgcagatag atggccttgt ggtattaaag ataatcaaac    180

attatcaaga agaaggacaa ggaactgaag ttgttcaagg agtgcttttg ggtctggttg    240

tagaagatcg gcttgaaatt accaactgct ttcctttccc tcagcacaca gaggatgatg    300

ctgactttga tgaagtccaa tatcagatgg aaatgatgcg gagccttcgc catgtaaaca    360
```

```
ttgatcatct tcacgtgggc tggtatcagt ccacatacta tggctcattc gttacccggg    420
cactcctgga ctctcagttt agttaccagc atgccattga agaatctgtc gttctcattt    480
atgatcccat aaaaactgcc caaggatctc tctcactaaa ggcatacaga ctgactccta    540
aactgatgga agtttgtaaa gaaaaggatt tttcccctga agcattgaaa aaagcaaata    600
tcacctttga gtacatgttt gaagaagtgc cgattgtaat taaaaattca catctgatca    660
atgtcctaat gtgggaactt gaaaagaagt cagctgttgc agataaacat gaattgctca    720
gccttgccag cagcaatcat ttggggaaga atctacagtt gctgatggac agagtggatg    780
aaatgagcca agatatagtt aaatacaaca catacatgag gaatactagt aaacaacagc    840
agcagaaaca tcagtatcag cagcgtcgcc agcaggagaa tatgcagcgc cagagccgag    900
gagaaccccc gctccctgag gaggacctgt ccaaactctt caaaccacca cagccgcctg    960
ccaggatgga ctcgctgctc attgcaggcc agataaacac ttactgccag aacatcaagg   1020
agttcactgc ccaaaactta ggcaagctct tcatggccca ggctcttcaa gaatacaaca   1080
actaagaaaa ggaagtttcc agaaaagaag ttaacatgaa ctcttgaagt cacaccaggg   1140
caactcttgg aagaaatata tttgcatatt gaaaagcaca gaggatttct ttagtgtcat   1200
tgccgatttt ggctataaca gtgtctttct agccataata aaataaaaca aaatcttgac   1260
tgcttgctca tttgatttta gatgtatttt ctctggctta cttttgtttg cttatacttg   1320
tttatttcta aaagctaaaa caagccctga ccggaagttt caccaggcag aaacctatag   1380
gctccaccac ttttgctgcc tctcaggtgc cacctttcaa cccacttctc ccaactactt   1440
atcccagctc ctgaccccga ggccctggca tctactgtga atattttttt tttgaatttt   1500
tatacttcgc tgctcccaaa tgagcacccc gagagaagtc caggcttcat gtacttgccc   1560
aggaattcct tgtccccgga cccggaatca cttggcctaa ttccggtcag tctgcctttt   1620
catttctgca ggtgatggtc aaccagtccc cgtactcata ggccatggga cacaagatta   1680
ttattatcat cattattttt aaagacagag tctcactttg ttgcccaggc tggagtgtag   1740
tggcacaatc tcagctcgct gcaacctcca ccttctgagt tcaagcgatt ctcccacctc   1800
agcctcccaa gtagctggga ctacaggcgt gtgccatcac gcctggctaa tttttgtatt   1860
tttagtagag atggggtttc accatgttgg ccaggctggt ctgcatctcc tgacctcaag   1920
tgattcacct gcttctgtct cccaaagtgc tgggaataca ggcatgagcc accactcctg   1980
gacaggccac agaaatttta aagaaaagaa tcatgccacc acaagtaaac ttcattttgt   2040
ttatattatt taggacttca catttgtctt ccgaaaccat gaagtataat tctgctaaca   2100
gcaagtgttg tgaatgagga attaggaatt aggagaatgg tagtacattg ggaaaaacat   2160
atttagtaa ttttatatt ttaaagataa tcacagattt tgctgtttgt gcatcaccaa    2220
aatcagtgag atctgccagc tggtgggggt gtgcctatga gaatttttga ttatgatccc   2280
ctaggagggt tatcaaaaaa ggagatgggt gaaagatcag gagagtcgag aaattcattt   2340
tttggacaac attgttttga aggcactact ggggctctgg gatcaggcag ccagattgaa   2400
acctggctcc tccttttcct aagttattta acctccctgt gcctcacttt ttgtcaacca   2460
gataagataa gaaatgagag caggtctgtt acctcacaag gtggctgtga gtgttgaaga   2520
cgtttgttgg gggtttgggt gaagcatgca aactctggtt ggtatgtggc agccactcag   2580
cctgtattta tgatgaggga ggcattctag gcaccccttc caggatgttg ggttgttggc   2640
tgggttttac tttaaaaagc tcagggccta gaacattcta gaatccaagt acttgctcac   2700
```

```
atatataatt atttctttag gataatcttt gatatagact tacgagtcaa agggtatgta   2760

aaatgtcagc ccttttacct gtattgccaa attgccttca aaagtttctg ctgttttgcc   2820

ctcctaccca tagtgataac cttaaattgg agtcaacaca aatttgagtg tgactgtgtt   2880

agacagaagg gatatattaa caggtaaaac tggccatggc ccctgccctt gtggagtata   2940

tgctctgttg gttcatttcc tctgcattct aattttctag acttgggatc ttattgtgga   3000

gttaaacaaa gcacccttaa agtagcaagc gagcaaaata aaagcaagga aaatcagttg   3060

gaacataact tatgtatttt ttaggattaa gagtaattta actgagtcaa ttcaatatgt   3120

ttttaaaggt gtgattctta aattctttat gattgtttag atttctatat cttggtaaca   3180

tgaatacaca cttaatgaaa gatttcagta atttttgatt tgggaattaa tcatagtggg   3240

aaaaactgtt taggaaaaca tgtcagtgga aattaactcg ccacagtatg tagtgttagg   3300

gaatagcttc tgttcggcat ttgatttgag tgctgtattc tgacattttt caggaacaaa   3360

tacatgtgat tcatcttcta taaatatttg cagtttcttc aagttgaaat gagaaaagct   3420

cgtaaattga gcaccaggtc taataaatca ttcacttacc caagaacaga aagacaggaa   3480

aagctagcat gttaatctaa tgaaaaaatc gaatgttaaa aaaccaagaa agtagaagat   3540

atttgacatt aactttctaa tcattgataa taatctaata atcataacat tattcttaaa   3600

acctgaaaga atggattcct gctcccaatg tgtttttaat atcaacttaa actaaaataa   3660

ttttttacc tatttttgga agcttggaaa ttgagatgta gttgtctaat gttaacctaa   3720

ttaagagagc ttggtgtgat ttctcatata cagcatctaa atatttaagt tttaatgtct   3780

tctaaaatat tattacattc ttcatactat agttttttaa catcctttag aaaacttgta   3840

tcagcttcac tttcaaacca tgctggcatc gaactcaggt gtagtggtat cagaatgtta   3900

tgaaataatt ttttatttc attataaact ccatttttac aataaacact tctcaaccaa   3960

a                                                                   3961
```

<210> SEQ ID NO 3
<211> LENGTH: 580
<212> TYPE: PRT
<213> ORGANISM: Homo Sapiens

<400> SEQUENCE: 3

```
Met Ser Asp Thr Trp Ser Ser Ile Gln Ala His Lys Lys Gln Leu Asp
1               5                   10                  15

Ser Leu Arg Glu Arg Leu Gln Arg Arg Arg Lys Gln Asp Ser Gly His
            20                  25                  30

Leu Asp Leu Arg Asn Pro Glu Ala Ala Leu Ser Pro Thr Phe Arg Ser
        35                  40                  45

Asp Ser Pro Val Pro Thr Ala Pro Thr Ser Gly Gly Pro Lys Pro Ser
    50                  55                  60

Thr Ala Ser Ala Val Pro Glu Leu Ala Thr Asp Pro Glu Leu Glu Lys
65                  70                  75                  80

Lys Leu Leu His His Leu Ser Asp Leu Ala Leu Thr Leu Pro Thr Asp
                85                  90                  95

Ala Val Ser Ile Cys Leu Ala Ile Ser Thr Pro Asp Ala Pro Ala Thr
            100                 105                 110

Gln Asp Gly Val Glu Ser Leu Leu Gln Lys Phe Ala Ala Gln Glu Leu
        115                 120                 125

Ile Glu Val Lys Arg Gly Leu Leu Gln Asp Asp Ala His Pro Thr Leu
    130                 135                 140
```

```
Val Thr Tyr Ala Asp His Ser Lys Leu Ser Ala Met Met Gly Ala Val
145                 150                 155                 160

Ala Glu Lys Lys Gly Pro Gly Glu Val Ala Gly Thr Val Thr Gly Gln
                165                 170                 175

Lys Arg Arg Ala Glu Gln Asp Ser Thr Thr Val Ala Ala Phe Ala Ser
            180                 185                 190

Ser Leu Val Ser Gly Leu Asn Ser Ser Ala Ser Glu Pro Ala Lys Glu
        195                 200                 205

Pro Ala Lys Lys Ser Arg Lys His Ala Ala Ser Asp Val Asp Leu Glu
    210                 215                 220

Ile Glu Ser Leu Leu Asn Gln Gln Ser Thr Lys Glu Gln Gln Ser Lys
225                 230                 235                 240

Lys Val Ser Gln Glu Ile Leu Glu Leu Leu Asn Thr Thr Thr Ala Lys
                245                 250                 255

Glu Gln Ser Ile Val Glu Lys Phe Arg Ser Arg Gly Arg Ala Gln Val
            260                 265                 270

Gln Glu Phe Cys Asp Tyr Gly Thr Lys Glu Glu Cys Met Lys Ala Ser
        275                 280                 285

Asp Ala Asp Arg Pro Cys Arg Lys Leu His Phe Arg Arg Ile Ile Asn
    290                 295                 300

Lys His Thr Asp Glu Ser Leu Gly Asp Cys Ser Phe Leu Asn Thr Cys
305                 310                 315                 320

Phe His Met Asp Thr Cys Lys Tyr Val His Tyr Glu Ile Asp Ala Cys
                325                 330                 335

Met Asp Ser Glu Ala Pro Gly Ser Lys Asp His Thr Pro Ser Gln Glu
            340                 345                 350

Leu Ala Leu Thr Gln Ser Val Gly Gly Asp Ser Ser Ala Asp Arg Leu
        355                 360                 365

Phe Pro Pro Gln Trp Ile Cys Cys Asp Ile Arg Tyr Leu Asp Val Ser
    370                 375                 380

Ile Leu Gly Lys Phe Ala Val Val Met Ala Asp Pro Pro Trp Asp Ile
385                 390                 395                 400

His Met Glu Leu Pro Tyr Gly Thr Leu Thr Asp Asp Glu Met Arg Arg
                405                 410                 415

Leu Asn Ile Pro Val Leu Gln Asp Asp Gly Phe Leu Phe Leu Trp Val
            420                 425                 430

Thr Gly Arg Ala Met Glu Leu Gly Arg Glu Cys Leu Asn Leu Trp Gly
        435                 440                 445

Tyr Glu Arg Val Asp Glu Ile Ile Trp Val Lys Thr Asn Gln Leu Gln
    450                 455                 460

Arg Ile Ile Arg Thr Gly Arg Thr Gly His Trp Leu Asn His Gly Lys
465                 470                 475                 480

Glu His Cys Leu Val Gly Val Lys Gly Asn Pro Gln Gly Phe Asn Gln
                485                 490                 495

Gly Leu Asp Cys Asp Val Ile Val Ala Glu Val Arg Ser Thr Ser His
            500                 505                 510

Lys Pro Asp Glu Ile Tyr Gly Met Ile Glu Arg Leu Ser Pro Gly Thr
        515                 520                 525

Arg Lys Ile Glu Leu Phe Gly Arg Pro His Asn Val Gln Pro Asn Trp
    530                 535                 540

Ile Thr Leu Gly Asn Gln Leu Asp Gly Ile His Leu Leu Asp Pro Asp
545                 550                 555                 560

Val Val Ala Arg Phe Lys Gln Arg Tyr Pro Asp Gly Ile Ile Ser Lys
```

```
                565                 570                 575

Pro Lys Asn Leu
            580


<210> SEQ ID NO 4
<211> LENGTH: 150
<212> TYPE: PRT
<213> ORGANISM: Homo Sapiens

<400> SEQUENCE: 4

Pro Val Pro Thr Ala Pro Thr Ser Gly Gly Pro Lys Pro Ser Thr Ala
1               5                   10                  15

Ser Ala Val Pro Glu Leu Ala Thr Asp Pro Glu Leu Glu Lys Lys Leu
            20                  25                  30

Leu His His Leu Ser Asp Leu Ala Leu Thr Leu Pro Thr Asp Ala Val
        35                  40                  45

Ser Ile Cys Leu Ala Ile Ser Thr Pro Asp Ala Pro Ala Thr Gln Asp
    50                  55                  60

Gly Val Glu Ser Leu Leu Gln Lys Phe Ala Ala Gln Glu Leu Ile Glu
65                  70                  75                  80

Val Lys Arg Gly Leu Leu Gln Asp Asp Ala His Pro Thr Leu Val Thr
                85                  90                  95

Tyr Ala Asp His Ser Lys Leu Ser Ala Met Met Gly Ala Val Ala Glu
            100                 105                 110

Lys Lys Gly Pro Gly Glu Val Ala Gly Thr Val Thr Gly Gln Lys Arg
        115                 120                 125

Arg Ala Glu Gln Asp Ser Thr Thr Val Ala Ala Phe Ala Ser Ser Leu
    130                 135                 140

Val Ser Gly Leu Asn Ser
145                 150


<210> SEQ ID NO 5
<211> LENGTH: 352
<212> TYPE: PRT
<213> ORGANISM: Homo Sapiens

<400> SEQUENCE: 5

Met Ala Ser Arg Lys Glu Gly Thr Gly Ser Thr Ala Thr Ser Ser Ser
1               5                   10                  15

Ser Thr Ala Gly Ala Ala Gly Lys Gly Lys Gly Lys Gly Gly Ser Gly
            20                  25                  30

Asp Ser Ala Val Lys Gln Val Gln Ile Asp Gly Leu Val Val Leu Lys
        35                  40                  45

Ile Ile Lys His Tyr Gln Glu Glu Gly Gln Gly Thr Glu Val Val Gln
    50                  55                  60

Gly Val Leu Leu Gly Leu Val Val Glu Asp Arg Leu Glu Ile Thr Asn
65                  70                  75                  80

Cys Phe Pro Phe Pro Gln His Thr Glu Asp Asp Ala Asp Phe Asp Glu
                85                  90                  95

Val Gln Tyr Gln Met Glu Met Met Arg Ser Leu Arg His Val Asn Ile
            100                 105                 110

Asp His Leu His Val Gly Trp Tyr Gln Ser Thr Tyr Tyr Gly Ser Phe
        115                 120                 125

Val Thr Arg Ala Leu Leu Asp Ser Gln Phe Ser Tyr Gln His Ala Ile
    130                 135                 140

Glu Glu Ser Val Val Leu Ile Tyr Asp Pro Ile Lys Thr Ala Gln Gly
```

```
145                 150                 155                 160

Ser Leu Ser Leu Lys Ala Tyr Arg Leu Thr Pro Lys Leu Met Glu Val
                165                 170                 175

Cys Lys Glu Lys Asp Phe Ser Pro Glu Ala Leu Lys Lys Ala Asn Ile
            180                 185                 190

Thr Phe Glu Tyr Met Phe Glu Glu Val Pro Ile Val Ile Lys Asn Ser
        195                 200                 205

His Leu Ile Asn Val Leu Met Trp Glu Leu Glu Lys Lys Ser Ala Val
    210                 215                 220

Ala Asp Lys His Glu Leu Leu Ser Leu Ala Ser Ser Asn His Leu Gly
225                 230                 235                 240

Lys Asn Leu Gln Leu Leu Met Asp Arg Val Asp Glu Met Ser Gln Asp
                245                 250                 255

Ile Val Lys Tyr Asn Thr Tyr Met Arg Asn Thr Ser Lys Gln Gln Gln
            260                 265                 270

Gln Lys His Gln Tyr Gln Gln Arg Arg Gln Gln Glu Asn Met Gln Arg
        275                 280                 285

Gln Ser Arg Gly Glu Pro Pro Leu Pro Glu Glu Asp Leu Ser Lys Leu
    290                 295                 300

Phe Lys Pro Pro Gln Pro Pro Ala Arg Met Asp Ser Leu Leu Ile Ala
305                 310                 315                 320

Gly Gln Ile Asn Thr Tyr Cys Gln Asn Ile Lys Glu Phe Thr Ala Gln
                325                 330                 335

Asn Leu Gly Lys Leu Phe Met Ala Gln Ala Leu Gln Glu Tyr Asn Asn
            340                 345                 350


<210> SEQ ID NO 6
<211> LENGTH: 193
<212> TYPE: PRT
<213> ORGANISM: Homo Sapiens

<400> SEQUENCE: 6

Gly Ser Gly Asp Ser Ala Val Lys Gln Val Gln Ile Asp Gly Leu Val
1               5                   10                  15

Val Leu Lys Ile Ile Lys His Tyr Gln Glu Glu Gly Gln Gly Thr Glu
            20                  25                  30

Val Val Gln Gly Val Leu Leu Gly Leu Val Val Glu Asp Arg Leu Glu
        35                  40                  45

Ile Thr Asn Cys Phe Pro Phe Pro Gln His Thr Glu Asp Asp Ala Asp
    50                  55                  60

Phe Asp Glu Val Gln Tyr Gln Met Glu Met Met Arg Ser Leu Arg His
65                  70                  75                  80

Val Asn Ile Asp His Leu His Val Gly Trp Tyr Gln Ser Thr Tyr Tyr
                85                  90                  95

Gly Ser Phe Val Thr Arg Ala Leu Leu Asp Ser Gln Phe Ser Tyr Gln
            100                 105                 110

His Ala Ile Glu Glu Ser Val Val Leu Ile Tyr Asp Pro Ile Lys Thr
        115                 120                 125

Ala Gln Gly Ser Leu Ser Leu Lys Ala Tyr Arg Leu Thr Pro Lys Leu
    130                 135                 140

Met Glu Val Cys Lys Glu Lys Asp Phe Ser Pro Glu Ala Leu Lys Lys
145                 150                 155                 160

Ala Asn Ile Thr Phe Glu Tyr Met Phe Glu Glu Val Pro Ile Val Ile
                165                 170                 175
```

```
Lys Asn Ser His Leu Ile Asn Val Leu Met Trp Glu Leu Glu Lys Lys
            180                 185                 190

Ser


<210> SEQ ID NO 7
<211> LENGTH: 3234
<212> TYPE: DNA
<213> ORGANISM: Homo Sapiens

<400> SEQUENCE: 7

agtgcgctgg cggcggcggc ggcggcggcg gcggcggctg ggctgtttgt tctggtctcc     60

cgcagccgag gagccgaagc agtggcggcg gcagcggctg cggcggctgc cggcggtgcc    120

cgcgggcgag cgcggcctgt gagctcggca gagcggcggg cgggccccgg cgccgcgcag    180

gcagctcggg gagggggcgg cggcagcggg cggacggccg gcgggggcgg cgtgcggcct    240

agcgtctcag agtgcctggt gaagaatgtg atgggatcac tagcatgtct gcggagagcg    300

gccctgggac gagattgaga aatctgccag taatgggggga tggactagaa acttcccaaa    360

tgtctacaac acaggcccag gcccaacccc agccagccaa cgcagccagc accaaccccc    420

cgcccccaga gacctccaac cctaacaagc ccaagaggca gaccaaccaa ctgcaatacc    480

tgctcagagt ggtgctcaag acactatgga aacaccagtt tgcatggcct ttccagcagc    540

ctgtggatgc cgtcaagctg aacctccctg attactataa gatcattaaa acgcctatgg    600

atatgggaac aataaagaag cgcttggaaa acaactatta ctggaatgct caggaatgta    660

tccaggactt caacactatg tttacaaatt gttacatcta caacaagcct ggagatgaca    720

tagtcttaat ggcagaagct ctggaaaagc tcttcttgca aaaaataaat gagctaccca    780

cagaagaaac cgagatcatg atagtccagg caaaaggaag aggacgtggg aggaaagaaa    840

cagggacagc aaaacctggc gtttccacgg taccaaacac aactcaagca tcgactcctc    900

cgcagaccca gacccctcag ccgaatcctc ctcctgtgca ggccacgcct caccccttcc    960

ctgccgtcac cccggacctc atcgtccaga cccctgtcat gacagtggtg cctccccagc   1020

cactgcagac gcccccgcca gtgccccccc agccacaacc cccacccgct ccagctcccc   1080

agcccgtaca gagccaccca cccatcatcg cggccacccc acagcctgtg aagacaaaga   1140

agggagtgaa gaggaaagca gacaccacca cccccaccac cattgacccc attcacgagc   1200

caccctcgct gcccccggag cccaagacca ccaagctggg ccagcggcgg gagagcagcc   1260

ggcctgtgaa acctccaaag aaggacgtgc ccgactctca gcagcaccca gcaccagaga   1320

agagcagcaa ggtctcggag cagctcaagt gctgcagcgg catcctcaag gagatgtttg   1380

ccaagaagca cgccgcctac gcctggccct tctacaagcc tgtggacgtg gaggcactgg   1440

gcctacacga ctactgtgac atcatcaagc accccatgga catgagcaca atcaagtcta   1500

aactggaggc ccgtgagtac cgtgatgctc aggagtttgg tgctgacgtc cgattgatgt   1560

tctccaactg ctataagtac aaccctcctg accatgaggt ggtggccatg gcccgcaagc   1620

tccaggatgt gttcgaaatg cgctttgcca agatgccgga cgagcctgag gagccagtgg   1680

tggccgtgtc ctccccggca gtgccccctc ccaccaaggt tgtggccccg ccctcatcca   1740

gcgacagcag cagcgatagc tcctcggaca gtgacagttc gactgatgac tctgaggagg   1800

agcgagccca gcggctggct gagctccagg agcagctcaa agccgtgcac gagcagcttg   1860

cagccctctc tcagccccag cagaacaaac caaagaaaaa ggagaaagac aagaaggaaa   1920

agaaaaaaga aaagcacaaa aggaaagagg aagtggaaga gaataaaaaa agcaaagcca   1980
```

```
aggaacctcc tcctaaaaag acgaagaaaa ataatagcag caacagcaat gtgagcaaga   2040

aggagccagc gcccatgaag agcaagcccc ctcccacgta tgagtcggag gaagaggaca   2100

agtgcaagcc tatgtcctat gaggagaagc ggcagctcag cttggacatc aacaagctcc   2160

ccggcgagaa gctgggccgc gtggtgcaca tcatccagtc acgggagccc tccctgaaga   2220

attccaaccc cgacgagatt gaaatcgact ttgagaccct gaagccgtcc acactgcgtg   2280

agctggagcg ctatgtcacc tcctgtttgc ggaagaaaag gaaacctcaa gctgagaaag   2340

ttgatgtgat tgccggctcc tccaagatga agggcttctc gtcctcagag tcggagagct   2400

ccagtgagtc cagctcctct gacagcgaag actccgaaac agctttctgc accagtggag   2460

acttcgtgtc cccagggcct tccccgtatc acagtcacgt gcagtgcggc cgcttcaggg   2520

agatgcttcg ctggtttctg gtggatgtgg agcagactgc agctggccag ccgcatcgcc   2580

agtctgctgc tggccctgcc atcacctggg ccccagccat tgcctacccc tccccagagt   2640

gtgctcgttg ctgtgttggc tgctcctgaa tctgccctaa ctccacacgc acctggactt   2700

gcgtgtccct cctgcagttc taactaacag tcccttcttt tcaagccccg tgggtctgca   2760

cgttggaccc tgggttcccc attagagccc accttctgag cagcagcctc agtgggaggt   2820

ggaggcaggt agtgatgctg ggtgccaggt gggagtggag aggggactgc tctcctccaa   2880

gtgtgcactt tcctcattat tctcaggggc gcagatgctc aggctggcgc aggggagagg   2940

ctagggaggg agccatggtg cccagaaggc ctggcgacca gcccctgctg agagatggag   3000

ctaacatcct gtgtttacgg ccaacggggt tgccgctagg ctggtgcagc tgtcagtgag   3060

ctggcgtgct gcagaccacc tgagagctgg ccctagggtc tcaggcagac tggggagtgg   3120

ggatccacag tgggaaacct gtgttttggc agtagactcc tgcatgttct cccacgggcc   3180

tgtcccatcc ctgggatttt attctaacta gaaataaatg ctaaccctca ataa         3234
```

<210> SEQ ID NO 8
<211> LENGTH: 4635
<212> TYPE: DNA
<213> ORGANISM: Homo Sapiens

<400> SEQUENCE: 8

```
attctttgga atactactgc tagaagtctg acttaagacc cagcttatgg gccacatggc     60

acccagctgc ttctgcagag aaggcaggcc actgatgggt acagcaaagt gtggtgctgc    120

tggccaagcc aaagacccgt gtaggatgac tgggcctctg ccccttgtgg gtgttgccac    180

tgtgcttgag tgcctggtga agaatgtgat gggatcacta gcatgtctgc ggagagcggc    240

cctgggacga gattgagaaa tctgccagta atgggggatg gactagaaac ttcccaaatg    300

tctacaacac aggcccaggc ccaaccccag ccagccaacg cagccagcac caaccccccg    360

cccccagaga cctccaaccc taacaagccc aagaggcaga ccaaccaact gcaatacctg    420

ctcagagtgg tgctcaagac actatggaaa caccagtttg catggccttt ccagcagcct    480

gtggatgccg tcaagctgaa cctccctgat tactataaga tcattaaaac gcctatggat    540

atgggaacaa taaagaagcg cttggaaaac aactattact ggaatgctca ggaatgtatc    600

caggacttca acactatgtt tacaaattgt tacatctaca acaagcctgg agatgacata    660

gtcttaatgg cagaagctct ggaaaagctc ttcttgcaaa aaataaatga gctacccaca    720

gaagaaaccg agatcatgat agtccaggca aaaggaagag gacgtgggag gaaagaaaca    780

gggacagcaa aacctggcgt ttccacggta ccaaacacaa ctcaagcatc gactcctccg    840

cagacccaga cccctcagcc gaatcctcct cctgtgcagg ccacgcctca ccccttccct    900
```

```
gccgtcaccc cggacctcat cgtccagacc cctgtcatga cagtggtgcc tccccagcca    960
ctgcagacgc cccgccagt gcccccccag ccacaacccc cacccgctcc agctccccag   1020
cccgtacaga gccacccacc catcatcgcg gccaccccac agcctgtgaa gacaaagaag   1080
ggagtgaaga ggaaagcaga caccaccacc cccaccacca ttgaccccat tcacgagcca   1140
ccctcgctgc ccccggagcc caagaccacc aagctgggcc agcggcggga gagcagccgg   1200
cctgtgaaac ctccaaagaa ggacgtgccc gactctcagc agcacccagc accagagaag   1260
agcagcaagg tctcggagca gctcaagtgc tgcagcggca tcctcaagga gatgtttgcc   1320
aagaagcacg ccgcctacgc ctggcccttc tacaagcctg tggacgtgga ggcactgggc   1380
ctacacgact actgtgacat catcaagcac cccatggaca tgagcacaat caagtctaaa   1440
ctggaggccc gtgagtaccg tgatgctcag gagtttggtg ctgacgtccg attgatgttc   1500
tccaactgct ataagtacaa ccctcctgac catgaggtgg tggccatggc ccgcaagctc   1560
caggatgtgt tcgaaatgcg ctttgccaag atgccggacg agcctgagga gccagtggtg   1620
gccgtgtcct ccccggcagt gccccctccc accaaggttg tggccccgcc ctcatccagc   1680
gacagcagca gcgatagctc ctcggacagt gacagttcga ctgatgactc tgaggaggag   1740
cgagcccagc ggctggctga gctccaggag cagctcaaag ccgtgcacga gcagcttgca   1800
gccctctctc agccccagca gaacaaacca aagaaaaagg agaaagacaa gaaggaaaag   1860
aaaaaagaaa agcacaaaag gaaagaggaa gtggaagaga ataaaaaaag caaagccaag   1920
gaacctcctc ctaaaaagac gaagaaaaat aatagcagca acagcaatgt gagcaagaag   1980
gagccagcgc ccatgaagag caagcccccct cccacgtatg agtcggagga agaggacaag   2040
tgcaagccta tgtcctatga ggagaagcgg cagctcagct tggacatcaa caagctcccc   2100
ggcgagaagc tgggccgcgt ggtgcacatc atccagtcac gggagccctc cctgaagaat   2160
tccaaccccg acgagattga aatcgacttt gagaccctga agccgtccac actgcgtgag   2220
ctggagcgct atgtcacctc ctgtttgcgg aagaaaagga aacctcaagc tgagaaagtt   2280
gatgtgattg ccggctcctc caagatgaag ggcttctcgt cctcagagtc ggagagctcc   2340
agtgagtcca gctcctctga cagcgaagac tccgaaacag gtcctgccta atcattggac   2400
acggactctt aataaaacgg tcttcagttc cagattcctt cccagcaagc tatagcttaa   2460
gtccattttc ttccgtgaaa gggacaggac tccatcaagt tatggaattc ctcagagccc   2520
tgggcctgtc ccccggggtg gattagtcat gtccagcagc acacgcctag tcccgccttc   2580
gggaaggctg cctgcctggc cagccgccca ggcctctctg tgtaaagact gcctggctgt   2640
cctgcccagc cttcctggtt ctctggggtc ctctgggtgg gtggcatctc ctggagggtg   2700
atgacaatcc ccaacacatg cattcatgtg gtgctactct gtgtgcaaag ccagacccca   2760
agtatgtttt ctctctttgt cccatccctc tttttctggg actttggacc ctaactactt   2820
ccctcctgaa ccttgcagtg acatcagtcc aggagagctc tcgttcagtg tgcggaagaa   2880
cactctgacc tctagagctg tcctagataa ggagtgggag ctttagaggc aaggcctcta   2940
gaccctggaa ggctcagtga ggctcttccc acagcatgct tctcactggt gccctgtaag   3000
gctcgagcca ccgctgactc tgagcctttt ggagtctttc ctccttcgtc tccattgttc   3060
ccgtgcattt ccaaaagctt aagttgcctg gtgggcattt ccccagtttc tttggcctcc   3120
gtcttctcaa gtcacatagg gaaagtacct cctggaacca ggctgcagta tgcaggacct   3180
gccaggcagg cactggtgaa gggccttggg cctatcatcc ccccaacccc acctcacccc   3240
```

-continued

```
acccgcctcc tctagtgggg tgagtctggg ctggtggacc agagagggtg tcacagaccc   3300
tcagggactg ccccatggac acctctgact ggtgttaaca gtgtgaacat tttccccgtc   3360
ttcagtccct tagaatgacg acagcccctg gggttggggc aggcgagtgt ggccacatca   3420
tccaagccct cccagagaca caaataggct tttttgctct aaaaataaat accagccctt   3480
ttttggtcac aaatccagca tctcagcaga aaactgcctg acatgaaaag tcccctgagg   3540
aactgcatct gcgtttcagg ggcttttcat tttttctcct tttttaaagt gtagattgtg   3600
ggtgcttcct agaggcctgc cttcttctgg aactggaagt gggctatcac catgggcaag   3660
cccttgggtg caggctcccc acctgcctgg gaactctggc agctctcctc agctccttgg   3720
gcttgagcag ctgcaactgc cccagatttg ctgtggaagc aggggctagc cctggcctca   3780
ccagggcctc ccggggccct gcattgatgc tcaggagttc ctgggctgct cttgatcctt   3840
tctgggcatc cagcttccag ttaagctctg tttgccaaac aaactattct cagctgccct   3900
ttggcctgcg cctgatgtgt tcctgttgca gtcccgcctg cctgagacag gagcaggcag   3960
gagagccttc atgcccagat tcccacagga caattgggga gctgctggca ttgtctttct   4020
gggaagattc tgctttcttg gaccaaatgg cagcctgatt accagtgtcg ggcctgcatg   4080
ctgcccccga cacacgcacg cacgcgcaca cacgtgtgca catgggccat agccacaagc   4140
cagctctcct ccagggtcct ttcaacctcg ctgtccaggg accctgtcct tcttgcccgt   4200
ggggcttcca tctggcagag aacgttcagg gcttgttgaa cttgaaagct cattagactt   4260
aagctgtcac ctgtgcttgg tgccccagga acagccagag aggacagtgc ccactcactt   4320
cttgttggca gcctcctgtg caggaagtgc cagccgggcc tcgacgcacc agctggctgt   4380
gggtcctgag gaggggcggg aggcggccgc tcagtgcaga tggggactcc tctcctctgc   4440
cctgacctta ccctccatta cctccttcac tggagtgggg ctggggggtg ggtggaatca   4500
gtgttttaat cggattttta aaaaacattt tatttctttg tacaattacc atcctatgta   4560
aagatgaaat ttgtgttgag ttgaagattg tcatggaata aagatcacac cgtacttgag   4620
gccatcttca tgtaa                                                     4635
```

<210> SEQ ID NO 9
<211> LENGTH: 5198
<212> TYPE: DNA
<213> ORGANISM: Homo Sapiens

<400> SEQUENCE: 9

```
attctttgga atactactgc tagaagtctg acttaagacc cagcttatgg gccacatggc     60
acccagctgc ttctgcagag aaggcaggcc actgatgggt acagcaaagt gtggtgctgc    120
tggccaagcc aaagacccgt gtaggatgac tgggcctctg ccccttgtgg gtgttgccac    180
tgtgcttgag tgcctggtga agaatgtgat gggatcacta gcatgtctgc ggagagcggc    240
cctgggacga gattgagaaa tctgccagta atgggggatg gactagaaac ttcccaaatg    300
tctacaacac aggcccaggc ccaaccccag ccagccaacg cagccagcac caaccccccg    360
cccccagaga cctccaaccc taacaagccc aagaggcaga ccaaccaact gcaatacctg    420
ctcagagtgg tgctcaagac actatggaaa caccagtttg catggccttt ccagcagcct    480
gtggatgccg tcaagctgaa cctccctgat tactataaga tcattaaaac gcctatggat    540
atgggaacaa taaagaagcg cttggaaaac aactattact ggaatgctca ggaatgtatc    600
caggacttca acactatgtt tacaaattgt tacatctaca acaagcctgg agatgacata    660
gtcttaatgg cagaagctct ggaaaagctc ttcttgcaaa aaataaatga gctacccaca    720
```

```
gaagaaaccg agatcatgat agtccaggca aaaggaagag gacgtgggag gaaagaaaca    780
gggacagcaa aacctggcgt ttccacggta ccaaacacaa ctcaagcatc gactcctccg    840
cagacccaga cccctcagcc gaatcctcct cctgtgcagg ccacgcctca ccccttccct    900
gccgtcaccc cggacctcat cgtccagacc cctgtcatga cagtggtgcc tccccagcca    960
ctgcagacgc cccgccagt gcccccccag ccacaacccc cacccgctcc agctccccag    1020
cccgtacaga gccacccacc catcatcgcg gccaccccac agcctgtgaa gacaaagaag    1080
ggagtgaaga ggaaagcaga caccaccacc cccaccacca ttgaccccat tcacgagcca    1140
ccctcgctgc ccccggagcc caagaccacc aagctgggcc agcggcggga gagcagccgg    1200
cctgtgaaac ctccaaagaa ggacgtgccc gactctcagc agcacccagc accagagaag    1260
agcagcaagg tctcggagca gctcaagtgc tgcagcggca tcctcaagga gatgtttgcc    1320
aagaagcacg ccgcctacgc ctggcccttc tacaagcctg tggacgtgga ggcactgggc    1380
ctacacgact actgtgacat catcaagcac cccatggaca tgagcacaat caagtctaaa    1440
ctggaggccc gtgagtaccg tgatgctcag gagtttggtg ctgacgtccg attgatgttc    1500
tccaactgct ataagtacaa ccctcctgac catgaggtgg tggccatggc ccgcaagctc    1560
caggatgtgt tcgaaatgcg ctttgccaag atgccggacg agcctgagga gccagtggtg    1620
gccgtgtcct ccccggcagt gccccctccc accaaggttg tggccccgcc ctcatccagc    1680
gacagcagca gcgatagctc ctcggacagt gacagttcga ctgatgactc tgaggaggag    1740
cgagcccagc ggctggctga gctccaggag cagctcaaag ccgtgcacga gcagcttgca    1800
gccctctctc agccccagca gaacaaacca aagaaaaagg agaaagacaa gaaggaaaag    1860
aaaaaagaaa agcacaaaag gaaagaggaa gtggaagaga ataaaaaaag caaagccaag    1920
gaacctcctc ctaaaaagac gaagaaaaat aatagcagca acagcaatgt gagcaagaag    1980
gagccagcgc ccatgaagag caagcccct cccacgtatg agtcggagga agaggacaag    2040
tgcaagccta tgtcctatga ggagaagcgg cagctcagct tggacatcaa caagctcccc    2100
ggcgagaagc tgggccgcgt ggtgcacatc atccagtcac gggagccctc cctgaagaat    2160
tccaaccccg acgagattga aatcgacttt gagaccctga agccgtccac actgcgtgag    2220
ctggagcgct atgtcacctc ctgtttgcgg aagaaaagga aacctcaagc tgagaaagtt    2280
gatgtgattg ccggctcctc caagatgaag ggcttctcgt cctcagagtc ggagagctcc    2340
agtgagtcca gctcctctga cagcgaagac tccgaaacag agatggctcc gaagtcaaaa    2400
aagaaggggc accccgggag ggagcagaag aagcaccatc atcaccacca tcagcagatg    2460
cagcaggccc cggctcctgt gccccagcag ccgcccccgc ctccccagca gcccccaccg    2520
cctccacctc cgcagcagca acagcagccg ccacccccgc ctcccccacc ctccatgccg    2580
cagcaggcag ccccggcgat gaagtcctcg cccccaccct tcattgccac ccaggtgccc    2640
gtcctggagc cccagctccc aggcagcgtc tttgacccca tcggccactt cacccagccc    2700
atcctgcacc tgccgcagcc tgagctgccc cctcacctgc cccagccgcc tgagcacagc    2760
actccacccc atctcaacca gcacgcagtg gtctctcctc cagctttgca caacgcacta    2820
ccccagcagc catcacggcc cagcaaccga gccgctgccc tgcctcccaa gcccgcccgg    2880
cccccagccg tgtcaccagc cttgacccaa acacccctgc tcccacagcc ccccatggcc    2940
caaccccccc aagtgctgct ggaggatgaa gagccacctg ccccacccct cacctccatg    3000
cagatgcagc tgtacctgca gcagctgcag aaggtgcagc cccctacgcc gctactccct    3060
```

```
tccgtgaagg tgcagtccca gcccccaccc cccctgccgc ccccacccca cccctctgtg   3120
cagcagcagc tgcagcagca gccgccacca cccccaccac cccagcccca gcctccaccc   3180
cagcagcagc atcagccccc tccacggccc gtgcacttgc agcccatgca gttttccacc   3240
cacatccaac agcccccgcc accccagggc cagcagcccc cccatccgcc cccaggccag   3300
cagccacccc cgccgcagcc tgccaagcct cagcaagtca tccagcacca ccattcaccc   3360
cggcaccaca agtcggaccc ctactcaacc ggtcacctcc gcgaagcccc ctccccgctt   3420
atgatacatt ccccccagat gtcacagttc cagagcctga cccaccagtc tccaccccag   3480
caaaacgtcc agcctaagaa acaggagctg cgtgctgcct ccgtggtcca gccccagccc   3540
ctcgtggtgg tgaaggagga gaagatccac tcacccatca tccgcagcga gcccttcagc   3600
ccctcgctgc ggccggagcc ccccaagcac ccggagagca tcaaggcccc cgtccacctg   3660
ccccagcggc cggaaatgaa gcctgtggat gtcgggaggc ctgtgatccg gcccccagag   3720
cagaacgcac cgccaccagg ggcccctgac aaggacaaac agaaacagga gccgaagact   3780
ccagttgcgc ccaaaaagga cctgaaaatc aagaacatgg gctcctgggc cagcctagtg   3840
cagaagcatc cgaccacccc ctcctccaca gccaagtcat ccagcgacag cttcgagcag   3900
ttccgccgcg ccgctcggga gaaagaggag cgtgagaagg ccctgaaggc tcaggccgag   3960
cacgctgaga aggagaagga gcggctgcgg caggagcgca tgaggagccg agaggacgag   4020
gatgcgctgg agcaggcccg gcgggcccat gaggaggcac gtcggcgcca ggagcagcag   4080
cagcagcagc gccaggagca acagcagcag cagcaacagc aagcagctgc ggtggctgcc   4140
gccgccaccc cacaggccca gagctcccag ccccagtcca tgctggacca gcagagggag   4200
ttggcccgga agcgggagca ggagcgaaga cgccgggaag ccatggcagc taccattgac   4260
atgaatttcc agagtgatct attgtcaata tttgaagaaa atcttttctg agcgcaccta   4320
ggtggcttct gactttgatt ttctggcaaa acattgactt tccatagtgt taggggcggt   4380
ggtggaggtg ggatcagcgg ccaggggatg cctcagggcc tggccctcct gcatgctatg   4440
cccggggcag gcctgacggg cagctgagga ttgcagagcc tgtctgcctt acggccagtc   4500
ggacagacgt cccgccaccc accacccctc acaggacgtc cgctcagcac acgccttgtt   4560
acgagcaagt gccggctgga cccaagccct gcatccccac atgcggggca gaggcccttc   4620
tctccgccaa atgtctacac agtatacaca ggacatcgtt gctgccgccg tgactggttt   4680
tctgtcccca agaacgtgac gttcgtgatg tcctgcccgc cgggagtctt tccccacacc   4740
ccagccatcg ccgcccgctc ccaggaggcc agggcaggcc tgcgtgggct ggaggcgggc   4800
gaggccggcc cacccccctcg ctggcactga ctttgccttg aacagacccc ccgaccctcc   4860
cccacaagcc tttaattgag agccgctctc tgtaagtgtt tgcttgtgca aaagggaata   4920
gtgccgtgga ggtgtgtgtg tccatggcat ccggagcgag gcgactgtcc tgcgtgggta   4980
gccctcggcc ggggagtgag gccaccaacc aaagtcagtt ccttcccacc tgtgtttctg   5040
tttcgttttt ttttttcttt tttttctata tatatttttt gttgaattct attttatttt   5100
taattctctc ttctcctcca gacacaatgg cactgcttat ctccgaaatg gtgtgatcgt   5160
ctcctcattg agcagcggct gccaccgcgc tgtgggta                           5198
```

<210> SEQ ID NO 10
<211> LENGTH: 22
<212> TYPE: RNA
<213> ORGANISM: Artificial Sequence
<220> FEATURE:
<223> OTHER INFORMATION: Synthetic

<400> SEQUENCE: 10
rgauagaugg ccuuguggua uu 22

<210> SEQ ID NO 11
<211> LENGTH: 22
<212> TYPE: RNA
<213> ORGANISM: Artificial Sequence
<220> FEATURE:
<223> OTHER INFORMATION: Synthetic

<400> SEQUENCE: 11
rgcggagccu ucgccaugua uu 22

<210> SEQ ID NO 12
<211> LENGTH: 22
<212> TYPE: DNA
<213> ORGANISM: Artificial Sequence
<220> FEATURE:
<223> OTHER INFORMATION: Synthetic

<400> SEQUENCE: 12
rugagaaagg aggagaggaa tt 22

<210> SEQ ID NO 13
<211> LENGTH: 22
<212> TYPE: DNA
<213> ORGANISM: Artificial Sequence
<220> FEATURE:
<223> OTHER INFORMATION: Synthetic

<400> SEQUENCE: 13
rucaaccucu uuacggauuu tt 22

<210> SEQ ID NO 14
<211> LENGTH: 22
<212> TYPE: RNA
<213> ORGANISM: Artificial Sequence
<220> FEATURE:
<223> OTHER INFORMATION: Synthetic

<400> SEQUENCE: 14
rgcaucaacc ugaaugacau uu 22

<210> SEQ ID NO 15
<211> LENGTH: 43
<212> TYPE: DNA
<213> ORGANISM: Artificial Sequence
<220> FEATURE:
<223> OTHER INFORMATION: Synthetic

<400> SEQUENCE: 15
ataagaatgc ggccgcgtcg gacacgtgga gctctatcca ggc 43

<210> SEQ ID NO 16
<211> LENGTH: 35
<212> TYPE: DNA
<213> ORGANISM: Artificial Sequence
<220> FEATURE:
<223> OTHER INFORMATION: Synthetic

<400> SEQUENCE: 16
gaagatctag atggacacag catcagtggg caatg 35

<210> SEQ ID NO 17

<211> LENGTH: 43
<212> TYPE: DNA
<213> ORGANISM: Artificial Sequence
<220> FEATURE:
<223> OTHER INFORMATION: Synthetic

<400> SEQUENCE: 17
ataagaatgc ggccgcgtcg gacacgtgga gctctatcca ggc 43

<210> SEQ ID NO 18
<211> LENGTH: 35
<212> TYPE: DNA
<213> ORGANISM: Artificial Sequence
<220> FEATURE:
<223> OTHER INFORMATION: Synthetic

<400> SEQUENCE: 18
gaagatctaa tggtcagcat aggttacaag agtag 35

<210> SEQ ID NO 19
<211> LENGTH: 34
<212> TYPE: DNA
<213> ORGANISM: Artificial Sequence
<220> FEATURE:
<223> OTHER INFORMATION: Synthetic

<400> SEQUENCE: 19
aacaagcggc cgcgtcggac acgtggagct ctat 34

<210> SEQ ID NO 20
<211> LENGTH: 39
<212> TYPE: DNA
<213> ORGANISM: Artificial Sequence
<220> FEATURE:
<223> OTHER INFORMATION: Synthetic

<400> SEQUENCE: 20
aacaaagatc ttaagagttc agaccagaga ctaacgaac 39

<210> SEQ ID NO 21
<211> LENGTH: 34
<212> TYPE: DNA
<213> ORGANISM: Artificial Sequence
<220> FEATURE:
<223> OTHER INFORMATION: Synthetic

<400> SEQUENCE: 21
aacaagcggc cgcgtcggac acgtggagct ctat 34

<210> SEQ ID NO 22
<211> LENGTH: 31
<212> TYPE: DNA
<213> ORGANISM: Artificial Sequence
<220> FEATURE:
<223> OTHER INFORMATION: Synthetic

<400> SEQUENCE: 22
aacaaagatc ttagcttggc gtgtggtctt t 31

<210> SEQ ID NO 23
<211> LENGTH: 43
<212> TYPE: DNA
<213> ORGANISM: Artificial Sequence
<220> FEATURE:
<223> OTHER INFORMATION: Synthetic

<400> SEQUENCE: 23
ataagaatgc ggccgcgtgt cttgccatct ccacgccaga tgc 43

<210> SEQ ID NO 24
<211> LENGTH: 49
<212> TYPE: DNA
<213> ORGANISM: Artificial Sequence
<220> FEATURE:
<223> OTHER INFORMATION: Synthetic

<400> SEQUENCE: 24
gaagatctct ataaattctt aggtttagag atgataccat ctgggtacc 49

<210> SEQ ID NO 25
<211> LENGTH: 31
<212> TYPE: DNA
<213> ORGANISM: Artificial Sequence
<220> FEATURE:
<223> OTHER INFORMATION: Synthetic

<400> SEQUENCE: 25
acgcgtcgac tcggacacgt ggagctctat c 31

<210> SEQ ID NO 26
<211> LENGTH: 48
<212> TYPE: DNA
<213> ORGANISM: Artificial Sequence
<220> FEATURE:
<223> OTHER INFORMATION: Synthetic

<400> SEQUENCE: 26
ataagaatgc ggccgcctat aaattcttag gtttagagat gataccat 48

<210> SEQ ID NO 27
<211> LENGTH: 42
<212> TYPE: DNA
<213> ORGANISM: Artificial Sequence
<220> FEATURE:
<223> OTHER INFORMATION: Synthetic

<400> SEQUENCE: 27
gtcatgctag cgccaccatg tcggacacgt ggagctctat cc 42

<210> SEQ ID NO 28
<211> LENGTH: 33
<212> TYPE: DNA
<213> ORGANISM: Artificial Sequence
<220> FEATURE:
<223> OTHER INFORMATION: Synthetic

<400> SEQUENCE: 28
aacaagcggc cgcctataaa ttcttaggtt tag 33

<210> SEQ ID NO 29
<211> LENGTH: 38
<212> TYPE: DNA
<213> ORGANISM: Artificial Sequence
<220> FEATURE:
<223> OTHER INFORMATION: Synthetic

<400> SEQUENCE: 29
tacttccaat ccaatgcaat gtcggacacg tggagctc 38

<210> SEQ ID NO 30
<211> LENGTH: 45
<212> TYPE: DNA

<213> ORGANISM: Artificial Sequence
<220> FEATURE:
<223> OTHER INFORMATION: Synthetic

<400> SEQUENCE: 30
ttatccactt ccaatgttat tagttcagac cagagactaa cgaac 45

<210> SEQ ID NO 31
<211> LENGTH: 35
<212> TYPE: DNA
<213> ORGANISM: Artificial Sequence
<220> FEATURE:
<223> OTHER INFORMATION: Synthetic

<400> SEQUENCE: 31
ggaagatctc ctactggaga ctttgattcg aagcc 35

<210> SEQ ID NO 32
<211> LENGTH: 36
<212> TYPE: DNA
<213> ORGANISM: Artificial Sequence
<220> FEATURE:
<223> OTHER INFORMATION: Synthetic

<400> SEQUENCE: 32
ccggaattct tagttggtgg acggcttggc ccactc 36

<210> SEQ ID NO 33
<211> LENGTH: 35
<212> TYPE: DNA
<213> ORGANISM: Artificial Sequence
<220> FEATURE:
<223> OTHER INFORMATION: Synthetic

<400> SEQUENCE: 33
cgcggatccg cgtcccgcaa ggaaggtacc ggctc 35

<210> SEQ ID NO 34
<211> LENGTH: 36
<212> TYPE: DNA
<213> ORGANISM: Artificial Sequence
<220> FEATURE:
<223> OTHER INFORMATION: Synthetic

<400> SEQUENCE: 34
ccggaattct tagttgttgt attcttgaag agcctg 36

<210> SEQ ID NO 35
<211> LENGTH: 35
<212> TYPE: DNA
<213> ORGANISM: Artificial Sequence
<220> FEATURE:
<223> OTHER INFORMATION: Synthetic

<400> SEQUENCE: 35
cgcggatcca gcgtcccggc cttcatcgac atcag 35

<210> SEQ ID NO 36
<211> LENGTH: 37
<212> TYPE: DNA
<213> ORGANISM: Artificial Sequence
<220> FEATURE:
<223> OTHER INFORMATION: Synthetic

<400> SEQUENCE: 36
ccggaattct caggtatcag aaagactcaa aaggctg 37

<210> SEQ ID NO 37
<211> LENGTH: 34
<212> TYPE: DNA
<213> ORGANISM: Artificial Sequence
<220> FEATURE:
<223> OTHER INFORMATION: Synthetic

<400> SEQUENCE: 37
ggaagatcta agccgatcct actgcagggc catg 34

<210> SEQ ID NO 38
<211> LENGTH: 37
<212> TYPE: DNA
<213> ORGANISM: Artificial Sequence
<220> FEATURE:
<223> OTHER INFORMATION: Synthetic

<400> SEQUENCE: 38
ccggaattct taagcctcaa actcaaattc gaagtac 37

<210> SEQ ID NO 39
<211> LENGTH: 33
<212> TYPE: DNA
<213> ORGANISM: Artificial Sequence
<220> FEATURE:
<223> OTHER INFORMATION: Synthetic

<400> SEQUENCE: 39
cgcggatccc acgctcacac ccggctcgag atg 33

<210> SEQ ID NO 40
<211> LENGTH: 36
<212> TYPE: DNA
<213> ORGANISM: Artificial Sequence
<220> FEATURE:
<223> OTHER INFORMATION: Synthetic

<400> SEQUENCE: 40
ccggaattct cacatgaagt cttcatagtc ttgtac 36

<210> SEQ ID NO 41
<211> LENGTH: 35
<212> TYPE: DNA
<213> ORGANISM: Artificial Sequence
<220> FEATURE:
<223> OTHER INFORMATION: Synthetic

<400> SEQUENCE: 41
cgcggatccg cgtcccgcaa ggaaggtacc ggctc 35

<210> SEQ ID NO 42
<211> LENGTH: 40
<212> TYPE: DNA
<213> ORGANISM: Artificial Sequence
<220> FEATURE:
<223> OTHER INFORMATION: Synthetic

<400> SEQUENCE: 42
ccggaattct tatgacttct tttcaagttc ccacattagg 40

<210> SEQ ID NO 43
<211> LENGTH: 36
<212> TYPE: DNA
<213> ORGANISM: Artificial Sequence
<220> FEATURE:

<223> OTHER INFORMATION: Synthetic

<400> SEQUENCE: 43
cgcggatccg gcggctcggg agattcagcc gtgaag 36

<210> SEQ ID NO 44
<211> LENGTH: 40
<212> TYPE: DNA
<213> ORGANISM: Artificial Sequence
<220> FEATURE:
<223> OTHER INFORMATION: Synthetic

<400> SEQUENCE: 44
ccggaattct tatgacttct tttcaagttc ccacattagg 40

<210> SEQ ID NO 45
<211> LENGTH: 30
<212> TYPE: DNA
<213> ORGANISM: Artificial Sequence
<220> FEATURE:
<223> OTHER INFORMATION: Synthetic

<400> SEQUENCE: 45
catgccatgg cgcgtacacg atcacggtac 30

<210> SEQ ID NO 46
<211> LENGTH: 29
<212> TYPE: DNA
<213> ORGANISM: Artificial Sequence
<220> FEATURE:
<223> OTHER INFORMATION: Synthetic

<400> SEQUENCE: 46
catgccatgg ccccgggagc atgggtgat 29

<210> SEQ ID NO 47
<211> LENGTH: 30
<212> TYPE: DNA
<213> ORGANISM: Artificial Sequence
<220> FEATURE:
<223> OTHER INFORMATION: Synthetic

<400> SEQUENCE: 47
ctagtctaga cgcgtacacg atcacggtac 30

<210> SEQ ID NO 48
<211> LENGTH: 28
<212> TYPE: DNA
<213> ORGANISM: Artificial Sequence
<220> FEATURE:
<223> OTHER INFORMATION: Synthetic

<400> SEQUENCE: 48
ccggaattcc cccgggagca tgggtgat 28

<210> SEQ ID NO 49
<211> LENGTH: 29
<212> TYPE: DNA
<213> ORGANISM: Artificial Sequence
<220> FEATURE:
<223> OTHER INFORMATION: Synthetic

<400> SEQUENCE: 49
ccggaattcg tgagcaaggg cgaggagct 29

<210> SEQ ID NO 50
<211> LENGTH: 30
<212> TYPE: DNA
<213> ORGANISM: Artificial Sequence
<220> FEATURE:
<223> OTHER INFORMATION: Synthetic

<400> SEQUENCE: 50
ctagtctaga cttgtacagc tcgtccatgc 30

<210> SEQ ID NO 51
<211> LENGTH: 30
<212> TYPE: DNA
<213> ORGANISM: Artificial Sequence
<220> FEATURE:
<223> OTHER INFORMATION: Synthetic

<400> SEQUENCE: 51
ctagtctaga gtgagcaagg gcgaggagct 30

<210> SEQ ID NO 52
<211> LENGTH: 29
<212> TYPE: DNA
<213> ORGANISM: Artificial Sequence
<220> FEATURE:
<223> OTHER INFORMATION: Synthetic

<400> SEQUENCE: 52
ccggaattcc ttgtacagct cgtccatgc 29

<210> SEQ ID NO 53
<211> LENGTH: 29
<212> TYPE: DNA
<213> ORGANISM: Artificial Sequence
<220> FEATURE:
<223> OTHER INFORMATION: Synthetic

<400> SEQUENCE: 53
ccggaattcc gcgtacacga tcacggtac 29

<210> SEQ ID NO 54
<211> LENGTH: 29
<212> TYPE: DNA
<213> ORGANISM: Artificial Sequence
<220> FEATURE:
<223> OTHER INFORMATION: Synthetic

<400> SEQUENCE: 54
ctagtctaga ccccgggagc atgggtgat 29

<210> SEQ ID NO 55
<211> LENGTH: 23
<212> TYPE: DNA
<213> ORGANISM: Artificial Sequence
<220> FEATURE:
<223> OTHER INFORMATION: Synthetic

<400> SEQUENCE: 55
caagctctct cccatgatgg gtg 23

<210> SEQ ID NO 56
<211> LENGTH: 20
<212> TYPE: DNA
<213> ORGANISM: Artificial Sequence
<220> FEATURE:
<223> OTHER INFORMATION: Synthetic

<400> SEQUENCE: 56
gaatggtcag cataggttac 20

<210> SEQ ID NO 57
<211> LENGTH: 31
<212> TYPE: DNA
<213> ORGANISM: Artificial Sequence
<220> FEATURE:
<223> OTHER INFORMATION: Synthetic

<400> SEQUENCE: 57
cattacgaga ttgatgcttg catggattct g 31

<210> SEQ ID NO 58
<211> LENGTH: 32
<212> TYPE: DNA
<213> ORGANISM: Artificial Sequence
<220> FEATURE:
<223> OTHER INFORMATION: Synthetic

<400> SEQUENCE: 58
tacgtattta caggtatcca tgtggaaaca tg 32

<210> SEQ ID NO 59
<211> LENGTH: 34
<212> TYPE: DNA
<213> ORGANISM: Artificial Sequence
<220> FEATURE:
<223> OTHER INFORMATION: Synthetic

<400> SEQUENCE: 59
acgcgtcgac gactacaaag acgatgacga caag 34

<210> SEQ ID NO 60
<211> LENGTH: 32
<212> TYPE: DNA
<213> ORGANISM: Artificial Sequence
<220> FEATURE:
<223> OTHER INFORMATION: Synthetic

<400> SEQUENCE: 60
acgacttaag ttatggtacc gatatcagat ct 32

<210> SEQ ID NO 61
<211> LENGTH: 56
<212> TYPE: DNA
<213> ORGANISM: Artificial Sequence
<220> FEATURE:
<223> OTHER INFORMATION: Synthetic

<400> SEQUENCE: 61
gactagtaat acgactcact ataggggcca ccatggaaga cgccaaaaac ataaag 56

<210> SEQ ID NO 62
<211> LENGTH: 25
<212> TYPE: DNA
<213> ORGANISM: Artificial Sequence
<220> FEATURE:
<223> OTHER INFORMATION: Synthetic

<400> SEQUENCE: 62
tctagacccc gggagcatgg gtgat 25

<210> SEQ ID NO 63
<211> LENGTH: 55

<212> TYPE: DNA
<213> ORGANISM: Artificial Sequence
<220> FEATURE:
<223> OTHER INFORMATION: Synthetic

<400> SEQUENCE: 63
tttttttttt tttttttttt tttttttttt tctagacccc gggagcatgg gtgat 55

<210> SEQ ID NO 64
<211> LENGTH: 20
<212> TYPE: DNA
<213> ORGANISM: Artificial Sequence
<220> FEATURE:
<223> OTHER INFORMATION: Synthetic

<400> SEQUENCE: 64
ggtactgttg gtaaagccac 20

<210> SEQ ID NO 65
<211> LENGTH: 20
<212> TYPE: DNA
<213> ORGANISM: Artificial Sequence
<220> FEATURE:
<223> OTHER INFORMATION: Synthetic

<400> SEQUENCE: 65
ctcttcatag ccttatgcag 20

<210> SEQ ID NO 66
<211> LENGTH: 20
<212> TYPE: DNA
<213> ORGANISM: Artificial Sequence
<220> FEATURE:
<223> OTHER INFORMATION: Synthetic

<400> SEQUENCE: 66
cactgggcag gtgtccactc 20

<210> SEQ ID NO 67
<211> LENGTH: 20
<212> TYPE: DNA
<213> ORGANISM: Artificial Sequence
<220> FEATURE:
<223> OTHER INFORMATION: Synthetic

<400> SEQUENCE: 67
gttctggatc ataaactttc 20

<210> SEQ ID NO 68
<211> LENGTH: 20
<212> TYPE: DNA
<213> ORGANISM: Artificial Sequence
<220> FEATURE:
<223> OTHER INFORMATION: Synthetic

<400> SEQUENCE: 68
gacatgagca caatcaagtc 20

<210> SEQ ID NO 69
<211> LENGTH: 20
<212> TYPE: DNA
<213> ORGANISM: Artificial Sequence
<220> FEATURE:
<223> OTHER INFORMATION: Synthetic

<400> SEQUENCE: 69
gaacacatcc tggagcttgc 20

<210> SEQ ID NO 70
<211> LENGTH: 20
<212> TYPE: DNA
<213> ORGANISM: Artificial Sequence
<220> FEATURE:
<223> OTHER INFORMATION: Synthetic

<400> SEQUENCE: 70
ctgaaagcca tccactatgc 20

<210> SEQ ID NO 71
<211> LENGTH: 20
<212> TYPE: DNA
<213> ORGANISM: Artificial Sequence
<220> FEATURE:
<223> OTHER INFORMATION: Synthetic

<400> SEQUENCE: 71
gtcgaagacc tctttgatgg 20

<210> SEQ ID NO 72
<211> LENGTH: 20
<212> TYPE: DNA
<213> ORGANISM: Artificial Sequence
<220> FEATURE:
<223> OTHER INFORMATION: Synthetic

<400> SEQUENCE: 72
cgtttgcgac ttggtacttg 20

<210> SEQ ID NO 73
<211> LENGTH: 20
<212> TYPE: DNA
<213> ORGANISM: Artificial Sequence
<220> FEATURE:
<223> OTHER INFORMATION: Synthetic

<400> SEQUENCE: 73
gagctttatt tcgtgcagac 20

<210> SEQ ID NO 74
<211> LENGTH: 20
<212> TYPE: DNA
<213> ORGANISM: Artificial Sequence
<220> FEATURE:
<223> OTHER INFORMATION: Synthetic

<400> SEQUENCE: 74
cttctgcaat tccgacctcg 20

<210> SEQ ID NO 75
<211> LENGTH: 20
<212> TYPE: DNA
<213> ORGANISM: Artificial Sequence
<220> FEATURE:
<223> OTHER INFORMATION: Synthetic

<400> SEQUENCE: 75
catcccctaa ggcttggaac 20

<210> SEQ ID NO 76
<211> LENGTH: 20
<212> TYPE: DNA
<213> ORGANISM: Artificial Sequence
<220> FEATURE:
<223> OTHER INFORMATION: Synthetic

<400> SEQUENCE: 76
ccactgaaga ttatgacatg 20

<210> SEQ ID NO 77
<211> LENGTH: 20
<212> TYPE: DNA
<213> ORGANISM: Artificial Sequence
<220> FEATURE:
<223> OTHER INFORMATION: Synthetic

<400> SEQUENCE: 77
gctctacctc taatggtttg 20

<210> SEQ ID NO 78
<211> LENGTH: 20
<212> TYPE: DNA
<213> ORGANISM: Artificial Sequence
<220> FEATURE:
<223> OTHER INFORMATION: Synthetic

<400> SEQUENCE: 78
gaatgacatt gccatcaacg 20

<210> SEQ ID NO 79
<211> LENGTH: 20
<212> TYPE: DNA
<213> ORGANISM: Artificial Sequence
<220> FEATURE:
<223> OTHER INFORMATION: Synthetic

<400> SEQUENCE: 79
gaggttggag ttccatcatc 20

<210> SEQ ID NO 80
<211> LENGTH: 20
<212> TYPE: DNA
<213> ORGANISM: Artificial Sequence
<220> FEATURE:
<223> OTHER INFORMATION: Synthetic

<400> SEQUENCE: 80
gcttcagcag caacaactgc 20

<210> SEQ ID NO 81
<211> LENGTH: 20
<212> TYPE: DNA
<213> ORGANISM: Artificial Sequence
<220> FEATURE:
<223> OTHER INFORMATION: Synthetic

<400> SEQUENCE: 81
catgaataac acagcacctg 20

<210> SEQ ID NO 82
<211> LENGTH: 20
<212> TYPE: DNA
<213> ORGANISM: Artificial Sequence
<220> FEATURE:
<223> OTHER INFORMATION: Synthetic

<400> SEQUENCE: 82
gctcacggag gaggattttg 20

```
<210> SEQ ID NO 83
<211> LENGTH: 20
<212> TYPE: DNA
<213> ORGANISM: Artificial Sequence
<220> FEATURE:
<223> OTHER INFORMATION: Synthetic

<400> SEQUENCE: 83

cgaaggcata gaagcaagtc                                                   20


<210> SEQ ID NO 84
<211> LENGTH: 196
<212> TYPE: PRT
<213> ORGANISM: Artificial Sequence
<220> FEATURE:
<223> OTHER INFORMATION: Synthetic

<400> SEQUENCE: 84

Met Ser Asp Thr Trp Ser Ser Ile Gln Ala His Lys Lys Gln Leu Asp
1               5                   10                  15

Ser Leu Arg Glu Arg Leu Gln Arg Arg Arg Lys Gln Asp Ser Gly His
            20                  25                  30

Leu Asp Leu Arg Asn Pro Glu Ala Ala Leu Ser Pro Thr Phe Arg Ser
        35                  40                  45

Asp Ser Pro Val Pro Thr Ala Pro Thr Ser Gly Gly Pro Lys Pro Ser
    50                  55                  60

Thr Ala Ser Ala Val Pro Glu Leu Ala Thr Asp Pro Glu Leu Glu Lys
65                  70                  75                  80

Lys Leu Leu His His Leu Ser Asp Leu Ala Leu Thr Leu Pro Thr Asp
                85                  90                  95

Ala Val Ser Ile Cys Leu Ala Ile Ser Thr Pro Asp Ala Pro Ala Thr
            100                 105                 110

Gln Asp Gly Val Glu Ser Leu Leu Gln Lys Phe Ala Ala Gln Glu Leu
        115                 120                 125

Ile Glu Val Lys Arg Gly Leu Leu Gln Asp Asp Ala His Pro Thr Leu
    130                 135                 140

Val Thr Tyr Ala Asp His Ser Lys Leu Ser Ala Met Met Gly Ala Val
145                 150                 155                 160

Ala Glu Lys Lys Gly Pro Gly Glu Val Ala Gly Thr Val Thr Gly Gln
                165                 170                 175

Lys Arg Arg Ala Glu Gln Asp Ser Thr Thr Val Ala Ala Phe Ala Ser
            180                 185                 190

Ser Leu Val Ser
        195
```